US009957503B2

(12) United States Patent
Collard et al.

(10) Patent No.: US 9,957,503 B2
(45) Date of Patent: May 1, 2018

(54) TREATMENT OF LCAT GENE RELATED DISEASES BY INHIBITION OF A NATURAL ANTISENSE TRANSCRIPT TO LCAT

(71) Applicant: CuRNA, Inc., Miami, FL (US)

(72) Inventors: Joseph Collard, Delray Beach, FL (US); Olga Khorkova Sherman, Tequesta, FL (US)

(73) Assignee: CuRNA, Inc., Miami, FL (US)

( * ) Notice: Subject to any disclaimer, the term of this patent is extended or adjusted under 35 U.S.C. 154(b) by 0 days. days.

(21) Appl. No.: 14/815,007

(22) Filed: Jul. 31, 2015

(65) Prior Publication Data

US 2016/0024506 A1 Jan. 28, 2016

Related U.S. Application Data

(60) Continuation of application No. 14/814,895, filed on Jul. 31, 2015, which is a division of application No. 13/318,713, filed as application No. PCT/US2010/033908 on May 6, 2010, now Pat. No. 9,155,754.

(60) Provisional application No. 61/248,212, filed on Oct. 2, 2009, provisional application No. 61/235,227, filed on Aug. 19, 2009, provisional application No. 61/180,646, filed on May 22, 2009, provisional application No. 61/176,267, filed on May 7, 2009, provisional application No. 61/175,930, filed on May 6, 2009.

(51) Int. Cl.

| | |
|---|---|
| ***C12N 15/113*** | (2010.01) |
| ***A61K 31/7115*** | (2006.01) |
| ***A61K 31/712*** | (2006.01) |
| ***A61K 31/713*** | (2006.01) |
| *A61K 48/00* | (2006.01) |

(52) U.S. Cl.

CPC .......... *C12N 15/113* (2013.01); *A61K 31/713* (2013.01); *C12N 15/1137* (2013.01); *C12N 15/1138* (2013.01); *C12Y 203/01043* (2013.01); *A61K 48/00* (2013.01); *C12N 2310/11* (2013.01); *C12N 2310/14* (2013.01); *C12N 2310/313* (2013.01); *C12N 2310/314* (2013.01); *C12N 2310/315* (2013.01); *C12N 2310/321* (2013.01); *C12N 2310/322* (2013.01)

(58) Field of Classification Search

None

See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,754,065 | A | 6/1988 | Levenson et al. |
| 4,800,159 | A | 1/1989 | Mullis et al. |
| 5,034,506 | A | 7/1991 | Summerton et al. |
| 5,138,045 | A | 8/1992 | Cook et al. |
| 5,218,105 | A | 6/1993 | Cook et al. |
| 5,288,512 | A | 2/1994 | Seiden |
| 5,288,514 | A | 2/1994 | Ellman |
| 5,319,080 | A | 6/1994 | Leumann |
| 5,393,878 | A | 2/1995 | Leumann |
| 5,432,272 | A | 7/1995 | Benner et al. |
| 5,457,189 | A | 10/1995 | Crooke et al. |
| 5,459,255 | A | 10/1995 | Cook et al. |
| 5,474,796 | A | 12/1995 | Brennan |
| 5,491,084 | A | 2/1996 | Chalfie et al. |
| 5,506,337 | A | 4/1996 | Summerton et al. |
| 5,519,134 | A | 5/1996 | Acevedo et al. |
| 5,525,735 | A | 6/1996 | Gallop et al. |
| 5,539,083 | A | 7/1996 | Cook et al. |
| 5,549,974 | A | 8/1996 | Holmes |
| 5,569,588 | A | 10/1996 | Ashby et al. |
| 5,576,302 | A | 11/1996 | Cook et al. |
| 5,593,853 | A | 1/1997 | Chen et al. |
| 5,605,662 | A | 2/1997 | Heller et al. |
| 5,661,134 | A | 8/1997 | Cook et al. |
| 5,708,161 | A | 1/1998 | Reese |
| 5,739,119 | A | 4/1998 | Galli et al. |
| 5,739,311 | A | 4/1998 | Lackey et al. |
| 5,756,710 | A | 5/1998 | Stein et al. |
| 5,849,902 | A | 12/1998 | Arrow et al. |
| 5,891,725 | A | 4/1999 | Soreq et al. |
| 5,902,880 | A | 5/1999 | Thompson |
| 5,908,779 | A | 6/1999 | Carmichael et al. |
| 5,965,721 | A | 10/1999 | Cook et al. |

(Continued)

FOREIGN PATENT DOCUMENTS

| | | |
|---|---|---|
| CA | 2686933 | 4/2008 |
| EP | 335451 A3 | 3/1988 |

(Continued)

OTHER PUBLICATIONS

Ahaneku et al (Leukemia. Nov. 1991;5(11):1004-5).*

(Continued)

*Primary Examiner* — Richard A Schnizer

(74) *Attorney, Agent, or Firm* — CuRNA, Inc.; Monte R. Browder

(57) ABSTRACT

The present invention relates to antisense oligonucleotides that modulate the expression of and/or function of a Lipid transport and metabolism gene, in particular, by targeting natural antisense polynucleotide of a Lipid transport and metabolism gene. The invention also relates to the identification of these antisense oligonucleotides and their use in treating diseases and disorders associated with the expression of a Lipid transport and metabolism genes.

12 Claims, 29 Drawing Sheets

(56) References Cited

U.S. PATENT DOCUMENTS

| | | | |
|---|---|---|---|
| 5,985,663 | A | 11/1999 | Bennett et al. |
| 6,005,095 | A | 12/1999 | Capaccioli et al. |
| 6,013,639 | A | 1/2000 | Peyman et al. |
| 6,013,786 | A | 1/2000 | Chen et al. |
| 6,034,233 | A | 3/2000 | Ecker et al. |
| 6,100,090 | A | 8/2000 | Monia et al. |
| 6,140,492 | A | 10/2000 | Morelli et al. |
| 6,147,200 | A | 11/2000 | Manoharan et al. |
| 6,165,712 | A | 12/2000 | Foulkes et al. |
| 6,165,990 | A | 12/2000 | Singh et al. |
| 6,175,409 | B1 | 1/2001 | Nielsen et al. |
| 6,221,587 | B1 | 4/2001 | Ecker et al. |
| 6,239,265 | B1 | 5/2001 | Cook |
| 6,242,589 | B1 | 6/2001 | Cook et al. |
| 6,268,490 | B1 | 7/2001 | Imanishi et al. |
| 6,303,374 | B1 | 10/2001 | Zhang et al. |
| 6,307,040 | B1 | 10/2001 | Cook et al. |
| 6,316,198 | B1 | 11/2001 | Skouv et al. |
| 6,335,434 | B1 | 1/2002 | Guzaev et al. |
| 6,376,541 | B1 | 4/2002 | Nixon et al. |
| 6,403,566 | B1 | 6/2002 | Wang |
| 6,444,464 | B1 | 9/2002 | Wyatt |
| 6,451,991 | B1 | 9/2002 | Martin et al. |
| 6,525,191 | B1 | 2/2003 | Ramassamy |
| 6,528,262 | B1 | 3/2003 | Gilad et al. |
| 6,528,631 | B1 | 3/2003 | Cook et al. |
| 6,617,122 | B1 | 9/2003 | Hayden et al. |
| 6,617,442 | B1 | 9/2003 | Crooke et al. |
| 6,630,315 | B1 | 10/2003 | Miwa et al. |
| 6,639,059 | B1 | 10/2003 | Kochkine et al. |
| 6,656,730 | B1 | 12/2003 | Manoharan |
| 6,667,337 | B2 | 12/2003 | Wilson |
| 6,670,461 | B1 | 12/2003 | Wengel et al. |
| 6,710,174 | B2 | 3/2004 | Bennett et al. |
| 6,734,291 | B2 | 5/2004 | Kochkine et al. |
| 6,762,169 | B1 | 7/2004 | Manoharan |
| 6,794,499 | B2 | 9/2004 | Wengel et al. |
| 6,833,361 | B2 | 12/2004 | Hong et al. |
| 6,861,514 | B2 | 3/2005 | Cook et al. |
| 6,867,294 | B1 | 3/2005 | Sanghvi et al. |
| 6,936,467 | B2 | 8/2005 | Kmiec et al. |
| 6,936,593 | B1 | 8/2005 | Agrawal et al. |
| 6,977,295 | B2 | 12/2005 | Belotserkovskii et al. |
| 6,986,988 | B2 | 1/2006 | Gilad et al. |
| 7,034,133 | B2 | 4/2006 | Wengel et al. |
| 7,034,145 | B2 | 4/2006 | Shen et al. |
| 7,053,195 | B1 | 5/2006 | Goff |
| 7,053,199 | B2 | 5/2006 | Imanishi et al. |
| 7,053,207 | B2 | 5/2006 | Wengel |
| 7,060,809 | B2 | 6/2006 | Wengel et al. |
| 7,084,125 | B2 | 8/2006 | Wengel |
| 7,087,589 | B2 | 8/2006 | Jacobson et al. |
| 7,125,982 | B1 | 10/2006 | Frayne |
| 7,144,995 | B2 | 12/2006 | Wise et al. |
| 7,144,999 | B2 | 12/2006 | Ward et al. |
| 7,148,204 | B2 | 12/2006 | Bennett et al. |
| 7,153,954 | B2 | 12/2006 | Koch et al. |
| 7,169,916 | B2 | 1/2007 | Krotz et al. |
| 7,199,107 | B2 | 4/2007 | Dobie et al. |
| 7,202,357 | B2 | 4/2007 | Crooke et al. |
| 7,217,572 | B2 | 5/2007 | Ward et al. |
| 7,220,549 | B2 | 5/2007 | Buzby |
| 7,226,785 | B2 | 6/2007 | Kmiec et al. |
| 7,229,974 | B2 | 6/2007 | Peyman et al. |
| 7,229,976 | B2 | 6/2007 | Dobie et al. |
| 7,235,534 | B2 | 6/2007 | Tauguay et al. |
| 7,235,653 | B2 | 6/2007 | Bennett et al. |
| 7,238,858 | B2 | 7/2007 | Marraccini et al. |
| 7,276,599 | B2 | 10/2007 | Moore et al. |
| 7,285,288 | B1 | 10/2007 | Tormo et al. |
| 7,297,786 | B2 | 11/2007 | McCray et al. |
| 7,314,923 | B2 | 1/2008 | Kaneko et al. |
| 7,320,965 | B2 | 1/2008 | Sah et al. |
| 7,321,828 | B2 | 1/2008 | Cowsert et al. |
| 7,335,764 | B2 | 2/2008 | Crooke et al. |
| 7,335,765 | B2 | 2/2008 | Kaneko et al. |
| 7,339,051 | B2 | 3/2008 | Crooke et al. |
| 7,371,833 | B1 | 5/2008 | Weiss |
| 7,399,845 | B2 | 7/2008 | Seth et al. |
| 7,402,434 | B2 | 7/2008 | Newman et al. |
| 7,402,574 | B2 | 7/2008 | Iversen et al. |
| 7,420,050 | B2 | 9/2008 | Park et al. |
| 7,423,142 | B2 | 9/2008 | Vornlocher |
| 7,425,545 | B2 | 9/2008 | Crooke et al. |
| 7,427,675 | B2 | 9/2008 | Capaldi et al. |
| 7,456,154 | B2 | 11/2008 | Soreq et al. |
| 7,462,642 | B2 | 12/2008 | Wang et al. |
| 7,468,431 | B2 | 12/2008 | Bhanot et al. |
| 7,510,830 | B2 | 3/2009 | Baguley et al. |
| 7,541,344 | B2 | 6/2009 | Bhat et al. |
| 7,547,684 | B2 | 6/2009 | Seth et al. |
| 7,569,575 | B2 | 8/2009 | Sorensen et al. |
| 7,569,686 | B1 | 8/2009 | Bhat et al. |
| 7,572,582 | B2 | 8/2009 | Wengel et al. |
| 7,582,745 | B2 | 9/2009 | Sah et al. |
| 7,585,893 | B2 | 9/2009 | Baguley et al. |
| 7,589,190 | B2 | 9/2009 | Westergaard et al. |
| 7,598,227 | B2 | 10/2009 | Crooke et al. |
| 7,605,251 | B2 | 10/2009 | Tan et al. |
| 7,622,453 | B2 | 11/2009 | Frieden et al. |
| 7,662,948 | B2 | 2/2010 | Kurreck et al. |
| 7,666,854 | B2 | 2/2010 | Seth et al. |
| 7,674,895 | B2 | 3/2010 | Reich et al. |
| 7,687,617 | B2 | 3/2010 | Thrue et al. |
| 7,691,995 | B2 | 4/2010 | Zamore et al. |
| 7,695,902 | B2 | 4/2010 | Crooke |
| 7,696,345 | B2 | 4/2010 | Allerson et al. |
| 7,709,456 | B2 | 5/2010 | Corey et al. |
| 7,709,630 | B2 | 5/2010 | Gaarde et al. |
| 7,713,738 | B2 | 5/2010 | Hansen et al. |
| 7,718,629 | B2 | 5/2010 | Bamcrot et al. |
| 7,723,508 | B2 | 5/2010 | Crooke et al. |
| 7,732,422 | B2 | 6/2010 | Gleave et al. |
| 7,732,590 | B2 | 6/2010 | Bhanot et al. |
| 7,737,264 | B2 | 6/2010 | Thrue et al. |
| 7,737,265 | B2 | 6/2010 | Akinc et al. |
| 7,741,305 | B2 | 6/2010 | Crooke et al. |
| 7,741,309 | B2 | 6/2010 | Hansen et al. |
| 7,741,457 | B2 | 6/2010 | Seth et al. |
| 7,745,609 | B2 | 6/2010 | Bennett et al. |
| 7,749,978 | B2 | 7/2010 | Sah et al. |
| 9,155,754 | B2 | 10/2015 | Collard et al. |
| 2003/0139359 | A1 | 7/2003 | Dobie |
| 2003/0186920 | A1 | 10/2003 | Sirois |
| 2003/0191075 | A1 | 10/2003 | Cook et al. |
| 2003/0228618 | A1 | 12/2003 | Levanon et al. |
| 2003/0233670 | A1 | 12/2003 | Edgerton et al. |
| 2004/0006031 | A1 | 1/2004 | Dean et al. |
| 2004/0033480 | A1 | 2/2004 | Wong |
| 2004/0101858 | A1 | 5/2004 | Ward et al. |
| 2004/0137423 | A1 | 7/2004 | Hayden et al. |
| 2004/0138155 | A1 | 7/2004 | Baird et al. |
| 2004/0175803 | A1 | 9/2004 | Meritet et al. |
| 2004/0180336 | A1 | 9/2004 | Gilad et al. |
| 2004/0254137 | A1 | 12/2004 | Ackermann et al. |
| 2005/0009771 | A1 | 1/2005 | Levanon et al. |
| 2005/0026160 | A1 | 2/2005 | Allerson et al. |
| 2005/0113326 | A1 | 5/2005 | Siwkowski et al. |
| 2005/0143357 | A1 | 6/2005 | Pousette et al. |
| 2005/0153286 | A1 | 7/2005 | Clements |
| 2005/0215504 | A1 | 9/2005 | Bennett et al. |
| 2005/0222029 | A1 | 10/2005 | Bartel et al. |
| 2006/0009410 | A1 | 1/2006 | Crooke et al. |
| 2006/0142196 | A1 | 6/2006 | Klein et al. |
| 2006/0178333 | A1 | 8/2006 | Soreq et al. |
| 2007/0082848 | A1 | 4/2007 | Alitalo et al. |
| 2007/0197459 | A1 | 8/2007 | Milner |
| 2007/0213274 | A1 | 9/2007 | Salonen |
| 2007/0213292 | A1 | 9/2007 | Stoffel et al. |
| 2007/0231816 | A1 | 10/2007 | Chaussabel et al. |
| 2007/0248590 | A1 | 10/2007 | Milne et al. |
| 2008/0146788 | A1 | 6/2008 | Bhat et al. |
| 2008/0206232 | A1 | 8/2008 | Spiegelman et al. |
| 2008/0221051 | A1 | 9/2008 | Becker et al. |

(56) References Cited

U.S. PATENT DOCUMENTS

| | | | |
|---|---|---|---|
| 2008/0293142 A1 | 11/2008 | Liu et al. |
| 2009/0191263 A1 | 7/2009 | Reich et al. |
| 2009/0192106 A1 | 7/2009 | Dobie et al. |
| 2009/0208479 A1 | 8/2009 | Jaye et al. |
| 2009/0258925 A1 | 10/2009 | Wahlestedt |
| 2009/0318536 A1 | 12/2009 | Freier et al. |
| 2009/0326041 A1 | 12/2009 | Bhanot et al. |
| 2010/0105760 A1 | 4/2010 | Collard et al. |
| 2012/0046344 A1 | 2/2012 | Collard et al. |

FOREIGN PATENT DOCUMENTS

| | | | |
|---|---|---|---|
| EP | 335451 | A2 | 10/1989 |
| WO | WO-1984/03564 | | 9/1984 |
| WO | WO-1991/19735 | | 12/1991 |
| WO | WO-1992/00091 | | 1/1992 |
| WO | WO-1992/08796 | | 5/1992 |
| WO | WO-1993/20242 | | 10/1993 |
| WO | WO-1994-026887 | A1 | 11/1994 |
| WO | WO-1994/28143 | | 12/1994 |
| WO | WO-1995-015373 | A2 | 6/1995 |
| WO | WO-1995/22618 | | 8/1995 |
| WO | WO-1995/25116 | | 10/1995 |
| WO | WO-1995/35505 | | 12/1995 |
| WO | WO-1996-027663 | A2 | 9/1996 |
| WO | WO-1997-039120 | A1 | 10/1997 |
| WO | WO-1999-014226 | A1 | 3/1999 |
| WO | WO-1999-039352 | A1 | 8/1999 |
| WO | WO-2000-057837 | A1 | 10/2000 |
| WO | WO-2000-061770 | A2 | 10/2000 |
| WO | WO-2001-000669 | A2 | 1/2001 |
| WO | WO-2001-21631 | A2 | 3/2001 |
| WO | WO-2001-025488 | A2 | 4/2001 |
| WO | WO-2001-051630 | A1 | 7/2001 |
| WO | WO-2002-062840 | A1 | 8/2002 |
| WO | WO-2002-068688 | A1 | 9/2002 |
| WO | WO-2004-016255 | A1 | 2/2004 |
| WO | WO-2004-024079 | A2 | 3/2004 |
| WO | WO-2004-030750 | A1 | 4/2004 |
| WO | WO-2004-041838 | A1 | 5/2004 |
| WO | WO-2004- 104161 | A2 | 12/2004 |
| WO | WO-2005-045034 | A2 | 5/2005 |
| WO | WO-2005-070136 | A2 | 8/2005 |
| WO | WO-2005-079862 | A1 | 9/2005 |
| WO | WO-2007-028065 | A2 | 3/2007 |
| WO | WO-2007-071182 | A1 | 6/2007 |
| WO | WO-2007-087113 | A2 | 8/2007 |
| WO | WO-2007-138023 | A1 | 12/2007 |
| WO | WO-2008-057556 | A2 | 5/2008 |
| WO | WO-2008-066672 | A2 | 6/2008 |
| WO | WO-2008-087561 | A2 | 7/2008 |
| WO | WO-2010-002984 | A1 | 1/2010 |
| WO | 2010040112 | A2 | 4/2010 |
| WO | 2010129799 | A2 | 4/2010 |
| WO | WO-2010-040571 | A2 | 4/2010 |
| WO | WO-2010-054364 | A1 | 5/2010 |
| WO | WO-2010-058227 | A2 | 5/2010 |

OTHER PUBLICATIONS

Rose et al (Atherosclerosis 229 (2013) 206e211).*

Ausubel, Current Protocols in Molecular Biology vol. 1, 1994, 6.0.1-6.4.10.

Barak, et al., "A β-Arrestin/Green Fluorescent Protein Biosensor for Detecting G Protein-Coupled Receptor Activation," J. Biol. Chem. 272:27497-27500 (1997).

Barber, et al., "Delivery of membrane-impermeant fluorescent probes into living neural cell populations by lipotransfer," Neuroscience Letters 207:17-20 (1996).

Baum, "Solid-phase synthesis of benzodiazepines," C&EN News, Jan. 18, page 33-34 (1993).

Bernstein, E., et al., "Role for a Bidentate Ribonuclease in the Initiation Step of RNA Interference," Nature 409:363-366 (2001).

Boutla, A., et al., "Short 5'-phosphorylated double-stranded RNAs induce RNA interference in *Drosophila*," Curr. Biol. 11:1776-1780 (2001).

Boyd-Kimball, et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).

Brazma & Vilo, "Gene expression data analysis," FEBS Lett., 480:17-24 (2000).

Bright, et al., "Chapter 6. Fluorescence Ratio Imaging Microscopy," Methods in Cell Biology vol. 30, Taylor and Wang (eds) p. 157-192 (1989).

Bright, et al., "Delivery of Macromolecules Into Adherent Cells via Electroporation for Use in Fluorescence Spectroscopic Imaging and Metabolic Studies," Cytometry 24:226-233 (1996).

Bright, et al., "Fluorescence Ratio Imaging Microscopy: Temporal and Spatial Measurements of Cytoplasmic pH," J. Cell Biology 104:1019-1033 (1987).

Campbell, et al., "Phosphonmate Ester Synthesis Using a Modified Mitsunobu Condensation," J. Org. Chem. 59:658-660 (1994).

Caplen, N. J., et al., "Specific inhibition of gene expression by small double-stranded RNAs in invertebrate and vertebrate systems," PNAS Sci. USA 98:9742-9747 (2001).

Carninci, et al., "The transcriptional landscape of the mammalian genome," Science 309:1559-1563 (2005).

Carulli, et al., "High Throughput Analysis of Differential Gene Expression," J. Cell Biochem. Suppl., 3:286-296 (1998).

Celis, et al., "Gene expression profiling: monitoring transcription and translation products using DNA microarrays and proteomics," FEBS Lett., 480:2-16 (2000).

Chabala, J.C., "Solid-phase combinatorial chemistry and novel tagging methods for i dentifying leads," Curr Opin Biotechnol. 6:632-639 (1995).

Cech, J., "Ribozymes and Their Medical Implications," American. Med Assoc. 260:3030-3035 (1988).

Chen, et al., "Expression of ssDNA in Mammalian Cells," BioTechniques 34:167-171 (2003).

Chen, et al., "Analogous Organic Synthesis of Small-Compound Libraries: Validation of Combinatorial Chemistry in Small-Molecule Synthesis," J. Amer. Chem. Soc. 116:2661-2662 (1994).

Cheng, J. et al., "Transcriptional maps of 10 human chromosomes at 5-nucleotide resolution," Science 308:5725:1149-1154 (2005).

Cho, et al., "An Unnatural Biopolymer," Science 261:1303-1305 (1993).

Christiensen, N.K. et al., "A Novel Class of Oligonucleotide Analogues Containing 2'-O,3'-C-Linked [3.2.0]Bicycloarabinonucleoside Monomers: Synthesis, Thermal Affinity Studies, and Molecular Modeling," J. Am. Chem. Soc., 120:5458-5463 (1998).

Cubitt, et al. , "Understanding, improving and using green fluorescent proteins," Trends in Biochemical Science 20:448-455 (1995).

Curiel, D. T. et al., "Adenovirus enhancement of transferrin-polylysine-mediated gene delivery," PNAS 88:8850-8854 (1991).

Dai et al., "SIRT1 Interacts With p73 and Suppresses p73-Dependent Transcriptional Activity," J Cell Physiol 210(1):161-165 (2007).

Davidson, et al., "A model system for in vivo gene transfer into the central nervous system using an adenoviral vector," Nat. Genet 3:219-223 (1993).

Davis, et al., "Direct Gene Transfer into Skeletal Muscle In Vivo: Factors Affecting Efficiency of Transfer and Stability of Expression," Hum Gene Ther 4:151-159 (1993).

De Mesmaeker, et al., "Antisense Oligonucleotides," Acc. Chem. Res. 28:366-374 (1995).

Deng et al., "Small Interfering RNA Targeting the PINK1 Induces Apoptosis in Dopaminergic Cells SH-SY5Y", Biochemical and Biophysical Research Communications, vol. 337, No. 4, pp. 1133-1138 (2005).

Dixon, et al., "Anthrax," New England J. Med. 341:815-826 (1999).

Dolle, "Discovery of Enzyme inhibitors through combinatorial chemistry," Mol Divers. 2:223-236 (1997).

(56) References Cited

OTHER PUBLICATIONS

Dykxhoorn, D., et al., "Determinants of Specific RNA Interference-Mediated Silencing of Human β-Globin Alleles Differing by a Single Nucleotide Polymorphism," PNAS, vol. 103, No. 15, pp. 5953-5958, (2006).
Eguchi, et al., "Antisense RNA," Annu Rev. Biochem 60:631-652 (1991).
Eichler, et al., "Generation and utilization of synthetic combinatorial libraries," Mol Med Today 1:174-180 (1995).
Eichler, et al., "Peptide Peptidomimetic and organic synthetic combinatorial libraries," Med Res Rev 15:481-496 (1995).
Espeseth, et al., A genome wide analysis of ubiquitin ligases in APP processing identifies a novel regulator of BACE1 mRNA levels, Mol. Cell Neurosci. 33: 227-235 (2006).
Faghihi, M. & Wahlestedt, C., "RNA interference is not involved in natural antisense mediated regulation of gene expression in mammals," Genome Biol (2005).
Fauchere, et al., "Peptide and nonpeptide lead discovery using robotically synthesized soluble libraries," Can J. Physiol Pharmacol 75:683-689 (1997).
Felgner and Holm, "Cationic Liposome-Mediated Transfection," Bethesda Res. Lab Focus, 11:2:21 (1989).
Fields, et al., "How many genes in the human genome?" Nature Genetics 7:345-346 (1994).
Freier & Altman, "The ups and downs of nucleic acid duplex stability: structure-stability studies on chemically-modified DNA:RNA duplexes," Nucl. Acid Res., 25:22:4429-4443 (1997).
Fuchs, et al., "Identification of Differentially Expressed Genes by Mutually Subtracted RNA Fingerprinting," Anal. Biochem., 286:91-98 (2000).
Gebeyehu, G., et al., "Novel biotinylated nucleotide-analogs for labeling and colorimetric detection of DNA," Nucl. Acids Res. 15:4513 (1987).
Geller, A.I. et al., "An HSV-1 Vector Expressing Tyrosine Hydroxylase Causes Production and Release of L-DOPA from Cultured Rat Striatal Cells," J. Neurochem 64:487-496 (1995).
Geller, A.I. et al., "Long-term increases in neurotransmitter release from neuronal cells expressing a constitutively active adenylate cyclase from a herpes simplex virus type 1 vector," PNAS U.S.A. :90:7603-7607 (1993).
Geller, A.I., et al., "Infection of cultured central nervous system neurons with a defective herpes simplex virus 1 vector results in stable expression of *Escherichia coli* β-galactosidase," PNAS USA 87:1149-1153 (1990).
GenBank Accession No. NM_000559, *Homo sapiens* Hemoglobin, Gamma A (HBG1), mRNA, (2008).
Giuliano, et al., "FLuorescent Protein Biosensors: Measurement of Molecular Dynamics in Living Cells," Ann. Rev. if Biophysics and Biomolecular Structure 24:405-434 (1995).
Giuliano, et al., "Light-Optical-Based Reagents for the Measurement and Manipulation of Ions, Metabolites, and Macromolecules in Living Cells," Methods in Neuroscience 27:1-16 (1995).
Giuliano, et al., "Determination of Intracellular pH of BALB/c-3T3 Cells Using the Fluorescence of Pyranine," Anal. Biochem 167:362-371 (1987).
Going & Gusterson, "Molecular Pathology and Future Developments," Eur. J. Cancer, 35:1895-1904 (1999).
Hagihara, et al., "Vinylogous Polypeptides: An Alternate Peptide Backbone," J. Amer. Chem. Soc. 114:6568-6571 (1992).
Haussecker, D., et al., "Dicer-Dependent Turnover of Intergenic from the Human β-Globin Gene Cluster," Molecular and Cellular Biology, vol. 25, No. 21, pp. 9724-9733, (2005).
Heller, et al., "Discovery and Analysis of Inflammatory Disease-Related Genes Using cDNA Microarrays," PNAS U.S.A. 94:2150-2155 (1997).
Herdewijn P., "Heterocyclic Modifications of Oligonucleotides and Antisense Technology," Antisense & Nucleic Acid Drug Dev., 10:297-310 (2000).
Hirschmann, et al., J. Amer. Chem. Soc., 114:9217-9218 (1992).
Hobbs-DeWitt, et al., "Diversomers: An approach to nonpeptide, nonoligomeric chemical diversity," Proc. Nat. Acad. Sci. USA 90;6909-6913 (1993).
Houghton AN, Gold JS, Blachere NE, Immunity against cancer: lessons learned from melanoma,. Curr Opin Immunol 13:134-140 (2001).
International Human Genome Sequencing Consortium "Finishing the euchromatic sequence of the human genome." Nature 431:7011:931-945 (2004).
Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigen RNAs," Nature Chemical Biology, 1(4):216-222 (2005).
Jungblut, et al., "Proteomics in human disease: Cancer, heart and infectious diseases," Electrophoresis 20:2100-2110 (1999).
Jurecic & Belmont, "Long-distance DD-PCR and cDNA microarrays," Curr. Opin. Microbiol., 3:316-321 (2000).
Kabanov, et al., "A new class of antivirals: antisense oligonucleotides combined with a hydrophobic substituent effectively inhibit influenza virus reproduction and synthesis of virus-specific proteins in MDCK cells," FEBS Lett. 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptome," Science 309:1564-1566 (2005).
Kawahara & Nishikura, "Extensive adenosine-to-inosine editing detected in Alu repeats of antisense RNAs reveals scarcity of sense-antisense duplex formation," FEBS Lett 580:2301-2305 (2006).
Kay, et al., "Identification of enzyme inhibitors from phage-displayed combinatorial peptide libraries," Comb Chem High Throughput Screen 4:535-543 (2001).
Kenan, et al., "Exploring molecular diversity with combinatorial shape libraries," Trends Biochem Sci 19:57-64 (1994).
Kornberg, A., DNA Replication, W.H. Freeman & Co., San Francisco, pp. 75-77, (1980).
Larson, et al., "Rapid DNA Fingerprinting of Pathogens by Flow Cytometry," Cytometry, 2000, 41:203-208 (2000).
Larsson, et al., "High-Throughput Protein Expression of cDNA Products as a Tool in Functional Genomics," J. Biotechnology., 80:143-157 (2000).
Lebl, et al., "One-bead-one-structure combinatorial libraries," Biopolymers 37:177-198 (1995).
LeGal Lasalle et al., "An Adenovirus Vector for Gene Transfer into Neurons and Glia in teh Brain," Science 259:988-990 (1993).
Letsinger, et al., "Cholesteryl-conjugated oligonucleotides: Synthesis, Properties, and Activity as Inhibitors of Replication of Human Immunodeficiency Virus in Cell Culture," PNAS 86:6553-6556 (1989).
Li et al., "Control of APP processing and Aβ generation level by BACE1 enzymatic activity and transcription," Faseb J 20; 285-292 (2006).
Li, et al., J. Neurochem 89 1308-1312 (2004).
Liang, et al., "Parallel Synthesis and Screening of a Solid Phase Carbohydrate Library," Science 274:1520-1522 (1996).
Luther, "Role of endogenous antisense RNA in cardiac gene regulation," J. Mol. Med. 83:26-32 (2005).
Madden, et al., "Serial analysis of gene expression: from gene discovery to target identification," Drug Discov. Today 5:415-425 (2000).
Makalowska I, Lin CF, Makalowski W., "Overlapping genes in vertebrate genomes," Comput Biol. Chem 29:1:1-12 (2005).
Mannino and Gould-Fogerite, "Liposome Mediated Gene Transfer," BioTechniques 6:682-690 (1988).
Manoharan et al., "Lipidic Nucleic Acids," Tetrahedron Lett 36:3651-3654 (1995).

(56) References Cited

OTHER PUBLICATIONS

Manoharan, et al., "Chemical Modifications to Improve Uptake and Bioavailability of Antisense Oligonucleotides," Ann. N.Y. Acad. Scie 660:306-309 (1992).
Manoharan, et al., "Introduction of a Lipophilic Thioether in teh Minor Groove of Nucleic Acids for Antisense Applications," Bioorg. Med. Chem. Let 3:2765-2770 (1993).
Manoharan, et al., "Cholic Acid-Oligonucleotide Conjugates for Antisense Applications," Bioorg. Med. Chem. Let 4;1053 (1994).
Manoharan, et al., "Oligonucleotide Conjugates: Alteration of the Pharmacokinetic Properties of Antisense Agents," Nucleosides & Nucleotides 14:969-973 (1995).
Manoharan, M., "2'-Carbohydrate modifications in antisense oligonucleotide therapy: importance of conformation, configurationj and conjugation," Biochemica et Biophysica Acta 1489:117-139 (1999).
Mattick, J. S. "RNA regulation: a new genetics?" Nat. Rev. Genet 5:4:316-323 (2004).
Maurer, R.A., "Cationic Liposome-Mediated Transfection of Primary Cultures of Rat Pituitary Cells," Bethesda Res. Lab. Focus 11:2:25 (1989).
McNeil in Methods in Cell Biology vol. 29, Taylor and Wang (eds.) p. 153-173 (1989).
Morelli et al., "The antisense bc1-2-IgH transcript is an optimal target for synthetic oligonucleotides," PNAS USA 94:8150-8155 (1997).
Nielsen, et al., "Sequence-Selective Recognition of DNA by Strand Displacement with a Thymine-Substituted Polyamide," Science 254:1497-1500 (1991).
Oberhauser, et al., "Effective incorporation of 2'-O-methyl-oligoribonucleotides into liposomes and enhanced cell association through modification with thiocholesterol," Nucl. Acids Res. 20:533-538 (1992).
Petit et al., "Wild-type PINK1 Prevents Basal and Induced Neuronal Apoptosis, a Protective Effect Abrogated by Parkinson Disease-Related Mutations", Journ. Biol. Chem., vol. 280, No. 40, pp. 34025-334032 (2005).
Prasanth, et al., "Regulating Gene Expression through RNA Nuclear Retention," Cell 123, 249-263 (2005).
Prashar & Weissman, "READS: A Method for Display of 3'-End Fragments of Restriction Enzyme-Digested cDNAs for Analysis of Differential Gene Expression," Methods Enzymol., 303:258-272 (1999).
Quantin, et al., "Adenovirus as an expression vector in muscle cells in vivo," PNAS 89:2581-2584 (1992).
Rosenfeld, et al., "In Vivo Transfer of the Human Cystic Fibrosis Transmembrane Conductance Regulator Gene to the Airway Epithelium," Cell, 68:143-155 (1992).
Rosok and Sioud, "Systematic identification of sense-antisense transcripts in mammalian cells," Nature Biotech. 22(1):104-108 (2004).
Saison-Behmoaras, et al., "Short modified antisense oligonucleotides directed against Ha-ras point mutation induce selective cleavage of the mRNA and inhibit T24 cells proliferation," EMBO J. 10:1111-1118 (1991).
Sanghvi, Y.S., in Crooke, S.T. and Lebleu, B., eds., Antisense Research and Applications, CRC Press, Boca Raton, 1993, p. 276-278.
Scheele et al., "The Human PINK1 Locus is Regulated and Vivo by a Non-Coding Natural Antisense RNA During Modulation of Mitochondrial Function", BMC Genomics, vol. 8, No. 1, p. 74 (2007).
Schena, et al., "Parallel human genome analysis: Microarray-based expression monitoring of 1000 genes," PNAS 93:10614-10619(1996).
Shea, et al., "Synthesis, hybridization properties and antiviral activity of lipid-oligodeoxynucleotide conjugates," Nucl. Acids Res 18:3777-3783 (1990).
Shen, T., et al., "Modification of Globin Gene Expression by RNA Targeting Strategies," Experimental Hematology, vol. 35, No. 8, pp. 1209-1218, (2007).
Shimomura, et al., "Semi-synthetic aequorin," J. of Biochemistry (Tokyo) 251:405-410 (1988).
Singer, et al., "Targeting BACE1 with siRNAs ameliorates Alzheimer disease neuropathology in a transgenic model," Nat Neurosci 8:1343-1349 (2005).
Southwick, et al., "Cyanine Dye Labeling Reagents-Carboxymethylindocyanine Succinimidyl Esters," Cytometry 11:418-430 (1990).
Stratford-Perricadet, et al., "Widespread Long-term Gene Transfer to Mouse Skeletal Muscles and Heart," J. Clin. Invest., 90:626-630 (1992).
Sullenger, et al., "Overexpression of TAR sequences Renders Cells Resistant to Human Immunodeficiency Virus Replication," Cell63:601-608 (1990).
Sun, et al., "Downregulation of Sirt1 by antisense oligonucleotides induces apoptosis and enhances radiations sensitization in A549 lung cancer cells," Lung Cancer 58(1):21-29 (2007).
Sutcliffe, et al., "TOGA: An automated parsing technology for analyzing expression of nearly all genes," PNAS, 97:1976-1981 (2000).
Sutton, et al., "TIGR Assembler: A New Tool for Assembling Large Shotgun Sequencing Projects," Genome Science & Tech., 1:9-19 (1995).
Svinarchuk, et al., "Inhibition of HIV proliferation in MT-4 cells by antisense oligonucleotide conjugated to lipophilic groups," Biochimie 75:49-54 (1993).
Tamagno, et al., "The various aggregation states of β-amyloid 1-42 mediate different effects on oxidative stress, neurodegeneration, and BACE-1 expression," Free Radic Biol Med 41:202-212 (2006).
Thakker, D.R., et al., "siRNA-mediated knockdown of the serotonin transporter in the adult mouse brain," Mol Psychiatry 10:782-789 (2005).
Thakker, et al., "Neurochemical and behavioral consequences of widespread gene knockdown in the adult mouse brain by using nonviral RNA interference," PNAS 101:17270-17275 (2004).
Thomas et al., "Intracellular pH Measurements in Ehrlich Ascites Tumor Cells Utilizing Spectroscopic Probes Generated in Situ," Biochemistry 18:2210-2218 (1979).
Thompson, et al., "Synthesis and Applications of Small Molecule Libraries" Chem Rev 96:555-600 (1996).
To, Ky, "Identification of Differential Gene Expressionm by High Throughput Analysis," Comb. Chem. High Throughput Screen 3:235-241 (2000).
Tong, et al., "Oxidative stress potentiates BACE1 gene expression," Neural Transm 112, 455-469 (2005).
Toulme, J.J., "New candidates for true antisense," Nature Biotechnology 19:17-18 (2001).
Tsien in Methods in Cell Biology vol. 30 Taylor and Wang (eds) p. 127-156 (1989).
Ulhman, E., "Recent advances in the medical chemistry of antisense oligonucleotide," Current Opinions in Drug Discovery & Development 3:203-213 (2000).
Van Den Eynde BJ, "T cell defined tumor antigens," Curr Opin Immunol 9:684-693 (1997).
Van Der Bruggen, et al., "Tumor-specific shared antigenic peptides recognized by human T cells," Immunol Rev188:51-64 (2002).
Vanhee-Brossolet and Vaquero, "Do natural antisense transcripts make sense in eukaryotes?" Gene 211:1-9 (1998).
Vaughn, et al., "Human Antibodies with Sub-nanomolar Affinities Isolated from a Large Non-immunized Phage Display Library," Nature Biotechnology, 14:3:309-314 (1996).
Velculescu, et al., "Serial Analysis of Gene Expression," Science 270:484-487 (1995).
Wahlestedt, "Natural antisense and noncoding RNA transcripts as potential drug targets," Drug Discovery Today 11 (11/12):503-508 (2006).
Wahlestedt, C., "Antisense oligonucleotide strategies in neuropharmacology," Trends Pharmacol Sci 15:2:42-46 (1994).
Walsh, et al., The role of cell-derived oligomers of Aβ in Alzheimer's disease and avenues for therapeutic intervention, Biochem Soc Trans 33: 1087-1090 (2005).

(56) References Cited

OTHER PUBLICATIONS

Wang, B.B. et al., "Identification of a nuclear-specific cyclophilin which interacts with the proteinase inhibitor eglin c," Biochem J. 314 (Pt 1) 313-319 (1996).
Wiesenhofer, et al., "Glial cell line-derived neurotrophic factor (GDNP) is a proliferation factor for rat C6 glioma cells: evidence from antisense experiments," Antisense & Nucleic Acid Drug Development 10(5):311-321 (2000).
Xue, et al., "Hypoxia and reoxygenation increased BACE1 mRNA and protein levels in human neuroblastoma SH-SY5Y cells," Neurosci Lett 405,231-235 (2006).
Yamada, et at, "Endothelial Nitric-Oxide Synthase Antisense (NOS3AS) Gene Encodes an Autophagy-Related Protein (APG9-like2) Highly Expressed in Trophoblast" (2005).
Yang, et al., "Cellular and Humoral Immune Responses to Viral Antigens Create Barriers to Lung-Directed Gene Therapy with Recombinant Adenoviruses," J. Virol 69:2004-2015 (1995).
Yoshigai, et al., "Characterization of Natural Antisense Transcripts Expressed from Interleukin 1β-inducible Genes in Rat Hepatocytes," HOAJ Biology; Jan. 10, 2012.
EP Application No. 06850393.7 Examination Report dated Oct. 18, 2011.
International Search Report and Written Opinion for PCT Application No. PCT/US2010/033078 dated Jun. 29, 2011.
PCT/US2010/026119 Search Report and Written Opinion dated Feb. 7, 2011.
PCT/US2010/024079 Search Report and Written Opinion dated Jan. 31, 2011.
PCT/US2010/027394 Search Report and Written Opinion dated Nov. 5, 2010.
PCT/US96/10287 (WO97/000271) The Regents of the University of California 1.3.97.
Database Accession No. ARA28420, "Human SiRNA, Seq. ID. 74" Institute of Biology Physics CA, (2008).
Schmitz, G., et al., "Role of ABSG1 and other ABCG Family Members in Lipid Metabolism", Journal of Lipid Research, vol. 42, pp. 1513-1520, (2001).
Barter, B., et el, "Cholesteryl Ester Transfer Protein: A Novel Target, for Raising HDL and Inhibiting Atherosclerosis", Arterioscier Thromb Vas Biology, vol. 23, pp. 160-0 167, (2003).
Esau, C., et al., "MiR-122 Regulation of Lipid Metabolism Revealed by In Vivo Antisense Targeting", Cell Metabolism, vol. 3, pp. 87-98, (2006).
Kuivenhoven, J., et al., "The Molecular Pathology of Lecithin" Cholesterol Acyltransferase (LCAT) Deficiency Syndromes, Journal of Lipid Research, vol. 38, pp. 191-205, (1997).
Genbank Accession No. NG_007981.1. "*Homo sapiens* ATP Binding Cassette Subfamily A Member 1 (ABCA1), RefSeqGene on Chromosome 9", (2015).
Genbank Accession No. BM_396690.1. "5009-0-24-C03.t.1 Chilcoat/Turkewitz cDNA (Large Fraction) Tetrahymena Thermophila cDNA, mRNA Sequence", (2002).
Seitz, A., et al., "Sense and Antisense Transcripts of the Apolipoprotein E Gene in Normal and ApoE Knockout Mice, Their Expression After Spinal Cord Injury and Corresponding Human Transcripts", Human Molecular Genetics, vol. 14, No. 18, pp. 2661-2670, (2005).
Klein, H., et al, "Fish Eye Syndrome: A Molecular Defect in the Lecithin-Cholesterol Acyltransferase (LCAT) Gene Associated with Normal a-LCAT-Specific Activity Implications for Classification and Prognosis", The Journal of Clinical Investigation, Inc., vol. 92, pp. 479-485, (1993).
Rousset, X., et al., "Lecithin:Cholesterol Acyltransferase: From Biochemisty to Role in Cardiovascular Disease", Current Opinion in Endocrinology, Diabetes and Obesity, vol. 16, No. 2, pp. 163-71, (2009).

* cited by examiner

Fold difference in mRNA copy number compared to control (primary monkey hepatocytes)

FIG.2

(SEQ ID NO: 1)

>gi|21536375 | ref |NM_005502 | Homo sapiens ATP-binding cassette, sub –family A (ABC1), member 1 (ABCA1), mRNA gtaattgcgagcgagagtgagtggggccgggacccgcagagccgagccgacccttctctcccgggctgcggcagggcagggcggggagctccgc
gcaccaacagagccggttctcagggcgctttgctccttgttttttccccggttctgttttctccccttctccggaaggcttgtcaaggggtaggagaaagaga
cgcaaacacaaaagtggaaaacagttaatgaccagccacggcgtccctgctgtgagctctggccgctgccttccagggctcccgagccacacgctggg
ggtgctggctgagggaacatggcttgttggcctcagctgaggttgctgctgtggaagaacctcactttcagaagaagacaaacatgtcagctgctgctgg
aagtggcctggccctctatttatcttcctgatcctgatctctgttcggctgagctacccaccctatgaacaacatgaatgccattttccaaataaagccatgccct
ctgcaggaacacttccttgggttcaggggattatctgtaatgccaacaacccctgtttccgttacccgactcctggggaggctcccggagttgttggaaact
ttaacaaatccattgtggctcgcctgttctcagatgctcggaggcttcttttatacagccagaaagacaccagcatgaaggacatgcgcaaagttctgagaa
cattacagcagatcaagaaatccagctcaaacttgaagcttcaagatttcctggtggacaatgaaaccttctctgggttcctgtatcacaacctctctctccca
aagtctactgtggacaagatgctgagggctgatgtcattctccacaaggtatttttgcaaggctaccagttacatttgacaagtctgtgcaatggatcaaaatc
agaagagatgattcaacttggtgaccaagaagtttctgagctttgtggcctaccaagggagaaactggctgcagcagagcgagtacttcgttccaacatg
gacatcctgaagccaatcctgagaacactaaactctacatctccctttcccgagcaaggagctggctgaagccacaaaaacattgctgcatagtcttggga
ctctggcccaggagctgttcagcatgagaagctggagtgacatgcgacaggaggtgatgtttctgaccaatgtgaacagctccagctcctccacccaaat
ctaccaggctgtgtctcgtattgtctgcgggcatcccgagggagggggggctgaagatcaagtctctcaactggtatgaggacaacaactacaaagccctc
tttggaggcaatggcactgaggaagatgctgaaaccttctatgacaactctacaactccttactgcaatgatttgatgaagaatttggagtctagtcctctttcc
cgcattatctggaaagctctgaagccgctgctcgttgggaagatcctgtatacacctgacactccagccacaaggcaggtcatggctgaggtgaacaag
accttccaggaactggctgtgttccatgatctggaaggcatgtgggaggaactcagccccaagatctggaccttcatggagaacagccaagaaatggac
cttgtccggatgctgttggacagcagggacaatgaccacttttgggaacagcagttggatggcttagattggacagcccaagacatcgtggcgtttttggc
caagcacccagaggatgtccagtccagtaatggttctgtgtacacctggagagaagctttcaacgagactaaccaggcaatccggaccatatctcgcttc
atggagtgtgtcaacctgaacaagctagaacccatagcaacagaagtctggctcatcaacaagtccatggagctgctggatgagaggaagttctgggct
ggtattgtgttcactggaattactccaggcagcattgagctgccccatcatgtcaagtacaagatccgaatggacattgacaatgtggagaggacaaataa
aatcaaggatgggtactgggaccctggtcctcgagctgacccctttgaggacatgcggtacgtctgggggggcttcgcctacttgcaggatgtggtgga
gcaggcaatcatcagggtgctgacgggcaccgagaagaaaactggtgtctatatgcaacagatgccctatccctgttacgttgatgacatctttctgcggg
tgatgagccggtcaatgcccctcttcatgacgctggcctggatttactcagtggctgtgatcatcaagggcatcgtgtatgagaaggaggcacggctgaa
agagaccatgcggatcatgggcctggacaacagcatcctctggtttagctggttcattagtagcctcattcctcttcttgtgagcgctggcctgctagtggtc
atcctgaagttaggaaacctgctgccctacagtgatcccagcgtggtgtttgtcttcctgtccgtgtttgctgtggtgacaatcctgcagtgcttcctgattagc
acactcttctccagagccaacctggcagcagcctgtgggggcatcatctacttcacgctgtacctgccctacgtcctgtgtgtggcatggcaggactacgt
gggcttcacactcaagatcttcgctagcctgctgtctcctgtggcttttgggtttggctgtgagtactttgcccttttgaggagcagggcattggagtgcagt
gggacaacctgtttgagagtcctgtggaggaagatggcttcaatctcaccacttcggtctccatgatgctgtttgacaccttcctctatggggtgatgacctg
gtacattgaggctgtctttccaggccagtacggaattcccaggccctggtatttccttgcaccaagtcctactggtttggcgaggaaagtgatgagaagag
ccaccctggttccaaccagaagagaatatcagaaatctgcatggaggaggaacccacccacttgaagctgggcgtgtccattcagaacctggtaaaagt
ctaccgagatgggatgaaggtggctgtcgatggcctggcactgaattttatgagggccagatcacctccttcctgggccacaatggagcggggaagac
gaccaccatgtcaatcctgaccgggttgttcccccccgacctcgggcaccgcctacatcctgggaaaagacattcgctctgagatgagcaccatccggca
gaacctgggggtctgtccccagcataacgtgctgtttgacatgctgactgtcgaagaacacatctggttctatgcccgcttgaaagggctctctgagaagc
acgtgaaggcggagatggagcagatggccctggatgttggtttgccatcaagcaagctgaaaagcaaaacaagccagctgtcaggtggaatgcagag
aaagctatctgtggccttggcctttgtcgggggatctaaggttgtcattctggatgaacccacagctggtgtggacccttactcccgcaggggaatatggg
agctgctgctgaaataccgacaaggccgcaccattattctctctacacaccacatggatgaagcggacgtcctgggggacaggattgccatcatctccca
tgggaagctgtgctgtgtgggctcctccctgtttctgaagaaccagctgggaacaggctactacctgaccttggtcaagaaagatgtggaatcctccctca
gttcctgcagaaacagtagtagcactgtgtcatacctgaaaaaggaggacagtgtttctcagagcagttctgatgctggcctgggcagcgaccatgagag
tgacacgctgaccatcgatgtctctgctatctccaacctcatcaggaagcatgtgtctgaagcccggctggtggaagacatagggcatgagctgacctatg
tgctgccatatgaagctgctaaggagggagcctttgtggaactctttcatgagattgatgaccggctctcagacctgggcatttctagttatggcatctcaga
gacgaccctggaagaaatattcctcaaggtggccgaagagagtggggtggatgctgagacctcagatggtaccttgccagcaagacgaaacaggcgg
gccttcggggacaagcagagctgtcttcgcccgttcactgaagatgatgctgctgatccaaatgattctgacatagacccagaatccagagagacagact

FIG.2 (Continued)

tgctcagtgggatggatggcaaagggtcctaccaggtgaaaggctggaaacttacacagcaacagtttgtggccctttgtggaagagactgctaattgc
cagacggagtcggaaaggatttttgctcagattgtcttgccagctgtgtttgtctgcattgcccttgtgttcagcctgatcgtgccacccttggcaagtaccc
cagcctggaacttcagccctggatgtacaacgaacagtacacatttgtcagcaatgatgctcctgaggacacgggaaccctggaactcttaaacgccctc
accaaagaccctggcttcgggacccgctgtatggaaggaaacccaatcccagacacgccctgccaggcaggggaggaagagtggaccactgcccca
gttccccagaccatcatggacctcttccagaatgggaactggacaatgcagaacccttcacctgcatgccagtgtagcagcgacaaaatcaagaagatg
ctgcctgtgtgtcccccaggggcaggggggctgcctcctccacaaagaaaacaaaacactgcagatatccttcaggacctgacaggaagaaacatttcg
gattatctggtgaagacgtatgtgcagatcatagccaaaagcttaaagaacaagatctgggtgaatgagtttaggtatggcggctttccctgggtgtcagt
aatactcaagcacttcctccgagtcaagaagttaatgatgccatcaaacaaatgaagaaacacctaaagctggccaaggacagttctgcagatcgatttct
caacagcttgggaagatttatgacaggactggacaccaaaaataatgtcaaggtgtggttcaataacaagggctggcatgcaatcagctctttcctgaatgt
catcaacaatgccattctccgggccaacctgcaaaagggagagaaccctagccattatggaattactgctttcaatcatcccctgaatctcaccaagcagc
agctctcagaggtggctctgatgaccacatcagtggatgtccttgtgtccatctgtgtcatctttgcaatgtccttcgtcccagccagctttgtcgtattcctgat
ccaggagcgggtcagcaaagcaaaacacctgcagttcatcagtggagtgaagcctgtcatctactggctctctaattttgtctgggatatgtgcaattacgtt
gtccctgccacactggtcattatcatcttcatctgcttccagcagaagtcctatgtgtcctccaccaatctgcctgtgctagcccttctactttgctgtatgggt
ggtcaatcacacctctcatgtacccagcctcctttgtgttcaagatccccagcacagcctatgtggtgctcaccagcgtgaacctcttcattggcattaatgg
cagcgtggccacctttgtgctggagctgttcaccgacaataagctgaataatatcaatgatatcctgaagtccgtgttcttgatcttcccacattttgcctggg
acgagggctcatcgacatggtgaaaaaccaggcaatggctgatgccctggaaaggtttggggagaatcgctttgtgtcaccattatcttgggacttggtgg
gacgaaacctcttcgccatggccgtggaagggggtggtgttcttcctcattactgttctgatccagtacagattcttcatcaggcccagacctgtaaatgcaaa
gctatctcctctgaatgatgaagatgaagatgtgaggcgggaaagacagagaattcttgatggtggaggccagaatgacatcttagaaatcaaggagttg
acgaagatatatagaaggaagcggaagcctgctgttgacaggatttgcgtgggcattcctcctggtgagtgctttgggctcctgggagttaatggggctg
gaaaatcatcaactttcaagatgttaacaggagataccactgttaccagaggagatgctttccttaacaaaaatagtatcttatcaaacatccatgaagtacat
cagaacatgggctactgccctcagtttgatgccatcacagagctgttgactgggagagaacacgtggagttctttgccctttgagaggagtcccagagaa
agaagttggcaaggttggtgagtgggcgattcggaaactgggcctcgtgaagtatggagaaaaatatgctggtaactatagtggaggcaacaaacgcaa
gctctctacagccatggctttgatcggcgggcctcctgtggtgtttctggatgaacccaccacaggcatggatcccaaagcccggcggttcttgtggaatt
gtgccctaagtgttgtcaaggaggggagatcagtagtgcttacatctcatagtatggaagaatgtgaagctctttgcactaggatggcaatcatggtcaatg
gaaggttcaggtgccttggcagtgtccagcatctaaaaaataggtttggagatggttatacaatagttgtacgaatagcagggtccaacccggacctgaag
cctgtccaggatttctttggacttgcatttcctggaagtgttctaaaagagaaacaccggaacatgctacaataccagcttccatcttcattatcttctctggcc
aggatattcagcatcctctcccagagcaaaaagcgactccacatagaagactactctgtttctcagacaacacttgaccaagtatttgtgaactttgccaag
gaccaaagtgatgatgaccacttaaaagacctctcattacacaaaaaccagacagtagtggacgttgcagttctcacatcttttctacaggatgagaaagtg
aaagaaagctatgtatgaagaatcctgttcatacggggtggctgaaagtaaagaggaactagactttcctttgcaccatgtgaagtgttgtggagaaaaga
gccagaagttgatgtgggaagaagtaaactggatactgtactgatactattcaatgcaatgcaattcaatgcaatgaaaacaaaattccattacaggggca
gtgcctttgtagcctatgtcttgtatggctctcaagtgaaagacttgaatttagtttttacctatacctatgtgaaactctattatggaacccaatggacatatgg
gtttgaactcacactttttttttttttttgttcctgtgtattctcattggggttgcaacaataattcatcaagtaatcatggccagcgattattgatcaaaatcaaaag
gtaatgcacatcctcattcactaagccatgccatgcccaggagactggtttcccggtgacacatccattgctggcaatgagtgtgccagagttattagtgcc
aagtttttcagaaagttgaagcaccatggtgtgtcatgctcactttgtgaaagctgctctgctcagagtctatcaacattgaatatcagttgacagaatggtgc
catgcgtggctaacatcctgctttgattccctctgataagctgttctggtggcagtaacatgcaacaaaaatgtgggtgtctccaggcacgggaaacttggtt
ccattgttatattgtcctatgcttcgagccatgggtctacagggtcatccttatgagactcttaaatatacttagatcctggtaagaggcaaagaatcaacagc
caaactgctggggctgcaagctgctgaagccagggcatgggattaaagagattgtgcgttcaaacctagggaagcctgtgcccatttgtcctgactgtct
gctaacatggtacactgcatctcaagatgtttatctgacacaagtgtattatttctggctttttgaattaatctagaaaatgaaaagatggagttgtattttgacaa
aaatgtttgtactttttaatgttatttggaatttaagttctatcagtgacttctgaatccttagaatggcctctttgtagaaccctgtggtatagaggagtatggcca
ctgccccactattttatttcttatgtaagtttgcatatcagtcatgactagtgcctagaaagcaatgtgatggtcaggatctcatgacattatatttgagtttcttt
cagatcatttaggatactcttaatctcacttcatcaatcaaatattttttgagtgtatgctgtagctgaaagagtatgtacgtacgtataagactagagagatatta
agtctcagtacacttcctgtgccatgttattcagctcactggtttacaaatataggttgtcttgtggttgtaggagcccactgtaacaatactgggcagcctttttt
tttttttttaattgcaacaatgcaaaagccaagaaagtataagggtcacaagtctaaacaatgaattcttcaacagggaaaacagctagcttgaaaacttgc
tgaaaaacacaacttgtgtttatggcatttagtaccttcaaataattggctttgcagatattggataccccattaaatctgacagtctcaaatttttcatctcttcaat
cactagtcaagaaaaatataaaaacaacaaatacttccatatggagcattttcagagtttctaacccagtcttatttttctagtcagtaaacatttgtaaaaata
ctgtttcactaatacttactgttaactgtcttgagagaaaagaaaaatatgagagaactattgtttggggaagttcaagtgatctttcaatatcattactaacttctt
ccacttttccagaatttgaatattaacgctaaaggtgtaagacttcagatttcaaattaatctttctatatttttaaatttacagaatattatataacccactgctga

FIG.2 (Continued)

aaaagaaaaaaaatgattgttttagaagttaaagtcaatattgatttaaatataagtaatgaaggcatatttccaataactagtgatatggcatcgttgcattttac
agtatcttcaaaaatacagaatttatagaataatttctcctcatttaatatttttcaaaatcaaagttatggtttcctcatttactaaaatcgtattctaattcttcattat
agtaaatctatgagcaactccttacttcggttcctctgatttcaaggccatatttaaaaaatcaaaaggcactgtgaactattttgaagaaaacacaacattta
atacagattgaaaggacctcttctgaagctagaaacaatctatagttatacatcttcattaatactgtgttacctttaaaatagtaatttttacatttcctgtgtaa
acctaattgtggtagaaatttttaccaactctatactcaatcaagcaaaatttctgtatattccctgtggaatgtacctatgtgagtttcagaaattctcaaaatac
gtgttcaaaaaatttctgctttgcatctttgggacacctcagaaaacttattaacaactgtgaatatgagaaatacagaagaaaataataagccctctatacata
aatgcccagcacaattcattgttaaaaaacaaccaaacctcacactactgtatttcattatctgtactgaaagcaaatgcttgtgactattaaatgttgcacatc
attcattcactgtatagtaatcattgactaaagccatttgtctgtgtttcttcttgtggttgtatatatcaggtaaaatattttccaaagagccatgtgtcatgtaata
ctgaaccactttgatattgagacattaatttgtacccttgttattatctactagtaataatgtaatactgtagaaatattgctctaattcttttcaaaattgttgcatccc
ccttagaatgtttctatttccataaggatttaggtatgctattatcccttcttataccctaagatgaagctgtttttgtgctctttgttcatcattggccctcattccaa
gcactttacgctgtctgtaatgggatctatttttgcactggaatatctgagaattgcaaaactagacaaaagtttcacaacagatttctaagttaaatcatttttcat
taaaaggaaaaaagaaaaaaaatttttgtatgtcaataactttatatgaagtattaaaatgcatatttctatgttgtaatataatgagtcacaaaataaagctgtga
cagttctgttggtctacagaaa

(SEQ ID NO: 2)

>gi|4557891| ref| NM_000229.1| Home sapiens lecithin-cholesterol acyltransferase (LCAT), Mrna CCAGGGCTGGAATGGGGCCGCCCGGCTCCCCATGGCAGTGGGTGACGCTGCTGCTGGGGCTGCTGCTCCCTCCTGCCGCCCCCTTC
TGGCTCCTCAATGTGCTCTTCCCCCCGCACACCACGCCCAAGGCTGAGCTCAGTAACCACACACGGCCCGTCATCCTCGTGCCCGG
CTGCCTGGGGAATCAGCTAGAAGCCAAGCTGGACAAACCAGATGTGGTGAACTGGATGTGCTACCGCAAGACAGAGGACTTCTTC
ACCATCTGGCTGGATCTCAACATGTTCCTACCCCTTGGGGTAGACTGCTGGATCGATAACACCAGGGTTGTCTACAACCGGAGCTC
TGGGCTCGTGTCCAACGCCCCTGGTGTCCAGATCCGCGTCCCTGGCTTTGGCAAGACCTACTCTGTGGAGTACCTGGACAGCAGCA
AGCTGGCAGGGTACCTGCACACACTGGTGCAGAACCTGGTCAACAATGGCTACGTGCGGGACGAGACTGTGCGCGCCGCCCCCTA
TGACTGGCGGCTGGAGCCCGGCCAGCAGGAGGAGTACTACCGCAAGCTCGCAGGGCTGGTGGAGGAGATGCACGCTGCCTATGG
GAAGCCTGTCTTCCTCATTGGCCACAGCCTCGGCTGTCTACACTTGCTCTATTTCCTGCTGCGCCAGCCCCAGGCCTGGAAGGACC
GCTTTATTGATGGCTTCATCTCTCTTGGGGCTCCCTGGGGTGGCTCCATCAAGCCCATGCTGGTCTTGGCCTCAGGTGACAACCAG
GGCATCCCCATCATGTCCAGCATCAAGCTGAAAGAGGAGCAGCGCATAACCACCACCTCCCCCTGGATGTTTCCCTCTCGCATGG
CGTGGCCTGAGGACCACGTGTTCATTTCCACACCCAGCTTCAACTACACAGGCCGTGACTTCCAACGCTTCTTTGCAGACCTGCAC
TTTGAGGAAGGCTGGTACATGTGGCTGCAGTCACGTGACCTCCTGGCAGGACTCCCAGCACCTGGTGTGGAAGTATACTGTCTTTA
CGGCGTGGGCCTGCCCACGCCCCGCACCTACATCTACGACCACGGCTTCCCCTACACGGACCCTGTGGGTGTGCTCTATGAGGAT
GGTGATGACACGGTGGCGACCCGCAGCACCGAGCTCTGTGGCCTGTGGCAGGGCCGCCAGCCACAGCCTGTGCACCTGCTGCCCC
TGCACGGGATACAGCATCTCAACATGGTCTTCAGCAACCTGACCCTGGAGCACATCAATGCCATCCTGCTGGGTGCCTACCGCCA
GGGTCCCCCTGCATCCCCGACTGCCAGCCCAGAGCCCCCGCCTCCTGAATAAAGACCTTCCTTTGCTACCGT

(SEQ ID NO: 3)

>gi|126012561| ref|NM_002332.21|Homo sapiens low density lipoprotein receptor-related protein 1 (LRP1), mRNA CAGCGGTGCGAGCTCCAGGCCCATGCACTGAGGAGGCGGAAACAAGGGGAGCCCCCAGAGCTCCATCAAGCCCCCTCCAAAGGC
TCCCCTACCCGGTCCACGCCCCCCACCCCCCCTCCCCGCCTCCTCCCAATTGTGCATTTTTGCAGCCGGAGGCGGCTCCGAGATGG
GGCTGTGAGCTTCGCCCGGGGAGGGGGAAAGAGCAGCGAGGAGTGAAGCGGGGGGGTGGGGTGAAGGGTTTGGATTTCGGGGC
AGGGGGCGCACCCCCGTCAGCAGGCCCTCCCCAAGGGGCTCGGAACTCTACCTCTTCACCCACGCCCCTGGTGCGCTTTGCCGAA
GGAAAGAATAAGAACAGAGAAGGAGGAGGGGGAAAGGAGGAAAAGGGGGACCCCCCAACTGGGGGGGGTGAAGGAGAGAAGT
AGCAGGACCAGAGGGGAAGGGGCTGCTGCTTGCATCAGCCCACACCATGCTGACCCCGCCGTTGCTCCTGCTGCTGCCCCTGCTC
TCAGCTCTGGTCGCGGCGGCTATCGACGCCCCTAAGACTTGCAGCCCCAAGCAGTTTGCCTGCAGAGATCAAATAACCTGTATCTC
AAAGGGCTGGCGGTGCGACGGTGAGAGGGACTGCCCAGACGGATCTGACGAGGCCCCTGAGATTTGTCCACAGAGTAAGGCCCA
GCGATGCCAGCCAAACGAGCATAACTGCCTGGGTACTGAGCTGTGTGTTCCCATGTCCCGCCTCTGCAATGGGGTCCAGGACTGC
ATGGACGGCTCAGATGAGGGGCCCCACTGCCGAGAGCTCCAAGGCAACTGCTCTCGCCTGGGCTGCCAGCACCATTGTGTCCCCA
CACTCGATGGGCCCACCTGCTACTGCAACAGCAGCTTTCAGCTTCAGGCAGATGGCAAGACCTGCAAAGATTTTGATGAGTGCTC
AGTGTACGGCACCTGCAGCCAGCTATGCACCAACACAGACGGCTCCTTCATATGTGGCTGTGTTGAAGGATACCTCCTGCAGCCG
GATAACCGCTCCTGCAAGGCCAAGAACGAGCCAGTAGACCGGCCCCCTGTGCTGTTGATAGCCAACTCCCAGAACATCTTGGCCA
CGTACCTGAGTGGGGCCCAGGTGTCTACCATCACACCTACGAGCACGCGGCAGACCACAGCCATGGACTTCAGCTATGCCAACGA
GACCGTATGCTGGGTGCATGTTGGGGACAGTGCTGCTCAGACGCAGCTCAAGTGTGCCCGCATGCCTGGCCTAAAGGGCTTCGTG

FIG.2 (Continued)

GATGAGCACACCATCAACATCTCCCTCAGTCTGCACCACGTGGAACAGATGGCCATCGACTGGCTGACAGGCAACTTCTACTTTG
TGGATGACATCGATGATAGGATCTTTGTCTGCAACAGAAATGGGGACACATGTGTCACATTGCTAGACCTGGAACTCTACAACCC
CAAGGGCATTGCCCTGGACCCTGCCATGGGGAAGGTGTTTTTCACTGACTATGGGCAGATCCCAAAGGTGGAACGCTGTGACATG
GATGGGCAGAACCGCACCAAGCTCGTCGACAGCAAGATTGTGTTTCCTCATGGCATCACGCTGGACCTGGTCAGCCGCCTTGTCT
ACTGGGCAGATGCCTATCTGGACTATATTGAAGTGGTGGACTATGAGGGCAAGGGCCGCCAGACCATCATCCAGGGCATCCTGAT
TGAGCACCTGTACGGCCTGACTGTGTTTGAGAATTATCTCTATGCCACCAACTCGGACAATGCCAATGCCCAGCAGAAGACGAGT
GTGATCCGTGTGAACCGCTTTAACAGCACCGAGTACCAGGTTGTCACCCGGGTGGACAAGGGTGGTGCCCTCCACATCTACCACC
AGAGGCGTCAGCCCCGAGTGAGGAGCCATGCCTGTGAAAACGACCAGTATGGGAAGCCGGGTGGCTGCTCTGACATCTGCCTGCT
GGCCAACAGCCACAAGGCGCGGACCTGCCGCTGCCGTTCCGGCTTCAGCCTGGGCAGTGACGGGAAGTCATGCAAGAAGCCGGA
GCATGAGCTGTTCCTCGTGTATGGCAAGGGCCGGCCAGGCATCATCCGGGGCATGGATATGGGGGCCAAGGTCCCGGATGAGCA
CATGATCCCCATTGAAAACCTCATGAACCCCCGAGCCCTGGACTTCCACGCTGAGACCGGCTTCATCTACTTTGCCGACACCACCA
GCTACCTCATTGGCCGCCAGAAGATTGATGGCACTGAGCGGGAGACCATCCTGAAGGACGGCATCCACAATGTGGAGGGTGTGG
CCGTGGACTGGATGGGAGACAATCTGTACTGGACGGACGATGGGCCCAAAAAGACAATCAGCGTGGCCAGGCTGGAGAAAGCTG
CTCAGACCCGCAAGACTTTAATCGAGGGCAAAATGACACACCCCAGGGCTATTGTGGTGGATCCACTCAATGGGTGGATGTACTG
GACAGACTGGGAGGAGGACCCCAAGGACAGTCGGCGTGGGCGGCTGGAGAGGGCGTGGATGGATGGCTCACACCGAGACATCTT
TGTCACCTCCAAGACAGTGCTTTGGCCCAATGGGCTAAGCCTGGACATCCCGGCTGGGCGCCTCTACTGGGTGGATGCCTTCTACG
ACCGCATCGAGACGATACTGCTCAATGGCACAGACCGGAAGATTGTGTATGAAGGTCCTGAGCTGAACCACGCCTTTGGCCTGTG
TCACCATGGCAACTACCTCTTCTGGACTGAGTATCGGAGTGGCAGTGTCTACCGCTTGGAACGGGGTGTAGGAGGCGCACCCCCC
ACTGTGACCCTTCTGCGCAGTGAGCGGCCCCCCATCTTTGAGATCCGAATGTATGATGCCCAGCAGCAGCAAGTTGGCACCAACA
AATGCCGGGTGAACAATGGCGGCTGCAGCAGCCTGTGCTTGGCCACCCCTGGGAGCCGCCAGTGCGCCTGTGCTGAGGACCAGGT
GTTGGACGCAGACGGCGTCACTTGCTTGGCGAACCCATCCTACGTGCCTCCACCCCAGTGCCAGCCAGGCGAGTTTGCCTGTGCC
AACAGCCGCTGCATCCAGGAGCGCTGGAAGTGTGACGGAGACAACGATTGCCTGGACAACAGTGATGAGGCCCCAGCCCTCTGC
CATCAGCACACCTGCCCCTCGGACCGATTCAAGTGCGAGAACAACCGGTGCATCCCCAACCGCTGGCTCTGCGACGGGGACAATG
ACTGTGGGAACAGTGAAGATGAGTCCAATGCCACTTGTTCAGCCCGCACCTGCCCCCCCAACCAGTTCTCCTGTGCCAGTGGCCG
CTGCATCCCCATCTCCTGGACGTGTGATCTGGATGACGACTGTGGGGACCGCTCTGATGAGTCTGCTTCGTGTGCCTATCCCACCT
GCTTCCCCCTGACTCAGTTTACCTGCAACAATGGCAGATGTATCAACATCAACTGGAGATGCGACAATGACAATGACTGTGGGGA
CAACAGTGACGAAGCCGGCTGCAGCCACTCCTGTTCTAGCACCCAGTTCAAGTGCAACAGCGGGCGTTGCATCCCCGAGCACTGG
ACCTGCGATGGGGACAATGACTGCGGAGACTACAGTGATGAGACACACGCCAACTGCACCAACCAGGCCACGAGGCCCCCTGGT
GGCTGCCACACTGATGAGTTCCAGTGCCGGCTGGATGGACTATGCATCCCCCTGCGGTGGCGCTGCGATGGGGACACTGACTGCA
TGGACTCCAGCGATGAGAAGAGCTGTGAGGGAGTGACCCACGTCTGCGATCCCAGTGTCAAGTTTGGCTGCAAGGACTCAGCTCG
GTGCATCAGCAAAGCGTGGGTGTGTGATGGCGACAATGACTGTGAGGATAACTCGGACGAGGAGAACTGCGAGTCCCTGGCCTG
CAGGCCACCCTCGCACCCTTGTGCCAACAACACCTCAGTCTGCCTGCCCCCTGACAAGCTGTGTGATGGCAACGACGACTGTGGC
GACGGCTCAGATGAGGGCGAGCTCTGCGACCAGTGCTCTCTGAATAACGGTGGCTGCAGCCACAACTGCTCAGTGGCACCTGGCG
AAGGCATTGTGTGTTCCTGCCCTCTGGGCATGGAGCTGGGGCCCGACAACCACACCTGCCAGATCCAGAGCTACTGTGCCAAGCA
TCTCAAATGCAGCCAAAAGTGCGACCAGAACAAGTTCAGCGTGAAGTGCTCCTGCTACGAGGGCTGGGTCCTGGAACCTGACGGC
GAGAGCTGCCGCAGCCTGGACCCCTTCAAGCCGTTCATCATTTTCTCCAACCGCCATGAAATCCGGCGCATCGATCTTCACAAAGG
AGACTACAGCGTCCTGGTGCCCGGCCTGCGCAACACCATCGCCCTGGACTTCCACCTCAGCCAGAGCGCCCTCTACTGGACCGAC
GTGGTGGAGGACAAGATCTACCGCGGGAAGCTGCTGGACAACGGAGCCCTGACTAGTTTCGAGGTGGTGATTCAGTATGGCCTGG
CCACACCCGAGGGCCTGGCTGTAGACTGGATTGCAGGCAACATCTACTGGGTGGAGAGTAACCTGGATCAGATCGAGGTGGCCA
AGCTGGATGGGACCCTCCGGACCACCCTGCTGGCCGGTGACATTGAGCACCCAAGGGCAATCGCACTGGATCCCCGGGATGGGAT
CCTGTTTTGGACAGACTGGGATGCCAGCCTGCCCCGCATTGAGGCAGCCTCCATGAGTGGGGCTGGGCGCCGCACCGTGCACCGG
GAGACCGGCTCTGGGGGCTGGCCCAACGGGCTCACCGTGGACTACCTGGAGAAGCGCATCCTTTGGATTGACGCCAGGTCAGATG
CCATTTACTCAGCCCGTTACGACGGCTCTGGCCACATGGAGGTGCTTCGGGGACACGAGTTCCTGTCGCACCCGTTTGCAGTGACG
CTGTACGGGGGGGAGGTCTACTGGACTGACTGGCGAACAAACACACTGGCTAAGGCCAACAAGTGGACCGGCCACAATGTCACC
GTGGTACAGAGGACCAACACCCAGCCCTTTGACCTGCAGGTGTACCACCCCTCCCGCCAGCCCATGGCTCCCAATCCCTGTGAGG
CCAATGGGGGCCAGGGCCCCTGCTCCCACCTGTGTCTCATCAACTACAACCGGACCGTGTCCTGCGCCTGCCCCCACCTCATGAAG
CTCCACAAGGACAACACCACCTGCTATGAGTTTAAGAAGTTCCTGCTGTACGCACGTCAGATGGAGATCCGAGGTGTGGACCTGG
ATGCTCCCTACTACAACTACATCATCTCCTTCACGGTGCCCGACATCGACAACGTCACAGTGCTAGACTACGATGCCCGCGAGCA
GCGTGTGTACTGGTCTGACGTGCGGACACAGGCCATCAAGCGGGCCTTCATCAACGGCACAGGCGTGGAGACAGTCGTCTCTGCA
GACTTGCCAAATGCCCACGGGCTGGCTGTGGACTGGGTCTCCCGAAACCTGTTCTGGACAAGCTATGACACCAATAAGAAGCAGA
TCAATGTGGCCCGGCTGGATGGCTCCTTCAAGAACGCAGTGGTGCAGGGCCTGGAGCAGCCCCATGGCCTTGTCGTCCACCCTCT
GCGTGGGAAGCTCTACTGGACCGATGGTGACAACATCAGCATGGCCAACATGGATGGCAGCAATCGCACCCTGCTCTTCAGTGGC
CAGAAGGGCCCCGTGGGCCTGGCTATTGACTTCCCTGAAAGCAAACTCTACTGGATCAGCTCCGGGAACCATACCATCAACCGCT
GCAACCTGGATGGGAGTGGGCTGGAGGTCATCGATGCCATGCGGAGCCAGCTGGGCAAGGCCACCGCCCTGGCCATCATGGGGG
ACAAGCTGTGGTGGGCTGATCAGGTGTCGGAAAAGATGGGCACATGCAGCAAGGCTGACGGCTCGGGCTCCGTGGTCCTTCGGA
ACAGCACCACCCTGGTGATGCACATGAAGGTCTATGACGAGAGCATCCAGCTGGACCATAAGGGCACCAACCCCTGCAGTGTCA
ACAACGGTGACTGCTCCCAGCTCTGCCTGCCCACGTCAGAGACGACCCGCTCCTGCATGTGCACAGCCGGCTATAGCCTCCGGAG
TGGCCAGCAGGCCTGCGAGGGCGTAGGTTCCTTTCTCCTGTACTCTGTGCATGAGGGAATCAGGGGAATTCCCCTGGATCCCAATG
ACAAGTCAGATGCCCTGGTCCCAGTGTCCGGGACCTCGCTGGCTGTCGGCATCGACTTCCACGCTGAAAATGACACCATCTACTG
GGTGGACATGGGCCTGAGCACGATCAGCCGGGCCAAGCGGGACCAGACGTGGCGTGAAGACGTGGTGACCAATGGCATTGGCCG
TGTGGAGGGCATTGCAGTGGACTGGATCGCAGGCAACATCTACTGGACAGACCAGGGCTTTGATGTCATCGAGGTCGCCCGGCTC
AATGGCTCCTTCCGCTACGTGGTGATCTCCCAGGGTCTAGACAAGCCCCGGGCCATCACCGTCCACCCGGAGAAAGGGTACTTGT
TCTGGACTGAGTGGGGTCAGTATCCGCGTATTGAGCGGTCTCGGCTAGATGGCACGGAGCGTGTGGTGCTGGTCAACGTCAGCAT
CAGCTGGCCCAACGGCATCTCAGTGGACTACCAGGATGGGAAGCTGTACTGGTGCGATGCACGGACAGACAAGATTGAACGGAT
CGACCTGGAGACAGGTGAGAACCGCGAGGTGGTTCTGTCCAGCAACAACATGGACATGTTTTCAGTGTCTGTGTTTGAGGATTTC
ATCTACTGGAGTGACAGGACTCATGCCAACGGCTCTATCAAGCGCGGGAGCAAAGACAATGCCACAGACTCCGTGCCCCTGCGA
ACCGGCATCGGCGTCCAGCTTAAAGACATCAAAGTCTTCAACCGGGACCGGCAGAAAGGCACCAACGTGTGCGCGGTGGCCAAT

FIG.2 (Continued)

GGCGGGTGCCAGCAGCTGTGCCTGTACCGGGGCCGTGGGCAGCGGGCCTGCGCCTGTGCCCACGGGATGCTGGCTGAAGACGGA
GCATCGTGCCGCGAGTATGCCGGCTACCTGCTCTACTCAGAGCGCACCATTCTCAAGAGTATCCACCTGTCGGATGAGCGCAACC
TCAATGCGCCCGTGCAGCCCTTCGAGGACCCTGAGCACATGAAGAACGTCATCGCCCTGGCCTTTGACTACCGGGCAGGCACCTC
TCCGGGCACCCCCAATCGCATCTTCTTCAGCGACATCCACTTTGGGAACATCCAACAGATCAACGACGATGGCTCCAGGAGGATC
ACCATTGTGGAAAACGTGGGCTCCGTGGAAGGCCTGGCCTATCACCGTGGCTGGGACACTCTCTATTGGACAAGCTACACGACAT
CCACCATCACGCGCCACACAGTGGACCAGACCCGCCCAGGGGCCTTCGAGCGTGAGACCGTCATCACTATGTCTGGAGATGACCA
CCCACGGGCCTTCGTTTTGGACGAGTGCCAGAACCTCATGTTCTGGACCAACTGGAATGAGCAGCATCCCAGCATCATGCGGGCG
GCGCTCTCGGGAGCCAATGTCCTGACCCTTATCGAGAAGGACATCCGTACCCCCAATGGCCTGGCCATCGACCACCGTGCCGAGA
AGCTCTACTTCTCTGACGCCACCCTGGACAAGATCGAGCGGTGCGAGTATGACGGCTCCCACCGCTATGTGATCCTAAAGTCAGA
GCCTGTCCACCCCTTCGGGCTGGCCGTGTATGGGGAGCACATTTTCTGGACTGACTGGGTGCGGCGGGCAGTGCAGCGGGCCAAC
AAGCACGTGGGCAGCAACATGAAGCTGCTGCGCGTGGACATCCCCCAGCAGCCCATGGGCATCATCGCCGTGGCCAACGACACC
AACAGCTGTGAACTCTCTCCATGCCGAATCAACAACGGTGGCTGCCAGGACCTGTGTCTGCTCACTCACCAGGGCCATGTCAACT
GCTCATGCCGAGGGGGCCGAATCCTCCAGGATGACCTCACCTGCCGAGCGGTGAATTCCTCTTGCCGAGCACAAGATGAGTTTGA
GTGTGCCAATGGCGAGTGCATCAACTTCAGCCTGACCTGCGACGGCGTCCCCCACTGCAAGGACAAGTCCGATGAGAAGCCATCC
TACTGCAACTCCCGCCGCTGCAAGAAGACTTTCCGGCAGTGCAGCAATGGGCGCTGTGTGTCCAACATGCTGTGGTGCAACGGGG
CCGACGACTGTGGGGATGGCTCTGACGAGATCCCTTGCAACAAGACAGCCTGTGGTGTGGGCGAGTTCCGCTGCCGGGACGGGAC
CTGCATCGGGAACTCCAGCCGCTGCAACCAGTTTGTGGATTGTGAGGACGCCTCAGATGAGATGAACTGCAGTGCCACCGACTGC
AGCAGCTACTTCCGCCTGGGCGTGAAGGGCGTGCTCTTCCAGCCCTGCGAGCGGACCTCACTCTGCTACGCACCCAGCTGGGTGT
GTGATGGCGCCAATGACTGTGGGGACTACAGTGATGAGCGCGACTGCCCAGGTGTGAAACGCCCCAGATGCCCTCTGAATTACTT
CGCCTGCCCTAGTGGGCGCTGCATCCCCATGAGCTGGACGTGTGACAAAGAGGATGACTGTGAACATGGCGAGGACGAGACCCA
CTGCAACAAGTTCTGCTCAGAGGCCCAGTTTGAGTGCCAGAACCATCGCTGCATCTCCAAGCAGTGGCTGTGTGACGGCAGCGAT
GACTGTGGGGATGGCTCAGACGAGGCTGCTCACTGTGAAGGCAAGACGTGCGGCCCCTCCTCCTTCTCCTGCCCTGGCACCCACG
TGTGCGTCCCCGAGCGCTGGCTCTGTGACGGTGACAAAGACTGTGCTGATGGTGCAGACGAGAGCATCGCAGCTGGTTGCTTGTA
CAACAGCACTTGTGACGACCGTGAGTTCATGTGCCAGAACCGCCAGTGCATCCCCAAGCACTTCGTGTGTGACCACGACCGTGAC
TGTGCAGATGGCTCTGATGAGTCCCCCGAGTGTGAGTACCCGACCTGCGGCCCCAGTGAGTTCCGCTGTGCCAATGGGCGCTGTCT
GAGCTCCCGCCAGTGGGAGTGTGATGGCGAGAATGACTGCCACGACCAGAGTGACGAGGCTCCCAAGAACCCACACTGCACCAG
CCAAGAGCACAAGTGCAATGCCTCGTCACAGTTCCTGTGCAGCAGTGGGCGCTGTGTGGCTGAGGCACTGCTCTGCAACGGCCAG
GATGACTGTGGCGACAGCTCGGACGAGCGTGGCTGCCACATCAATGAGTGTCTCAGCCGCAAGCTCAGTGGCTGCAGCCAGGACT
GTGAGGACCTCAAGATCGGCTTCAAGTGCCGCTGTCGCCCTGGCTTCCGGCTGAAGGACGACGGCCGGACGTGTGCTGATGTGGA
CGAGTGCAGCACCACCTTCCCCTGCAGCCAGCGCTGCATCAACACTCATGGCAGCTATAAGTGTCTGTGTGTGGAGGGCTATGCA
CCCCGCGGCGGCGACCCCCACAGCTGCAAGGCTGTGACTGACGAGGAACCGTTTCTGATCTTCGCCAACCGGTACTACCTGCGCA
AGCTCAACCTGGACGGGTCCAACTACACGTTACTTAAGCAGGGCCTGAACAACGCCGTTGCCTTGGATTTTGACTACCGAGAGCA
GATGATCTACTGGACAGATGTGACCACCCAGGGCAGCATGATCCGAAGGATGCACCTTAACGGGAGCAATGTGCAGGTCCTACA
CCGTACAGGCCTCAGCAACCCCGATGGGCTGGCTGTGGACTGGGTGGGTGGCAACCTGTACTGGTGCGACAAAGGCCGGGACAC
CATCGAGGTGTCCAAGCTCAATGGGGCCTATCGGACGGTGCTGGTCAGCTCTGGCCTCCGTGAGCCCAGGGCTCTGGTGGTGGAT
GTGCAGAATGGGTACCTGTACTGGACAGACTGGGGTGACCATTCACTGATCGGCCGCATCGGCATGGATGGGTCCAGCCGCAGCG
TCATCGTGGACACCAAGATCACATGGCCCAATGGCCTGACGCTGGACTATGTCACTGAGCGCATCTACTGGGCCGACGCCCGCGA
GGACTACATTGAATTTGCCAGCCTGGATGGCTCCAATCGCCACGTTGTGCTGAGCCAGGACATCCCGCACATCTTTGCACTGACCC
TGTTTGAGGACTACGTCTACTGGACCGACTGGGAAACAAAGTCCATTAACCGAGCCCACAAGACCACGGGCACCAACAAAACGC
TCCTCATCAGCACGCTGCACCGGCCCATGGACCTGCATGTCTTCCATGCCCTGCGCCAGCCAGACGTGCCCATCACCCCTGCAAGG
TCAACAATGGTGGCTGCAGCAACCTGTGCCTGCTGTCCCCCGGGGGAGGGCACAAATGTGCCTGCCCCACCAACTTCTACCTGGG
CAGCGATGGGCGCACCTGTGTGTCCAACTGCACGGCTAGCCAGTTTGTATGCAAGAACGACAAGTGCATCCCCTTCTGGTGGAAG
TGTGACACCGAGGACGACTGCGGGGACCACTCAGACGAGCCCCCGGACTGCCCTGAGTTCAAGTGCCGGCCCGGACAGTTCCAGT
GCTCCACAGGTATCTGCACAAACCCTGCCTTCATCTGCGATGGCGACAATGACTGCCAGGACAACAGTGACGAGGCCAACTGTGA
CATCCACGTCTGCTTGCCCAGTCAGTTCAAATGCACCAACACCAACCGCTGTATTCCCGGCATCTTCCGCTGCAATGGGCAGGACA
ACTGCGGAGATGGGGAGGATGAGAGGGACTGCCCCGAGGTGACCTGCGCCCCCAACCAGTTCCAGTGCTCCATTACCAAACGGT
GCATCCCCCGGGTCTGGGTCTGCGACCGGGACAATGACTGTGTGGATGGCAGTGATGAGCCCGCCAACTGCACCCAGATGACCTG
TGGTGTGGACGAGTTCCGCTGCAAGGATTCGGGCCGCTGCATCCCAGCGCGTTGGAAGTGTGACGGAGAGGATGACTGTGGGGAT
GGCTCGGATGAGCCCAAGGAAGAGTGTGATGAACGCACCTGTGAGCCATACCAGTTCCGCTGCAAGAACAACCGCTGCGTGCCC
GGCCGCTGGCAGTGCGACTACGACAACGATTGCGGTGACAACTCCGATGAAGAGAGCTGCACCCCTCGGCCCTGCTCCGAGAGTG
AGTTCTCCTGTGCCAACGGCCGCTGCATCGCGGGGCGCTGGAAATGCGATGGAGACCACGACTGCGCGGACGGCTCGGACGAGA
AAGACTGCACCCCCCGCTGTGACATGGACCAGTTCCAGTGCAAGAGCGGCCACTGCATCCCCCTGCGCTGGCGCTGTGACGCAGA
CGCCGACTGCATGGACGGCAGCGACGAGGAGGCCTGCGGCACTGGCGTGCGGACCTGCCCCCTGGACGAGTTCCAGTGCAACAA
CACCTTGTGCAAGCCGCTGGCCTGGAAGTGCGATGGCGAGGATGACTGTGGGGACAACTCAGATGAGAACCCCGAGGAGTGTGC
CCGGTTCGTGTGCCCTCCCAACCGGCCCTTCCGTTGCAAGAATGACCGCGTCTGTCTGTGGATCGGGCGCCAATGCGATGGCACG
GACAACTGTGGGGATGGGACTGATGAAGAGGACTGTGAGCCCCCCACAGCCCACACCACCCACTGCAAAGACAAGAAGGAGTTT
CTGTGCCGGAACCAGCGCTGCCTCTCCTCCTCCCTGCGCTGCAACATGTTCGATGACTGCGGGGACGGCTCTGACGAGGAGGACT
GCAGCATCGACCCCAAGCTGACCAGCTGCGCCACCAATGCCAGCATCTGTGGGGACGAGGCACGCTGCGTGCGCACCGAGAAAG
CGGCCTACTGTGCCTGCCGCTCGGGCTTCCACACCGTGCCCGGCCAGCCCGGATGCCAAGACATCAACGAGTGCCTGCGCTTCGG
CACCTGCTCCCAGCTCTGCAACAACACCAAGGGCGGCCACCTCTGCAGCTGCGCTCGGAACTTCATGAAGACGCACAACACCTGC
AAGGCCGAAGGCTCTGAGTACCAGGTCCTGTACATCGCTGATGACAATGAGATCCGCAGCCTGTTCCCCGGCCACCCCCATTCGG
CTTACGAGCAGGCATTCCAGGGTGACGAGAGTGTCCGCATTGATGCTATGGATGTCCATGTCAAGGCTGGCCGTGTCTATTGGAC
CAACTGGCACACGGGCACCATCTCCTACCGCAGCCTGCCACCTGCTGCGCCTCCTACCACTTCCAACCGCCACCGGCGACAGATT
GACCGGGGTGTCACCCACCTCAACATTTCAGGGCTGAAGATGCCCAGAGGCATCGCCATCGACTGGGTGGCCGGAAACGTGTACT
GGACCGACTCGGGCCGAGATGTGATTGAGGTGGCGCAGATGAAGGGCGAGAACCGCAAGACGCTCATCTCGGGCATGATTGACG
AGCCCCACGCCATTGTGGTGGACCCACTGAGGGGGACCATGTACTGGTCAGACTGGGGCAACCACCCCAAGATTGAGACGGCAG
CGATGGATGGGACGCTTCGGGAGACACTGGTGCAGGACAACATTCAGTGGCCCACAGGCCTGGCCGTGGATTATCACAATGAGC

FIG.2 (Continued)

GGCTGTACTGGGCAGACGCCAAGCTTTCAGTCATCGGCAGCATCCGGCTCAATGGCACGGACCCCATTGTGGCTGCTGACAGCAA
ACGAGGCCTAAGTCACCCCTTCAGCATCGACGTCTTTGAGGATTACATCTATGGTGTCACCTACATCAATAATCGTGTCTTCAAGA
TCCATAAGTTTGGCCACAGCCCCTTGGTCAACCTGACAGGGGGCCTGAGCCACGCCTCTGACGTGGTCCTTTACCATCAGCACAA
GCAGCCCGAAGTGACCAACCCATGTGACCGCAAGAAATGCGAGTGGCTCTGCCTGCTGAGCCCCAGTGGGCCTGTCTGCACCTGT
CCCAATGGGAAGCGGCTGGACAACGGCACATGCGTGCCTGTGCCCTCTCCAACGCCCCCCCAGATGCTCCCCGGCCTGGAACCT
GTAACCTGCAGTGCTTCAACGGTGGCAGCTGTTTCCTCAATGCACGGAGGCAGCCCAAGTGCCGCTGCCAACCCCGCTACACGGG
TGACAAGTGTGAACTGGACCAGTGCTGGGAGCACTGTCGCAATGGGGGCACCTGTGCTGCCTCCCCCTCTGGCATGCCCACGTGC
CGGTGCCCCACGGGCTTCACGGGCCCCAAATGCACCCAGCAGGTGTGTGCGGGCTACTGTGCCAACAACAGCACCTGCACTGTCA
ACCAGGGCAACCAGCCCCAGTGCCGATGCCTACCCGGCTTCCTGGGCGACCGCTGCCAGTACCGGCAGTGCTCTGGCTACTGTGA
GAACTTTGGCACATGCCAGATGGCTGCTGATGGCTCCCGACAATGCCGCTGCACTGCCTACTTTGAGGGATCGAGGTGTGAGGTG
AACAAGTGCAGCCGCTGTCTCGAAGGGGCCTGTGTGGTCAACAAGCAGAGTGGGGATGTCACCTGCAACTGCACGGATGGCCGG
GTGGCCCCCAGCTGTCTGACCTGCGTCGGCCACTGCAGCAATGGCGGCTCCTGTACCATGAACAGCAAAATGATGCCTGAGTGCC
AGTGCCCACCCCACATGACAGGGCCCCGGTGTGAGGAGCACGTCTTCAGCCAGCAGCAGCCAGGACATATAGCCTCCATCCTAAT
CCCTCTGCTGTTGCTGCTGCTGCTGGTTCTGGTGGCCGGAGTGGTATTCTGGTATAAGCGGCGAGTCCAAGGGGCTAAGGGCTTCC
AGCACCAACGGATGACCAACGGGGCCATGAACGTGGAGATTGGAAACCCCACCTACAAGATGTACGAAGGCGGAGAGCCTGATG
ATGTGGGAGGCCTACTGGACGCTGACTTTGCCCTGGACCCTGACAAGCCCACCAACTTCACCAACCCCGTGTATGCCACACTCTAC
ATGGGGGGCCATGGCAGTCGCCACTCCCTGGCCAGCACGGACGAGAAGCGAGAACTCCTGGGCCGGGGCCCTGAGGACGAGATA
GGGGACCCCTTGGCATAGGGCCCTGCCCCGTCGGACTGCCCCCAGAAAGCCTCCTGCCCCCTGCCGGTGAAGTCCTTCAGTGAGC
CCCTCCCCAGCCAGCCCTTCCCTGGCCCCGCCGGATGTATAAATGTAAAAATGAAGGAATTACATTTTATATGTGAGCGAGCAAG
CCGGCAAGCGAGCACAGTATTATTTCTCCATCCCCTCCCTGCCTGCTCCTTGGCACCCCCATGCTGCCTTCAGGGAGACAGGCAGG
GAGGGCTTGGGGCTGCACCTCCTACCCTCCCACCAGAACGCACCCCACTGGGAGAGCTGGTGGTGCAGCCTTCCCCTCCCTGTAT
AAGACACTTTGCCAAGGCTCTCCCCTCTCGCCCCATCCCTGCTTGCCCGCTCCCACAGCTTCCTGAGGGCTAATTCTGGGAAGGGA
GAGTTCTTTGCTGCCCCTGTCTGGAAGACGTGGCTCTGGGTGAGGTAGGCGGGAAAGGATGGAGTGTTTTAGTTCTTGGGGGAGG
CCACCCCAAACCCCAGCCCCAACTCCAGGGGCACCTATGAGATGGCCATGCTCAACCCCCCTCCCAGACAGGCCCTCCCTGTCTC
CAGGGCCCCCACCGAGGTTCCCAGGGCTGGAGACTTCCTCTGGTAAACATTCCTCCAGCCTCCCCTCCCCTGGGGACGCCAAGGA
GGTGGGCCACACCCAGGAAGGGAAAGCGGGCAGCCCCGTTTTGGGGACGTGAACGTTTTAATAATTTTTGCTGAATTCCTTTACA
ACTAAATAACACAGATATTGTTATAAATAAAATTGTAAAAAAAAAAAAAAAAAA

(SEQ ID NO: 4)

>gi|124494255|ref|NM_008512.2| Mus musculus low density lipoprotein receptor- related protein (Lrpl), mRNA AGTCAGGGGAGCAGCGGTGCGAGCTCCAGGCCAGTGCACTGAGGAGGCGGAAACGGGGGAGCCCCTAGTGCTCCATCAGGCCCC
TACCAAGGCACCCCCATCGGGTCCACGCCCCCCACCCCCCACCCCGCCTCCTCCCAATTGTGCATTTTTGCAGCCAGAGGCGGCTC
CGAGATGGGGCTGTGAGCTTCGCCCTGGGAGGGGGAGAGGAGCGAGGAGTAAAGCAGGGGTGAAGGGTTCGAATTTGGGGGCA
GGGGGCGCACCCGCGTCAGCAGGCCCTTCCCAGGGGGCTCGGAACTGTACCATTTCACCTATGCCCCTGGTTCGCTTTGCTTAAGG
AAAGGATAAGAATAGAAGAGTCGGGGAGAGGAAGATAAAGGGGGACCCCCCAATTGGGGGGGGCGAGGACAAGAAGTAACAG
GACCAGAGGGTGGGGGCTGCTGTTTGCATCGGCCCACACCATGCTGACCCCGCCGTTGCTGCTGCTGCTGCCGCTGCTTTCAGCTC
TGGTCTCCGGGGCCACTATGGATGCCCCTAAAACTTGCAGCCCTAAGCAGTTTGCCTGCAGAGACCAAATCACCTGTATCTCAAA
GGGCTGGCGGTGTGACGGTGAAAGAGATTGCCCCGACGGCTCTGATGAAGCCCCTGAGATCTGTCCACAGAGTAAAGCCCAGAG
ATGCCCGCCAAATGAGCACAGTTGTCTGGGGACTGAGCTATGTGTCCCCATGTCTCGTCTCTGCAACGGGATCCAGGACTGCATG
GATGGCTCAGACGAGGGTGCTCACTGCCGAGAGCTCCGAGCCAACTGTTCTCGAATGGGTTGTCAACACCATTGTGTACCTACAC
CCAGTGGGCCCACGTGCTACTGTAACAGCAGCTTCCAGCTGCAGGCAGATGGCAAGACGTGCAAAGATTTTGACGAGTGTTCCGT
GTATGGCACCTGCAGCCAGCTTTGCACCAACACAGATGGCTCCTTCACATGTGGCTGTGTTGAAGGCTACCTGCTGCAACCGGAC
AACCGCTCCTGCAAGGCCAAGAATGAGCCAGTAGATCGGCCGCCAGTGCTACTGATTGCCAACTCTCAGAACATCCTAGCTACGT
ACCTGAGTGGGGCCCAAGTGTCTACCATCACACCCACCAGCACCCGACAAACCACGGCCATGGACTTCAGTTATGCCAATGAGAC
CGTATGCTGGGTGCACGTTGGGGACAGTGCTGCCCAGACACAGCTCAAGTGTGCCCGGATGCCTGGCCTGAAGGGCTTTGTGGAT
GAGCATACCATCAACATCTCCCTCAGCCTGCACCACGTGGAGCAGATGGCAATCGACTGGCTGACGGGAAACTTCTACTTTGTCG
ACGACATTGACGACAGGATCTTTGTCTGTAACCGAAACGGGGACACCTGTGTCACTCTGCTGGACCTGGAACTCTACAACCCCAA
AGGCATCGCCTTGGACCCCGCCATGGGGAAGGTGTTCTTCACTGACTACGGGCAGATCCCAAAGGTGGAGCGCTGTGACATGGAT
GGACAGAACCGCACCAAGCTGGTGGATAGCAAGATCGTGTTTCCACACGGCATCACCCTGGACCTGGTCAGCCGCCTCGTCTACT
GGGCGGACGCCTACCTAGACTACATCGAGGTGGTAGACTACGAAGGGAAGGGTCGGCAGACCATCATCCAAGGCATCCTGATCG
AGCACCTGTACGGCCTGACCGTGTTTGAGAACTATCTCTACGCCACCAACTCGGACAATGCCAACACGCAGCAGAAGACGAGCGT
GATCCGAGTGAACCGGTTCAACAGTACTGAGTACCAGGTCGTCACCCGTGTGGACAAGGGTGGTGCCCTGCATATCTACCACCAG
CGACGCCAGCCCCGAGTGCGGAGTCACGCCTGTGAGAATGACCAGTACGGGAAGCCAGGTGGCTGCTCCGACATCTGCCTCCTGG
CCAACAGTCACAAGGCAAGGACCTGCAGGTGCAGGTCTGGCTTCAGCCTGGGAAGTGATGGGAAGTCTTGTAAGAAACCTGAAC
ATGAGCTGTTCCTCGTGTATGGCAAGGGCCGACCAGGCATCATTAGAGGCATGGACATGGGGGCCAAGGTCCCAGATGAGCACAT
GATCCCCATCGAGAACCTTATGAATCCACGCGCTCTGGACTTCCACGCCGAGACCGGCTTCATCTACTTTGCTGACACCACCAGCT
ACCTCATTGGCCGCCAGAAAATTGATGGCACGGAGAGAGAGACTATCCTGAAGGATGGCATCCACAATGTGGAGGGCGTAGCCG
TGGACTGGATGGGAGACAATCTTTACTGGACTGATGATGGCCCCAAGAAGACCATTAGTGTGGCCAGGCTGGAGAAAGCCGCTCA
GACCCGGAAGACTCTAATTGAGGGCAAGATGACACACCCCAGGGCCATTGTAGTGGATCCACTCAAGGGTGGATGTACTGGACA
GACTGGGAGGAGGACCCCAAGGACAGTCGGCGAGGGCGGCTCGAGAGGGCTTGGATGGACGGCTCACACCGAGATATCTTTGTC
ACCTCCAAGACAGTGCTTTGGCCCAATGGGCTAAGCCTGGATATCCCAGCCGGACGCCTCTACTGGGTGGATGCCTTCTATGACC
GAATTGAGACCATACTGCTCAATGGCACAGACCGGAAGATTGTATATGAGGGTCCTGAACTGAATCATGCCTTCGGCCTGTGTCA
CCATGGCAACTACCTCTTTTGGACCGAGTACCGGAGCGGCAGCGTCTACCGCTTGGAACGGGGCGTGGCAGGCGCACCGCCCACT

FIG.2 (Continued)

GTGACCCTTCTGCGCAGCGAGAGACCGCCTATCTTTGAGATCCGAATGTACGACGCGCAGCAGCAGCAAGTGGGTACCAACAAAT
GCCGGGTAAATAACGGAGGCTGCAGCAGCCTGTGCCTCGCCACCCCCGGGAGCCGCCAGTGTGCCTGTGCCGAGGACCAGGTGTT
GGACACAGATGGTGTCACCTGCTTGGCGAACCCATCCTACGTGCCCCCACCCCAGTGCCAGCCGGGCGAGTTTGCCTGTGCCAAC
AACCGCTGCATCCAGGAGCGCTGGAAGTGTGACGGAGACAACGACTGTCTGGACAACAGCGATGAGGCCCCAGCACTGTGCCAT
CAACACACCTGTCCCTCGGACCGATTCAAGTGTGAGAACAACCGGTGTATCCCCAACCGCTGGCTCTGTGATGGGGATAATGATT
GTGGCAACAGCGAGGACGAATCCAATGCCACGTGCTCAGCCCGCACCTGTCCACCCAACCAGTTCTCCTGTGCCAGTGGCCGATG
CATTCCTATCTCATGGACCTGTGATCTGGATGATGACTGTGGGGACCGGTCCGATGAGTCAGCCTCATGCGCCTACCCCACCTGCT
TCCCCCTGACTCAATTTACCTGCAACAATGGCAGATGTATTAACATCAACTGGCGGTGTGACAACGACAATGACTGTGGGGACAA
CAGCGACGAAGCCGGCTGCAGTCACTCCTGCTCCAGTACCCAGTTCAAGTGCAACAGTGGCAGATGCATCCCCGAGCACTGGACG
TGTGATGGGGACAATGATTGTGGGGACTACAGCGACGAGACACACGCCAACTGTACCAACCAGGCTACAAGACCTCCTGGTGGC
TGCCACTCGGATGAGTTCCAGTGCCGCCTAGATGGCCTGTGCATCCCCCTGAGGTGGCGCTGCGACGGGGACACCGACTGCATGG
ATTCCAGCGATGAGAAGAGCTGTGAGGGCGTGACCCATGTTTGTGACCCGAATGTCAAGTTTGGCTGCAAGGACTCCGCCCGGTG
CATCAGCAAGGCGTGGGTGTGTGATGGCGACAGCGACTGTGAAGATAACTCCGACGAGGAGAACTGTGAGGCCCTGGCCTGCAG
GCCACCCTCCCATCCCTGCGCCAACAACACCTCTGTCTGCCTGCCTCCTGACAAGCTGTGCGACGGCAAGGATGACTGTGGAGAC
GGCTCGGATGAGGGCGAGCTCTGTGACCAGTGTTCTCTGAATAATGGTGGCTGTAGTCACAACTGCTCAGTGGCCCCTGGTGAAG
GCATCGTGTGCTCTTGCCCTCTGGGCATGGAGCTGGGCTCTGACAACCACACCTGCCAGATCCAGAGCTACTGTGCCAAGCACCTC
AAATGCAGCCAGAAGTGTGACCAGAACAAGTTCAGTGTGAAGTGCTCCTGCTACGAGGGCTGGGTCTTGGAGCCTGACGGGGAA
AGCTGCCGCAGTCTGGATCCCTTCAAACCGTTCATCATCTTCTCCAACCGCCACGAGATCAGGCGCATTGACCTTCACAAGGGGG
ACTACAGCGTCCTAGTGCCTGGCCTGCGCAACACTATTGCCCTGGACTTCCACCTCAGCCAGAGTGCCCTCTACTGGACCGACGTG
GTAGAGGACAAGATCTACCGTGGGAAACTCCTGGACAACGGAGCCCTGACCAGCTTTGAGGTGGTGATTCAGTATGGCTTGGCCA
CACCAGAGGGCCTGGCTGTAGATTGGATTGCAGGCAACATCTACTGGGTGGAGAGCAACCTGGACCAGATCGAAGTGGCCAAGC
TGGACGGAACCCTCCGAACCACTCTGCTGGCGGGTGACATTGAGCACCCGAGGGCCATCGCTCTGGACCCTCGGGATGGGATTCT
GTTTTGGACAGACTGGGATGCCAGCCTGCCACGAATCGAGGCTGCGTCCATGAGTGGGGCTGGCCGCCGAACCATCCACCGGGAG
ACAGGCTCTGGGGGCTGGCCCAACGGGCTCACCGTGGATTACCTGGAGAAGCGCATCCTCTGGATTGATGCTAGGTCAGATGCCA
TCTATTCAGCCCGGTATGACGGCTCCGGCCACATGGAGGTGCTTCGGGGACACGAGTTCCTGTCACACCCATTTGCCGTGACACTG
TACGGTGGGGAGGTGTACTGGACCGACTGGCGAACAAATACACTGGCTAAGGCCAACAAGTGGACTGGCCACAACGTCACCGTG
GTACAGAGGACCAACACCCAGCCCTTCGACCTGCAGGTGTATCACCCTTCCCGGCAGCCCATGGCTCCAAACCCATGTGAGGCCA
ATGGCGGCCGGGGCCCCTGTTCCCATCTGTGCCTCATCAACTACAACCGGACCGTCTCCTGCGCCTGTCCCCACCTCATGAAGCTG
CACAAGGACAACACCACCTGCTATGAGTTTAAGAAGTTCCTGCTGTACGCACGTCAGATGGAGATCCGGGGCGTGGACCTGGATG
CCCCGTACTACAATTATATCATCTCCTTCACGGTGCCTGATATCGACAATGTCACGGTGCTGGACTATGATGCCCGAGAGCAGCGA
GTTTACTGGTCTGATGTGCGGACTCAAGCCATCAAAAGGGCATTTATCAACGGCACTGGCGTGGAGACCGTTGTCTCTGCAGACTT
GCCCAACGCCCACGGGCTGGCTGTGGACTGGGTCTCCCGAAATCTGTTTTGGACAAGTTACGACACCAACAAGAAGCAGATTAAC
GTGGCCCGGCTGGACGGCTCCTTCAAGAATGCGGTGGTGCAGGGCCTGGAGCAGCCCCACGGCCTGGTCGTCCACCCGCTTCGTG
GCAAGCTCTACTGGACTGATGGGGACAACATCAGCATGGCCAACATGGATGGGAGCAACCACACTCTGCTCTTCAGTGGCCAGAA
GGGCCCTGTGGGGTTGGCCATTGACTTCCCTGAGAGCAAACTCTACTGGATCAGCTCTGGGAACCACACAATCAACCGTTGCAAT
CTGGATGGGAGCGAGCTGGAGGTCATCGACACCATGCGGAGCCAGCTGGGCAAGGCCACTGCCCTGGCCATCATGGGGGACAAG
CTGTGGTGGGCAGATCAGGTGTCAGAGAAGATGGGCACGTGCAACAAAGCCGATGGCTCTGGGTCCGTGGTGCTGCGGAACAGT
ACCACGTTGGTTATGCACATGAAGGTGTATGACGAGAGCATCCAGCTAGAGCATGAGGGCACCAACCCCTGCAGTGTCAACAAC
GGAGACTGTTCCCAGCTCTGCCTGCCAACATCAGAGACGACTCGCTCCTGTATGTGTACAGCCGGTTACAGCCTCCGGAGCGGAC
AGCAGGCCTGTGAGGGTGTGGGCTCTTTTCTCCTGTACTCTGTACATGAGGGAATTCGGGGGATTCCACTAGATCCCAATGACAAG
TCGGATGCCCTGGTCCCAGTGTCCGGAACTTCACTGGCTGTCGGAATCGACTTCCATGCCGAAAATGACACTATTTATTGGGTGGA
TATGGGCCTAAGCACCATCAGCAGGGCCAAGCGTGACCAGACATGGCGAGAGGATGTGGTGACCAACGGTATTGGCCGTGTGGA
GGGCATCGCGGTGGACTGGATCGCAGGCAACATATACTGGACGGACCAGGGCTTCGATGTCATCGAGGTTGCCCGGCTCAATGGC
TCTTTTCGTTATGTGGTCATTTCCCAGGGTCTGGACAAGCCTCGGGCCATCACTGTCCACCCAGAGAAGGGGTACTTGTTCTGGAC
CGAGTGGGGTCATTACCCACGTATTGAGCGGTCTCGCCTTGATGGCACAGAGAGAGTGGTGTTGGTTAATGTCAGCATCAGCTGG
CCCAATGGCATCTCAGTAGACTATCAGGGCGGCAAGCTCTACTGGTGTGATGCTCGGATGGACAAGATCGAGCGCATCGACCTGG
AAACGGGCGAGAACCGGGAGGTGGTCCTGTCCAGCAATAACATGGATATGTTCTCCGTGTCCGTGTTTGAGGACTTCATCTACTG
GAGTGACAGAACTCACGCCAATGGCTCCATCAAGCGCGGCTGCAAAGACAATGCTACAGACTCCGTGCCTCTGAGGACAGGCATT
GGTGTTCAGCTTAAAGACATCAAGGTCTTCAACAGGGACAGGCAGAAGGGTACCAATGTGTGCGCGGTAGCCAACGGCGGGTGC
CAGCAGCTCTGCTTGTATCGGGGTGGCGGACAGCGAGCCTGTGCCTGTGCCCACGGGATGCTGGCAGAAGACGGGGCCTCATGCC
GAGAGTACGCTGGCTACCTGCTCTACTCAGAGCGGACCATCCTCAAGAGCATCCACCTGTCGGATGAGCGTAACCTCAACGCACC
GGTGCAGCCCTTTGAAGACCCCGAGCACATGAAAAATGTCATCGCCCTGGCCTTTGACTACCGAGCAGGCACCTCCCCGGGGACC
CCTAACCGCATCTTCTTCAGTGACATCCACTTTGGGAACATCCAGCAGATCAATGACGATGGCTCGGGCAGGACCACCATCGTGG
AAAATGTGGGCTCTGTGGAAGGCCTGGCCTATCACCGTGGCTGGGACACACTGTACTGGACAAGCTACACCACATCCACCATCAC
CCGCCACACCGTGGACCAGACTCGCCCAGGGGCCTTCGAGAGGGAGACAGTCATCACCATGTCCGGAGACGACCACCCGAGAGC
CTTTGTGCTGGATGAGTGCCAGAACCTGATGTTCTGGACCAATTGGAACGAGCTCCATCCAAGCATCATGCGGGCAGCCCTATCC
GGAGCCAACGTCCTGACCCTCATTGAGAAGGACATCCGCACGCCCAATGGGTTGGCCATCGACCACCGGGCGGAGAAGCTGTACT
TCTCGGATGCCACCTTGGACAAGATCGAGCGCTGCGAGTACGACGGCTCCCACCGCTATGTGATCCTAAAGTCGGAGCCCGTCCA
CCCCTTTGGGTTGGCGGTGTACGGAGAGCACATTTTCTGGACTGACTGGGTGCGGCGGGCTGTGCAGCGAGCCAACAAGTATGTG
GGCAGCGACATGAAGCTGCTTCGGGTGGACATTCCCCAGCAACCCATGGGCATCATCGCCGTGGCCAACGACACCAACAGCTGTG
AACTCTCCCCCTGCCGTATCAACAATGGAGGCTGCCAGGATCTGTGTCTGCTCACCCACCAAGGCCACGTCAACTGTTCCTGTCGA
GGGGGCCGGATCCTCCAGGAGGACTTCACCTGCCGGGCTGTGAACTCCTCTTGTCGGGCACAAGATGAGTTTGAGTGTGCCAATG
GGGAATGTATCAGCTTCAGCCTCACCTGTGATGGCGTCTCCCACTGCAAGGACAAGTCCGATGAGAAGCCCTCCTACTGCAACTC
ACGCCGCTGCAAGAAGACTTTCCGCCAGTGTAACAATGGTCGCTGTGTATCCAACATGCTGTGGTGCAATGGGGTGGATGACTGT
GGGGATGGCTCTGATGAGATTCCTTGCAACAAGACTGCCTGTGGTGTGGGTGAGTTCCGCTGCCGGGATGGGTCCTGCATCGGGA
ACTCCAGTCGCTGCAACCAGTTTGTGGATTGTGAGGATGCCTCGGATGAGATGAATTGCAGTACCACAGACTGCAGCAGCTATTT

FIG.2 (Continued)

CCGCCTGGGCGTGAAAGGTGTCCTCTTCCAGCCGTGCGAGCGGACATCCCTGTGCTACGCACCTAGCTGGGTGTGTGATGGCGCC
AACGACTGTGGAGACTACAGCGATGAACGTGACTGTCCAGGTGTGAAGCGCCCTAGGTGCCCGCTCAATTACTTTGCCTGCCCCA
GCGGGCGCTGTATCCCCATGAGCTGGACGTGTGACAAGGAGGATGACTGTGAGAACGGCGAGGACGAGACCCACTGCAACAAGT
TCTGCTCAGAGGCACAGTTCGAGTGCCAGAACCACCGGTGTATCTCCAAGCAGTGGCTGTGTGACGGTAGCGATGATTGCGGGGA
TGGCTCCGATGAGGCAGCTCACTGTGAAGGCAAGACATGTGGCCCCTCCTCCTTCTCCTGTCCCGGCACCCACGTGTGTGTCCCTG
AGCGCTGGCTCTGTGATGGCGACAAGGACTGTACCGATGGCGCGGATGAGAGTGTCACTGCTGGCTGCCTGTACAACAGCACCTG
TGATGACCGTGAGTTCATGTGCCAGAACCGCTTGTGTATTCCCAAGCATTTCGTGTGCGACCATGACCGTGACTGTGCTGATGGCT
CTGATGAATCCCCTGAGTGTGAGTACCCAACCTGCGGCCCCAATGAATTCCGCTGTGCCAATGGGCGTTGTCTGAGCTCCCGTCAG
TGGGAATGTGATGGGGAGAATGACTGTCACGACCACAGCGATGAGGCTCCCAAGAACCCACACTGCACCAGCCCAGAGCACAAA
TGCAATGCCTCATCACAGTTCCTGTGCAGCAGCGGGCGCTGCGTGGCTGAGGCGTTGCTCTGCAACGGCCAGGACGACTGTGGGG
ACGGTTCAGACGAACGCGGGTGCCATGTCAACGAGTGTCTCAGCCGCAAGCTCAGTGGCTGCAGTCAGGACTGCGAGGACCTCA
AGATAGGCTTTAAGTGCCGCTGTCGCCCGGGCTTCCGGCTAAAGGACGATGGCAGGACCTGTGCCGACCTGGATGAGTGCAGCAC
CACCTTCCCCTGCAGCCAGCTCTGCATCAACACCCACGGAAGTTACAAGTGTCTGTGTGTGGAGGGCTATGCACCCCGTGGCGGT
GACCCCCACAGCTGCAAAGCTGTGACCGATGAGGAGCCATTTCTCATCTTTGCCAACCGGTACTACCTGCGGAAGCTCAACCTGG
ACGGCTCCAACTACACACTGCTTAAGCAGGGCCTGAACAATGCGGTCGCCTTGGACTTTGACTACCGAGAGCAGATGATCTACTG
GACGGACGTGACCACCCAGGGCAGCATGATTCGCAGGATGCACCTCAACGGCAGCAACGTGCAGGTTCTGCACCGGACGGGCCT
TAGTAACCCAGATGGGCTGGCTGTGGACTGGGTGGGTGGCAACCTGTACTGGTGTGACAAGGGCAGAGATACCATTGAGGTGTCC
AAGCTTAACGGGGCCTATCGGACAGTGCTGGTCAGCTCTGGCCTCCGGGAGCCCAGAGCTCTGGTAGTGGATGTACAGAATGGGT
ACCTGTACTGGACAGACTGGGGTGACCACTCACTGATCGGCCGGATTGGCATGGATGGATCTGGCCGCAGCATCATCGTGGACAC
TAAGATCACATGGCCCAATGGCCTGACCGTGGACTACGTCACGGAACGCATCTACTGGGCTGACGCCCGTGAGGACTACATCGAG
TTCGCCAGCCTGGATGGCTCCAACCGTCACGTTGTGCTGAGCCAAGACATCCCACACATCTTTGCGCTGACCCTATTTGAAGACTA
CGTCTACTGGACAGACTGGGAAACGAAGTCCATCAACCGGGCCCACAAGACCACGGGTGCCAACAAAACACTCCTCATCAGCAC
CCTGCACCGGCCCATGGACTTACATGTATTCCACGCCCTGCGCCAGCCAGATGTGCCCAATCACCCCTGCAAAGTCAACAATGGT
GGCTGCAGCAACCTGTGCCTGCTGTCCCCTGGGGGTGGTCATAAATGCGCCTGCCCCACCAACTTCTATCTGGGTGGCGATGGCCG
TACCTGTGTGTCCAACTGCACAGCAAGCCAGTTTGTGTGCAAAAATGACAAGTGCATCCCCTTCTGGTGGAAGTGTGACACGGAG
GACGACTGTGGGGATCACTCAGACGAGCCTCCAGACTGTCCCGAGTTCAAGTGCCGCCCAGGCCAGTTCCAGTGCTCCACCGGCA
TCTGCACCAACCCTGCCTTCATCTGTGATGGGGACAATGACTGCCAAGACAATAGTGATGAGGCCAATTGCGACATTCACGTCTG
CTTGCCCAGCCAATTCAAGTGCACCAACACCAACCGCTGCATTCCTGGCATCTTCCGTTGCAATGGGCAGGACAACTGCGGGGAC
GGCGAGGATGAGCGGGATTGCCCTGAGGTGACCTGCGCCCCCAACCAGTTCCAGTGCTCCATCACCAAGCGCTGCATCCCTCGCG
TCTGGGTCTGTGACAGGGATAATGACTGTGTGGACGGCAGTGATGAGCCTGCCAACTGTACCCAAATGACCTGTGGAGTGGATGA
GTTCCGCTGCAAGGATTCTGGCCGCTGCATCCCCGCGCGCTGGAAGTGTGACGGAGAAGATGACTGTGGGGATGGTTCAGATGAG
CCCAAGGAAGAGTGTGATGAGCGCACCTGTGAGCCATACCAGTTCCGCTGCAAAAACAACCGCTGTGTCCCAGGCCGTTGGCAAT
GTGACTACGACAACGACTGCGGAGATAACTCGGACGAGGAGAGCTGCACACCTCGGCCCTGCTCTGAGAGTGAGTTTTCCTGTGC
CAATGGCCGCTGCATCGCTGGGCGCTGGAAGTGTGATGGGGACCATGACTGTGCCGACGGCTCAGACGAGAAAGACTGCACCCC
CCGCTGTGATATGGACCAGTTCCAGTGCAAGAGTGGCCACTGCATCCCCCTGCGCTGGCGCTGTGACGCGGATGCTGACTGTATG
GACGGCAGTGACGAGGAAGCCTGTGGCACTGGGGTGAGGACCTGCCCATTGGATGAGTTTCAATGTAACAACACCTTGTGCAAGC
CGCTGGCCTGGAAGTGTGATGGAGAGGACGACTGTGGGGACAACTCAGATGAGAACCCCGAGGAATGCGCCCGGTTCATCTGCC
CTCCCAACCGGCCTTTCCGCTGCAAGAATGACCGAGTCTGCCTGTGGATTGGGCGCCAGTGTGATGGCGTGGACAACTGTGGAGA
TGGGACTGACGAGGAGGACTGTGAGCCCCCCACGGCCCAGAACCCCCACTGCAAAGACAAGAAGGAGTTCCTGTGCCGAAACCA
GCGCTGTCTATCATCCTCCCTGCGCTGTAACATGTTCGATGACTGCGGCGATGGCTCCGATGAAGAAGATTGCAGCATCGACCCCA
AGCTGACCAGCTGTGCCACCAATGCCAGCATGTGTGGGGACGAAGCTCGTTGTGTGCGCACTGAGAAAGCTGCCTACTGTGCCTG
CCGCTCGGGCTTCCATACTGTGCCGGGCCAGCCCGGATGCCAGGACATCAACGAGTGCCTGCGCTTTGGTACCTGCTCTCAGCTCT
GCAACAACACCAAGGGAGGCCACCTCTGCAGCTGTGCCCGCAACTTCATGAAGACACACAACACCTGCAAAGCTGAAGGCTCCG
AGTACCAGGTGCTATACATCGCGGATGACAACGAGATCCGCAGCTTGTTCCCGGGCCACCCCCACTCAGCCTACGAGCAGACATT
CCAGGGCGATGAGAGTGTCCGCATAGATGCCATGGATGTCCATGTCAAGGCCGGCCGTGTCTACTGGACTAACTGGCACACGGGC
ACAATCTCCTACAGGAGCCTGCCCCCTGCCGCCCCTCCTACCACTTCCAACCGCCACCGGAGGCAGATCGACCGGGGTGTCACCC
ACCTCAATATTTCAGGGCTGAAGATGCCGAGGGGTATCGCTATCGACTGGGTGGCCGGGAATGTGTACTGGACCGATTCCGGCCG
AGACGTGATTGAGGTGGCGCAAATGAAGGGCGAGAACCGCAAGACGCTCATCTCGGGCATGATTGATGAGCCCCATGCCATCGT
GGTGGACCCTCTGAGGGGCACCATGTACTGGTCAGACTGGGGGAACCACCCCAAGATTGAAACAGCAGCGATGGATGGCACCCT
TCGGGAGACTCTCGTGCAAGACAACATTCAGTGGCCTACAGGGCTGGCTGTGGACTATCACAATGAACGGCTCTACTGGGCAGAT
GCCAAGCTTTCGGTCATCGGCAGCATCCGGCTCAACGGCACTGACCCCATTGTGGCTGCTGACAGCAAACGAGGCCTAAGTCACC
CCTTCAGCATCGATGTGTTTGAAGACTACATCTACGGAGTCACTTACATCAATAATCGTGTCTTCAAGATCCACAAGTTTGGACAC
AGCCCCTTGATCAACCTAACTGGGGGCCTGAGCCATGCCTCTGATGTAGTCCTTTACCATCAACACAAGCAGCCTGAAGTGACCA
ACCCCTGTGACCGCAAGAAATGTGAATGGCTGTGTCTGCTGAGCCCCAGCGGGCCTGTCTGCACCTGTCCCAATGGAAAGAGGCT
GGATAATGGCACCTGTGTGCCTGTGCCCTCTCCAACACCCCCTCCAGATGCCCCTAGGCCTGGAACCTGCACTCTGCAGTGCTTCA
ATGGTGGTAGTTGTTTCCTCAATGCTCGGAGGCAGCCCAAGTGCCGTTGCCAGCCCCGTTACACAGGCGATAAGTGTGAGCTGGA
TCAGTGCTGGGAATACTGTCACAACGGAGGCACCTGTGCGGCTTCCCCATCTGGCATGCCCACGTGCCGCTGTCCCACTGGCTTCA
CGGGCCCCAAATGCACCGCACAGGTGTGTGCAGGCTACTGCTCTAACAACAGCACCTGCACCGTCAACCAGGGCAACCAGCCCCA
GTGCCGATGTCTACCTGGCTTCCTGGGCGACCGTTGCCAGTACCGGCAGTGCTCTGGCTTCTGTGAGAACTTTGGCACCTGTCAGA
TGGCTGCTGATGGCTCCCGACAATGTCGCTGCACCGTCTACTTTGAGGGACCAAGGTGTGAGGTGAACAAGTGTAGTCGCTGTCTC
CAAGGCGCCTGTGTGGTCAATAAGCAGACCGGAGATGTCACATGCAACTGCACTGATGGCCGGGTAGCCCCCAGTTGTCTGACCT
GCATCGATCACTGTAGCAATGGTGGCTCCTGCACCATGAACAGCAAGATGATGCCTGAGTGCCAGTGCCCGCCCCATATGACAGG
ACCCCGGTGCGAGGAGCAGGTTGTTAGTCAGCAACAGCCTGGGCATATGGCCTCCATCCTGATCCCTCTGCTGCTGCTTCTCCTGC
TGCTTCTGGTGGCTGGCGTGGTGTTCTGGTATAAGCGGCGAGTCCGAGGGGCTAAGGGCTTCCAGCACCAGCGGATGACCAATGG
GGCCATGAATGTGGAAATTGGAAACCCTACCTACAAGATGTATGAAGGTGGAGAGCCCGATGATGTCGGGGGCCTACTGGATGCT
GATTTTGCCCTTGACCCTGACAAGCCTACCAACTTCACCAACCCAGTGTATGCCACGCTCTACATGGGGGGCCACGGCAGCCGCC

FIG.2 (Continued)

ATTCCCTGGCCAGCACGGACGAGAAGCGAGAACTGCTGGGCCGGGGACCTGAAGACGAGATAGGAGATCCCTTGGCATAGGGCC
CTGCCCCGACGGATGTCCCCAGAAAGCCCCCTGCCACATGAGTCTTTCAATGAACCCCCTCCCCAGCCGGCCCTTCTCCGGCCCTG
CCGGGTGTACAAATGTAAAAATGAAGGAATTACTTTTTATATGTGAGCGAGCAAGCGAGCAAGCACAGTATTATCTCTTTGCATTT
CCTTCCTGCCTGCTCCTCAGTATCCCCCCCATGCTGCCTTGAGGGGGCGGGGAGGGCTTTGTGGCTCAAAGGTATGAAGGAGTCCA
CATGTTCCCTACCGAGCATACCCCTGGAAGCTGGCGGCACGGCCTCCCCACCACGCCTGTGCAAGACACTCAACGGGGCTCCGTG
TCCCAGCTTTCCTTTCCTTGGCTCTCTGGGGTTAGTTCAGGGGAGGTGGAGTCCTCTGCTGACCCTGTCTGGAAGATTTGGCTCTAG
CTGAGGAAGGAGTCTTTTAGTTGAGGGAAGTCACCCCAAACCCCAGCTCCCACTTTCAGGGGCACCTCTCAGATGGCCATGCTCA
GTATCCCTTCCAGACAGGCCCTCCCCTCTCTAGCGCCCCCTCTGTGGCTCCTAGGGCTGAACACATTCTTTGGTAACTGTCCCCCAA
GCCTCCCATCCCCCTGAGGGCCAGGAAGAGTCGGGGCACACCAAGGAAGGGCAAGCGGGCAGCCCCATTTTGGGGACGTGAACG
TTTTAATAATTTTTGCTGAATTCCTTTACAACTAAATAACACAGATATTGTTATAAATAAAATTGTAAAAAAGGAAAAAAAAAAG
AAAAGAAAAGAAAAGAAAAAAAAAAAAAAAAAA

(SEQ ID NO: 5)

>gi|170932496|ref|NM_000527.3| Homo sapiens low density lipoprotein receptor (LDLR), mRNA ACATTTGAAAATCACCCCACTGCAAACTCCTCCCCCTGCTAGAAACCTCACATTGAAATGCTGTAAATGACGTGGGCCCCGAGTG
CAATCGCGGGAAGCCAGGGTTTCCAGCTAGGACACAGCAGGTCGTGATCCGGGTCGGGACACTGCCTGGCAGAGGCTGCGAGCA
TGGGGCCCTGGGGCTGGAAATTGCGCTGGACCGTCGCCTTGCTCCTCGCCGCGGCGGGGACTGCAGTGGGCGACAGATGCGAAA
GAAACGAGTTCCAGTGCCAAGACGGGAAATGCATCTCCTACAAGTGGGTCTGCGATGGCAGCGCTGAGTGCCAGGATGGCTCTGA
TGAGTCCCAGGAGACGTGCTTGTCTGTCACCTGCAAATCCGGGGACTTCAGCTGTGGGGGCCGTGTCAACCGCTGCATTCCTCAGT
TCTGGAGGTGCGATGGCCAAGTGGACTGCGACAACGGCTCAGACGAGCAAGGCTGTCCCCCCAAGACGTGCTCCCAGGACGAGT
TTCGCTGCCACGATGGGAAGTGCATCTCTCGGCAGTTCGTCTGTGACTCAGACCGGGACTGCTTGGACGGCTCAGACGAGGCCTC
CTGCCCGGTGCTCACCTGTGGTCCCGCCAGCTTCCAGTGCAACAGCTCCACCTGCATCCCCCAGCTGTGGGCCTGCGACAACGACC
CCGACTGCGAAGATGGCTCGGATGAGTGGCCGCAGCGCTGTAGGGGTCTTTACGTGTTCCAAGGGGACAGTAGCCCCTGCTCGGC
CTTCGAGTTCCACTGCCTAAGTGGCGAGTGCATCCACTCCAGCTGGCGCTGTGATGGTGGCCCCGACTGCAAGGACAAATCTGAC
GAGGAAAACTGCGCTGTGGCCACCTGTCGCCCTGACGAATTCCAGTGCTCTGATGGAAACTGCATCCATGGCAGCCGGCAGTGTG
ACCGGGAATATGACTGCAAGGACATGAGCGATGAAGTTGGCTGCGTTAATGTGACACTCTGCGAGGGACCCAACAAGTTCAAGT
GTCACAGCGGCGAATGCATCACCCTGGACAAAGTCTGCAACATGGCTAGAGACTGCCGGGACTGGTCAGATGAACCCATCAAAG
AGTGCGGGACCAACGAATGCTTGGACAACAACGGCGGCTGTTCCCACGTCTGCAATGACCTTAAGATCGGCTACGAGTGCCTGTG
CCCCGACGGCTTCCAGCTGGTGGCCCAGCGAAGATGCGAAGATATCGATGAGTGTCAGGATCCCGACACCTGCAGCCAGCTCTGC
GTGAACCTGGAGGGTGGCTACAAGTGCCAGTGTGAGGAAGGCTTCCAGCTGGACCCCCACACGAAGGCCTGCAAGGCTGTGGGC
TCCATCGCCTACCTCTTCTTCACCAACCGGCACGAGGTCAGGAAGATGACGCTGGACCGGAGCGAGTACACCAGCCTCATCCCCA
ACCTGAGGAACGTGGTCGCTCTGGACACGGAGGTGGCCAGCAATAGAATCTACTGGTCTGACCTGTCCCAGAGAATGATCTGCAG
CACCCAGCTTGACAGAGCCCACGGCGTCTCTTCCTATGACACCGTCATCAGCAGAGACATCCAGGCCCCCGACGGGCTGGCTGTG
GACTGGATCCACAGCAACATCTACTGGACCGACTCTGTCCTGGGCACTGTCTCTGTTGCGGATACCAAGGGCGTGAAGAGGAAAA
CGTTATTCAGGGAGAACGGCTCCAAGCCAAGGGCCATCGTGGTGGATCCTGTTCATGGCTTCATGTACTGGACTGACTGGGGAAC
TCCCGCCAAGATCAAGAAAGGGGGCCTGAATGGTGTGGACATCTACTCGCTGGTGACTGAAAACATTCAGTGGCCCAATGGCATC
ACCCTAGATCTCCTCAGTGGCCGCCTCTACTGGGTTGACTCCAAACTTCACTCCATCTCAAGCATCGATGTCAACGGGGGCAACCG
GAAGACCATCTTGGAGGATGAAAAGAGGCTGGCCCACCCCTTCTCCTTGGCCGTCTTTGAGGACAAAGTATTTTGGACAGATATC
ATCAACGAAGCCATTTTCAGTGCCAACCGCCTCACAGGTTCCGATGTCAACTTGTTGGCTGAAAACCTACTGTCCCCAGAGGATAT
GGTTCTCTTCCACAACCTCACCCAGCCAAGAGGAGTGAACTGGTGTGAGAGGACCACCCTGAGCAATGGCGGCTGCCAGTATCTG
TGCCTCCCTGCCCCGCAGATCAACCCCCACTCGCCCAAGTTTACCTGCGCCTGCCCGGACGGCATGCTGCTGGCCAGGGACATGA
GGAGCTGCCTCACAGAGGCTGAGGCTGCAGTGGCCACCCAGGAGACATCCACCGTCAGGCTAAAGGTCAGCTCCACAGCCGTAA
GGACACAGCACACAACCACCCGACCTGTTCCCGACACCTCCCGGCTGCCTGGGGCCACCCCTGGGCTCACCACGGTGGAGATAGT
GACAATGTCTCACCAAGCTCTGGGCGACGTTGCTGGCAGAGGAAATGAGAAGAAGCCCAGTAGCGTGAGGGCTCTGTCCATTGTC
CTCCCCATCGTGCTCCTCGTCTTCCTTTGCCTGGGGGTCTTCCTTCTATGGAAGAACTGGCGGCTTAAGAACATCAACAGCATCAA
CTTTGACAACCCCGTCTATCAGAAGACCACAGAGGATGAGGTCCACATTTGCCACAACCAGGACGGCTACAGCTACCCCTCGAGA
CAGATGGTCAGTCTGGAGGATGACGTGGCGTGAACATCTGCCTGGAGTCCCGTCCCTGCCCAGAACCCTTCCTGAGACCTCGCCG
GCCTTGTTTTATTCAAAGACAGAGAAGACCAAAGCATTGCCTGCCAGAGCTTTGTTTTATATATTTATTCATCTGGGAGGCAGAAC
AGGCTTCGGACAGTGCCCATGCAATGGCTTGGGTTGGGATTTTGGTTTCTTCCTTTCCTCGTGAAGGATAAGAGAAACAGGCCCGG
GGGGACCAGGATGACACCTCCATTTCTCTCCAGGAAGTTTTGAGTTTCTCTCCACCGTGACACAATCCTCAAACATGGAAGATGAA
AGGGGAGGGGATGTCAGGCCCAGAGAAGCAAGTGGCTTTCAACACACAACAGCAGATGGCACCAACGGGACCCCCTGGCCCTGC
TCATCCACCAATCTCTAAGCCAAACCCCTAAACTCAGGAGTCAACGTGTTTACCTCTTCTATGCAAGCCTTGCTAGACAGCCAGGT
TAGCCTTTGCCCTGTCACCCCCGAATCATGACCCACCCAGTGTCTTTCGAGGTGGGTTTGTACCTTCCTTAAGCCAGGAAAGGGAT
TCATGGCGTCGGAAATGATCTGGCTGAATCCGTGGTGGCACCGAGACCAAACTCATTCACCAAATGATGCCACTTCCCAGAGGCA
GAGCCTGAGTCACTGGTCACCCTTAATATTTATTAAGTGCCTGAGACACCCGGTTACCTTGGCCGTGAGGACACGTGGCCTGCACC
CAGGTGTGGCTGTCAGGACACCAGCCTGGTGCCCATCCTCCCGACCCCTACCCACTTCCATTCCCGTGGTCTCCTTGCACTTTCTCA
GTTCAGAGTTGTACACTGTGTACATTTGGCATTTGTGTTATTATTTTGCACTGTTTTCTGTCGTGTGTGTTGGGATGGGATCCCAGG
CCAGGGAAAGCCCGTGTCAATGAATGCCGGGGACAGAGAGGGGCAGGTTGACCGGGACTTCAAAGCCGTGATCGTGAATATCGA
GAACTGCCATTGTCGTCTTTATGTCCGCCCACCTAGTGCTTCCACTTCTATGCAAATGCCTCCAAGCCATTCACTTCCCCAATCTTG
TCGTTGATGGGTATGTGTTTAAAACATGCACGGTGAGGCCGGGCGCAGTGGCTCACGCCTGTAATCCCAGCACTTTGGGAGGCCG
AGGCGGGTGGATCATGAGGTCAGGAGATCGAGACCATCCTGGCTAACACGTGAAACCCCGTCTCTACTAAAAATACAAAAAATT
AGCCGGGCGTGGTGGCGGGCACCTGTAGTCCCAGCTACTCGGGAGGCTGAGGCAGGAGAATGGTGTGAACCCGGGAAGCGGAGC

FIG.2 (Continued)

TTGCAGTGAGCCGAGATTGCGCCACTGCAGTCCGCAGTCTGGCCTGGGCGACAGAGCGAGACTCCGTCTCAAAAAAAAAAAACA
AAAAAAAACCATGCATGGTGCATCAGCAGCCCATGGCCTCTGGCCAGGCATGGCGAGGCTGAGGTGGGAGGATGGTTTGAGCTC
AGGCATTTGAGGCTGTCGTGAGCTATGATTATGCCACTGCTTTCCAGCCTGGGCAACATAGTAAGACCCCATCTCTTAAAAAATGA
ATTTGGCCAGACACAGGTGCCTCACGCCTGTAATCCCAGCACTTTGGGAGGCTGAGCTGGATCACTTGAGTTCAGGAGTTGGAGA
CCAGGCCTGAGCAACAAAGCGAGATCCCATCTCTACAAAAACCAAAAAGTTAAAAATCAGCTGGGTACGGTGGCACGTGCCTGT
GATCCCAGCTACTTGGGAGGCTGAGGCAGGAGGATCGCCTGAGCCCAGGAGGTGGAGGTTGCAGTGAGCCATGATCGAGCCACT
GCACTCCAGCCTGGGCAACAGATGAAGACCCTATTTCAGAAATACAACTATAAAAAAATAAATAAATCCTCCAGTCTGGATCGTT
TGACGGGACTTCAGGTTCTTTCTGAAATCGCCGTGTTACTGTTGCACTGATGTCCGGAGAGACAGTGACAGCCTCCGTCAGACTCC
CGCGTGAAGATGTCACAAGGGATTGGCAATTGTCCCCAGGGACAAAACACTGTGTCCCCCCCAGTGCAGGGAACCGTGATAAGC
CTTTCTGGTTTCGGAGCACGTAAATGCGTCCCTGTACAGATAGTGGGGATTTTTTGTTATGTTTGCACTTTGTATATTGGTTGAAAC
TGTTATCACTTATATATATATATATACACACATATATATAAAATCTATTTATTTTTGCAAACCCTGGTTGCTGTATTTGTTCAGTGA
CTATTCTCGGGGCCCTGTGTAGGGGGTTATTGCCTCTGAAATGCCTCTTCTTTATGTACAAAGATTATTTGCACGAACTGGACTGTG
TGCAACGCTTTTTGGGAGAATGATGTCCCCGTTGTATGTATGAGTGGCTTCTGGGAGATGGGTGTCACTTTTTAAACCACTGTATA
GAAGGTTTTTGTAGCCTGAATGTCTTACTGTGATCAATTAAATTTCTTAAATGAACCAATTTGTCTAAA

(SEQ ID NO: 6)

>gi|48762938|ref|NM_000041.2| Homo sapiens apolipoprotein receptor E (APOE), mRNA GGGATCCTTGAGTCCTACTCAGCCCCAGCGGAGGTGAAGGACGTCCTTCCCCAGGAGCCGACTGGCCAATCACAGGCAGGAAGA
TGAAGGTTCTGTGGGCTGCGTTGCTGGTCACATTCCTGGCAGGATGCCAGGCCAAGGTGGAGCAAGCGGTGGAGACAGAGCCGG
AGCCCGAGCTGCGCCAGCAGACCGAGTGGCAGAGCGGCCAGCGCTGGGAACTGGCACTGGGTCGCTTTTGGGATTACCTGCGCTG
GGTGCAGACACTGTCTGAGCAGGTGCAGGAGGAGCTGCTCAGCTCCCAGGTCACCCAGGAACTGAGGGCGCTGATGGACGAGAC
CATGAAGGAGTTGAAGGCCTACAAATCGGAACTGGAGGAACAACTGACCCCGGTGGCGGAGGAGACGCGGGCACGGCTGTCCAA
GGAGCTGCAGGCGGCGCAGGCCCGGCTGGGCGCGGACATGGAGGACGTGTGCGGCCGCCTGGTGCAGTACCGCGGCGAGGTGCA
GGCCATGCTCGGCCAGAGCACCGAGGAGCTGCGGGTGCGCCTCGCCTCCCACCTGCGCAAGCTGCGTAAGCGGCTCCTCCGCGAT
GCCGATGACCTGCAGAAGCGCCTGGCAGTGTACCAGGCCGGGGCCCGCGAGGGCGCCGAGCGCGGCCTCAGCGCCATCCGCGAG
CGCCTGGGGCCCCTGGTGGAACAGGGCCGCGTGCGGGCCGCCACTGTGGGCTCCCTGGCCGCCAGCCGCTACAGGAGCGGGCCCA
GGCCTGGGGCGAGCGGCTGCGCGCGCGGATGGAGGAGATGGGCAGCCGGACCCGCGACCGCCTGGACGAGGTGAAGGAGCAGG
TGGCGGAGGTGCGCGCCAAGCTGGAGGAGCAGGCCCAGCAGATACGCCTGCAGGCCGAGGCCTTCCAGGCCCGCCTCAAGAGCT
GGTTCGAGCCCCTGGTGGAAGACATGCAGCGCCAGTGGGCCGGGCTGGTGGAGAAGGTGCAGGCTGCCGTGGGCACCAGCGCCG
CCCCTGTGCCCAGCGACAATCACTGAACGCCGAAGCCTGCAGCCATGCGACCCCACGCCACCCCGTGCCTCCTGCCTCCGCGCAG
CCTGCAGCGGGAGACCCTGTCCCCGCCCCAGCCGTCCTCCTGGGGTGGACCCTAGTTTAATAAAGATTCACCAAGTTTCACGCAA
AAAAAAAAAAAAAAAAAAAAAAAAAAAAAAAAAAAAAAAAA

(SEQ ID NO: 7)

>gi|4557320|ref|NM_000039| Homo sapiens apolipoprotein A-I (APOA1), mRNA

AGAGACTGCGAGAAGGAGGTCCCCCACGGCCCTTCAGGATGAAAGCTGCGGTGCTGACCTTGGCCGTGCTCTTCCTGACGGGGAG
CCAGGCTCGGCATTTCTGGCAGCAAGATGAACCCCCCCAGAGCCCCTGGGATCGAGTGAAGGACCTGGCCACTGTGTACGTGGAT
GTGCTCAAAGACAGCGGCAGAGACTATGTGTCCCAGTTTGAAGGCTCCGCCTTGGGAAAACAGCTAAACCTAAAGCTCCTTGACA
ACTGGGACAGCGTGACCTCCACCTTCAGCAAGCTGCGCGAACAGCTCGGCCCTGTGACCCAGGAGTTCTGGGATAACCTGGAAAA
GGAGACAGAGGGCCTGAGGCAGGAGATGAGCAAGGATCTGGAGGAGGTGAAGGCCAAGGTGCAGCCCTACCTGGACGACTTCC
AGAAGAAGTGGCAGGAGGAGATGGAGCTCTACCGCCAGAAGGTGGAGCCGCTGCGCGCAGAGCTCCAAGAGGGCGCGCGCCAG
AAGCTGCACGAGCTGCAAGAGAAGCTGAGCCCACTGGGCGAGGAGATGCGCGACCGCGCGCGCGCCCATGTGGACGCGCTGCGC
ACGCATCTGGCCCCCTACAGCGACGAGCTGCGCCAGCGCTTGGCCGCGCGCCTTGAGGCTCTCAAGGAGAACGGCGGCGCCAGA
CTGGCCGAGTACCACGCCAAGGCCACCGAGCATCTGAGCACGCTCAGCGAGAAGGCCAAGCCCGCGCTCGAGGACCTCCGCCAA
GGCCTGCTGCCCGTGCTGGAGAGCTTCAAGGTCAGCTTCCTGAGCGCTCTCGAGGAGTACACTAAGAAGCTCAACACCCAGTGAG
GCGCCCGCCGCCGCCCCCCTTCCCGGTGCTCAGAATAAACGTTTCCAAAGTGGG

FIG.3

Natural antisense sequence (AK311445): SEQ ID NO: 8

ACGCCCGGGAACCCCCGACCCCTCTGAGCCCGGGGTACTGCGCCCGGGTCTCCACGCCCAGAGATGCTCCCCGGTCTCCACCGTC
GGGCAAGCCCCAAGCGCAGCAGCGCAGAGTCCTGGGGTCACCAGAGCTCGTACTAGGACATCGTCTCCCCATTTAACACCGCCTC
CGGTCCCATCTGAGTTGCAAGTGGTGGGGATGTGGGGCTCCGGATCAAAGTCCCCGAAACCGAGCACTTCCCGAAGCCTCCTTGG
CCTCGAAACAAAACAATAACGCCCAACTCCATCATATTCCAGAACTCCCACCACCTGCATACAGACATTCAGCTGCACAAGCCCC
CTCCATGCTACAGTCAACAGATCTCCAGGCCACGGCTCAAGCCCAGGTACTCACATCAGTGGTTCTATCAACACTCAGGACAGAC
CCATAGAAGAGGCCCAAGCAGGCCCTGGAAGTGCATGTGGAGGCCACCAGGCAAGGAATTCTGGAGTCCCAGGTACTCATAACT
CTGGGTGGCATGGCCCCTTTGCACCATGGACTGTTTGCCCTTAGAAAGGGATGGATCTGAGCTGGGCGCAGTGGCTCATGCCTGTA
ATCCCAGCACTTTGGGAGGCCAAGGTGGGCAGCTCACCTCAGGTCAGGTTGGTCTCAAACTCCTGACCTCAGGCGATCCACCTCA
GCCTCTCAAAGTGCTGGAATTATAGGTGTGAGCCACTGTGCCCAGCCCAAAATCATTCTTTTTGGAATTTTGAAGCATATAATTCC
AAAAGGTATGAAGGTAATCACTTAGATTGCTCTAATAAGGGAATGGGAACAGTTAAGTCCTATACAAATAAGACAAAGATAAGA
TACTACAAAAAGGGGATGAGCCCAAGAAAAAAATCAAAGTCCCAGAGAGAGAACAGCCATTGATTCTAAATACACAAGTCTATG
GCCCCAACCCAAACTTGTTTCACTAAGAACAACCTGTGGTTTCGAGAATCTGGTCATCCCCCACAGTGAATACATGAACACATTGT
AATGTTTGAAATGTTTATTTTTCTTGTTGATTTCTTACTGTTAGAAGAGCTAAGTGATTTGGCCCAAAGTGGCTAAGTGATTCGGCC
AGTTTGTACACAGGGATATAAGTTTGCTGACACCAAGCTCATACTTTACAAATGTAATATCTTCATAAAACAAAAATACTGGGCC
GGGCGCGGTGGCTCACGCCTGTAATCCCAGCATTTTGGGAGGCCGAGGCGGGCGGATCATGAGATCAGGAGATCGAGACCATCC
TGGCTAGCAGGGTGAAGCCCCG

Natural antisense sequence (BF133827): SEQ ID NO: 9

CAAAATGGCGTGCTACCCTGTCCAACCTTGTCTGTAGACAGAGTCAATTGAACACTGTCTTTGGGACTTCCGTGCAACTGAGGTGG
GCGGGCTTGAAGCACAAAGCTTTCAGGGAGAACCAAACTTTATGCCCAAGCTGCTCTCTGCCACCCACAGGGTAAATGAATCTCA
TACAGGAAAGGCAAGAGACATGTGACACTGTTGTCTGATGGTCACAAGTCAAGCTTTTTAAAAAGCAGCCTGATATTGTGAGCTA
ACATGGCTTTCTGTAATTGAATGCAATGTATTTTCTATGCTTGTCTGGGTAAAGTTGACCTTGGTTTGATTTAGCTCAAGCAATATT
TCAACAGTGCACTGGGGCTCTGAGTCCCCTGACTACTGTTTGACTAGAGCCAGGCTCTGCCCTGGATGGCAACCAACAGCCCAGG
CTCTGGGGCACAGCCGGGCTTTGACAGGTCTGGGGAAATGTTCACCGGAGATGAAAGGTTTCAAACTATGAAACTCTAAAATCTC
AAGTCAAAACTTTTGACAAGCACACACAGGACATGAATTACAATCACCCGAAGATTTTTACAGGCTTCTCAATTTTAATGACATGC
TGACACGTGTCATCAGATCTCACAACAAGATGACACATGGGTGTCAGGTATGGCGCAGAAGACTAGAGTCGGGGTGTAACCAAT
GAGCATTGTCTGTTGGACACAGGCGAATTCGGCAAACGGACAGTGCTGGAGGCAGAAGGGTTTAAAGAAGGCAGGAAAGCCCAT
GTTTAACAGAATGGGGTGACGAAGAGGGATGGGAAGGTCTAACTCACCCGGGGGTGGGGGCACCAGGGGGGGCCCACGGACACA
GAAAACCACGCAGGTCAGGCACCTACAAAGACCGAAGGAAAAAGGGACCACGCAGAAATCACTCACG

Natural antisense sequence (Hs.668679): SEQ ID NO: 10

AAAGTCCAAGGTGGGAACAGATAGGTCTGGGGGCATGGGGGCTGGGCCTAATAGGGGCCGGGCATGGATGGGCCTCTCCTGCTC
ACCGATCCTGGGCTGGGCATCTTGTCCTTGGTGGGTGGGGGCCAAGGAAGGAGTGGTGGGGCTTGGCCCAGAGTCTGGTGTGGCT
GTGACTGACCACAGCTTGTGATGCCCCAGCCAAGACCTCAGGCACACCCCGTCCCCCACTCCGCCCCCCCTGGGTTAGACAACTG
AGAGTCACAGTGTGGTGGGAGAAGGGACGTCATTCCTCTAAGGGACAAGCTTTTGGCCCCTCCCCACACCAGGGCAGGTACTTAT
GTCGGGGCTTATGCAGGGCAGAAGGGCTTTGGCCAGGTCAGCTGCCAGGGGCTGGGGCCCAGGCTCCCCAGGGTCTGGCGTGGT
GCATCAGGGGCCTGGTGGGGGCTTACCGAGGATGACGGGCCGTGTGTGGTTACTGAGCTCAGCCTTGGGCGTGGTGTGCGGGGGG
AAGAGCACATTGAGGAGCCAGAAGGGGGCGGCAGGAGGGAGCAGCAGCCCCAGCAGCAGCGTCACCCACTGCCATGGGGAGCC
GGGCGGCCCCATTCCAGCCCTGGTGCCTACTGCCAGAGAAAGCGGCACTGGGCTGTCCTTATCTGGTGTGGGAGTGGGAGGGGCC
CTAGGGCCAGTGGGAGGGACGGCCTGGCCAGTGGGGGTTGTGGCCAGAGATTGCCGGAAAGGGGCACAGCCTCAGGGAGCCGGC
TCTGGGCCTGGGTTCAGTTCCGCCTTCTTCTCTTGGCGCCAGGGGAAACAGAGCCGGGGCAGCAGGAGGCCCAGAACTACACAAT
GTTTTATTGAAAAAGTCAGGCCTCAGCTCAGCTGTCTCCATTCGGCTCAGCTTGGTGGGGGGCCCTGCCCATAGTAGACTGAGCCA
GATCTTCCTGCAGGCAGCTGGGCTGGACTCCCTCCCTGGCTACCCTTCCCTTCGTCTCTGATGGTGACATCCAAACAATAAATATG
CAATAAATAGCGCTCCTGGGCTGGGCCGGGCCGGCTGCCTTCAAACCCCACTCGGCCCCTACCAGTCTTCTCTGGCCAGGACAGG
CCTACTGGGGTGCTAGATAGTAAAGTCCCCAAACATCCCAGGGTCCCACAAGACCTGGGATCCATCTCCATTTTGAGGCCCAGGC
CTGGTTTCCAAGGAGACCTAGCAAAGCTGGGTCCAGGACAGGGCCAGGCAAGCAGGGCTGGCAGGTGGGTGCTGGGAAGAGGCT
GTTACCCCAGACCACAGCTTGTTATGTCCTGGCCAAGACCTCGACTCCAGGCCACAAGATGACACTGGGCTCAGGAGTAGATGGT
GATGACTTCACGGCCACCACCGCGCACCAACAGCACCCGCTCAAGGCCCTCGGTCAGCACCTCGAGGAACTCCATGTAGTTCTCG
TCGCCCTCACTGTTCCTGGGTGGGCCAGGCATGTTTAGGAGAACCAGGCGGGCGTCGTGGGAGCGCGTGACAATGACTTCATTGA
GCTTCACAGCAGTGTGCATGCGCC

Natural antisense sequence (Hs.593769): SEQ ID NO: 11

TTTAANGTTTGATGTTTATTGGTGGTGTCTGATGAGCGTTTCTCTTGTCCAGACTGTGTTTCTCTCTCCAGACCAGCTCCCAGGGTA
CAGGGGGTGGGGAGTAGGTGGTAGCTGTGTCAGTGCTGGGCCCTGGNGCCACTCCCTAGGGAAGAGCAGGTGGGGCCTCGGGGG
GTCTGGCCCTAGCTCTGGCAGATCCATCCTCAGTGAAGCACATCCCTGGGGCAAAGGCACTCCTGAGGCCAAGACCAGCATGGGC
TTGATGGAGCCACCCCAGGGAGCCCCAAGAGAGATGAAGCCATCAATAAAGCGGNCCTTCCAGGCCTGGGNCT

FIG.3 (Continued)

Natural antisense sequence (Hs.387239): SEQ ID NO: 12

TGTCACTCTGACCTCAGTGTAGGCACTGCCTCCTCTGGGAAGTCTTTGCTGACCTGAAAGGCTCAGCCTCTTGTGCTTCCTAAGCTT
TTCTCAGAGCATTTAGCTTCATTAGTAATTAAACTTCCATTAGTGAAATGATCTGATTAATGGTTGTCACTCCCAGATTTTAATTCT
AACTTTTTTTTTTTTTTTTTTTTTTTTGAGACCCAGTCTCTTTTTTTTTGAGACAGTCTCATTCTGCCGCCCAGTCTGGAGTGCAACGAC
GTGATCTCGGCTCACGGTGACCTCCACCTCCCAGGTTCAAGTGATTCTCGTGCCTCAGCCTCCTGAGTAGCTGGGACGACAGATGC
ATGCCACCACGCCTGGCAAATATTTTGTATTTTAGTAGAGACGGGGGTTTCTGCCGTGTTGGCCTGGCTGGTCTCAAACTCCTGAG
TTCGGGTGATCCGCCTGCCTCGGTCTCCCGGGGTGCCGGGATTACAGGCGTGAGCCACCGTGCCCGGCCTCTAAACACTTGTGGCC
CTGTCATTCACCCAGCACTCAAAAGGTCGTCTCACCTGCCCTTTTGGGAGCTGGGAGAGACAGCTCAAATTGTCACCGCCCCCCCA
CCGCCCCGTGCTCCTCTGACAGGGCTGTGGGTGGAGCCAGCTCCAGTCCCCGCGCCCAGCACAGAGGCAGGCACGGTGCACACTG
CCTCAACAGCTCGACCAGGAGAGTGGGCAGCTGTACATCTAGGGTGCCCAGCTCAGTCCCAGGCCTCAGCAGAGCCCATCTTGCC
TCACTGCACACAGCACTGAGCCTGTGGCTGGTGAGGAGTGAAACCTAGTGTGGGACTCTAGTGCCTCCCTTCAACCTGAAACATA
GCCATCAGGGCTTACGGTAGCAAAGGAAGGTCTTTATTCAGGAGGCGGGGGCTCTGGGCTGGCAGTCGGGGATGCAGGGGGACC
CTGGCGGTAGGCACCCAGCAGGATGGCATTGATGTGCTCCAGGGTCAGGTTGCTGAAGACCATGTTCAGATGCTGTATCCCGTGC
AGGGGCAGCAGGTGCACAGGCTGTGGCTGGCGGCCCTGCCACAGGCCACAGAGCTCGGTGCTGCGGGTCGCCACCGTGTCATCA
CCATCCTCATAGAGCACACCCACAGGGTCCGTGTAGGGGAAGCCGTGGTCGTAGATGTAGGTGCGGGGCGTGGGCAGGCCCACG
CCGTAAAGACAGTATACTTCCACACCAGGTGCTGGGAGTCCTGCCAGGAGGTCACGTGACTGCAGCCACATGTACCAGCCTTCCT
CAAAGTGCAGGTCTGCAAAGAAGCGTTGGAAGTCACGGCCTGTGTAGTTGAAGCTGGGTGTGGAAATGAACACGTGGTCCTCAG
GCCACGCCATGCGAGAGGGAAACATCCAGGGGGAGGTGGTGGTTATGCGCTGCTCCTCTTTCAGCTTGATGCTGGACATGATGGG
GATGCCCTGGTTGTCACCTGTGGATATGGAGCAAGGTGGGACAGGGAGCCAGGCCTGGCTACCCCTGGCCCACAACCTGCTGAGT
GTAGGCTCAGCCAGATGCTCAATCTTGTCCCTGCCCAATCTAGACACAGACTCTAAGCCACAGGCTTGAGCAGGCCTGATATTCA
ATGATGCTCAGTGTCAGCTTACTCAATGAGAAGCCCTGATAAGACCTCTGTTGGGTGGAGCTGTAGGGCTTCAAAAGGATGGCAG
GGACAGGCACCATGGCTCACCCCTGTAATCCCGGCACTTTGGGAGGCTGAGGCAGGAGGATCACTTGAGGCCAGGAGTCCGTGA
CCAGACTGGGCAATGCAGTGAGACCCTGTCTCTAC

Natural antisense sequence (Hs.711951): SEQ ID NO: 13

TGTTTTTTTTTTTTTTTTTTTAAAGAGATGGAGTCCTGATCTGTCGCCCAGGCTGGAGTTCAGTGGCACAATATTGGCCCACTGCAAC
CCTTGAACCTTCCCGGTTCAAGTGATTCTCCTGCCTAGGTCTTCTGAGTAGCTGGGATTACAGGTGCCCACCACCACGCCCAGCTA
ATTTTTGTGGTTTTAGTAGAGACGGAGTTTTGCCATGTTGGCCAAGCTAGTCTCAAACTCCTGACCTCAAGTGATCGGCCGGCCTC
AGCCTCCCAAAGTGCTGGGATTACAGGCTTGAGCCACTGCGCCTGGCCCAGTTTTCCCATGTCTTGAGGCACCACTACCCATGCAC
CTCAGAATCCTCCCTTGCCTTTATCCCTTTGATACAGCACATCCCAAAGTGAATCCCCACATGGTCCCTGGTTGCTCAGACTCAGT
GAAAAAAAAATGAATGGTCAAGTGAGTTTTGGAAAACCCCAAACGCTTGAAAAATTCTTGGCACACATAAACATATTCAAGGCTC
TGAGAAGTTCTGCAGCACAA

Natural antisense sequence (DC401271): SEQ ID NO: 14

ACCATTCAGCTGCACCCAGATGCCCCAAGAGCAATGAGCCCACACGCAGAGCTGGAGGACCTGAAAGGCAACCTCCAAGTCCCA
GATCATGTCTCTGTGGGGTCTGGTCTCCAAGATGCCCCCAGAAAAAGTGCAGCGGCTCTATGTCGACTTTCCCCAACACCTGCGGC
ATCTTCTGGGTGACTGGCTGGAGAGCCAGCCCTGGGAGTTCCTGGTCGGCTCCGACGCCTTCTGCTGCAACTTGGCTAGTGCCCTA
CTTTCAGACACTGTCCAGCACCTTCAGGCCTCGGTGGGAGAGCAGGGGGAGGGGAGCACCATCTTGCAACACATCAGCACCCTTG
AGAGCATATATCAGAGGGACCCCCTGAAGCTGGTGGCCACTTTCAGACAAATACTTCAAGGAGAGAAAAAAGCTGTTATGGAAC
AGTTCCGCCACTTGCCAATGCCTTTCCACTGGAAGCAGGAAGAACTCAAGTTTAAGACAGGCTTGCGGAGGCTGCAGCACCGAGT
AGGGGAGATCCACCTTCTCCGAGAAGCCCTGCAGAAGGGGG

Natural antisense sequence (BM933147): SEQ ID NO: 15

TGTGACACCCTTCCTCACGCTTAGACAGCAAAGTTGCCTCGGAAGAGAAGAGAAGCCTGCATGGGAATGGCCAGCACATCCTAAA
TGCTCCAGTGGCCCGTGGTTCGTCCCTTCGTCTCATTGACTGCCACAGACAGGAAGTAGGCTCAGGGACTTGGCACCTACCCAACA
GCAGGACGTCCTTTCTGGCCATACTCCTGAGGGTAACAAAATCACATGGAAGCCCAAAGCAAGCCAGGCTCAGGCTCCTCTGCCC
TCTGCTACTTAACAATGTCCGTCCTTCCCCAGCCCCCCTGCAGATGCTTCTGTATGGGAAAGCCCCTCTGCATCTAATGACACTCTG
CTTTCAAAGACGGGACAGTCCCTGGTCTCTGGAGAGTGACCATTCGTGGCCTTCTCAGTTGACACTTCTCCGCTGAGGCATCCCTT
AGCCCTGAACCAGAAATGAAAGAGCCGGCTCAGAGTGAAAAGGAAGAATAGCCATCAATCTGCTCCTGTGTGCAAGGAGCACAG
ACCTGGTCTCAGACTCTGCCCGTCTCCCCCGCTTCCCTGCCCTCTGAGTGACTCACGGTGCAGGCTGAGGGAGATGTTGATGGTAT
GCTCATCCACAAAGCCCTTCAGGCCAGGCATCCGGGCAACTTGAGCTGTGTCTGGGCACACTGTCCCAACGTG

Natural antisense sequence (CK626173): SEQ ID NO: 16

GACTTTTATCTGCACTGTTTCAACAGCAGGTAGCCAGCCGTCTTTTTACTGCCTGCCTCTGGCTGAAGCTCGGCCCACACTATCAG
GACTCAGCCCTGTAGGGATGACTCTGCCACACAGCTACAGCACCAGCTGGCACAAATGGCTTTCTCTCCAACTTCCTCAGGCTTCC
CTGAGTCACTGCCCAGCCCTAGGACTGGCAACACCCTGGCCCTGCTCACCCATCCACCCTTGGCAAGAGGGAAAGAGGAAGAAG
CCTGCAGAGAGCTGGTGCCCTGCTTCCAGATGCTGCTCCATTCTCAGGCCAAGCCTCAAGATGGGGGGAACCTGAGTGGGAGCCT
CTCTCCTGGCTTGCGTTCCCTCCCACTTCTGGGAAAGCAGGGCAGTGACAGTCCCTGTTCTCATGTGTCTGCCCTTGGCTGGGCTCC
CCTCACCTCCCCAAAGACCAGGCAGGGTCCCATTCAGCAGACCTGACTGTAAGGAATTGGCAAGAAATGACGTCCCTAGCCAGCC
TGGCCTCCCCTTTGGTATTTTTGCAGCTGGAGATTATTAGTCTCAAGCAAAACTCCTTTGTTATCCAAGCCCACTCCACCACATTAT
TTTCCTCTCTCCTAAA

FIG.3 (Continued)

Natural antisense sequence (AW544265): SEQ ID NO: 17

GACAGGGTCTTATTCTGCAGCTCGGGTTGACCTGGAATTCTCCAGGCAGACCATTCTGGCCTTACGTTCACTGACATCCACCTGCC
TCTGCCTCCTGAGTGCTGCTGTTAAGGAGTAGTTCCAGCCTATAGTGTTCTGAAATACTGTTATTTTACTGTAATGATAGCCAAAG
CTAAAATGAGTTAAGAATAGTTCCTTTCTTACTCGCTGTCTCGTTCCTCATTCACTTGCCCCATCTTCGTGCCCTCAGAACTACCCC
ACCCCCAATCCTCCTTTAGCCCCAGAGCCTTCTCTGAACCCTACCCCTTGCTTCCTGTCAGCATCTCAGGGCCCCCTCTTTGCTTCC
TTAATCTCTACTGGAAACACAGAGAACTCCCCTGCCCTCTGCCATTCTTCTGCTGGAGCTACCTTCCCACCCTTGTGCAAGCCAGG
CCCCTCATACCCAAGCAGGTGACACCATCTGTGTCCAAC

Natural antisense sequence (bloflor.aApr07): SEQ ID NO: 18

GAGCTGCGCTCACCGCTGTTGCCTGATTTTGGTCTAAGTGAAGGCTTGCGGTTCAGATTCCAACAACTTCCCTTTGTAAAGGAAAT
GGACAAGAAACTCCCCCCTGGATATGCCTTGAAGCCAGCTACAGCGTGAGGTGGTGCAGCTAGAAAGTGCTAGAAACACACACC
AGCTCTCAGAAGTCTGGAGGAAAACATCAGGGGTGTAGTCTCCTTGACAACAGAGGAAACATCACATTCTCAGCCATCCCGGGAG
AGAGAAACTAAAGTGATGAACAAACAAGGCCTTGCCTAAGACTTCCTTAACATTTTCTCTTAAGGAAGAGGTTGATTGAGGAAAA
ATCGCCGCTTGGACAGCTGAACCGAAGCCATTCACAGCCTCTGAAGAAGCGAGGCCACCCCAGGGGGTCGGTCCCGGGGGATAG
CTGCCCCACCGTGGCTGAAGATCTCGGCTGCAGACCAAGGAGGGGCGGGGAGATTCTGAGGCAACGTTTCAACCTCGTAAGGAA
CCGAGGCCTTGAGGGTGGCCGGGGGCCCCTCTGTGAACTTGATCGGGGCTGGTGGGGCGAGGGCGCCCCCCAGGACAAGGTGGG
GACGGAGGTGTCGCCACAGAGCACAGCGGAAACCGGGGACTTCGCCAGGAGGGCCCAGGATAACGGAGGGCGACTCGTGTATGT
CGCGGAGGCGGCTCCGGGGACCCGGGACTTG

Natural antisense sequence (sherflor.aApr07): SEQ ID NO: 19

GGGGCTCCCTCTCAACCTATTCTGGCGCCTGGAGCAAGCCTTACCTGCAGTCCCCGCCCGCGGCGAGGAGCAAGGCGACGGTCCAG
CGCAATTTCCAGCCCCAGGGCCCCATGCTCGCAGCCTCTGCCAGGCAGTGTCCCGACCCGGATCACGACCTGCTGTGTCCTAGCTG
GAAACCCTGGCTTCCCGCGATTGCACTCGGGGCCCACGTCATTTACAGCATTTCAATGTGAGGTTTCTAGCAGGGGGAGGAGTTTG
CAGTGGGGTGATTTTCAAATGTCTTCACCTCACTGCAAGAGGAGGAGTTTCGAACGGCCGATGTGACATCGGCTTTTTAACCCGTG
AAGCTCTGATTCCCACTCCAGTCCTTCGAAAGTGTCGCCAGGGCAGGCGACTTGATTTGTTGTATTTGGGTCTCCGGTGAAGAGCT
GACGCCCCCTCAAAATTGGAAACGCATCTTCTGAAAGATCCTCCTGAAATTTCTCGATGTTTAACTGTTAACATTTTGCTGTTGTTG
TCCACAGAAGGATAACAACAGCCTTTCAAGATCCTCCAATAGCCTAATGCCATTGTCCTCTCTGCCTCAAAAGGAAAACACTAAA
AATGTTGGGAACTTCCGCCACTTTCTATATTTGCCTTTTCCTTTCTAGGAATTGTGTATAGATTTTTAGCTTCCTTTCGTTGTATATT
GTTTTTACATTGTTATTCCAAATCACCTAATAGACACTGATCAATCAGGAAT

Natural antisense sequence (Hs.626623): SEQ ID NO: 20

CCCACGTATATTTTTTGTTGTTTTTTGTTTTTTTTCTGTAAAATGTCCCGGTTCTTCCATAACTTATAAACATGATTTATACCGAGGA
GATGGGAAAGTGGACGGGGCAGGGTGGACTGACCGGGGATGGGGAAGCTCCTCTCGCTGCCCCCTCGGGGCGGGCCCAGGCCCT
TTGGAGGATGGGGACGCCAGGACACTCCTCCCTGAGGTTGCTGGCCGCCTCTGCCCTGGTGCTGTGAAGTCAGAGCCCCGATACT
CCCCGTCCACCTGCCAGTTCACAAACTTCGACTGCTGGGTCTGGATGGCCATCTTGGACCTGAGACCGGGGCCCAGCTGGTGAAT
GACC

Natural antisense sequence (Hs.714236): SEQ ID NO: 21

ACCATCTTTTTTTTTTTTCTTTTATGCGTGAAACTTGGTGAATCTTTATTAAACTAGGGTCCACCCCAGGAGGACGGCTGGGGCGGG
GACAGGGTCTCCCGCTGCAGGCTGCGCGGAGGCAGGAGGCACGGGGTGGCGTGGGGTCGCATGGCTGCAGGCTTCGGCGTTCAG
TGATTGTCGCTGGGCACAGGGGCGGCGCTGGTGCCCACGGCAGCCTGCACCTTCTCCACCAGCCCGGCCCACTGGCGCTGCATGT
CTTCCACCAGGGGCTCGAACCAGCTCTTGAGGCGGGCCTGGAAGGCCTCGGCCTGCAGGCGTATCTGCTGGGCCTGCTCCTCCAG
CTTGGCGCGCACCTCCGCCACCTGCTCCTTCACCTCGTCCAGGCGGTCGCGGGTCCGGCTGCCCATCTCCTCCATCCGCGCGCGCA
GCCGCTCGCCCCAGGCCTGGGCCCGCTCCTGTAGCGGCTGGCCGGCCAGGGAGCCCACAGTGGCGGCCCGCACGCGGCCCTGTTC
CACCAGGGGCCCCAGGCGCTCGCGGATGCGCTGAGGCCGCGCTCGGCGCCCTCGCGGGCCCCGGCCTGGTACACTGCCAGGCGCT
TCTGCAGGTCATCGGCATCGCGGAGGAGCCGCTTACGCAGCTTGCGCAGGTGGGAGGCGAGGCGCACCCGCAGCTCCTCGGTGCT
CTGGCCGAGCATGGCCTGCACCTCGCCGCGGTACTGCACCAGGCGGCCGCACACGTCCTCCATGTCCGCGCCCAGCCGGGCCTGC
GCCGCCTGCAGCTCCTTGGACAGCCGTGCCCGCGTCTCCTCCGCCACCGGGGTCAGTTGTTCCTCCAGTTCCGATTTGTAGGCCTT
CAACTCCTTCATG

Natural antisense sequence (DA327409 extended): SEQ ID NO: 22

CAGCTTCTCTTGCAGCTCGTGCAGCTTCTGGCGCGCGCCCTCTTGGAGCTCTGCGCGCAGCGGCTCCACCTTCTGGCGGTAGAGCT
CCATCTCCTCCTGCCACTTCTTCTGGAAGTCGTCCAGATCCAAATGGCAAACCTTCTTCATCCACCAGGACCCAACCCACAGGCTA
CTTATTGCTGGAAACCTACGTTGTTCCTTGGATTGAAGTAATCTCTCCCTCTTCTGGTGCGCCCACAGCACTTGCACCAACAGTGG
GTACCCAACAGACTAGCGTGCCTGCCGAAGAAGGGGTCCTCTGACAATCAGGGGACAATGGGGAATTATGCTCTCCAGACTTTCT
ACACACACAAGTCACACAGGAAGGAAGGTAAAGAGAAACTAGAGAAAATAATTTTTGAAGAAAAACATTTCAGGAAGTATTGAA
AGTACACGGTAACTCAGCCTGGGGCAGGGGTGGAGGGCAGCAGCACTGTTTGCTGCAGCTATGCTCCTTCCTCAGTGCCCTGCAC
ACCCGGGACTTGCTCGGTGAGCATCTCTCGTGTCAGTGACAGCTAGTGTGA

FIG.4

| Sequence ID | Sequence Name | Sequence |
|---|---|---|
| SEQ ID NO: 23 | CUR-0521 | UUGUAAAGUAUGAGCUUGGUGUCAGCA |
| SEQ ID NO: 24 | CUR-0519 | AAUCAAUGGCUGUUCUCUCUCUGGGAC |
| SEQ ID NO: 25 | CUR-0523 | ACCUAUAAUUCCAGCACUUUGAGAGGC |
| SEQ ID NO: 26 | CUR-1214 | C*C*C*A*C*C*A*C*T*T*G*C*A*A*C*T*C*A*G*A |
| SEQ ID NO: 27 | CUR-1215 | T*T*C*G*G*G*A*A*G*T*G*C*T*C*G*G*T*T*T*C*G |
| SEQ ID NO: 28 | CUR-1216 | C*C*C*A*G*C*T*C*A*G*A*T*C*C*A*T*C*C*C*T*T |
| SEQ ID NO: 29 | CUR-1217 | G*C*C*T*C*T*T*C*T*A*T*G*G*G*T*C*T*G*T*C |
| SEQ ID NO: 30 | CUR-1218 | G*C*C*A*T*G*C*C*A*C*C*C*A*G*A*G*T*T*A |
| SEQ ID NO: 31 | CUR-1219 | G*C*T*G*T*T*C*T*C*T*CT*C*T*G*G*G*A*C*T*T |
| SEQ ID NO: 32 | CUR-1220 | G*T*T*C*C*C*A*T*T*C*C*C*T*T*A*T*T*A*G |
| SEQ ID NO: 33 | CUR-1221 | C*G*A*A*T*C*A*C*T*T*A*G*C*C*A*C*T*T*T*G |
| SEQ ID NO: 34 | CUR-1222 | C*T*G*G*G*A*T*T*A*C*A*G*G*C*G*T*G*A*G*C |
| SEQ ID NO: 35 | CUR-1087 | C*A*T*G*T*C*T*C*C*T*G*C*C*T*T*T*C*C*T*G*T |
| SEQ ID NO: 36 | CUR-1088 | G*C*T*C*A*C*A*A*T*A*T*C*A*G*G*C*T*G*C*T*T |
| SEQ ID NO: 37 | CUR-1089 | T*C*A*A*C*T*T*T*A*C*C*C*A*G*A*C*A*A*G*C*A |
| SEQ ID NO: 38 | CUR-1090 | G*G*A*C*A*G*G*G*T*A*G*C*A*A*C*G*C*C*A*T*T |
| SEQ ID NO: 39 | CUR-1091 | C*C*A*C*C*T*C*A*G*T*T*G*C*A*C*G*G*A*A |
| SEQ ID NO: 40 | CUR-1092 | T*T*G*G*G*C*A*T*A*G*A*G*T*T*T*G*G*T*T*C |

FIG.5

| Sequence ID | Sequence Name | Sequence |
|---|---|---|
| SEQ ID NO: 41 | CUR-0476 | GUGGUCAGUCACAGCCACACCAGACUU |
| SEQ ID NO: 42 | CUR-0478 | GUCCCUUCUCCCACCACACUGUGACUC |
| SEQ ID NO: 43 | CUR-0480 | CAGCACUGACACAGCUACCACCUACUC |
| SEQ ID NO: 44 | CUR-0444 | UGUGCUUCACUGAGGAUGGAUCUGCCA |
| SEQ ID NO: 45 | CUR-0446 | AGAGAAACGCUCAUCAGACACCACCAA |
| SEQ ID NO: 46 | CUR-0448 | CUUAGGAAGCACAAGAGGCUGAGCCUU |
| SEQ ID NO: 47 | CUR-0450 | CCUGGCUCCCUGUCCCACCUUGCUCCA |
| SEQ ID NO: 48 | CUR-0452 | GUUCAUUUCCACACCCAGCUUCAACUA |
| SEQ ID NO: 49 | CUR-0541 | A*G*A*C*C*T*A*T*C*T*G*T*T*C*C*C*A*C*C |
| SEQ ID NO: 50 | CUR-0542 | G*T*C*A*G*T*C*A*C*A*G*C*C*A*C*A*C*C*A*G |
| SEQ ID NO: 51 | CUR-0815 | C*C*T*A*T*C*T*G*T*T*C*C*C*A*C*C*T*T*G |
| SEQ ID NO: 52 | CUR-0816 | G*T*C*A*C*A*G*C*C*A*C*A*C*C*A*G*A*C*T*C*T |
| SEQ ID NO: 53 | CUR-0817 | T*C*C*C*T*T*C*T*C*C*C*A*C*C*A*C*A*C*T*G*T |
| SEQ ID NO: 54 | CUR-0818 | C*T*C*C*T*C*A*A*T*G*T*G*C*T*C*T*T*C*C*C |
| SEQ ID NO: 55 | CUR-0819 | C*C*C*A*C*T*C*C*C*A*C*A*C*C*A*G*A*T*A |
| SEQ ID NO: 56 | CUR-0820 | A*A*C*A*G*C*C*T*C*T*T*C*C*C*A*G*C*A*C*C |
| SEQ ID NO: 57 | CUR-0821 | C*A*C*C*A*T*C*T*A*C*T*C*C*T*G*A*G*C*C*C |
| SEQ ID NO: 58 | CUR-0822 | T*C*A*T*T*G*T*C*A*C*G*C*G*C*T*C*C*C*A*C |

FIG.6

| Sequence ID | Antisense Sequence Name | Sequence |
|---|---|---|
| SEQ ID NO: 59 | CUR-0767 | T*C*C*C*A*G*C*T*A*C*T*C*A*G*A*A*G*A*C*C*T |
| SEQ ID NO: 60 | CUR-0768 | T*G*G*G*C*G*A*C*A*G*A*T*C*A*G*G*A*C*T*C |
| SEQ ID NO: 61 | CUR-0769 | C*T*G*A*G*G*T*G*C*A*T*G*G*G*T*A*G*T*G*G*T |
| SEQ ID NO: 62 | CUR-0770 | G*C*C*G*A*T*C*A*C*T*T*G*A*G*G*T*C*A*G*G*A |
| SEQ ID NO: 63 | CUR-0771 | A*T*T*A*G*C*T*G*G*G*C*G*T*G*G*T*G*G*T*G |
| SEQ ID NO: 64 | CUR-0772 | G*C*T*C*T*G*C*G*T*G*T*G*G*G*C*T*C*A*T*T |
| SEQ ID NO: 65 | CUR-0773 | G*T*C*C*C*T*C*T*G*A*T*A*T*A*T*G*C*T*C*T*C |
| SEQ ID NO: 66 | CUR-0774 | C*T*T*G*A*G*T*T*C*T*T*C*C*T*G*C*T*T*C*C*A |
| SEQ ID NO: 67 | CUR-0775 | T*C*T*C*C*A*G*C*C*A*G*T*C*A*C*C*C*A*G*A |
| SEQ ID NO: 68 | CUR-1017 | C*C*A*T*C*A*A*C*A*T*C*T*C*C*C*T*C*A*G*C*C |
| SEQ ID NO: 69 | CUR-1018 | C*T*T*C*T*T*C*C*T*C*T*T*T*C*C*C*T*C*T*T |
| SEQ ID NO: 70 | CUR-1019 | A*C*A*G*C*A*G*C*A*C*T*C*A*G*G*A*G*G*C*A |
| SEQ ID NO: 71 | CUR-1020 | G*G*G*T*A*G*T*T*C*T*G*A*G*G*G*C*A*C*G*A |
| SEQ ID NO: 72 | CUR-1021 | A*G*G*C*A*G*G*T*G*G*A*T*G*T*C*A*G*T*G |
| SEQ ID NO: 73 | CUR-1022 | G*G*G*T*A*G*G*G*T*T*C*A*G*A*G*A*A*G*G*C |

FIG.7

| Sequence ID | Antisense Sequence Name | Sequence |
|---|---|---|
| SEQ ID NO: 74 | CUR-1054 | A*C*T*C*C*T*C*C*T*C*T*T*G*C*A*G*T*G*A*G |
| SEQ ID NO: 75 | CUR-1055 | G*C*T*G*T*T*G*T*T*A*T*C*C*T*T*C*T*G*T*G |
| SEQ ID NO: 76 | CUR-1056 | A*T*C*G*C*G*G*G*A*A*G*C*C*A*G*G*G*T*T*T |
| SEQ ID NO: 77 | CUR-1057 | G*C*C*A*G*A*A*T*A*G*G*T*T*G*A*G*A*G*G*G*A |
| SEQ ID NO: 78 | CUR-1058 | G*C*C*G*T*T*C*G*A*A*A*C*T*C*C*T*C*C*T*C*T |
| SEQ ID NO: 79 | CUR-1059 | G*G*T*T*T*C*C*G*C*T*G*T*G*C*T*C*T*G*T*G |
| SEQ ID NO: 80 | CUR-1060 | A*C*G*T*T*G*C*C*T*C*A*G*A*A*T*C*T*C*C*C |
| SEQ ID NO: 81 | CUR-1061 | T*T*C*C*T*C*A*A*T*C*A*A*C*C*T*C*T*T*C*C*T |
| SEQ ID NO: 82 | CUR-1062 | G*T*G*A*T*G*T*T*T*C*C*T*C*T*G*T*T*G*T*C |
| SEQ ID NO: 83 | CUR-1063 | C*A*C*T*T*T*C*T*A*G*C*T*G*C*A*C*C*A*C*C |

FIG.8

| Sequence ID | Antisense Sequence Name | Sequence |
|---|---|---|
| SEQ ID NO: 84 | CUR-0973 | C*C*G*T*C*C*A*C*T*T*T*C*C*C*A*T*C*T*C*C*T |
| SEQ ID NO: 85 | CUR-0974 | C*C*C*G*T*C*C*A*C*T*T*T*C*C*C*A*T*C*T*C |
| SEQ ID NO: 86 | CUR-0975 | C*T*T*C*A*C*A*G*C*A*C*C*A*G*G*G*C*A*G*A |
| SEQ ID NO: 87 | CUR-0976 | C*C*C*A*G*C*A*G*T*C*G*A*A*G*T*T*T*G*T*G*A |
| SEQ ID NO: 88 | CUR-0977 | C*C*G*G*T*C*T*C*A*G*G*T*C*C*A*A*G*A*T*G |
| SEQ ID NO: 89 | CUR-0978 | T*G*G*T*G*G*A*G*A*A*G*G*T*G*C*A*G*G*C*T |
| SEQ ID NO: 90 | CUR-0979 | G*A*T*T*C*A*C*C*A*A*G*T*T*T*C*A*C*G*C*A*T |
| SEQ ID NO: 91 | CUR-0980 | G*A*C*G*A*G*G*T*G*A*A*G*G*A*G*C*A*G*G*T |
| SEQ ID NO: 92 | CUR-0981 | T*C*G*G*A*A*C*T*G*G*A*G*G*A*A*C*A*A*C*T*G |

FIG.9

SEQ ID NO: 93- TGGAGCTCAG TTT
SEQ ID NO: 94- TTTCTCGTGC AGCT
SEQ ID NO: 95- TTCTGGCGCG TGCC
SEQ ID NO: 96- CCCTCGTGGA GCTC
SEQ ID NO: 97- GCCCGCGCGC AGCG
SEQ ID NO: 98- CGGCTCCACC TTCT
SEQ ID NO: 99- CTGGCGGTAG AGCT
SEQ ID NO: 100- GCTCGTGCAG CTTC
SEQ ID NO: 101- CAGCTTCTGG CGCG
SEQ ID NO: 102- GCGCGCAGCG GCTC
SEQ ID NO: 103- TCCACCTTCT GGCG
SEQ ID NO: 104- CGGTGTAGAG CTCC
SEQ ID NO: 105- CCATCTCCTC CTGC
SEQ ID NO: 106- GAAGTCGTCC AGATCCAAA
SEQ ID NO: 107- AAGTCGTCCA GATCCAAAT
SEQ ID NO: 108- AGTCGTCCAG ATCCAAATG
SEQ ID NO: 109- GTCGTCCAGA TCCAAATGG
SEQ ID NO: 110- TCGTCCAGAT CCAAATGGC
SEQ ID NO: 111- CGTCCAGATC CAAATGGCA
SEQ ID NO: 112- GTCCAGATCC AAATGGCAA
SEQ ID NO: 113- TCCAGATCCA AATGGCAAA
SEQ ID NO: 114- CAGATCCAAA TG
SEQ ID NO: 115- AGATCCAAAT GGCAAA
SEQ ID NO: 116- AGATCCAAAT GG
SEQ ID NO: 117- GATCCAAATG GC
SEQ ID NO: 118- ATCCAAATGG CA
SEQ ID NO: 119- TCCAAATGGC AA
SEQ ID NO: 120- CCAAATGGCA AA
SEQ ID NO: 121- CCAAATGGCA AACCTTCTT
SEQ ID NO: 122- ATGGCAAATC TTCTTCATC
SEQ ID NO: 123- AAATGGCAAA CCTTCTTCA
SEQ ID NO: 124- AAATGGCAAA TCTTCTTCA
SEQ ID NO: 125- ATGGCAAACC TTCTTCATC
SEQ ID NO: 126- CCAAATGGCA AATCTTCTT
SEQ ID NO: 127- ATGGCAAACC TTCTT
SEQ ID NO: 128- ATGGCAAATC TTCTT
SEQ ID NO: 129- CTTCTTCATC C
SEQ ID NO: 130- CCAGGACCCA ACCCACA
SEQ ID NO: 131- GCTACTTATT GCTG
SEQ ID NO: 132- TGCTGGAAAC CTAC
SEQ ID NO: 133- TTCCTTGGAT TGAA
SEQ ID NO: 134- GCCCACAGCA CTTGCA
SEQ ID NO: 135- CACCAACAGT GGGTAC
SEQ ID NO: 136- CAACAGACTA GC
SEQ ID NO: 137- GAAGAAGGGG TCCT
SEQ ID NO: 138- GAATTATGCT CTCC
SEQ ID NO: 139- CTCCAGACTT TCTA
SEQ ID NO: 140- AAGTCACACA GGAAGG
SEQ ID NO: 141- GAAACTAGAG AAAA
SEQ ID NO: 142- AATAATTTTT GAAG
SEQ ID NO: 143- GAAGTATTGA AAGT
SEQ ID NO: 144- TGAAAGTACA CGGT
SEQ ID NO: 145- CTGGGGCAGG GGTG
SEQ ID NO: 146- GGGGTGGAGG GCAG
SEQ ID NO: 147- TGCTCCTTCC TCAG
SEQ ID NO: 148- ACCCGGGACT TGCTC
SEQ ID NO: 149- TGTCAGTGAC AGCT
SEQ ID NO: 150- TGTCAGTGAC AGCTAGTGT
SEQ ID NO: 151- GTCAGTGACA GCTAGTGTG

FIG.9 (Continued)

SEQ ID NO: 152- TCAGTGACAG CTAGTGTGA
SEQ ID NO: 153- AGTGACAGCT AGTGTGAGT
SEQ ID NO: 154- TGACAGCTAG TGTGA
SEQ ID NO: 155- TGACAGCTAG TGTGAGTAC
SEQ ID NO: 156- GACAGCTAGT GTGAGTACT
SEQ ID NO: 157- CAGCTAGTGT GAGTACTCT
SEQ ID NO: 158- AGCTAGTGTG AGTACTCTT
SEQ ID NO: 159- GCTAGTGTGA GTACTCTTA
SEQ ID NO: 160- CTAGTGTGAG TACTCTTAT
SEQ ID NO: 161- CTAGTGTGAG TACT
SEQ ID NO: 162- TAGTGTGAGT ACTCTTATG
SEQ ID NO: 163- AGTGTGAGTA CTCTTATGT
SEQ ID NO: 164- GTGTGAGTAC TCTTATGTT
SEQ ID NO: 165- TGTGAGTACT CTTATGTTC
SEQ ID NO: 166- GTGAGTACTC TTATGTTCA
SEQ ID NO: 167- TGAGTACTCT TATGTTCAG
SEQ ID NO: 168- ACTCTTATGT TCAG
SEQ ID NO: 169- TACCTCTTGA CTTT
SEQ ID NO: 170- GACTTTGGGG ACAA
SEQ ID NO: 171- A*A*A*C*T*G*A*G*C*T* C*C*A
SEQ ID NO: 172- A*G*C*T*G*C*A*C*G*A *G*A*A*A
SEQ ID NO: 173- G*G*C*A*C*G*C*G*C*C *A*G*A*A
SEQ ID NO: 174- G*A*G*C*T*C*C*A*C*G *A*G*G*G
SEQ ID NO: 175- C*G*C*T*G*C*G*C*G*C* G*G*G*C
SEQ ID NO: 176- A*G*A*A*G*G*T*G*G*A *G*C*C*G
SEQ ID NO: 177- A*G*C*T*C*T*A*C*C*G* C*C*A*G
SEQ ID NO: 178- G*A*A*G*C*T*G*C*A*C *G*A*G*C
SEQ ID NO: 179- C*G*C*G*C*C*A*G*A*A *G*C*T*G
SEQ ID NO: 180- G*A*G*C*C*G*C*T*G*C *G*C*G*C
SEQ ID NO: 181- C*G*C*C*A*G*A*A*G*G* T*G*G*A
SEQ ID NO: 182- G*G*A*G*C*T*C*T*A*C *A*C*C*G
SEQ ID NO: 183- G*C*A*G*G*A*G*G*A*G* A*T*G*G
SEQ ID NO: 184- T*T*T*G*G*A*T*C*T*G* G*A*C*G*A*C*T*T*C
SEQ ID NO: 185- A*T*T*T*G*G*A*T*C*T* G*G*A*C*G*A*C*T*T
SEQ ID NO: 186- C*A*T*T*T*G*G*A*T*C* T*G*G*A*C*G*A*C*T
SEQ ID NO: 187- C*C*A*T*T*T*G*G*A*T *C*T*G*G*A*C*G*A*C
SEQ ID NO: 188- G*C*C*A*T*T*T*G*G*A T*C*T*G*G*A*C*G*A
SEQ ID NO: 189- T*G*C*C*A*T*T*T*G*G *A*T*C*T*G*G*A*C*G
SEQ ID NO: 190- T*T*G*C*C*A*T*T*T*G *G*A*T*C*T*G*G*A*C
SEQ ID NO: 191- T*T*T*G*C*C*A*T*T*T* G*G*A*T*C*T*G*G*A
SEQ ID NO: 192- C*A*T*T*T*G*G*A*T*C* T*G
SEQ ID NO: 193- TTTGCCATTT GGATCT
SEQ ID NO: 194- C*C*A*T*T*T*G*G*A*T* C*T
SEQ ID NO: 195- G*C*C*A*T*T*T*G*G*A *T*C
SEQ ID NO: 196- T*G*C*C*A*T*T*T*G*G* A*T
SEQ ID NO: 197- T*G*C*C*A*T*T*TG*G* A*T
SEQ ID NO: 198- T*T*T*G*C*C*A*T*T*T* G*G
SEQ ID NO: 199- A*A*G*A*A*G*G*T*T*T* G*C*C*A*T*T*T*G*G
SEQ ID NO: 200- G*A*T*G*A*A*G*A*A*G* A*T*T*T*G*C*C*A*T
SEQ ID NO: 201- T*G*A*A*G*A*A*G*G*T *T*T*G*C*C*A*T*T*T
SEQ ID NO: 202- T*G*A*A*G*A*A*G*A*T *T*T*G*C*C*A*T*T*T
SEQ ID NO: 203- G*A*T*G*A*A*G*A*A*G* G*T*T*T*G*C*C*A*T
SEQ ID NO: 204- A*A*G*A*A*G*A*T*T*T *G*C*C*A*T*T*T*G*G
SEQ ID NO: 205- A*A*G*A*A*G*G*T*T*T* G*C*C*A*T
SEQ ID NO: 206- A*A*G*A*A*G*A*T*T*T *G*C*C*A*T
SEQ ID NO: 207- G*G*A*T*G*A*A*G*A*A* G
SEQ ID NO: 208- T*G*T*G*G*G*T*T*G*G *G*T*C*C*T*G*G
SEQ ID NO: 209- C*A*G*C*A*A*T*A*AG* T*A*G*C
SEQ ID NO: 210- G*T*A*G*G*T*T*T*C*C *A*G*C*A

FIG.9 (Continued)

SEQ ID NO: 211- T*T*C*A*A*T*C*C*A*A*G*G*A*A
SEQ ID NO: 212- T*G*C*A*A*G*T*G*C*T* G*T*G*G*G*C
SEQ ID NO: 213- G*T*A*C*C*C*A*C*T*G T*T*G*G*T*G
SEQ ID NO: 214- G*C*T*A*G*T*C*T*G*T *T*G
SEQ ID NO: 215- A*G*G*A*C*C*C*C*T*T *C*T*T*C
SEQ ID NO: 216- G*G*A*G*A*G*C*A*T*A* A*T*T*C
SEQ ID NO: 217- T*A*G*A*A*A*G*T*C*T* G*G*A*G
SEQ ID NO: 218- C*C*T*T*C*C*T*G*T*G* T*G*A*C*T*T
SEQ ID NO: 219- T*T*T*T*C*T*C*T*A*G *T*T*T*C
SEQ ID NO: 220- C*T*T*C*A*A*A*A*A*T *T*A*T*T
SEQ ID NO: 221- A*C*T*T*TC*A*A*T*A *C*T*T*C
SEQ ID NO: 222- A*C*C*G*T*G*T*A*C*T *T*T*C*A
SEQ ID NO: 223- C*A*C*C*C*C*T*G*C*C *C*C*A*G
SEQ ID NO: 224- C*T*G*C*C*C*T*C*C*A*C*C*C*C
SEQ ID NO: 225- C*T*G*A*G*G*A*A*G*G *A*G*C*A
SEQ ID NO: 226- G*A*G*C*A*A*G*T*C*C *C*G*G*G*T
SEQ ID NO: 227- A*G*C*T*G*T*C*A*C*T* G*A*C*A
SEQ ID NO: 228- A*C*A*C*T*A*G*C*T*G* T*C*A*C*T*G*A*C*A
SEQ ID NO: 229- C*A*C*A*C*T*A*G*C*T *G*T*C*A*C*T*G*A*C
SEQ ID NO: 230- T*C*A*C*A*C*T*A*G*C *T*G*T*C*A*C*T*G*A
SEQ ID NO: 231- A*C*T*C*A*C*A*C*T*A* G*C*T*G*T*C*A*C*T
SEQ ID NO: 232- T*C*A*C*A*C*T*A*G*C *T*G*T*C*A
SEQ ID NO: 233- G*T*A*C*T*C*A*C*A*C *T*A*G*C*T*G*T*C*A
SEQ ID NO: 234- A*G*T*A*C*T*C*A*C*A *C*T*A*G*C*T*G*T*C
SEQ ID NO: 235- A*G*A*G*T*A*C*T*C*A* C*A*C*T*A*G*C*T*G
SEQ ID NO: 236- A*A*G*A*G*T*A*C*T*C *A*C*A*C*T*A*G*C*T
SEQ ID NO: 237- T*A*A*G*A*G*T*A*C*T *C*A*C*A*C*T*A*G*C
SEQ ID NO: 238- A*T*A*A*G*A*G*T*A*C *T*C*A*C*A*C*T*A*G
SEQ ID NO: 239- A*G*T*A*C*T*C*A*C*A* C*T*A*G
SEQ ID NO: 240- C*A*T*A*A*G*A*G*T*A *C*T*C*A*C*A*C*T*A
SEQ ID NO: 241- A*C*A*T*A*A*G*A*G*T *A*C*T*C*A*C*A*C*T
SEQ ID NO: 242- A*A*C*A*T*A*A*G*A*G* T*A*C*T*C*A*C*A*C
SEQ ID NO: 243- G*A*A*C*A*T*A*A*G*A* G*T*A*C*T*C*A*C*A
SEQ ID NO: 244- T*G*A*A*C*A*T*A*A*G*A*G*T*A*C*T*C*A*C
SEQ ID NO: 245- C*T*G*A*A*C*A*T*A*A*G*A*G*T*A*C*T*C*A
SEQ ID NO: 246- C*T*G*A*A*C*A*T*A*A*G*A*G*T
SEQ ID NO: 247- A*A*A*G*T*C*A*A*G*A*G*G*T*A
SEQ ID NO: 248- T*T*G*T*C*C*C*C*A*A*A*G*T*C
SEQ ID NO: 249- +A*+A*+G*A*A*G*G*T*T*T*G*C*+C*+A*+T
SEQ ID NO: 250- +T*+C*+AC*A*C*T*A*G*C*T*G*+T*+C*+A
SEQ ID NO: 251- A*A*G*A*A*G*G*T*T*T* G*C*C*A*T
SEQ ID NO: 252- T*C*A*C*A*C*T*A*G*C*T*G*T*C*A
SEQ ID NO: 253- CTCCTCCTGC CACTTCTTCT G
SEQ ID NO: 254- CTGGTGGATGAAGAAGGTTTGC
SEQ ID NO: 255- TTTGGATCTGGACGACTTC
SEQ ID NO: 256- +C*+A*+A*T*A*A*G*T*A*G*C*C*+T*+G*+T
SEQ ID NO: 257- +C*+A*+C*G*C*T*A*G*T*C*T*G*+T*+T*+G
SEQ ID NO: 258- +C*+T*+T*C*C*T*T*C*C*T* G*T*+G*+T*+G
SEQ ID NO: 259- +C*+A*+G*G*C*T*G*A*G*T*T*A*+C*+C*+G
SEQ ID NO: 260- +G*+C*T*A*G*T*C*T*G*+T *+T*+G
SEQ ID NO: 261- +G*+T*C*T*G*A*T*G*G*+A* G*+A
SEQ ID NO: 262- GCTAGT
SEQ ID NO: 263- T*G*C*C*A*T*T*T*G*G *A*T*C*T*G*G*A*C*G

FIG.10

| Sequence ID | Sense Sequence Name | Sequence |
|---|---|---|
| SEQ ID NO: 264 | CUR-0521 | CUGACACCAAGCUCAUACUUUACAA |
| SEQ ID NO: 265 | CUR-0519 | CCCAGAGAGAGAACAGCCAUUGATT |
| SEQ ID NO: 266 | CUR-0523 | CUCUCAAAGUGCUGGAAUUAUAGGT |

FIG.11

| Sequence ID | Antisense Sequence Name | Sequence |
|---|---|---|
| SEQ ID NO: 267 | CUR-0476 | GUCUGGUGUGGCUGUGACUGACCAC |
| SEQ ID NO: 268 | CUR-0478 | GUCACAGUGUGGUGGGAGAAGGGAC |
| SEQ ID NO: 269 | CUR-0480 | GUAGGUGGUAGCUGUGUCAGUGCTG |
| SEQ ID NO: 270 | CUR-0444 | GCAGAUCCAUCCUCAGUGAAGCACA |
| SEQ ID NO: 271 | CUR-0446 | GGUGGUGUCUGAUGAGCGUUUCUCT |
| SEQ ID NO: 272 | CUR-0448 | GGCUCAGCCUCUUGUGCUUCCUAAG |
| SEQ ID NO: 273 | CUR-0450 | GAGCAAGGUGGGACAGGGAGCCAGG |
| SEQ ID NO: 274 | CUR-0452 | GUUGAAGCUGGGUGUGGAAAUGAAC |

FIG.12

SEQ ID NO: 275- TTTGGATCTGGACGACTTC

SEQ ID NO: 276- CTCCTCCTGCCACTTCTTCTG

SEQ ID NO: 277- CTGGTGGATGAAGAAGGTTTGC

SEQ ID NO: 278- +G*+C*T*A*G*T*C*T*G*+T*+T*+G (CUR-962)

SEQ ID NO: 279- +G*+T*C*T*G*A*T*G*G*+A*+G*+A (CUR-963)

SEQUENCE LISTING

```
<160> NUMBER OF SEQ ID NOS: 279

<210> SEQ ID NO 1
<211> LENGTH: 10412
<212> TYPE: DNA
<213> ORGANISM: Homo sapiens
<300> PUBLICATION INFORMATION:
<308> DATABASE ACCESSION NUMBER: NM_005502
<309> DATABASE ENTRY DATE: 2010-08-15
<313> RELEVANT RESIDUES IN SEQ ID NO: (1)..(10412)

<400> SEQUENCE: 1

gtaattgcga gcgagagtga gtggggccgg gacccgcaga gccgagccga cccttctctc     60

ccgggctgcg gcagggcagg gcggggagct ccgcgcacca acagagccgg ttctcagggc    120

gctttgctcc ttgttttttc cccggttctg ttttctcccc ttctccggaa ggcttgtcaa    180

ggggtaggag aaagagacgc aaacacaaaa gtggaaaaca gttaatgacc agccacggcg    240

tccctgctgt gagctctggc cgctgccttc cagggctccc gagccacacg ctgggggtgc    300

tggctgaggg aacatggctt gttggcctca gctgaggttg ctgctgtgga agaacctcac    360

tttcagaaga agacaaacat gtcagctgct gctggaagtg gcctggcctc tatttatctt    420

cctgatcctg atctctgttc ggctgagcta cccaccctat gaacaacatg aatgccattt    480

tccaaataaa gccatgccct ctgcaggaac acttccttgg gttcagggga ttatctgtaa    540

tgccaacaac ccctgtttcc gttacccgac tcctggggag gctcccggag ttgttggaaa    600

ctttaacaaa tccattgtgg ctcgcctgtt ctcagatgct cggaggcttc ttttatacag    660

ccagaaagac accagcatga aggacatgcg caaagttctg agaacattac agcagatcaa    720

gaaatccagc tcaaacttga agcttcaaga tttcctggtg gacaatgaaa ccttctctgg    780
```

-continued

```
gttcctgtat cacaacctct ctctcccaaa gtctactgtg gacaagatgc tgagggctga    840
tgtcattctc cacaaggtat ttttgcaagg ctaccagtta catttgacaa gtctgtgcaa    900
tggatcaaaa tcagaagaga tgattcaact tggtgaccaa gaagtttctg agctttgtgg    960
cctaccaagg gagaaactgg ctgcagcaga gcgagtactt cgttccaaca tggacatcct   1020
gaagccaatc ctgagaacac taaactctac atctcccttc ccgagcaagg agctggctga   1080
agccacaaaa acattgctgc atagtcttgg gactctggcc caggagctgt tcagcatgag   1140
aagctggagt gacatgcgac aggaggtgat gtttctgacc aatgtgaaca gctccagctc   1200
ctccacccaa atctaccagg ctgtgtctcg tattgtctgc gggcatcccg agggaggggg   1260
gctgaagatc aagtctctca actggtatga ggacaacaac tacaaagccc tctttggagg   1320
caatggcact gaggaagatg ctgaaacctt ctatgacaac tctacaactc cttactgcaa   1380
tgatttgatg aagaatttgg agtctagtcc tctttcccgc attatctgga aagctctgaa   1440
gccgctgctc gttgggaaga tcctgtatac acctgacact ccagccacaa ggcaggtcat   1500
ggctgaggtg aacaagacct tccaggaact ggctgtgttc catgatctgg aaggcatgtg   1560
ggaggaactc agccccaaga tctggacctt catggagaac agccaagaaa tggaccttgt   1620
ccggatgctg ttggacagca gggacaatga ccacttttgg gaacagcagt tggatggctt   1680
agattggaca gcccaagaca tcgtggcgtt tttggccaag cacccagagg atgtccagtc   1740
cagtaatggt tctgtgtaca cctggagaga agctttcaac gagactaacc aggcaatccg   1800
gaccatatct cgcttcatgg agtgtgtcaa cctgaacaag ctagaaccca tagcaacaga   1860
agtctggctc atcaacaagt ccatggagct gctggatgag aggaagttct gggctggtat   1920
tgtgttcact ggaattactc caggcagcat tgagctgccc catcatgtca agtacaagat   1980
ccgaatggac attgacaatg tggagaggac aaataaaatc aaggatgggt actgggaccc   2040
tggtcctcga gctgacccct ttgaggacat gcggtacgtc tgggggggct tcgcctactt   2100
gcaggatgtg gtggagcagg caatcatcag ggtgctgacg ggcaccgaga agaaaactgg   2160
tgtctatatg caacagatgc cctatccctg ttacgttgat gacatctttc tgcgggtgat   2220
gagccggtca atgcccctct tcatgacgct ggcctggatt tactcagtgg ctgtgatcat   2280
caagggcatc gtgtatgaga aggaggcacg gctgaaagag accatgcgga tcatgggcct   2340
ggacaacagc atcctctggt ttagctggtt cattagtagc ctcattcctc ttcttgtgag   2400
cgctggcctg ctagtggtca tcctgaagtt aggaaacctg ctgccctaca gtgatcccag   2460
cgtggtgttt gtcttcctgt ccgtgtttgc tgtggtgaca atcctgcagt gcttcctgat   2520
tagcacactc ttctccagag ccaacctggc agcagcctgt gggggcatca tctacttcac   2580
gctgtacctg ccctacgtcc tgtgtgtggc atggcaggac tacgtgggct tcacactcaa   2640
gatcttcgct agcctgctgt ctcctgtggc ttttgggttt ggctgtgagt actttgccct   2700
ttttgaggag cagggcattg gagtgcagtg ggacaacctg tttgagagtc ctgtggagga   2760
agatggcttc aatctcacca cttcggtctc catgatgctg tttgacacct tcctctatgg   2820
ggtgatgacc tggtacattg aggctgtctt tccaggccag tacggaattc ccaggccctg   2880
gtattttcct tgcaccaagt cctactggtt tggcgaggaa agtgatgaga agagccaccc   2940
tggttccaac cagaagagaa tatcagaaat ctgcatggag gaggaaccca cccacttgaa   3000
gctgggcgtg tccattcaga acctggtaaa agtctaccga gatgggatga aggtggctgt   3060
cgatggcctg gcactgaatt tttatgaggg ccagatcacc tccttcctgg gccacaatgg   3120
```

-continued

```
agcggggaag acgaccacca tgtcaatcct gaccgggttg ttccccccga cctcgggcac   3180
cgcctacatc ctgggaaaag acattcgctc tgagatgagc accatccggc agaacctggg   3240
ggtctgtccc cagcataacg tgctgtttga catgctgact gtcgaagaac acatctggtt   3300
ctatgcccgc ttgaaagggc tctctgagaa gcacgtgaag gcggagatgg agcagatggc   3360
cctggatgtt ggtttgccat caagcaagct gaaaagcaaa acaagccagc tgtcaggtgg   3420
aatgcagaga aagctatctg tggccttggc ctttgtcggg ggatctaagg ttgtcattct   3480
ggatgaaccc acagctggtg tggaccctta ctcccgcagg ggaatatggg agctgctgct   3540
gaaataccga caaggccgca ccattattct ctctacacac cacatggatg aagcggacgt   3600
cctgggggac aggattgcca tcatctccca tgggaagctg tgctgtgtgg gctcctccct   3660
gtttctgaag aaccagctgg gaacaggcta ctacctgacc ttggtcaaga aagatgtgga   3720
atcctccctc agttcctgca gaaacagtag tagcactgtg tcatacctga aaaaggagga   3780
cagtgtttct cagagcagtt ctgatgctgg cctgggcagc gaccatgaga gtgacacgct   3840
gaccatcgat gtctctgcta tctccaacct catcaggaag catgtgtctg aagcccggct   3900
ggtggaagac atagggcatg agctgaccta tgtgctgcca tatgaagctg ctaaggaggg   3960
agcctttgtg gaactctttc atgagattga tgaccggctc tcagacctgg gcatttctag   4020
ttatggcatc tcagagacga ccctggaaga aatattcctc aaggtggccg aagagagtgg   4080
ggtggatgct gagacctcag atggtacctt gccagcaaga cgaaacaggc gggccttcgg   4140
ggacaagcag agctgtcttc gcccgttcac tgaagatgat gctgctgatc caaatgattc   4200
tgacatagac ccagaatcca gagagacaga cttgctcagt gggatggatg gcaaagggtc   4260
ctaccaggtg aaaggctgga aacttacaca gcaacagttt gtggcccttt tgtggaagag   4320
actgctaatt gccagacgga gtcggaaagg atttttttgct cagattgtct tgccagctgt   4380
gtttgtctgc attgcccttg tgttcagcct gatcgtgcca ccctttggca agtaccccag   4440
cctggaactt cagccctgga tgtacaacga acagtacaca tttgtcagca atgatgctcc   4500
tgaggacacg ggaaccctgg aactcttaaa cgccctcacc aaagaccctg gcttcgggac   4560
ccgctgtatg gaaggaaacc caatcccaga cacgccctgc caggcagggg aggaagagtg   4620
gaccactgcc ccagttcccc agaccatcat ggacctcttc cagaatggga actggacaat   4680
gcagaaccct tcacctgcat gccagtgtag cagcgacaaa atcaagaaga tgctgcctgt   4740
gtgtcccccca ggggcagggg ggctgcctcc tccacaaaga aaacaaaaca ctgcagatat   4800
ccttcaggac ctgacaggaa gaaacatttc ggattatctg gtgaagacgt atgtgcagat   4860
catagccaaa agcttaaaga acaagatctg ggtgaatgag tttaggtatg gcggcttttc   4920
cctgggtgtc agtaatactc aagcacttcc tccgagtcaa gaagttaatg atgccatcaa   4980
acaaatgaag aaacacctaa agctggccaa ggacagttct gcagatcgat ttctcaacag   5040
cttgggaaga tttatgacag gactggacac caaaaataat gtcaaggtgt ggttcaataa   5100
caagggctgg catgcaatca gctctttcct gaatgtcatc aacaatgcca ttctccgggc   5160
caacctgcaa aagggagaga accctagcca ttatggaatt actgctttca atcatcccct   5220
gaatctcacc aagcagcagc tctcagaggt ggctctgatg accacatcag tggatgtcct   5280
tgtgtccatc tgtgtcatct ttgcaatgtc cttcgtccca gccagctttg tcgtattcct   5340
gatccaggag cgggtcagca aagcaaaaca cctgcagttc atcagtggag tgaagcctgt   5400
catctactgg ctctctaatt ttgtctggga tatgtgcaat tacgttgtcc ctgccacact   5460
ggtcattatc atcttcatct gcttccagca gaagtcctat gtgtcctcca ccaatctgcc   5520
```

```
tgtgctagcc cttctacttt tgctgtatgg gtggtcaatc acacctctca tgtacccagc   5580
ctcctttgtg ttcaagatcc ccagcacagc ctatgtggtg ctcaccagcg tgaacctctt   5640
cattggcatt aatggcagcg tggccacctt tgtgctggag ctgttcaccg acaataagct   5700
gaataatatc aatgatatcc tgaagtccgt gttcttgatc ttcccacatt tttgcctggg   5760
acgagggctc atcgacatgg tgaaaaacca ggcaatggct gatgccctgg aaaggtttgg   5820
ggagaatcgc tttgtgtcac cattatcttg ggacttggtg ggacgaaacc tcttcgccat   5880
ggccgtggaa ggggtggtgt tcttcctcat tactgttctg atccagtaca gattcttcat   5940
caggcccaga cctgtaaatg caaagctatc tcctctgaat gatgaagatg aagatgtgag   6000
gcgggaaaga cagagaattc ttgatggtgg aggccagaat gacatcttag aaatcaagga   6060
gttgacgaag atatatagaa ggaagcggaa gcctgctgtt gacaggattt gcgtgggcat   6120
tcctcctggt gagtgctttg ggctcctggg agttaatggg gctggaaaat catcaacttt   6180
caagatgtta acaggagata ccactgttac cagaggagat gctttcctta acaaaaatag   6240
tatcttatca aacatccatg aagtacatca gaacatgggc tactgccctc agtttgatgc   6300
catcacagag ctgttgactg ggagagaaca cgtggagttc tttgcccttt tgagaggagt   6360
cccagagaaa gaagttggca aggttggtga gtgggcgatt cggaaactgg gcctcgtgaa   6420
gtatggagaa aaatatgctg gtaactatag tggaggcaac aaacgcaagc tctctacagc   6480
catggctttg atcggcgggc ctcctgtggt gtttctggat gaacccacca caggcatgga   6540
tcccaaagcc cggcggttct tgtggaattg tgccctaagt gttgtcaagg aggggagatc   6600
agtagtgctt acatctcata gtatggaaga atgtgaagct ctttgcacta ggatggcaat   6660
catggtcaat ggaaggttca ggtgccttgg cagtgtccag catctaaaaa ataggtttgg   6720
agatggttat acaatagttg tacgaatagc agggtccaac ccggacctga agcctgtcca   6780
ggatttcttt ggacttgcat ttcctggaag tgttctaaaa gagaaacacc ggaacatgct   6840
acaataccag cttccatctt cattatcttc tctggccagg atattcagca tcctctccca   6900
gagcaaaaag cgactccaca tagaagacta ctctgtttct cagacaacac ttgaccaagt   6960
atttgtgaac tttgccaagg accaaagtga tgatgaccac ttaaaagacc tctcattaca   7020
caaaaaccag acagtagtgg acgttgcagt tctcacatct ttttctacagg atgagaaagt   7080
gaaagaaagc tatgtatgaa gaatcctgtt catacggggt ggctgaaagt aaagaggaac   7140
tagactttcc tttgcaccat gtgaagtgtt gtggagaaaa gagccagaag ttgatgtggg   7200
aagaagtaaa ctggatactg tactgatact attcaatgca atgcaattca atgcaatgaa   7260
aacaaaattc cattacaggg gcagtgcctt tgtagcctat gtcttgtatg gctctcaagt   7320
gaaagacttg aatttagttt tttacctata cctatgtgaa actctattat ggaacccaat   7380
ggacatatgg gtttgaactc acactttttt tttttttttt gttcctgtgt attctcattg   7440
gggttgcaac aataattcat caagtaatca tggccagcga ttattgatca aaatcaaaag   7500
gtaatgcaca tcctcattca ctaagccatg ccatgcccag gagactggtt tcccggtgac   7560
acatccattg ctggcaatga gtgtgccaga gttattagtg ccaagttttt cagaaagttt   7620
gaagcaccat ggtgtgtcat gctcactttt gtgaaagctg ctctgctcag agtctatcaa   7680
cattgaatat cagttgacag aatggtgcca tgcgtggcta acatcctgct ttgattccct   7740
ctgataagct gttctggtgg cagtaacatg caacaaaaat gtgggtgtct ccaggcacgg   7800
gaaacttggt tccattgtta tattgtccta tgcttcgagc catgggtcta cagggtcatc   7860
```

-continued

```
cttatgagac tcttaaatat acttagatcc tggtaagagg caaagaatca acagccaaac   7920
tgctggggct gcaagctgct gaagccaggg catgggatta aagagattgt gcgttcaaac   7980
ctagggaagc ctgtgcccat ttgtcctgac tgtctgctaa catggtacac tgcatctcaa   8040
gatgtttatc tgacacaagt gtattatttc tggctttttg aattaatcta gaaaatgaaa   8100
agatggagtt gtattttgac aaaaatgttt gtacttttta atgttatttg gaattttaag   8160
ttctatcagt gacttctgaa tccttagaat ggcctctttg tagaaccctg tggtatagag   8220
gagtatggcc actgccccac tatttttatt ttcttatgta agtttgcata tcagtcatga   8280
ctagtgccta gaaagcaatg tgatggtcag gatctcatga cattatattt gagtttcttt   8340
cagatcattt aggatactct taatctcact tcatcaatca aatatttttt gagtgtatgc   8400
tgtagctgaa agagtatgta cgtacgtata agactagaga gatattaagt ctcagtacac   8460
ttcctgtgcc atgttattca gctcactggt ttacaaatat aggttgtctt gtggttgtag   8520
gagcccactg taacaatact gggcagcctt tttttttttt tttttaattg caacaatgca   8580
aaagccaaga aagtataagg gtcacaagtc taaacaatga attcttcaac agggaaaaca   8640
gctagcttga aaacttgctg aaaaacacaa cttgtgttta tggcatttag taccttcaaa   8700
taattggctt tgcagatatt ggatacccca ttaaatctga cagtctcaaa tttttcatct   8760
cttcaatcac tagtcaagaa aaatataaaa acaacaaata cttccatatg gagcattttt   8820
cagagtttc taacccagtc ttatttttct agtcagtaaa catttgtaaa aatactgttt    8880
cactaatact tactgttaac tgtcttgaga gaaaagaaaa atatgagaga actattgttt   8940
ggggaagttc aagtgatctt tcaatatcat tactaacttc ttccactttt tccagaattt   9000
gaatattaac gctaaaggtg taagacttca gatttcaaat taatctttct atatttttta   9060
aatttacaga atattatata acccactgct gaaaaagaaa aaaatgattg ttttagaagt   9120
taaagtcaat attgatttta aatataagta atgaaggcat atttccaata actagtgata   9180
tggcatcgtt gcattttaca gtatcttcaa aaatacagaa tttatagaat aatttctcct   9240
catttaatat ttttcaaaat caaagttatg gtttcctcat tttactaaaa tcgtattcta   9300
attcttcatt atagtaaatc tatgagcaac tccttacttc ggttcctctg atttcaaggc   9360
catattttaa aaaatcaaaa ggcactgtga actattttga agaaaacaca acattttaat   9420
acagattgaa aggacctctt ctgaagctag aaacaatcta tagttataca tcttcattaa   9480
tactgtgtta ccttttaaaa tagtaatttt ttacattttc ctgtgtaaac ctaattgtgg   9540
tagaaatttt taccaactct atactcaatc aagcaaaatt tctgtatatt ccctgtggaa   9600
tgtacctatg tgagtttcag aaattctcaa aatacgtgtt caaaaatttc tgcttttgca   9660
tctttgggac acctcagaaa acttattaac aactgtgaat atgagaaata cagaagaaaa   9720
taataagccc tctatacata aatgcccagc acaattcatt gttaaaaaac aaccaaacct   9780
cacactactg tatttcatta tctgtactga aagcaaatgc tttgtgacta ttaaatgttg   9840
cacatcattc attcactgta tagtaatcat tgactaaagc catttgtctg tgttttcttc   9900
ttgtggttgt atatatcagg taaaatattt tccaaagagc catgtgtcat gtaatactga   9960
accactttga tattgagaca ttaatttgta cccttgttat tatctactag taataatgta  10020
atactgtaga aatattgctc taattctttt caaaattgtt gcatccccct tagaatgttt  10080
ctatttccat aaggatttag gtatgctatt atcccttctt ataccctaag atgaagctgt  10140
ttttgtgctc tttgttcatc attggccctc attccaagca ctttacgctg tctgtaatgg  10200
gatctatttt tgcactggaa tatctgagaa ttgcaaaact agacaaaagt ttcacaacag  10260
```

-continued atttctaagt taaatcattt tcattaaaag gaaaaaagaa aaaaaatttt gtatgtcaat 10320
aactttatat gaagtattaa aatgcatatt tctatgttgt aatataatga gtcacaaaat 10380
aaagctgtga cagttctgtt ggtctacaga aa 10412

<210> SEQ ID NO 2
<211> LENGTH: 1354
<212> TYPE: DNA
<213> ORGANISM: Homo sapiens
<300> PUBLICATION INFORMATION:
<308> DATABASE ACCESSION NUMBER: NM_000229.1
<309> DATABASE ENTRY DATE: 2010-08-02
<313> RELEVANT RESIDUES IN SEQ ID NO: (1)..(1354)

<400> SEQUENCE: 2
ccagggctgg aatggggccg cccggctccc catggcagtg ggtgacgctg ctgctggggc 60
tgctgctccc tcctgccgcc cccttctggc tcctcaatgt gctcttcccc ccgcacacca 120
cgcccaaggc tgagctcagt aaccacacac ggcccgtcat cctcgtgccc ggctgcctgg 180
ggaatcagct agaagccaag ctggacaaac cagatgtggt gaactggatg tgctaccgca 240
agacagagga cttcttcacc atctggctgg atctcaacat gttcctaccc cttggggtag 300
actgctggat cgataacacc agggttgtct acaaccggag ctctgggctc gtgtccaacg 360
cccctggtgt ccagatccgc gtccctggct ttggcaagac ctactctgtg gagtacctgg 420
acagcagcaa gctggcaggg tacctgcaca cactggtgca gaacctggtc aacaatggct 480
acgtgcggga cgagactgtg cgcgccgccc cctatgactg gcggctggag cccggccagc 540
aggaggagta ctaccgcaag ctcgcagggc tggtggagga gatgcacgct gcctatggga 600
agcctgtctt cctcattggc cacagcctcg gctgtctaca cttgctctat ttcctgctgc 660
gccagcccca ggcctggaag gaccgcttta ttgatggctt catctctctt ggggctccct 720
ggggtggctc catcaagccc atgctggtct tggcctcagg tgacaaccag ggcatcccca 780
tcatgtccag catcaagctg aaagaggagc agcgcataac caccacctcc ccctggatgt 840
ttccctctcg catggcgtgg cctgaggacc acgtgttcat ttccacaccc agcttcaact 900
acacaggccg tgacttccaa cgcttctttg cagacctgca ctttgaggaa ggctggtaca 960
tgtggctgca gtcacgtgac ctcctggcag gactcccagc acctggtgtg gaagtatact 1020
gtctttacgg cgtgggcctg cccacgcccc gcacctacat ctacgaccac ggcttcccct 1080
acacggaccc tgtgggtgtg ctctatgagg atggtgatga cacggtggcg acccgcagca 1140
ccgagctctg tggcctgtgg cagggccgcc agccacagcc tgtgcacctg ctgcccctgc 1200
acgggataca gcatctcaac atggtcttca gcaacctgac cctggagcac atcaatgcca 1260
tcctgctggg tgcctaccgc cagggtcccc ctgcatcccc gactgccagc ccagagcccc 1320
cgcctcctga ataaagacct tcctttgcta ccgt 1354

<210> SEQ ID NO 3
<211> LENGTH: 14905
<212> TYPE: DNA
<213> ORGANISM: Homo sapiens
<300> PUBLICATION INFORMATION:
<308> DATABASE ACCESSION NUMBER: NM_002332.2
<309> DATABASE ENTRY DATE: 2010-08-04
<313> RELEVANT RESIDUES IN SEQ ID NO: (1)..(14905)

<400> SEQUENCE: 3
cagcggtgcg agctccaggc ccatgcactg aggaggcgga aacaagggga gcccccagag 60

-continued

```
ctccatcaag cccccctccaa aggctcccct acccggtcca cgccccccac cccccctccc    120
cgcctcctcc caattgtgca tttttgcagc cggaggcggc tccgagatgg ggctgtgagc    180
ttcgcccggg gagggggaaa gagcagcgag gagtgaagcg ggggggtggg gtgaagggtt    240
tggatttcgg ggcagggggc gcacccccgt cagcaggccc tccccaaggg gctcggaact    300
ctacctcttc acccacgccc ctggtgcgct ttgccgaagg aaagaataag aacagagaag    360
gaggaggggg aaaggaggaa aagggggacc ccccaactgg ggggggtgaa ggagagaagt    420
agcaggacca gaggggaagg ggctgctgct tgcatcagcc cacaccatgc tgaccccgcc    480
gttgctcctg ctgctgcccc tgctctcagc tctggtcgcg gcggctatcg acgcccctaa    540
gacttgcagc cccaagcagt ttgcctgcag agatcaaata acctgtatct caaagggctg    600
gcggtgcgac ggtgagaggg actgcccaga cggatctgac gaggcccctg agatttgtcc    660
acagagtaag gcccagcgat gccagccaaa cgagcataac tgcctgggta ctgagctgtg    720
tgttcccatg tcccgcctct gcaatggggt ccaggactgc atggacggct cagatgaggg    780
gccccactgc cgagagctcc aaggcaactg ctctcgcctg ggctgccagc accattgtgt    840
ccccacactc gatgggccca cctgctactg caacagcagc tttcagcttc aggcagatgg    900
caagacctgc aaagattttg atgagtgctc agtgtacggc acctgcagcc agctatgcac    960
caacacagac ggctccttca tatgtggctg tgttgaagga tacctcctgc agccggataa   1020
ccgctcctgc aaggccaaga acgagccagt agaccggccc cctgtgctgt tgatagccaa   1080
ctcccagaac atcttggcca cgtacctgag tggggcccag gtgtctacca tcacacctac   1140
gagcacgcgg cagaccacag ccatggactt cagctatgcc aacgagaccg tatgctgggt   1200
gcatgttggg gacagtgctg ctcagacgca gctcaagtgt gcccgcatgc ctggcctaaa   1260
gggcttcgtg gatgagcaca ccatcaacat ctccctcagt ctgcaccacg tggaacagat   1320
ggccatcgac tggctgacag gcaacttcta ctttgtggat gacatcgatg ataggatctt   1380
tgtctgcaac agaaatgggg acacatgtgt cacattgcta gacctggaac tctacaaccc   1440
caagggcatt gccctggacc ctgccatggg gaaggtgttt ttcactgact atgggcagat   1500
cccaaaggtg gaacgctgtg acatggatgg gcagaaccgc accaagctcg tcgacagcaa   1560
gattgtgttt cctcatggca tcacgctgga cctggtcagc cgccttgtct actgggcaga   1620
tgcctatctg gactatattg aagtggtgga ctatgagggc aagggccgcc agaccatcat   1680
ccagggcatc ctgattgagc acctgtacgg cctgactgtg tttgagaatt atctctatgc   1740
caccaactcg gacaatgcca atgcccagca gaagacgagt gtgatccgtg tgaaccgctt   1800
taacagcacc gagtaccagg ttgtcacccg ggtggacaag ggtggtgccc tccacatcta   1860
ccaccagagg cgtcagcccc gagtgaggag ccatgcctgt gaaaacgacc agtatgggaa   1920
gccgggtggc tgctctgaca tctgcctgct ggccaacagc cacaaggcgc ggacctgccg   1980
ctgccgttcc ggcttcagcc tgggcagtga cgggaagtca tgcaagaagc cggagcatga   2040
gctgttcctc gtgtatggca agggccggcc aggcatcatc cggggcatgg atatgggggc   2100
caaggtcccg gatgagcaca tgatccccat tgaaaacctc atgaaccccc gagccctgga   2160
cttccacgct gagaccggct tcatctactt tgccgacacc accagctacc tcattggccg   2220
ccagaagatt gatggcactg agcgggagac catcctgaag gacggcatcc acaatgtgga   2280
gggtgtggcc gtggactgga tgggagacaa tctgtactgg acggacgatg ggcccaaaaa   2340
gacaatcagc gtggccaggc tggagaaagc tgctcagacc cgcaagactt taatcgaggg   2400
caaaatgaca caccccaggg ctattgtggt ggatccactc aatgggtgga tgtactggac   2460
```

-continued

```
agactgggag gaggacccca aggacagtcg gcgtgggcgg ctggagaggg cgtggatgga   2520
tggctcacac cgagacatct ttgtcacctc caagacagtg ctttggccca atgggctaag   2580
cctggacatc ccggctgggc gcctctactg ggtggatgcc ttctacgacc gcatcgagac   2640
gatactgctc aatggcacag accggaagat tgtgtatgaa ggtcctgagc tgaaccacgc   2700
ctttggcctg tgtcaccatg gcaactacct cttctggact gagtatcgga gtggcagtgt   2760
ctaccgcttg gaacggggtg taggaggcgc accccccact gtgacccttc tgcgcagtga   2820
gcggcccccc atctttgaga tccgaatgta tgatgcccag cagcagcaag ttggcaccaa   2880
caaatgccgg gtgaacaatg gcggctgcag cagcctgtgc ttggccaccc ctgggagccg   2940
ccagtgcgcc tgtgctgagg accaggtgtt ggacgcagac ggcgtcactt gcttggcgaa   3000
cccatcctac gtgcctccac cccagtgcca gccaggcgag tttgcctgtg ccaacagccg   3060
ctgcatccag gagcgctgga agtgtgacgg agacaacgat tgcctggaca acagtgatga   3120
ggccccagcc ctctgccatc agcacacctg cccctcggac cgattcaagt gcgagaacaa   3180
ccggtgcatc cccaaccgct ggctctgcga cggggacaat gactgtggga acagtgaaga   3240
tgagtccaat gccacttgtt cagcccgcac ctgccccccc aaccagttct cctgtgccag   3300
tggccgctgc atccccatct cctggacgtg tgatctggat gacgactgtg gggaccgctc   3360
tgatgagtct gcttcgtgtg cctatcccac ctgcttcccc ctgactcagt ttacctgcaa   3420
caatggcaga tgtatcaaca tcaactggag atgcgacaat gacaatgact gtggggacaa   3480
cagtgacgaa gccggctgca gccactcctg ttctagcacc cagttcaagt gcaacagcgg   3540
gcgttgcatc cccgagcact ggacctgcga tggggacaat gactgcggag actacagtga   3600
tgagacacac gccaactgca ccaaccaggc cacgaggccc cctggtggct gccacactga   3660
tgagttccag tgccggctgg atggactatg catccccctg cggtggcgct gcgatgggga   3720
cactgactgc atggactcca gcgatgagaa gagctgtgag ggagtgaccc acgtctgcga   3780
tcccagtgtc aagtttggct gcaaggactc agctcggtgc atcagcaaag cgtgggtgtg   3840
tgatggcgac aatgactgtg aggataactc ggacgaggag aactgcgagt ccctggcctg   3900
caggccaccc tcgcaccctt gtgccaacaa cacctcagtc tgcctgcccc ctgacaagct   3960
gtgtgatggc aacgacgact gtggcgacgg ctcagatgag ggcgagctct gcgaccagtg   4020
ctctctgaat aacggtggct gcagccacaa ctgctcagtg gcacctggcg aaggcattgt   4080
gtgttcctgc cctctgggca tggagctggg gcccgacaac cacacctgcc agatccagag   4140
ctactgtgcc aagcatctca aatgcagcca aaagtgcgac cagaacaagt tcagcgtgaa   4200
gtgctcctgc tacgagggct gggtcctgga acctgacggc gagagctgcc gcagcctgga   4260
ccccttcaag ccgttcatca ttttctccaa ccgccatgaa atccggcgca tcgatcttca   4320
caaaggagac tacagcgtcc tggtgcccgg cctgcgcaac accatcgccc tggacttcca   4380
cctcagccag agcgccctct actggaccga cgtggtggag gacaagatct accgcgggaa   4440
gctgctggac aacggagccc tgactagttt cgaggtggtg attcagtatg gcctggccac   4500
acccgagggc ctggctgtag actggattgc aggcaacatc tactgggtgg agagtaacct   4560
ggatcagatc gaggtggcca agctggatgg gaccctccgg accaccctgc tggccggtga   4620
cattgagcac cccaagggca tcgcactgga tccccgggat gggatcctgt tttggacaga   4680
ctgggatgcc agcctgcccc gcattgaggc agcctccatg agtggggctg ggcgccgcac   4740
cgtgcaccgg gagaccggct ctgggggctg gcccaacggg ctcaccgtgg actacctgga   4800
```

-continued

```
gaagcgcatc ctttggattg acgccaggtc agatgccatt tactcagccc gttacgacgg   4860
ctctggccac atggaggtgc ttcggggaca cgagttcctg tcgcacccgt ttgcagtgac   4920
gctgtacggg ggggaggtct actggactga ctggcgaaca aacacactgg ctaaggccaa   4980
caagtggacc ggccacaatg tcaccgtggt acagaggacc aacacccagc cctttgacct   5040
gcaggtgtac cacccctccc gccagcccat ggctcccaat ccctgtgagg ccaatggggg   5100
ccagggcccc tgctcccacc tgtgtctcat caactacaac cggaccgtgt cctgcgcctg   5160
cccccacctc atgaagctcc acaaggacaa caccacctgc tatgagttta agaagttcct   5220
gctgtacgca cgtcagatgg agatccgagg tgtggacctg gatgctccct actacaacta   5280
catcatctcc ttcacggtgc ccgacatcga caacgtcaca gtgctagact acgatgcccg   5340
cgagcagcgt gtgtactggt ctgacgtgcg gacacaggcc atcaagcggg ccttcatcaa   5400
cggcacaggc gtggagacag tcgtctctgc agacttgcca aatgcccacg ggctggctgt   5460
ggactgggtc tcccgaaacc tgttctggac aagctatgac accaataaga agcagatcaa   5520
tgtggcccgg ctggatggct ccttcaagaa cgcagtggtg cagggcctgg agcagcccca   5580
tggccttgtc gtccaccctc tgcgtgggaa gctctactgg accgatggtg acaacatcag   5640
catggccaac atggatggca gcaatcgcac cctgctcttc agtggccaga agggccccgt   5700
gggcctggct attgacttcc ctgaaagcaa actctactgg atcagctccg ggaaccatac   5760
catcaaccgc tgcaacctgg atgggagtgg gctggaggtc atcgatgcca tgcggagcca   5820
gctgggcaag gccaccgccc tggccatcat gggggacaag ctgtggtggg ctgatcaggt   5880
gtcggaaaag atgggcacat gcagcaaggc tgacggctcg ggctccgtgg tccttcggaa   5940
cagcaccacc ctggtgatgc acatgaaggt ctatgacgag agcatccagc tggaccataa   6000
gggcaccaac ccctgcagtg tcaacaacgg tgactgctcc cagctctgcc tgcccacgtc   6060
agagacgacc cgctcctgca tgtgcacagc cggctatagc ctccggagtg gccagcaggc   6120
ctgcgagggc gtaggttcct ttctcctgta ctctgtgcat gagggaatca ggggaattcc   6180
cctggatccc aatgacaagt cagatgccct ggtcccagtg tccgggacct cgctggctgt   6240
cggcatcgac ttccacgctg aaaatgacac catctactgg gtggacatgg gcctgagcac   6300
gatcagccgg gccaagcggg accagacgtg gcgtgaagac gtggtgacca atggcattgg   6360
ccgtgtggag ggcattgcag tggactggat cgcaggcaac atctactgga cagaccaggg   6420
ctttgatgtc atcgaggtcg cccggctcaa tggctccttc cgctacgtgg tgatctccca   6480
gggtctagac aagccccggg ccatcaccgt ccacccggag aaagggtact tgttctggac   6540
tgagtggggt cagtatccgc gtattgagcg gtctcggcta gatggcacgg agcgtgtggt   6600
gctggtcaac gtcagcatca gctggcccaa cggcatctca gtggactacc aggatgggaa   6660
gctgtactgg tgcgatgcac ggacagacaa gattgaacgg atcgacctgg agacaggtga   6720
gaaccgcgag gtggttctgt ccagcaacaa catggacatg ttttcagtgt ctgtgtttga   6780
ggatttcatc tactggagtg acaggactca tgccaacggc tctatcaagc gcgggagcaa   6840
agacaatgcc acagactccg tgcccctgcg aaccggcatc ggcgtccagc ttaaagacat   6900
caaagtcttc aaccgggacc ggcagaaagg caccaacgtg tgcgcggtgg ccaatggcgg   6960
gtgccagcag ctgtgcctgt accggggccg tgggcagcgg gcctgcgcct gtgcccacgg   7020
gatgctggct gaagacggag catcgtgccg cgagtatgcc ggctacctgc tctactcaga   7080
gcgcaccatt ctcaagagta tccacctgtc ggatgagcgc aacctcaatg cgcccgtgca   7140
gcccttcgag gaccctgagc acatgaagaa cgtcatcgcc ctggcctttg actaccgggc   7200
```

aggcacctct ccgggcaccc ccaatcgcat cttcttcagc gacatccact ttgggaacat 7260
ccaacagatc aacgacgatg gctccaggag gatcaccatt gtggaaaacg tgggctccgt 7320
ggaaggcctg gcctatcacc gtggctggga cactctctat tggacaagct acacgacatc 7380
caccatcacg cgccacacag tggaccagac ccgcccaggg gccttcgagc gtgagaccgt 7440
catcactatg tctggagatg accacccacg ggccttcgtt ttggacgagt gccagaacct 7500
catgttctgg accaactgga atgagcagca tcccagcatc atgcgggcgg cgctctcggg 7560
agccaatgtc ctgaccctta tcgagaagga catccgtacc cccaatggcc tggccatcga 7620
ccaccgtgcc gagaagctct acttctctga cgccaccctg gacaagatcg agcggtgcga 7680
gtatgacggc tcccaccgct atgtgatcct aaagtcagag cctgtccacc ccttcgggct 7740
ggccgtgtat ggggagcaca ttttctggac tgactgggtg cggcgggcag tgcagcgggc 7800
caacaagcac gtgggcagca acatgaagct gctgcgcgtg gacatccccc agcagcccat 7860
gggcatcatc gccgtggcca acgacaccaa cagctgtgaa ctctctccat gccgaatcaa 7920
caacggtggc tgccaggacc tgtgtctgct cactcaccag ggccatgtca actgctcatg 7980
ccgagggggc cgaatcctcc aggatgacct cacctgccga gcggtgaatt cctcttgccg 8040
agcacaagat gagtttgagt gtgccaatgg cgagtgcatc aacttcagcc tgacctgcga 8100
cggcgtcccc cactgcaagg acaagtccga tgagaagcca tcctactgca actcccgccg 8160
ctgcaagaag actttccggc agtgcagcaa tgggcgctgt gtgtccaaca tgctgtggtg 8220
caacggggcc gacgactgtg gggatggctc tgacgagatc ccttgcaaca agacagcctg 8280
tggtgtgggc gagttccgct gccgggacgg gacctgcatc gggaactcca gccgctgcaa 8340
ccagtttgtg gattgtgagg acgcctcaga tgagatgaac tgcagtgcca ccgactgcag 8400
cagctacttc cgcctgggcg tgaagggcgt gctcttccag ccctgcgagc ggacctcact 8460
ctgctacgca cccagctggg tgtgtgatgg cgccaatgac tgtggggact acagtgatga 8520
gcgcgactgc ccaggtgtga aacgccccag atgccctctg aattacttcg cctgccctag 8580
tgggcgctgc atccccatga gctggacgtg tgacaaagag gatgactgtg aacatggcga 8640
ggacgagacc cactgcaaca agttctgctc agaggcccag tttgagtgcc agaaccatcg 8700
ctgcatctcc aagcagtggc tgtgtgacgg cagcgatgac tgtggggatg gctcagacga 8760
ggctgctcac tgtgaaggca agacgtgcgg cccctcctcc ttctcctgcc ctggcaccca 8820
cgtgtgcgtc cccgagcgct ggctctgtga cggtgacaaa gactgtgctg atggtgcaga 8880
cgagagcatc gcagctggtt gcttgtacaa cagcacttgt gacgaccgtg agttcatgtg 8940
ccagaaccgc cagtgcatcc ccaagcactt cgtgtgtgac cacgaccgtg actgtgcaga 9000
tggctctgat gagtcccccg agtgtgagta cccgacctgc ggccccagtg agttccgctg 9060
tgccaatggg cgctgtctga gctcccgcca gtgggagtgt gatggcgaga atgactgcca 9120
cgaccagagt gacgaggctc ccaagaaccc acactgcacc agccaagagc acaagtgcaa 9180
tgcctcgtca cagttcctgt gcagcagtgg gcgctgtgtg gctgaggcac tgctctgcaa 9240
cggccaggat gactgtggcg acagctcgga cgagcgtggc tgccacatca atgagtgtct 9300
cagccgcaag ctcagtggct gcagccagga ctgtgaggac ctcaagatcg gcttcaagtg 9360
ccgctgtcgc cctggcttcc ggctgaagga cgacggccgg acgtgtgctg atgtggacga 9420
gtgcagcacc accttcccct gcagccagcg ctgcatcaac actcatggca gctataagtg 9480
tctgtgtgtg gagggctatg caccccgcgg cggcgacccc cacagctgca aggctgtgac 9540

-continued

```
tgacgaggaa ccgtttctga tcttcgccaa ccggtactac ctgcgcaagc tcaacctgga   9600
cgggtccaac tacacgttac ttaagcaggg cctgaacaac gccgttgcct tggattttga   9660
ctaccgagag cagatgatct actggacaga tgtgaccacc cagggcagca tgatccgaag   9720
gatgcacctt aacgggagca atgtgcaggt cctacaccgt acaggcctca gcaaccccga   9780
tgggctggct gtggactggg tgggtggcaa cctgtactgg tgcgacaaag gccgggacac   9840
catcgaggtg tccaagctca atggggccta tcggacggtg ctggtcagct ctggcctccg   9900
tgagcccagg gctctggtgg tggatgtgca gaatgggtac ctgtactgga cagactgggg   9960
tgaccattca ctgatcggcc gcatcggcat ggatgggtcc agccgcagcg tcatcgtgga  10020
caccaagatc acatggccca atggcctgac gctggactat gtcactgagc gcatctactg  10080
ggccgacgcc cgcgaggact acattgaatt tgccagcctg gatggctcca atcgccacgt  10140
tgtgctgagc caggacatcc cgcacatctt tgcactgacc ctgtttgagg actacgtcta  10200
ctggaccgac tgggaaacaa agtccattaa ccgagcccac aagaccacgg gcaccaacaa  10260
aacgctcctc atcagcacgc tgcaccggcc catggacctg catgtcttcc atgccctgcg  10320
ccagccagac gtgcccaatc acccctgcaa ggtcaacaat ggtggctgca gcaacctgtg  10380
cctgctgtcc cccgggggag ggcacaaatg tgcctgcccc accaacttct acctgggcag  10440
cgatgggcgc acctgtgtgt ccaactgcac ggctagccag tttgtatgca agaacgacaa  10500
gtgcatcccc ttctggtgga agtgtgacac cgaggacgac tgcggggacc actcagacga  10560
gcccccggac tgccctgagt tcaagtgccg gcccggacag ttccagtgct ccacaggtat  10620
ctgcacaaac cctgccttca tctgcgatgg cgacaatgac tgccaggaca acagtgacga  10680
ggccaactgt gacatccacg tctgcttgcc cagtcagttc aaatgcacca acaccaaccg  10740
ctgtattccc ggcatcttcc gctgcaatgg gcaggacaac tgcggagatg gggaggatga  10800
gagggactgc cccgaggtga cctgcgcccc caaccagttc cagtgctcca ttaccaaacg  10860
gtgcatcccc cgggtctggg tctgcgaccg ggacaatgac tgtgtggatg gcagtgatga  10920
gcccgccaac tgcacccaga tgacctgtgg tgtggacgag ttccgctgca aggattcggg  10980
ccgctgcatc ccagcgcgtt ggaagtgtga cggagaggat gactgtgggg atggctcgga  11040
tgagcccaag gaagagtgtg atgaacgcac ctgtgagcca taccagttcc gctgcaagaa  11100
caaccgctgc gtgcccggcc gctggcagtg cgactacgac aacgattgcg gtgacaactc  11160
cgatgaagag agctgcaccc ctcggccctg ctccgagagt gagttctcct gtgccaacgg  11220
ccgctgcatc gcggggcgct ggaaatgcga tggagaccac gactgcgcgg acggctcgga  11280
cgagaaagac tgcacccccc gctgtgacat ggaccagttc cagtgcaaga gcggccactg  11340
catccccctg cgctggcgct gtgacgcaga cgccgactgc atggacggca gcgacgagga  11400
ggcctgcggc actggcgtgc ggacctgccc cctggacgag ttccagtgca acaacacctt  11460
gtgcaagccg ctggcctgga agtgcgatgg cgaggatgac tgtggggaca actcagatga  11520
gaaccccgag gagtgtgccc ggttcgtgtg ccctcccaac cggcccttcc gttgcaagaa  11580
tgaccgcgtc tgtctgtgga tcgggcgcca atgcgatggc acggacaact gtggggatgg  11640
gactgatgaa gaggactgtg agccccccac agcccacacc acccactgca aagacaagaa  11700
ggagtttctg tgccggaacc agcgctgcct ctcctcctcc ctgcgctgca acatgttcga  11760
tgactgcggg gacggctctg acgaggagga ctgcagcatc gaccccaagc tgaccagctg  11820
cgccaccaat gccagcatct gtggggacga ggcacgctgc gtgcgcaccg agaaagcggc  11880
ctactgtgcc tgccgctcgg gcttccacac cgtgcccggc cagcccggat gccaagacat  11940
```

-continued

```
caacgagtgc ctgcgcttcg gcacctgctc ccagctctgc aacaacacca agggcggcca  12000
cctctgcagc tgcgctcgga acttcatgaa gacgcacaac acctgcaagg ccgaaggctc  12060
tgagtaccag gtcctgtaca tcgctgatga caatgagatc cgcagcctgt tccccggcca  12120
cccccattcg gcttacgagc aggcattcca gggtgacgag agtgtccgca ttgatgctat  12180
ggatgtccat gtcaaggctg gccgtgtcta ttggaccaac tggcacacgg gcaccatctc  12240
ctaccgcagc ctgccacctg ctgcgcctcc taccacttcc aaccgccacc ggcgacagat  12300
tgaccggggt gtcacccacc tcaacatttc agggctgaag atgcccagag gcatcgccat  12360
cgactgggtg gccggaaacg tgtactggac cgactcgggc cgagatgtga ttgaggtggc  12420
gcagatgaag ggcgagaacc gcaagacgct catctcgggc atgattgacg agccccacgc  12480
cattgtggtg gacccactga gggggaccat gtactggtca gactggggca accaccccaa  12540
gattgagacg gcagcgatgg atgggacgct tcgggagaca ctggtgcagg acaacattca  12600
gtggcccaca ggcctggccg tggattatca caatgagcgg ctgtactggg cagacgccaa  12660
gctttcagtc atcggcagca tccggctcaa tggcacggac cccattgtgg ctgctgacag  12720
caaacgaggc ctaagtcacc ccttcagcat cgacgtcttt gaggattaca tctatggtgt  12780
cacctacatc aataatcgtg tcttcaagat ccataagttt ggccacagcc ccttggtcaa  12840
cctgacaggg ggcctgagcc acgcctctga cgtggtcctt taccatcagc acaagcagcc  12900
cgaagtgacc aacccatgtg accgcaagaa atgcgagtgg ctctgcctgc tgagccccag  12960
tgggcctgtc tgcacctgtc ccaatgggaa gcggctggac aacggcacat gcgtgcctgt  13020
gccctctcca acgccccccc cagatgctcc ccggcctgga acctgtaacc tgcagtgctt  13080
caacggtggc agctgtttcc tcaatgcacg gaggcagccc aagtgccgct gccaaccccg  13140
ctacacgggt gacaagtgtg aactggacca gtgctgggag cactgtcgca atgggggcac  13200
ctgtgctgcc tccccctctg gcatgcccac gtgccggtgc cccacgggct tcacgggccc  13260
caaatgcacc cagcaggtgt gtgcgggcta ctgtgccaac aacagcacct gcactgtcaa  13320
ccagggcaac cagccccagt gccgatgcct acccggcttc ctgggcgacc gctgccagta  13380
ccggcagtgc tctggctact gtgagaactt tggcacatgc cagatggctg ctgatggctc  13440
ccgacaatgc cgctgcactg cctactttga gggatcgagg tgtgaggtga acaagtgcag  13500
ccgctgtctc gaaggggcct gtgtggtcaa caagcagagt ggggatgtca cctgcaactg  13560
cacggatggc cgggtggccc ccagctgtct gacctgcgtc ggccactgca gcaatggcgg  13620
ctcctgtacc atgaacagca aaatgatgcc tgagtgccag tgcccacccc acatgacagg  13680
gccccggtgt gaggagcacg tcttcagcca gcagcagcca ggacatatag cctccatcct  13740
aatccctctg ctgttgctgc tgctgctggt tctggtggcc ggagtggtat tctggtataa  13800
gcggcgagtc caaggggcta agggcttcca gcaccaacgg atgaccaacg gggccatgaa  13860
cgtggagatt ggaaacccca cctacaagat gtacgaaggc ggagagcctg atgatgtggg  13920
aggcctactg gacgctgact ttgccctgga ccctgacaag cccaccaact tcaccaaccc  13980
cgtgtatgcc acactctaca tgggggggcca tggcagtcgc cactccctgg ccagcacgga  14040
cgagaagcga gaactcctgg gccggggccc tgaggacgag ataggggacc ccttggcata  14100
gggccctgcc ccgtcggact gcccccagaa agcctcctgc cccctgccgg tgaagtcctt  14160
cagtgagccc ctccccagcc agcccttccc tggccccgcc ggatgtataa atgtaaaaat  14220
gaaggaatta cattttatat gtgagcgagc aagccggcaa gcgagcacag tattatttct  14280
```

-continued

```
ccatcccctc cctgcctgct ccttggcacc cccatgctgc cttcagggag acaggcaggg  14340

agggcttggg gctgcacctc ctaccctccc accagaacgc accccactgg gagagctggt  14400

ggtgcagcct tcccctccct gtataagaca ctttgccaag gctctcccct ctcgccccat  14460

ccctgcttgc ccgctcccac agcttcctga gggctaattc tgggaaggga gagttctttg  14520

ctgcccctgt ctggaagacg tggctctggg tgaggtaggc gggaaaggat ggagtgtttt  14580

agttcttggg ggaggccacc ccaaacccca gccccaactc caggggcacc tatgagatgg  14640

ccatgctcaa ccccccctccc agacaggccc tccctgtctc cagggccccc accgaggttc  14700

ccagggctgg agacttcctc tggtaaacat tcctccagcc tcccctcccc tggggacgcc  14760

aaggaggtgg gccacaccca ggaagggaaa gcgggcagcc ccgttttggg gacgtgaacg  14820

ttttaataat ttttgctgaa ttcctttaca actaaataac acagatattg ttataaataa  14880

aattgtaaaa aaaaaaaaaa aaaaa                                       14905
```

<210> SEQ ID NO 4
<211> LENGTH: 14907
<212> TYPE: DNA
<213> ORGANISM: Mus musculus
<300> PUBLICATION INFORMATION:
<308> DATABASE ACCESSION NUMBER: NM_008512.2
<309> DATABASE ENTRY DATE: 2010-05-16
<313> RELEVANT RESIDUES IN SEQ ID NO: (1)..(14907)

<400> SEQUENCE: 4

```
agtcagggga gcagcggtgc gagctccagg ccagtgcact gaggaggcgg aaacggggga     60

gcccctagtg ctccatcagg cccctaccaa ggcaccccca tcgggtccac gccccccacc    120

ccccaccccg cctcctccca attgtgcatt tttgcagcca gaggcggctc cgagatgggg    180

ctgtgagctt cgccctggga gggggagagg agcgaggagt aaagcagggg tgaagggttc    240

gaatttgggg gcagggggcg cacccgcgtc agcaggccct tcccaggggg ctcggaactg    300

taccatttca cctatgcccc tggttcgctt tgcttaagga aaggataaga atagaagagt    360

cggggagagg aagataaagg gggacccccc aattgggggg ggcgaggaca agaagtaaca    420

ggaccagagg gtgggggctg ctgtttgcat cggcccacac catgctgacc ccgccgttgc    480

tgctgctgct gccgctgctt tcagctctgg tctccggggc cactatggat gcccctaaaa    540

cttgcagccc taagcagttt gcctgcagag accaaatcac ctgtatctca aagggctggc    600

ggtgtgacgg tgaaagagat tgccccgacg gctctgatga agcccctgag atctgtccac    660

agagtaaagc ccagagatgc ccgccaaatg agcacagttg tctggggact gagctatgtg    720

tccccatgtc tcgtctctgc aacgggatcc aggactgcat ggatggctca gacgagggtg    780

ctcactgccg agagctccga gccaactgtt ctcgaatggg ttgtcaacac cattgtgtac    840

ctacacccag tgggcccacg tgctactgta acagcagctt ccagctgcag gcagatggca    900

agacgtgcaa agattttgac gagtgttccg tgtatggcac ctgcagccag ctttgcacca    960

acacagatgg ctccttcaca tgtggctgtg ttgaaggcta cctgctgcaa ccggacaacc   1020

gctcctgcaa ggccaagaat gagccagtag atcggccgcc agtgctactg attgccaact   1080

ctcagaacat cctagctacg tacctgagtg gggcccaagt gtctaccatc acacccacca   1140

gcacccgaca aaccacggcc atggacttca gttatgccaa tgagaccgta tgctgggtgc   1200

acgttgggga cagtgctgcc cagacacagc tcaagtgtgc ccggatgcct ggcctgaagg   1260

gctttgtgga tgagcatacc atcaacatct ccctcagcct gcaccacgtg gagcagatgg   1320

caatcgactg gctgacggga aacttctact ttgtcgacga cattgacgac aggatctttg   1380
```

-continued

```
tctgtaaccg aaacggggac acctgtgtca ctctgctgga cctggaactc tacaacccca   1440

aaggcatcgc cttggacccc gccatgggga aggtgttctt cactgactac gggcagatcc   1500

caaaggtgga gcgctgtgac atggatggac agaaccgcac caagctggtg gatagcaaga   1560

tcgtgtttcc acacggcatc accctggacc tggtcagccg cctcgtctac tgggcggacg   1620

cctacctaga ctacatcgag gtggtagact acgaagggaa gggtcggcag accatcatcc   1680

aaggcatcct gatcgagcac ctgtacggcc tgaccgtgtt tgagaactat ctctacgcca   1740

ccaactcgga caatgccaac acgcagcaga agacgagcgt gatccgagtg aaccggttca   1800

acagtactga gtaccaggtc gtcacccgtg tggacaaggg tggtgccctg catatctacc   1860

accagcgacg ccagccccga gtgcggagtc acgcctgtga gaatgaccag tacgggaagc   1920

caggtggctg ctccgacatc tgcctcctgg ccaacagtca caaggcaagg acctgcaggt   1980

gcaggtctgg cttcagcctg ggaagtgatg ggaagtcttg taagaaacct gaacatgagc   2040

tgttcctcgt gtatggcaag ggccgaccag gcatcattag aggcatggac atgggggcca   2100

aggtcccaga tgagcacatg atccccatcg agaaccttat gaatccacgc gctctggact   2160

tccacgccga gaccggcttc atctactttg ctgacaccac cagctacctc attggccgcc   2220

agaaaattga tggcacggag agagagacta tcctgaagga tggcatccac aatgtggagg   2280

gcgtagccgt ggactggatg ggagacaatc tttactggac tgatgatggc cccaagaaga   2340

ccattagtgt ggccaggctg gagaaagccg ctcagacccg gaagactcta attgagggca   2400

agatgacaca ccccagggcc attgtagtgg atccactcaa tgggtggatg tactggacag   2460

actgggagga ggaccccaag gacagtcggc gagggcggct cgagagggct tggatggacg   2520

gctcacaccg agatatcttt gtcacctcca agacagtgct ttggcccaat gggctaagcc   2580

tggatatccc agccggacgc ctctactggg tggatgcctt ctatgaccga attgagacca   2640

tactgctcaa tggcacagac cggaagattg tatatgaggg tcctgaactg aatcatgcct   2700

tcggcctgtg tcaccatggc aactacctct tttggaccga gtaccggagc ggcagcgtct   2760

accgcttgga acggggcgtg gcaggcgcac cgcccactgt gacccttctg cgcagcgaga   2820

gaccgcctat ctttgagatc cgaatgtacg acgcgcagca gcagcaagtg ggtaccaaca   2880

aatgccgggt aaataacgga ggctgcagca gcctgtgcct cgccaccccc gggagccgcc   2940

agtgtgcctg tgccgaggac caggtgttgg acacagatgg tgtcacctgc ttggcgaacc   3000

catcctacgt gcccccaccc cagtgccagc cgggcgagtt tgcctgtgcc aacaaccgct   3060

gcatccagga gcgctggaag tgtgacggag acaacgactg tctggacaac agcgatgagg   3120

ccccagcact gtgccatcaa cacacctgtc cctcggaccg attcaagtgt gagaacaacc   3180

ggtgtatccc caaccgctgg ctctgtgatg gggataatga ttgtggcaac agcgaggacg   3240

aatccaatgc cacgtgctca gcccgcacct gtccacccaa ccagttctcc tgtgccagtg   3300

gccgatgcat tcctatctca tggacctgtg atctggatga tgactgtggg gaccggtccg   3360

atgagtcagc ctcatgcgcc taccccacct gcttccccct gactcaattt acctgcaaca   3420

atggcagatg tattaacatc aactggcggt gtgacaacga caatgactgt ggggacaaca   3480

gcgacgaagc cggctgcagt cactcctgct ccagtaccca gttcaagtgc aacagtggca   3540

gatgcatccc cgagcactgg acgtgtgatg gggacaatga ttgtggggac tacagcgacg   3600

agacacacgc caactgtacc aaccaggcta caagacctcc tggtggctgc cactcggatg   3660

agttccagtg ccgcctagat ggcctgtgca tcccctgag gtggcgctgc gacggggaca   3720
```

-continued ccgactgcat ggattccagc gatgagaaga gctgtgaggg cgtgacccat gtttgtgacc 3780
cgaatgtcaa gtttggctgc aaggactccg cccggtgcat cagcaaggcg tgggtgtgtg 3840
atggcgacag cgactgtgaa gataactccg acgaggagaa ctgtgaggcc ctggcctgca 3900
ggccaccctc ccatccctgc gccaacaaca cctctgtctg cctgcctcct gacaagctgt 3960
gcgacggcaa ggatgactgt ggagacggct cggatgaggg cgagctctgt gaccagtgtt 4020
ctctgaataa tggtggctgt agtcacaact gctcagtggc ccctggtgaa ggcatcgtgt 4080
gctcttgccc tctgggcatg gagctgggct ctgacaacca cacctgccag atccagagct 4140
actgtgccaa gcacctcaaa tgcagccaga agtgtgacca gaacaagttc agtgtgaagt 4200
gctcctgcta cgagggctgg gtcttggagc ctgacgggga aagctgccgc agtctggatc 4260
ccttcaaacc gttcatcatc ttctccaacc gccacgagat caggcgcatt gaccttcaca 4320
agggggacta cagcgtccta gtgcctggcc tgcgcaacac tattgccctg gacttccacc 4380
tcagccagag tgccctctac tggaccgacg tggtagagga caagatctac cgtgggaaac 4440
tcctggacaa cggagccctg accagctttg aggtggtgat tcagtatggc ttggccacac 4500
cagagggcct ggctgtagat tggattgcag gcaacatcta ctgggtggag agcaacctgg 4560
accagatcga agtggccaag ctggacggaa ccctccgaac cactctgctg gcgggtgaca 4620
ttgagcaccc gagggccatc gctctggacc ctcgggatgg gattctgttt tggacagact 4680
gggatgccag cctgccacga atcgaggctg cgtccatgag tggggctggc cgccgaacca 4740
tccaccggga gacaggctct gggggctggc ccaacgggct caccgtggat tacctggaga 4800
agcgcatcct ctggattgat gctaggtcag atgccatcta ttcagcccgg tatgacggct 4860
ccggccacat ggaggtgctt cggggacacg agttcctgtc acacccattt gccgtgacac 4920
tgtacggtgg ggaggtgtac tggaccgact ggcgaacaaa tacactggct aaggccaaca 4980
agtggactgg ccacaacgtc accgtggtac agaggaccaa cacccagccc ttcgacctgc 5040
aggtgtatca cccttcccgg cagcccatgg ctccaaaccc atgtgaggcc aatggcggcc 5100
ggggcccctg ttcccatctg tgcctcatca actacaaccg gaccgtctcc tgcgcctgtc 5160
cccacctcat gaagctgcac aaggacaaca ccacctgcta tgagtttaag aagttcctgc 5220
tgtacgcacg tcagatggag atccggggcg tggacctgga tgccccgtac tacaattata 5280
tcatctcctt cacggtgcct gatatcgaca atgtcacggt gctggactat gatgcccgag 5340
agcagcgagt ttactggtct gatgtgcgga ctcaagccat caaaagggca tttatcaacg 5400
gcactggcgt ggagaccgtt gtctctgcag acttgcccaa cgcccacggg ctggctgtgg 5460
actgggtctc ccgaaatctg ttttggacaa gttacgacac caacaagaag cagattaacg 5520
tggcccggct ggacggctcc ttcaagaatg cggtggtgca gggcctggag cagccccacg 5580
gcctggtcgt ccacccgctt cgtggcaagc tctactggac tgatggggac aacatcagca 5640
tggccaacat ggatgggagc aaccacactc tgctcttcag tggccagaag ggccctgtgg 5700
ggttggccat tgacttccct gagagcaaac tctactggat cagctctggg aaccacacaa 5760
tcaaccgttg caatctggat gggagcgagc tggaggtcat cgacaccatg cggagccagc 5820
tgggcaaggc cactgccctg gccatcatgg gggacaagct gtggtgggca gatcaggtgt 5880
cagagaagat gggcacgtgc aacaaagccg atggctctgg gtccgtggtg ctgcggaaca 5940
gtaccacgtt ggttatgcac atgaaggtgt atgacgagag catccagcta gagcatgagg 6000
gcaccaaccc ctgcagtgtc aacaacggag actgttccca gctctgcctg ccaacatcag 6060
agacgactcg ctcctgtatg tgtacagccg gttacagcct ccggagcgga cagcaggcct 6120

-continued

```
gtgagggtgt gggctctttt ctcctgtact ctgtacatga gggaattcgg gggattccac   6180
tagatcccaa tgacaagtcg gatgccctgg tcccagtgtc cggaacttca ctggctgtcg   6240
gaatcgactt ccatgccgaa aatgacacta tttattgggt ggatatgggc ctaagcacca   6300
tcagcagggc caagcgtgac cagacatggc gagaggatgt ggtgaccaac ggtattggcc   6360
gtgtggaggg catcgcggtg gactggatcg caggcaacat atactggacg gaccagggct   6420
tcgatgtcat cgaggttgcc cggctcaatg gctcttttcg ttatgtggtc atttcccagg   6480
gtctggacaa gcctcgggcc atcactgtcc acccagagaa ggggtacttg ttctggaccg   6540
agtggggtca ttacccacgt attgagcggt ctcgccttga tggcacagag agagtggtgt   6600
tggttaatgt cagcatcagc tggcccaatg gcatctcagt agactatcag ggcggcaagc   6660
tctactggtg tgatgctcgg atggacaaga tcgagcgcat cgacctggaa acgggcgaga   6720
accgggaggt ggtcctgtcc agcaataaca tggatatgtt ctccgtgtcc gtgtttgagg   6780
acttcatcta ctggagtgac agaactcacg ccaatggctc catcaagcgc ggctgcaaag   6840
acaatgctac agactccgtg cctctgagga caggcattgg tgttcagctt aaagacatca   6900
aggtcttcaa cagggacagg cagaagggta ccaatgtgtg cgcggtagcc aacggcgggt   6960
gccagcagct ctgcttgtat cggggtggcg gacagcgagc ctgtgcctgt gcccacggga   7020
tgctggcaga agacggggcc tcatgccgag agtacgctgg ctacctgctc tactcagagc   7080
ggaccatcct caagagcatc cacctgtcgg atgagcgtaa cctcaacgca ccggtgcagc   7140
cctttgaaga ccccgagcac atgaaaaatg tcatcgccct ggcctttgac taccgagcag   7200
gcacctcccc ggggacccct aaccgcatct tcttcagtga catccacttt gggaacatcc   7260
agcagatcaa tgacgatggc tcgggcagga ccaccatcgt ggaaaatgtg ggctctgtgg   7320
aaggcctggc ctatcaccgt ggctgggaca cactgtactg gacaagctac accacatcca   7380
ccatcacccg ccacaccgtg gaccagactc gcccaggggc cttcgagagg gagacagtca   7440
tcaccatgtc cggagacgac cacccgagag cctttgtgct ggatgagtgc cagaacctga   7500
tgttctggac caattggaac gagctccatc caagcatcat gcgggcagcc ctatccggag   7560
ccaacgtcct gaccctcatt gagaaggaca tccgcacgcc caatgggttg gccatcgacc   7620
accgggcgga gaagctgtac ttctcggatg ccaccttgga caagatcgag cgctgcgagt   7680
acgacggctc ccaccgctat gtgatcctaa agtcggagcc cgtccacccc tttgggttgg   7740
cggtgtacgg agagcacatt ttctggactg actgggtgcg gcgggctgtg cagcgagcca   7800
acaagtatgt gggcagcgac atgaagctgc ttcgggtgga cattccccag caacccatgg   7860
gcatcatcgc cgtggccaac gacaccaaca gctgtgaact ctccccctgc cgtatcaaca   7920
atggaggctg ccaggatctg tgtctgctca cccaccaagg ccacgtcaac tgttcctgtc   7980
gagggggccg gatcctccag gaggacttca cctgccgggc tgtgaactcc tcttgtcggg   8040
cacaagatga gtttgagtgt gccaatgggg aatgtatcag cttcagcctc acctgtgatg   8100
gcgtctccca ctgcaaggac aagtccgatg agaagccctc ctactgcaac tcacgccgct   8160
gcaagaagac tttccgccag tgtaacaatg gtcgctgtgt atccaacatg ctgtggtgca   8220
atggggtgga tgactgtggg gatggctctg atgagattcc ttgcaacaag actgcctgtg   8280
gtgtgggtga gttccgctgc cgggatgggt cctgcatcgg gaactccagt cgctgcaacc   8340
agtttgtgga ttgtgaggat gcctcggatg agatgaattg cagtaccaca gactgcagca   8400
gctatttccg cctgggcgtg aaaggtgtcc tcttccagcc gtgcgagcgg acatccctgt   8460
```

-continued

```
gctacgcacc tagctgggtg tgtgatggcg ccaacgactg tggagactac agcgatgaac   8520
gtgactgtcc aggtgtgaag cgccctaggt gcccgctcaa ttactttgcc tgccccagcg   8580
ggcgctgtat ccccatgagc tggacgtgtg acaaggagga tgactgtgag aacggcgagg   8640
acgagaccca ctgcaacaag ttctgctcag aggcacagtt cgagtgccag aaccaccggt   8700
gtatctccaa gcagtggctg tgtgacggta gcgatgattg cggggatggc tccgatgagg   8760
cagctcactg tgaaggcaag acatgtggcc cctcctcctt ctcctgtccc ggcacccacg   8820
tgtgtgtccc tgagcgctgg ctctgtgatg gcgacaagga ctgtaccgat ggcgcggatg   8880
agagtgtcac tgctggctgc ctgtacaaca gcacctgtga tgaccgtgag ttcatgtgcc   8940
agaaccgctt gtgtattccc aagcatttcg tgtgcgacca tgaccgtgac tgtgctgatg   9000
gctctgatga atcccctgag tgtgagtacc caacctgcgg ccccaatgaa ttccgctgtg   9060
ccaatgggcg ttgtctgagc tcccgtcagt gggaatgtga tggggagaat gactgtcacg   9120
accacagcga tgaggctccc aagaacccac actgcaccag cccagagcac aaatgcaatg   9180
cctcatcaca gttcctgtgc agcagcgggc gctgcgtggc tgaggcgttg ctctgcaacg   9240
gccaggacga ctgtggggac ggttcagacg aacgcgggtg ccatgtcaac gagtgtctca   9300
gccgcaagct cagtggctgc agtcaggact gcgaggacct caagataggc tttaagtgcc   9360
gctgtcgccc gggcttccgg ctaaaggacg atggcaggac ctgtgccgac ctggatgagt   9420
gcagcaccac cttcccctgc agccagctct gcatcaacac ccacggaagt tacaagtgtc   9480
tgtgtgtgga gggctatgca ccccgtggcg gtgacccccca cagctgcaaa gctgtgaccg   9540
atgaggagcc atttctcatc tttgccaacc ggtactacct gcggaagctc aacctggacg   9600
gctccaacta cacactgctt aagcagggcc tgaacaatgc ggtcgccttg gactttgact   9660
accgagagca gatgatctac tggacggacg tgaccaccca gggcagcatg attcgcagga   9720
tgcacctcaa cggcagcaac gtgcaggttc tgcaccggac gggccttagt aacccagatg   9780
ggctggctgt ggactgggtg ggtggcaacc tgtactggtg tgacaagggc agagatacca   9840
ttgaggtgtc caagcttaac ggggcctatc ggacagtgct ggtcagctct ggcctccggg   9900
agcccagagc tctggtagtg gatgtacaga atgggtacct gtactggaca gactggggtg   9960
accactcact gatcggccgg attggcatgg atggatctgg ccgcagcatc atcgtggaca  10020
ctaagatcac atggcccaat ggcctgaccg tggactacgt cacggaacgc atctactggg  10080
ctgacgcccg tgaggactac atcgagttcg ccagcctgga tggctccaac cgtcacgttg  10140
tgctgagcca agacatccca cacatctttg cgctgaccct atttgaagac tacgtctact  10200
ggacagactg ggaaacgaag tccatcaacc gggcccacaa gaccacgggt gccaacaaaa  10260
cactcctcat cagcaccctg caccggccca tggacttaca tgtattccac gccctgcgcc  10320
agccagatgt gcccaatcac ccctgcaaag tcaacaatgg tggctgcagc aacctgtgcc  10380
tgctgtcccc tgggggtggt cataaatgcg cctgccccac caacttctat ctgggtggcg  10440
atggccgtac ctgtgtgtcc aactgcacag caagccagtt tgtgtgcaaa aatgacaagt  10500
gcatcccctt ctggtggaag tgtgacacgg aggacgactg tggggatcac tcagacgagc  10560
ctccagactg tcccgagttc aagtgccgcc caggccagtt ccagtgctcc accggcatct  10620
gcaccaaccc tgccttcatc tgtgatgggg acaatgactg ccaagacaat agtgatgagg  10680
ccaattgcga cattcacgtc tgcttgccca gccaattcaa gtgcaccaac accaaccgct  10740
gcattcctgg catcttccgt tgcaatgggc aggacaactg cggggacggc gaggatgagc  10800
gggattgccc tgaggtgacc tgcgccccca accagttcca gtgctccatc accaagcgct  10860
```

gcatccctcg cgtctgggtc tgtgacaggg ataatgactg tgtggacggc agtgatgagc 10920
ctgccaactg tacccaaatg acctgtggag tggatgagtt ccgctgcaag gattctggcc 10980
gctgcatccc cgcgcgctgg aagtgtgacg gagaagatga ctgtggggat ggttcagatg 11040
agcccaagga agagtgtgat gagcgcacct gtgagccata ccagttccgc tgcaaaaaca 11100
accgctgtgt cccaggccgt tggcaatgtg actacgacaa cgactgcgga gataactcgg 11160
acgaggagag ctgcacacct cggccctgct ctgagagtga gttttcctgt gccaatggcc 11220
gctgcatcgc tgggcgctgg aagtgtgatg gggaccatga ctgtgccgac ggctcagacg 11280
agaaagactg cacccccgc tgtgatatgg accagttcca gtgcaagagt ggccactgca 11340 tcccctgcg ctggcgctgt gacgcggatg ctgactgtat ggacggcagt gacgaggaag 11400
cctgtggcac tggggtgagg acctgcccat tggatgagtt tcaatgtaac aacaccttgt 11460
gcaagccgct ggcctggaag tgtgatggag aggacgactg tggggacaac tcagatgaga 11520
accccgagga atgcgcccgg ttcatctgcc ctcccaaccg gcctttccgc tgcaagaatg 11580
accgagtctg cctgtggatt gggcgccagt gtgatggcgt ggacaactgt ggagatggga 11640
ctgacgagga ggactgtgag cccccacgg cccagaaccc ccactgcaaa gacaagaagg 11700
agttcctgtg ccgaaaccag cgctgtctat catcctccct gcgctgtaac atgttcgatg 11760
actgcggcga tggctccgat gaagaagatt gcagcatcga ccccaagctg accagctgtg 11820
ccaccaatgc cagcatgtgt ggggacgaag ctcgttgtgt gcgcactgag aaagctgcct 11880
actgtgcctg ccgctcgggc ttccatactg tgccgggcca gcccggatgc caggacatca 11940
acgagtgcct gcgctttggt acctgctctc agctctgcaa caacaccaag ggaggccacc 12000
tctgcagctg tgcccgcaac ttcatgaaga cacacaacac ctgcaaagct gaaggctccg 12060
agtaccaggt gctatacatc gcggatgaca acgagatccg cagcttgttc ccgggccacc 12120
cccactcagc ctacgagcag acattccagg gcgatgagag tgtccgcata gatgccatgg 12180
atgtccatgt caaggccggc cgtgtctact ggactaactg gcacacgggc acaatctcct 12240
acaggagcct gcccctgcc gcccctccta ccacttccaa ccgccaccgg aggcagatcg 12300
accggggtgt cacccacctc aatatttcag ggctgaagat gccgaggggt atcgctatcg 12360
actgggtggc cgggaatgtg tactggaccg attccggccg agacgtgatt gaggtggcgc 12420
aaatgaaggg cgagaaccgc aagacgctca tctcgggcat gattgatgag ccccatgcca 12480
tcgtggtgga ccctctgagg ggcaccatgt actggtcaga ctgggggaac caccccaaga 12540
ttgaaacagc agcgatggat ggcacccttc gggagactct cgtgcaagac aacattcagt 12600
ggcctacagg gctggctgtg gactatcaca atgaacggct ctactgggca gatgccaagc 12660
tttcggtcat cggcagcatc cggctcaacg gcactgaccc cattgtggct gctgacagca 12720
aacgaggcct aagtcacccc ttcagcatcg atgtgtttga agactacatc tacggagtca 12780
cttacatcaa taatcgtgtc ttcaagatcc acaagtttgg acacagcccc ttgatcaacc 12840
taactggggg cctgagccat gcctctgatg tagtccttta ccatcaacac aagcagcctg 12900
aagtgaccaa cccctgtgac cgcaagaaat gtgaatggct gtgtctgctg agccccagcg 12960
ggcctgtctg cacctgtccc aatggaaaga ggctggataa tggcacctgt gtgcctgtgc 13020
cctctccaac accccctcca gatgccccta ggcctggaac ctgcactctg cagtgcttca 13080
atggtggtag ttgtttcctc aatgctcgga ggcagcccaa gtgccgttgc cagccccgtt 13140
acacaggcga taagtgtgag ctggatcagt gctgggaata ctgtcacaac ggaggcacct 13200
gtgcggcttc cccatctggc atgcccacgt gccgctgtcc cactggcttc acgggcccca 13260
aatgcaccgc acaggtgtgt gcaggctact gctctaacaa cagcacctgc accgtcaacc 13320
agggcaacca gccccagtgc cgatgtctac ctggcttcct gggcgaccgt tgccagtacc 13380
ggcagtgctc tggcttctgt gagaactttg gcacctgtca gatggctgct gatggctccc 13440
gacaatgtcg ctgcaccgtc tactttgagg gaccaaggtg tgaggtgaac aagtgtagtc 13500
gctgtctcca aggcgcctgt gtggtcaata agcagaccgg agatgtcaca tgcaactgca 13560
ctgatggccg ggtagccccc agttgtctga cctgcatcga tcactgtagc aatggtggct 13620
cctgcaccat gaacagcaag atgatgcctg agtgccagtg cccgccccat atgacaggac 13680
cccggtgcga ggagcaggtt gttagtcagc aacagcctgg gcatatggcc tccatcctga 13740
tccctctgct gctgcttctc ctgctgcttc tggtggctgg cgtggtgttc tggtataagc 13800
ggcgagtccg aggggctaag ggcttccagc accagcggat gaccaatggg gccatgaatg 13860
tggaaattgg aaaccctacc tacaagatgt atgaaggtgg agagcccgat gatgtcgggg 13920
gcctactgga tgctgatttt gcccttgacc ctgacaagcc taccaacttc accaacccag 13980
tgtatgccac gctctacatg gggggccacg gcagccgcca ttccctggcc agcacggacg 14040
agaagcgaga actgctgggc cggggacctg aagacgagat aggagatccc ttggcatagg 14100
gccctgcccc gacggatgtc cccagaaagc cccctgccac atgagtcttt caatgaaccc 14160
cctccccagc cggcccttct ccggccctgc cgggtgtaca aatgtaaaaa tgaaggaatt 14220
actttttata tgtgagcgag caagcgagca agcacagtat tatctctttg catttccttc 14280
ctgcctgctc ctcagtatcc cccccatgct gccttgaggg ggcggggagg gctttgtggc 14340
tcaaaggtat gaaggagtcc acatgttccc taccgagcat acccctggaa gctggcggca 14400
cggcctcccc accacgcctg tgcaagacac tcaacggggc tccgtgtccc agctttcctt 14460
tccttggctc tctggggtta gttcagggga ggtggagtcc tctgctgacc ctgtctggaa 14520
gatttggctc tagctgagga aggagtcttt tagttgaggg aagtcacccc aaaccccagc 14580
tcccactttc aggggcacct ctcagatggc catgctcagt atcccttcca gacaggccct 14640
cccctctcta gcgccccctc tgtggctcct agggctgaac acattctttg gtaactgtcc 14700
cccaagcctc ccatccccct gagggccagg aagagtcggg gcacaccaag gaagggcaag 14760
cgggcagccc cattttgggg acgtgaacgt tttaataatt tttgctgaat tcctttacaa 14820
ctaaataaca cagatattgt tataaataaa attgtaaaaa aggaaaaaaa aaagaaaaga 14880
aaagaaaaga aaaaaaaaaa aaaaaaa 14907

<210> SEQ ID NO 5
<211> LENGTH: 5265
<212> TYPE: DNA
<213> ORGANISM: Homo sapiens
<300> PUBLICATION INFORMATION:
<308> DATABASE ACCESSION NUMBER: NM_000527
<309> DATABASE ENTRY DATE: 2010-08-01
<313> RELEVANT RESIDUES IN SEQ ID NO: (1)..(5265)

<400> SEQUENCE: 5
acatttgaaa atcaccccac tgcaaactcc tccccctgct agaaacctca cattgaaatg 60
ctgtaaatga cgtgggcccc gagtgcaatc gcgggaagcc agggtttcca gctaggacac 120
agcaggtcgt gatccgggtc gggacactgc ctggcagagg ctgcgagcat ggggccctgg 180
ggctggaaat tgcgctggac cgtcgccttg ctcctcgccg cggcggggac tgcagtgggc 240
gacagatgcg aaagaaacga gttccagtgc caagacggga aatgcatctc ctacaagtgg 300

-continued

```
gtctgcgatg gcagcgctga gtgccaggat ggctctgatg agtcccagga gacgtgcttg    360
tctgtcacct gcaaatccgg ggacttcagc tgtgggggcc gtgtcaaccg ctgcattcct    420
cagttctgga ggtgcgatgg ccaagtggac tgcgacaacg gctcagacga gcaaggctgt    480
ccccccaaga cgtgctccca ggacgagttt cgctgccacg atgggaagtg catctctcgg    540
cagttcgtct gtgactcaga ccgggactgc ttggacggct cagacgaggc ctcctgcccg    600
gtgctcacct gtggtcccgc cagcttccag tgcaacagct ccacctgcat cccccagctg    660
tgggcctgcg acaacgaccc cgactgcgaa gatggctcgg atgagtggcc gcagcgctgt    720
aggggtcttt acgtgttcca aggggacagt agcccctgct cggccttcga gttccactgc    780
ctaagtggcg agtgcatcca ctccagctgg cgctgtgatg gtggccccga ctgcaaggac    840
aaatctgacg aggaaaactg cgctgtggcc acctgtcgcc ctgacgaatt ccagtgctct    900
gatggaaact gcatccatgg cagccggcag tgtgaccggg aatatgactg caaggacatg    960
agcgatgaag ttggctgcgt taatgtgaca ctctgcgagg gacccaacaa gttcaagtgt   1020
cacagcggcg aatgcatcac cctggacaaa gtctgcaaca tggctagaga ctgccgggac   1080
tggtcagatg aacccatcaa agagtgcggg accaacgaat gcttggacaa caacggcggc   1140
tgttcccacg tctgcaatga ccttaagatc ggctacgagt gcctgtgccc cgacggcttc   1200
cagctggtgg cccagcgaag atgcgaagat atcgatgagt gtcaggatcc cgacacctgc   1260
agccagctct gcgtgaacct ggagggtggc tacaagtgcc agtgtgagga aggcttccag   1320
ctggaccccc acacgaaggc ctgcaaggct gtgggctcca tcgcctacct cttcttcacc   1380
aaccggcacg aggtcaggaa gatgacgctg gaccggagcg agtacaccag cctcatcccc   1440
aacctgagga acgtggtcgc tctggacacg gaggtggcca gcaatagaat ctactggtct   1500
gacctgtccc agagaatgat ctgcagcacc cagcttgaca gagcccacgg cgtctcttcc   1560
tatgacaccg tcatcagcag agacatccag gcccccgacg ggctggctgt ggactggatc   1620
cacagcaaca tctactggac cgactctgtc ctgggcactg tctctgttgc ggataccaag   1680
ggcgtgaaga ggaaaacgtt attcagggag aacggctcca agccaagggc catcgtggtg   1740
gatcctgttc atggcttcat gtactggact gactggggaa ctcccgccaa gatcaagaaa   1800
gggggcctga atggtgtgga catctactcg ctggtgactg aaaacattca gtggcccaat   1860
ggcatcaccc tagatctcct cagtggccgc ctctactggg ttgactccaa acttcactcc   1920
atctcaagca tcgatgtcaa cgggggcaac cggaagacca tcttggagga tgaaaagagg   1980
ctggcccacc ccttctcctt ggccgtcttt gaggacaaag tattttggac agatatcatc   2040
aacgaagcca ttttcagtgc caaccgcctc acaggttccg atgtcaactt gttggctgaa   2100
aacctactgt ccccagagga tatggttctc ttccacaacc tcacccagcc aagaggagtg   2160
aactggtgtg agaggaccac cctgagcaat ggcggctgcc agtatctgtg cctccctgcc   2220
ccgcagatca acccccactc gcccaagttt acctgcgcct gcccggacgg catgctgctg   2280
gccagggaca tgaggagctg cctcacagag gctgaggctg cagtggccac ccaggagaca   2340
tccaccgtca ggctaaaggt cagctccaca gccgtaagga cacagcacac aaccacccga   2400
cctgttcccg acacctcccg gctgcctggg gccacccctg ggctcaccac ggtggagata   2460
gtgacaatgt ctcaccaagc tctgggcgac gttgctggca gaggaaatga gaagaagccc   2520
agtagcgtga gggctctgtc cattgtcctc cccatcgtgc tcctcgtctt cctttgcctg   2580
ggggtcttcc ttctatggaa gaactggcgg cttaagaaca tcaacagcat caactttgac   2640
```

-continued

```
aaccccgtct atcagaagac cacagaggat gaggtccaca tttgccacaa ccaggacggc   2700
tacagctacc cctcgagaca gatggtcagt ctggaggatg acgtggcgtg aacatctgcc   2760
tggagtcccg tccctgccca gaacccttcc tgagacctcg ccggccttgt tttattcaaa   2820
gacagagaag accaaagcat tgcctgccag agctttgttt tatatattta ttcatctggg   2880
aggcagaaca ggcttcggac agtgcccatg caatggcttg ggttgggatt ttggtttctt   2940
cctttcctcg tgaaggataa gagaaacagg cccgggggga ccaggatgac acctccattt   3000
ctctccagga agttttgagt ttctctccac cgtgacacaa tcctcaaaca tggaagatga   3060
aaggggaggg gatgtcaggc ccagagaagc aagtggcttt caacacacaa cagcagatgg   3120
caccaacggg accccctggc cctgcctcat ccaccaatct ctaagccaaa cccctaaact   3180
caggagtcaa cgtgtttacc tcttctatgc aagccttgct agacagccag gttagccttt   3240
gccctgtcac ccccgaatca tgacccaccc agtgtctttc gaggtgggtt tgtaccttcc   3300
ttaagccagg aaagggattc atggcgtcgg aaatgatctg gctgaatccg tggtggcacc   3360
gagaccaaac tcattcacca aatgatgcca cttcccagag gcagagcctg agtcactggt   3420
caccccttaat atttattaag tgcctgagac acccggttac cttggccgtg aggacacgtg   3480
gcctgcaccc aggtgtggct gtcaggacac cagcctggtg cccatcctcc cgacccctac   3540
ccacttccat tcccgtggtc tccttgcact ttctcagttc agagttgtac actgtgtaca   3600
tttggcattt gtgttattat tttgcactgt tttctgtcgt gtgtgttggg atgggatccc   3660
aggccaggga aagcccgtgt caatgaatgc cggggacaga gaggggcagg ttgaccggga   3720
cttcaaagcc gtgatcgtga atatcgagaa ctgccattgt cgtctttatg tccgcccacc   3780
tagtgcttcc acttctatgc aaatgcctcc aagccattca cttccccaat cttgtcgttg   3840
atgggtatgt gtttaaaaca tgcacggtga ggccgggcgc agtggctcac gcctgtaatc   3900
ccagcacttt gggaggccga ggcgggtgga tcatgaggtc aggagatcga gaccatcctg   3960
gctaacacgt gaaaccccgt ctctactaaa aatacaaaaa attagccggg cgtggtggcg   4020
ggcacctgta gtcccagcta ctcgggaggc tgaggcagga gaatggtgtg aacccgggaa   4080
gcggagcttg cagtgagccg agattgcgcc actgcagtcc gcagtctggc ctgggcgaca   4140
gagcgagact ccgtctcaaa aaaaaaaaac aaaaaaaaac catgcatggt gcatcagcag   4200
cccatggcct ctggccaggc atggcgaggc tgaggtggga ggatggtttg agctcaggca   4260
tttgaggctg tcgtgagcta tgattatgcc actgctttcc agcctgggca acatagtaag   4320
accccatctc ttaaaaaatg aatttggcca gacacaggtg cctcacgcct gtaatcccag   4380
cactttggga ggctgagctg gatcacttga gttcaggagt tggagaccag gcctgagcaa   4440
caaagcgaga tcccatctct acaaaaacca aaaagttaaa aatcagctgg gtacggtggc   4500
acgtgcctgt gatcccagct acttgggagg ctgaggcagg aggatcgcct gagcccagga   4560
ggtggaggtt gcagtgagcc atgatcgagc cactgcactc cagcctgggc aacagatgaa   4620
gaccctattt cagaaataca actataaaaa aataaataaa tcctccagtc tggatcgttt   4680
gacgggactt caggttcttt ctgaaatcgc cgtgttactg ttgcactgat gtccggagag   4740
acagtgacag cctccgtcag actcccgcgt gaagatgtca caagggattg gcaattgtcc   4800
ccagggacaa aacactgtgt cccccccagt gcagggaacc gtgataagcc tttctggttt   4860
cggagcacgt aaatgcgtcc ctgtacagat agtggggatt ttttgttatg tttgcacttt   4920
gtatattggt tgaaactgtt atcacttata tatatatata tacacacata tatataaaat   4980
ctatttattt ttgcaaaccc tggttgctgt atttgttcag tgactattct cggggccctg   5040
```

tgtagggggt tattgcctct gaaatgcctc ttctttatgt acaaagatta tttgcacgaa 5100
ctggactgtg tgcaacgctt tttgggagaa tgatgtcccc gttgtatgta tgagtggctt 5160
ctgggagatg ggtgtcactt tttaaaccac tgtatagaag gtttttgtag cctgaatgtc 5220
ttactgtgat caattaaatt tcttaaatga accaatttgt ctaaa 5265

<210> SEQ ID NO 6
<211> LENGTH: 1223
<212> TYPE: DNA
<213> ORGANISM: Homo sapiens
<300> PUBLICATION INFORMATION:
<308> DATABASE ACCESSION NUMBER: NM_000041.2
<309> DATABASE ENTRY DATE: 2010-08-15
<313> RELEVANT RESIDUES IN SEQ ID NO: (1)..(1223)

<400> SEQUENCE: 6
gggatccttg agtcctactc agccccagcg gaggtgaagg acgtccttcc ccaggagccg 60
actggccaat cacaggcagg aagatgaagg ttctgtgggc tgcgttgctg gtcacattcc 120
tggcaggatg ccaggccaag gtggagcaag cggtggagac agagccggag cccgagctgc 180
gccagcagac cgagtggcag agcggccagc gctgggaact ggcactgggt cgcttttggg 240
attacctgcg ctgggtgcag acactgtctg agcaggtgca ggaggagctg ctcagctccc 300
aggtcaccca ggaactgagg gcgctgatgg acgagaccat gaaggagttg aaggcctaca 360
aatcggaact ggaggaacaa ctgaccccgg tggcggagga gacgcgggca cggctgtcca 420
aggagctgca ggcggcgcag gcccggctgg gcgcggacat ggaggacgtg tgcggccgcc 480
tggtgcagta ccgcggcgag gtgcaggcca tgctcggcca gagcaccgag gagctgcggg 540
tgcgcctcgc ctcccacctg cgcaagctgc gtaagcggct cctccgcgat gccgatgacc 600
tgcagaagcg cctggcagtg taccaggccg gggcccgcga gggcgccgag cgcggcctca 660
gcgccatccg cgagcgcctg gggcccctgg tggaacaggg ccgcgtgcgg gccgccactg 720
tgggctccct ggccggccag ccgctacagg agcgggccca ggcctggggc gagcggctgc 780
gcgcgcggat ggaggagatg ggcagccgga cccgcgaccg cctggacgag gtgaaggagc 840
aggtggcgga ggtgcgcgcc aagctggagg agcaggccca gcagatacgc ctgcaggccg 900
aggccttcca ggcccgcctc aagagctggt tcgagcccct ggtggaagac atgcagcgcc 960
agtgggccgg gctggtggag aaggtgcagg ctgccgtggg caccagcgcc gcccctgtgc 1020
ccagcgacaa tcactgaacg ccgaagcctg cagccatgcg accccacgcc accccgtgcc 1080
tcctgcctcc gcgcagcctg cagcgggaga ccctgtcccc gccccagccg tcctcctggg 1140
gtggacccta gtttaataaa gattcaccaa gtttcacgca aaaaaaaaaa aaaaaaaaaa 1200
aaaaaaaaaa aaaaaaaaaa aaa 1223

<210> SEQ ID NO 7
<211> LENGTH: 897
<212> TYPE: DNA
<213> ORGANISM: Homo sapiens
<300> PUBLICATION INFORMATION:
<308> DATABASE ACCESSION NUMBER: NM_000039
<309> DATABASE ENTRY DATE: 2010-08-15
<313> RELEVANT RESIDUES IN SEQ ID NO: (1)..(897)

<400> SEQUENCE: 7
agagactgcg agaaggaggt cccccacggc ccttcaggat gaaagctgcg gtgctgacct 60
tggccgtgct cttcctgacg gggagccagg ctcggcattt ctggcagcaa gatgaacccc 120

-continued

```
cccagagccc ctgggatcga gtgaaggacc tggccactgt gtacgtggat gtgctcaaag    180

acagcggcag agactatgtg tcccagtttg aaggctccgc cttgggaaaa cagctaaacc    240

taaagctcct tgacaactgg gacagcgtga cctccacctt cagcaagctg cgcgaacagc    300

tcggccctgt gacccaggag ttctgggata acctggaaaa ggagacagag ggcctgaggc    360

aggagatgag caaggatctg gaggaggtga aggccaaggt gcagccctac ctggacgact    420

tccagaagaa gtggcaggag gagatggagc tctaccgcca gaaggtggag ccgctgcgcg    480

cagagctcca agagggcgcg cgccagaagc tgcacgagct gcaagagaag ctgagcccac    540

tgggcgagga gatgcgcgac cgcgcgcgcg cccatgtgga cgcgctgcgc acgcatctgg    600

ccccctacag cgacgagctg cgccagcgct tggccgcgcg ccttgaggct ctcaaggaga    660

acggcggcgc cagactggcc gagtaccacg ccaaggccac cgagcatctg agcacgctca    720

gcgagaaggc caagcccgcg ctcgaggacc tccgccaagg cctgctgccc gtgctggaga    780

gcttcaaggt cagcttcctg agcgctctcg aggagtacac taagaagctc aacacccagt    840

gaggcgcccg ccgccgcccc ccttcccggt gctcagaata aacgtttcca aagtggg       897


<210> SEQ ID NO 8
<211> LENGTH: 1299
<212> TYPE: DNA
<213> ORGANISM: Homo sapiens

<400> SEQUENCE: 8

acgcccggga acccccgacc cctctgagcc cggggtactg cgcccgggtc tccacgccca     60

gagatgctcc ccggtctcca ccgtcgggca agccccaagc gcagcagcgc agagtcctgg    120

ggtcaccaga gctcgtacta ggacatcgtc tccccattta acaccgcctc cggtcccatc    180

tgagttgcaa gtggtgggga tgtggggctc cggatcaaag tccccgaaac cgagcacttc    240

ccgaagcctc cttggcctcg aaacaaaaca ataacgccca actccatcat attccagaac    300

tcccaccacc tgcatacaga cattcagctg cacaagcccc ctccatgcta cagtcaacag    360

gatctccagg ccacggctca agcccaggta ctcacatcag tggttctatc aacactcagg    420

acagacccat agaagaggcc caagcaggcc ctggaagtgc atgtggaggc caccaggcaa    480

ggaattctgg agtcccaggt actcataact ctgggtggca tggccccttt gcaccatgga    540

ctgtttgccc ttagaaaggg atggatctga gctgggcgca gtggctcatg cctgtaatcc    600

cagcactttg ggaggccaag gtgggcagct cacctcaggt caggttggtc tcaaactcct    660

gacctcaggc gatccacctc agcctctcaa agtgctggaa ttataggtgt gagccactgt    720

gcccagccca aaatcattct ttttggaatt ttgaagcata taattccaaa aggtatgaag    780

gtaatcactt agattgctct aataagggaa tgggaacagt taagtcctat acaaataaga    840

caaagataag atactacaaa aaggggatga gcccaagaaa aaaatcaaag tcccagagag    900

agaacagcca ttgattctaa atacacaagt ctatggcccc aacccaaact tgtttcacta    960

agaacaacct gtggtttcga gaatctggtc atccccccaca gtgaatacat gaacacattg  1020

taatgtttga aatgtttatt tttcttgttg atttcttact gttagaagag ctaagtgatt   1080

tggcccaaag tggctaagtg attcggccag tttgtacaca gggatataag tttgctgaca   1140

ccaagctcat actttacaaa tgtaatatct tcataaaaca aaaatactgg gccgggcgcg   1200

gtggctcacg cctgtaatcc cagcattttg ggaggccgag gcgggcggat catgagatca   1260

ggagatcgag accatcctgg ctagcagggt gaagccccg                          1299
```

<210> SEQ ID NO 9
<211> LENGTH: 917
<212> TYPE: DNA
<213> ORGANISM: Mus musculus

<400> SEQUENCE: 9
caaaatggcg tgctaccctg tccaaccttg tctgtagaca gagtcaattg aacactgtct 60
ttgggacttc cgtgcaactg aggtgggcgg gcttgaagca caaagctttc agggagaacc 120
aaactttatg cccaagctgc tctctgccac ccacagggta aatgaatctc atacaggaaa 180
ggcaagagac atgtgacact gttgtctgat ggtcacaagt caagcttttt aaaaagcagc 240
ctgatattgt gagctaacat ggctttctgt aattgaatgc aatgtatttt ctatgcttgt 300
ctgggtaaag ttgaccttgg tttgatttag ctcaagcaat atttcaacag tgcactgggg 360
ctctgagtcc cctgactact gtttgactag agccaggctc tgccctggat ggcaaccaac 420
agcccaggct ctggggcaca gccgggcttt gacaggtctg ggaaatgtt caccggagat 480 gaaaggtttc aaactatgaa actctaaaat ctcaagtcaa aacttttgac aagcacacac 540
aggacatgaa ttacaatcac ccgaagattt ttacaggctt ctcaatttta atgacatgct 600
gacacgtgtc atcagatctc acaacaagat gacacatggg tgtcaggtat ggcgcagaag 660
actagagtcg ggtgtaacc aatgagcatt gtctgttgga cacaggcgaa ttcggcaaac 720
ggacagtgct ggaggcagaa gggtttaaag aaggcaggaa agcccatgtt taacagaatg 780
gggtgacgaa gagggatggg aaggtctaac tcacccgggg gtgggggcac caggggggcc 840
cacggacaca gaaaaccacg caggtcaggc acctacaaag accgaaggaa aaagggacca 900
cgcagaaatc actcacg 917

<210> SEQ ID NO 10
<211> LENGTH: 1550
<212> TYPE: DNA
<213> ORGANISM: Homo sapiens

<400> SEQUENCE: 10
aaagtccaag gtgggaacag ataggtctgg gggcatgggg gctgggccta ataggggccg 60
ggcatggatg ggcctctcct gctcaccgat cctgggctgg gcatcttgtc cttggtgggt 120
gggggccaag gaaggagtgg tggggcttgg cccagagtct ggtgtggctg tgactgacca 180
cagcttgtga tgccccagcc aagacctcag gcacaccccg tcccccactc cgccccccct 240
gggttagaca actgagagtc acagtgtggt gggagaaggg acgtcattcc tctaagggac 300
aagcttttgg cccctcccca caccagggca ggtacttatg tcggggctta tgcagggcag 360
aagggctttg gccaggtcag ctgccagggg ctggggccca ggctccccag ggtctggcgt 420
ggtgcatcag gggcctggtg ggggcttacc gaggatgacg ggccgtgtgt ggttactgag 480
ctcagccttg ggcgtggtgt gcggggggaa gagcacattg aggagccaga agggggcggc 540
aggagggagc agcagcccca gcagcagcgt cacccactgc catggggagc cgggcggccc 600
cattccagcc ctggtgccta ctgccagaga aagcggcact gggctgtcct tatctggtgt 660
gggagtggga ggggccctag ggccagtggg agggacggcc tggccagtgg gggttgtggc 720
cagagattgc cggaaagggg cacagcctca gggagccggc tctgggcctg ggttcagttc 780
cgccttcttc tcttggcgcc aggggaaaca gagccggggc agcaggaggc ccagaactac 840
acaatgtttt attgaaaaag tcaggcctca gctcagctgt ctccattcgg ctcagcttgg 900
tggggggccc tgcccatagt agactgagcc agatcttcct gcaggcagct gggctggact 960
ccctccctgg ctacccttcc cttcgtctct gatggtgaca tccaaacaat aaatatgcaa 1020
taaatagcgc tcctgggctg ggccgggccg gctgccttca aaccccactc ggcccctacc 1080
agtcttctct ggccaggaca ggcctactgg ggtgctagat agtaaagtcc ccaaacatcc 1140
cagggtccca caagacctgg gatccatctc cattttgagg cccaggcctg gtttccaagg 1200
agacctagca aagctgggtc caggacaggg ccaggcaagc agggctggca ggtgggtgct 1260
gggaagaggc tgttacccca gaccacagct tgttatgtcc tggccaagac ctcgactcca 1320
ggccacaaga tgacactggg ctcaggagta gatggtgatg acttcacggc caccaccgcg 1380
caccaacagc acccgctcaa ggccctcggt cagcacctcg aggaactcca tgtagttctc 1440
gtcgccctca ctgttcctgg gtgggccagg catgtttagg agaaccaggc gggcgtcgtg 1500
ggagcgcgtg acaatgactt cattgagctt cacagcagtg tgcatgcgcc 1550

<210> SEQ ID NO 11
<211> LENGTH: 329
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (311)..(311)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t

<400> SEQUENCE: 11
tttaangttt gatgtttatt ggtggtgtct gatgagcgtt tctcttgtcc agactgtgtt 60
tctctctcca gaccagctcc cagggtacag ggggtgggga gtaggtggta gctgtgtcag 120
tgctgggccc tggngccact ccctagggaa gagcaggtgg ggcctcgggg ggtctggccc 180
tagctctggc agatccatcc tcagtgaagc acatccctgg ggcaaaggca ctcctgaggc 240
caagaccagc atgggcttga tggagccacc ccagggagcc ccaagagaga tgaagccatc 300
aataaagcgg nccttccagg cctgggnct 329

<210> SEQ ID NO 12
<211> LENGTH: 1826
<212> TYPE: DNA
<213> ORGANISM: Homo sapiens

<400> SEQUENCE: 12
tgtcactctg acctcagtgt aggcactgcc tcctctggga agtctttgct gacctgaaag 60
gctcagcctc ttgtgcttcc taagcttttc tcagagcatt tagcttcatt agtaattaaa 120
cttccattag tgaaatgatc tgattaatgg ttgtcactcc cagattttaa ttctaacttt 180 ttttttttt tttttttttg agacccagtc tcttttttttt tgagacagtc tcattctgcc 240
gcccagtctg gagtgcaacg acgtgatctc ggctcacggt gacctccacc tcccaggttc 300
aagtgattct cgtgcctcag cctcctgagt agctgggacg acagatgcat gccaccacgc 360
ctggcaaata ttttgtattt tagtagagac gggggtttct gccgtgttgg cctggctggt 420
ctcaaactcc tgagttcggg tgatccgcct gcctcggtct cccggggtgc cgggattaca 480

```
ggcgtgagcc accgtgcccg gcctctaaac acttgtggcc ctgtcattca cccagcactc    540
aaaaggtcgt ctcacctgcc cttttgggag ctgggagaga cagctcaaat tgtcaccgcc    600
cccccaccgc cccgtgctcc tctgacaggg ctgtgggtgg agccagctcc agtccccgcg    660
cccagcacag aggcaggcac ggtgcacact gcctcaacag ctcgaccagg agagtgggca    720
gctgtacatc tagggtgccc agctcagtcc caggcctcag cagagcccat cttgcctcac    780
tgcacacagc actgagcctg tggctggtga ggagtgaaac ctagtgtggg actctagtgc    840
ctcccttcaa cctgaaacat agccatcagg gcttacggta gcaaaggaag gtctttattc    900
aggaggcggg ggctctgggc tggcagtcgg ggatgcaggg ggaccctggc ggtaggcacc    960
cagcaggatg gcattgatgt gctccagggt caggttgctg aagaccatgt tcagatgctg   1020
tatcccgtgc aggggcagca ggtgcacagg ctgtggctgg cggccctgcc acaggccaca   1080
gagctcggtg ctgcgggtcg ccaccgtgtc atcaccatcc tcatagagca cacccacagg   1140
gtccgtgtag gggaagccgt ggtcgtagat gtaggtgcgg ggcgtgggca ggcccacgcc   1200
gtaaagacag tatacttcca caccaggtgc tgggagtcct gccaggaggt cacgtgactg   1260
cagccacatg taccagcctt cctcaaagtg caggtctgca aagaagcgtt ggaagtcacg   1320
gcctgtgtag ttgaagctgg gtgtggaaat gaacacgtgg tcctcaggcc acgccatgcg   1380
agagggaaac atccaggggg aggtggtggt tatgcgctgc tcctctttca gcttgatgct   1440
ggacatgatg ggatgccct ggttgtcacc tgtggatatg gagcaaggtg ggacagggag    1500
ccaggcctgg ctacccctgg cccacaacct gctgagtgta ggctcagcca gatgctcaat   1560
cttgtccctg cccaatctag acacagactc taagccacag gcttgagcag gcctgatatt   1620
caatgatgct cagtgtcagc ttactcaatg agaagccctg ataagacctc tgttgggtgg   1680
agctgtaggg cttcaaaagg atggcaggga caggcaccat ggctcacccc tgtaatcccg   1740
gcactttggg aggctgaggc aggaggatca cttgaggcca ggagtccgtg accagactgg   1800
gcaatgcagt gagaccctgt ctctac                                         1826
```

<210> SEQ ID NO 13
<211> LENGTH: 536
<212> TYPE: DNA
<213> ORGANISM: Homo sapiens

<400> SEQUENCE: 13

```
tgtttttttt tttttttttt aaagagatgg agtcctgatc tgtcgcccag gctggagttc     60
agtggcacaa tattggccca ctgcaaccct tgaaccttcc cggttcaagt gattctcctg    120
cctaggtctt ctgagtagct gggattacag gtgcccacca ccacgcccag ctaatttttg    180
tggttttagt agagacggag ttttgccatg ttggccaagc tagtctcaaa ctcctgacct    240
caagtgatcg gccggcctca gcctcccaaa gtgctgggat tacaggcttg agccactgcg    300
cctggcccag ttttcccatg tcttgaggca ccactaccca tgcacctcag aatcctccct    360
tgcctttatc cctttgatac agcacatccc aaagtgaatc cccacatggt ccctggttgc    420
tcagactcag tgaaaaaaaa atgaatggtc aagtgagttt tggaaaaccc caaacgcttg    480
aaaaattctt ggcacacata aacatattca aggctctgag aagttctgca gcacaa        536
```

<210> SEQ ID NO 14
<211> LENGTH: 551
<212> TYPE: DNA
<213> ORGANISM: Homo sapiens -continued

<400> SEQUENCE: 14
accattcagc tgcacccaga tgccccaaga gcaatgagcc cacacgcaga gctggaggac 60
ctgaaaggca acctccaagt cccagatcat gtctctgtgg ggtctggtct ccaagatgcc 120
cccagaaaaa gtgcagcggc tctatgtcga ctttccccaa cacctgcggc atcttctggg 180
tgactggctg gagagccagc cctgggagtt cctggtcggc tccgacgcct tctgctgcaa 240
cttggctagt gccctacttt cagacactgt ccagcacctt caggcctcgg tgggagagca 300
gggggagggg agcaccatct tgcaacacat cagcaccctt gagagcatat atcagaggga 360
ccccctgaag ctggtggcca ctttcagaca aatacttcaa ggagagaaaa aagctgttat 420
ggaacagttc cgccacttgc caatgccttt ccactggaag caggaagaac tcaagtttaa 480
gacaggcttg cggaggctgc agcaccgagt aggggagatc caccttctcc gagaagccct 540
gcagaagggg g 551

<210> SEQ ID NO 15
<211> LENGTH: 672
<212> TYPE: DNA
<213> ORGANISM: Mus musculus

<400> SEQUENCE: 15
tgtgacaccc ttcctcacgc ttagacagca aagttgcctc ggaagagaag agaagcctgc 60
atgggaatgg ccagcacatc ctaaatgctc cagtggcccg tggttcgtcc cttcgtctca 120
ttgactgcca cagacaggaa gtaggctcag ggacttggca cctacccaac agcaggacgt 180
cctttctggc catactcctg agggtaacaa aatcacatgg aagcccaaag caagccaggc 240
tcaggctcct ctgccctctg ctacttaaca atgtccgtcc ttccccagcc cccctgcaga 300
tgcttctgta tgggaaagcc cctctgcatc taatgacact ctgctttcaa agacgggaca 360
gtccctggtc tctggagagt gaccattcgt ggccttctca gttgacactt ctccgctgag 420 gcatcccctta gccctgaacc agaaatgaaa gagccggctc agagtgaaaa ggaagaatag 480
ccatcaatct gctcctgtgt gcaaggagca cagacctggt ctcagactct gcccgtctcc 540
cccgcttccc tgccctctga gtgactcacg gtgcaggctg agggagatgt tgatggtatg 600
ctcatccaca aagcccttca ggccaggcat ccgggcaact tgagctgtgt ctgggcacac 660
tgtcccaacg tg 672

<210> SEQ ID NO 16
<211> LENGTH: 616
<212> TYPE: DNA
<213> ORGANISM: Mus musculus

<400> SEQUENCE: 16
gacttttatc tgcactgttt caacagcagg tagccagccg tctttttact gcctgcctct 60
ggctgaagct cggcccacac tatcaggact cagccctgta gggatgactc tgccacacag 120
ctacagcacc agctggcaca aatggctttc tctccaactt cctcaggctt ccctgagtca 180
ctgcccagcc ctaggactgg caacaccctg gccctgctca cccatccacc cttggcaaga 240
gggaaagagg aagaagcctg cagagagctg gtgccctgct tccagatgct gctccattct 300
caggccaagc ctcaagatgg ggggaacctg agtgggagcc tctctcctgg cttgcgttcc 360
ctcccacttc tgggaaagca gggcagtgac agtccctgtt ctcatgtgtc tgcccttggc 420
tgggctcccc tcacctcccc aaagaccagg cagggtccca ttcagcagac ctgactgtaa 480
ggaattggca agaaatgacg tccctagcca gcctggcctc ccctttggta tttttgcagc 540

```
tggagattat tagtctcaag caaaactcct ttgttatcca agcccactcc accacattat    600

tttcctctct cctaaa                                                    616


<210> SEQ ID NO 17
<211> LENGTH: 471
<212> TYPE: DNA
<213> ORGANISM: Mus musculus

<400> SEQUENCE: 17

gacagggtct tattctgcag ctcgggttga cctggaattc tccaggcaga ccattctggc     60

cttacgttca ctgacatcca cctgcctctg cctcctgagt gctgctgtta aggagtagtt    120

ccagcctata gtgttctgaa atactgttat tttactgtaa tgatagccaa agctaaaatg    180

agttaagaat agttcctttc ttactcgctg tctcgttcct cattcacttg ccccatcttc    240

gtgccctcag aactacccca cccccaatcc tcctttagcc ccagagcctt ctctgaaccc    300

taccccttgc ttcctgtcag catctcaggg ccccctcttt gcttccttaa tctctactgg    360

aaacacagag aactcccctg ccctctgcca ttcttctgct ggagctacct tcccaccctt    420

gtgcaagcca ggcccctcat acccaagcag gtgacaccat ctgtgtccaa c             471


<210> SEQ ID NO 18
<211> LENGTH: 707
<212> TYPE: DNA
<213> ORGANISM: Homo sapiens

<400> SEQUENCE: 18

gagctgcgct caccgctgtt gcctgatttt ggtctaagtg aaggcttgcg gttcagattc     60

caacaacttc cctttgtaaa ggaaatggac aagaaactcc cccctggata tgccttgaag    120

ccagctacag cgtgaggtgg tgcagctaga aagtgctaga aacacacacc agctctcaga    180

agtctggagg aaaacatcag gggtgtagtc tccttgacaa cagaggaaac atcacattct    240

cagccatccc gggagagaga aactaaagtg atgaacaaac aaggccttgc ctaagacttc    300

cttaacattt tctcttaagg aagaggttga ttgaggaaaa atcgccgctt ggacagctga    360

accgaagcca ttcacagcct ctgaagaagc gaggccaccc caggggggtcg gtcccggggg    420

atagctgccc caccgtggct gaagatctcg gctgcagacc aaggaggggc ggggagattc    480

tgaggcaacg tttcaacctc gtaaggaacc gaggccttga gggtggccgg gggcccctct    540

gtgaacttga tcggggctgg tggggcgagg gcgcccccca ggacaaggtg gggacggagg    600

tgtcgccaca gagcacagcg gaaaccgggg acttcgccag gagggcccag gataacggag    660

ggcgactcgt gtatgtcgcg gaggcggctc cggggacccg ggacttg                  707


<210> SEQ ID NO 19
<211> LENGTH: 741
<212> TYPE: DNA
<213> ORGANISM: Homo sapiens

<400> SEQUENCE: 19

ggggctccct ctcaacctat tctggcgcct ggagcaagcc ttacctgcag tccccgccgc     60

ggcgaggagc aaggcgacgg tccagcgcaa tttccagccc cagggcccca tgctcgcagc    120

ctctgccagg cagtgtcccg acccggatca cgacctgctg tgtcctagct ggaaaccctg    180

gcttcccgcg attgcactcg gggcccacgt catttacagc atttcaatgt gaggtttcta    240

gcagggggag gagtttgcag tggggtgatt ttcaaatgtc ttcacctcac tgcaagagga    300
```

```
ggagtttcga acggccgatg tgacatcggc tttttaaccc gtgaagctct gattcccact    360

ccagtccttc gaaagtgtcg ccagggcagg cgacttgatt tgttgtattt gggtctccgg    420

tgaagagctg acgccccctc aaaattggaa acgcatcttc tgaaagatcc tcctgaaatt    480

tctcgatgtt taactgttaa cattttgctg ttgttgtcca cagaaggata acaacagcct    540

ttcaagatcc tccaatagcc taatgccatt gtcctctctg cctcaaaagg aaaacactaa    600

aaatgttggg aacttccgcc actttctata tttgcctttt cctttctagg aattgtgtat    660

agatttttag cttcctttcg ttgtatattg tttttacatt gttattccaa atcacctaat    720

agacactgat caatcaggaa t                                              741
```

<210> SEQ ID NO 20
<211> LENGTH: 346
<212> TYPE: DNA
<213> ORGANISM: Homo sapiens

<400> SEQUENCE: 20

```
cccacgtata tttttttgttg tttttttgttt tttttctgta aaatgtcccg gttcttccat     60

aacttataaa catgatttat accgaggaga tgggaaagtg gacggggcag ggtggactga    120

ccggggatgg ggaagctcct ctcgctgccc cctcggggcg ggcccaggcc ctttggagga    180

tggggacgcc aggacactcc tccctgaggt tgctggccgc ctctgccctg gtgctgtgaa    240

gtcagagccc cgatactccc cgtccacctg ccagttcaca aacttcgact gctgggtctg    300

gatggccatc ttggacctga gaccggggcc cagctggtga atgacc                   346
```

<210> SEQ ID NO 21
<211> LENGTH: 867
<212> TYPE: DNA
<213> ORGANISM: Homo sapiens

<400> SEQUENCE: 21

```
accatctttt tttttttct tttatgcgtg aaacttggtg aatctttatt aaactagggt     60

ccaccccagg aggacggctg gggcggggac agggtctccc gctgcaggct gcgcggaggc    120

aggaggcacg gggtggcgtg gggtcgcatg gctgcaggct tcggcgttca gtgattgtcg    180

ctgggcacag gggcggcgct ggtgcccacg gcagcctgca ccttctccac cagcccggcc    240

cactggcgct gcatgtcttc caccaggggc tcgaaccagc tcttgaggcg ggcctggaag    300

gcctcggcct gcaggcgtat ctgctgggcc tgctcctcca gcttggcgcg cacctccgcc    360

acctgctcct tcacctcgtc caggcggtcg cgggtccggc tgcccatctc ctccatccgc    420

gcgcgcagcc gctcgcccca ggcctgggcc cgctcctgta gcggctggcc ggccagggag    480

cccacagtgg cggcccgcac gcggccctgt tccaccaggg gccccaggcg ctcgcggatg    540

gcgctgaggc cgcgctcggc gccctcgcgg gccccggcct ggtacactgc caggcgcttc    600

tgcaggtcat cggcatcgcg gaggagccgc ttacgcagct tgcgcaggtg ggaggcgagg    660

cgcacccgca gctcctcggt gctctggccg agcatggcct gcacctcgcc gcggtactgc    720

accaggcggc cgcacacgtc ctccatgtcc gcgcccagcc gggcctgcgc cgcctgcagc    780

tccttggaca gccgtgcccg cgtctcctcc gccaccgggg tcagttgttc ctccagttcc    840

gatttgtagg ccttcaactc cttcatg                                        867
```

<210> SEQ ID NO 22
<211> LENGTH: 563
<212> TYPE: DNA
<213> ORGANISM: Homo sapiens

<400> SEQUENCE: 22
cagcttctct tgcagctcgt gcagcttctg gcgcgcgccc tcttggagct ctgcgcgcag 60
cggctccacc ttctggcggt agagctccat ctcctcctgc cacttcttct ggaagtcgtc 120
cagatccaaa tggcaaacct tcttcatcca ccaggaccca acccacaggc tacttattgc 180
tggaaaccta cgttgttcct tggattgaag taatctctcc ctcttctggt gcgcccacag 240
cacttgcacc aacagtgggt acccaacaga ctagcgtgcc tgccgaagaa ggggtcctct 300
gacaatcagg ggacaatggg gaattatgct ctccagactt tctacacaca caagtcacac 360
aggaaggaag gtaaagagaa actagagaaa ataatttttg aagaaaaaca tttcaggaag 420
tattgaaagt acacggtaac tcagcctggg gcaggggtgg agggcagcag cactgtttgc 480
tgcagctatg ctccttcctc agtgccctgc acacccggga cttgctcggt gagcatctct 540
cgtgtcagtg acagctagtg tga 563

<210> SEQ ID NO 23
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 23
uuguaaagua ugagcuuggu gucagca 27

<210> SEQ ID NO 24
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 24
aaucaauggc uguucucucu cugggac 27

<210> SEQ ID NO 25
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 25
accuauaauu ccagcacuuu gagaggc 27

<210> SEQ ID NO 26
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 26
cccaccactt gcaactcaga 20

<210> SEQ ID NO 27
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 27
ttcgggaagt gctcggtttc g 21

<210> SEQ ID NO 28
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 28
cccagctcag atccatccct t 21

<210> SEQ ID NO 29
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 29
gcctcttcta tgggtctgtc 20

<210> SEQ ID NO 30
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 30
gccatgccac ccagagtta 19

<210> SEQ ID NO 31
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 31
gctgttctct ctctgggact t 21

<210> SEQ ID NO 32
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 32
gttcccattc ccttattag 19

<210> SEQ ID NO 33
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 33
cgaatcactt agccactttg 20

<210> SEQ ID NO 34
<211> LENGTH: 20

<212> TYPE: DNA
<213> ORGANISM: Artificial Sequence
<220> FEATURE:
<223> OTHER INFORMATION: Antisense oligonucleotide

<400> SEQUENCE: 34
ctgggattac aggcgtgagc 20

<210> SEQ ID NO 35
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 35
catgtctcct gcctttcctg t 21

<210> SEQ ID NO 36
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 36
gctcacaata tcaggctgct t 21

<210> SEQ ID NO 37
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 37
tcaactttac ccagacaagc a 21

<210> SEQ ID NO 38
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 38
ggacagggta gcaacgccat t 21

<210> SEQ ID NO 39
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 39
ccacctcagt tgcacggaa 19

<210> SEQ ID NO 40
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 40

-continued

```
ttgggcatag agtttggttc                                                20


<210> SEQ ID NO 41
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 41

guggucaguc acagccacac cagacuu                                        27


<210> SEQ ID NO 42
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 42

gucccuucuc ccaccacacu gugacuc                                        27


<210> SEQ ID NO 43
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 43

cagcacugac acagcuacca ccuacuc                                        27


<210> SEQ ID NO 44
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 44

ugugcuucac ugaggaugga ucugcca                                        27


<210> SEQ ID NO 45
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 45

agagaaacgc ucaucagaca ccaccaa                                        27


<210> SEQ ID NO 46
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 46

cuuaggaagc acaagaggcu gagccuu                                        27


<210> SEQ ID NO 47
<211> LENGTH: 27
<212> TYPE: DNA
<213> ORGANISM: Artificial Sequence
```

<220> FEATURE:
<223> OTHER INFORMATION: Antisense oligonucleotide

<400> SEQUENCE: 47
ccuggcuccc ugucccaccu ugcucca 27

<210> SEQ ID NO 48
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 48
guucauuucc acacccagcu ucaacua 27

<210> SEQ ID NO 49
<211> LENGTH: 19
<212> TYPE: DNA
<213> ORGANISM: Artificial sequence
<220> FEATURE:
<223> OTHER INFORMATION: Antisense oligonucleotide

<400> SEQUENCE: 49
agacctatct gttcccacc 19

<210> SEQ ID NO 50
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 50
gtcagtcaca gccacaccag 20

<210> SEQ ID NO 51
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 51
cctatctgtt cccaccttg 19

<210> SEQ ID NO 52
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 52
gtcacagcca caccagactc t 21

<210> SEQ ID NO 53
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 53
tcccttctcc caccacactg t 21

-continued

<210> SEQ ID NO 54
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 54
ctcctcaatg tgctcttccc 20

<210> SEQ ID NO 55
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 55
cccactccca caccagata 19

<210> SEQ ID NO 56
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 56
aacagcctct tcccagcacc 20

<210> SEQ ID NO 57
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 57
caccatctac tcctgagccc 20

<210> SEQ ID NO 58
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 58
tcattgtcac gcgctcccac 20

<210> SEQ ID NO 59
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 59
tcccagctac tcagaagacc t 21

<210> SEQ ID NO 60
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 60
tgggcgacag atcaggactc 20

<210> SEQ ID NO 61
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 61
ctgaggtgca tgggtagtgg t 21

<210> SEQ ID NO 62
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 62
gccgatcact tgaggtcagg a 21

<210> SEQ ID NO 63
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 63
attagctggg cgtggtggtg 20

<210> SEQ ID NO 64
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 64
gctctgcgtg tgggctcatt 20

<210> SEQ ID NO 65
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 65
gtccctctga tatatgctct c 21

<210> SEQ ID NO 66
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 66
cttgagttct tcctgcttcc a 21

<210> SEQ ID NO 67

<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 67
tctccagcca gtcacccaga 20

<210> SEQ ID NO 68
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 68
ccatcaacat ctccctcagc c 21

<210> SEQ ID NO 69
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 69
cttcttcctc tttccctctt 20

<210> SEQ ID NO 70
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 70
acagcagcac tcaggaggca 20

<210> SEQ ID NO 71
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 71
gggtagttct gagggcacga 20

<210> SEQ ID NO 72
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 72
aggcaggtgg atgtcagtg 19

<210> SEQ ID NO 73
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 73
gggtagggtt cagagaaggc 20

<210> SEQ ID NO 74
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 74
actcctcctc ttgcagtgag 20

<210> SEQ ID NO 75
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 75
gctgttgtta tccttctgtg 20

<210> SEQ ID NO 76
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 76
atcgcgggaa gccagggttt 20

<210> SEQ ID NO 77
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 77
gccagaatag gttgagaggg a 21

<210> SEQ ID NO 78
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 78
gccgttcgaa actcctcctc t 21

<210> SEQ ID NO 79
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 79
ggtttccgct gtgctctgtg 20

<210> SEQ ID NO 80
<211> LENGTH: 20
<212> TYPE: DNA

<213> ORGANISM: Artificial Sequence
<220> FEATURE:
<223> OTHER INFORMATION: Antisense oligonucleotide

<400> SEQUENCE: 80
acgttgcctc agaatctccc 20

<210> SEQ ID NO 81
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 81
ttcctcaatc aacctcttcc t 21

<210> SEQ ID NO 82
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 82
gtgatgtttc ctctgttgtc 20

<210> SEQ ID NO 83
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 83
cactttctag ctgcaccacc 20

<210> SEQ ID NO 84
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 84
ccgtccactt tcccatctcc t 21

<210> SEQ ID NO 85
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 85
cccgtccact ttcccatctc 20

<210> SEQ ID NO 86
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 86
cttcacagca ccagggcaga 20

<210> SEQ ID NO 87
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 87
cccagcagtc gaagtttgtg a 21

<210> SEQ ID NO 88
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 88
ccggtctcag gtccaagatg 20

<210> SEQ ID NO 89
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 89
tggtggagaa ggtgcaggct 20

<210> SEQ ID NO 90
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 90
gattcaccaa gtttcacgca t 21

<210> SEQ ID NO 91
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 91
gacgaggtga aggagcaggt 20

<210> SEQ ID NO 92
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 92
tcggaactgg aggaacaact g 21

<210> SEQ ID NO 93
<211> LENGTH: 13
<212> TYPE: DNA
<213> ORGANISM: Artificial Sequence
<220> FEATURE:

<223> OTHER INFORMATION: Antisense oligonucleotide

<400> SEQUENCE: 93
tggagctcag ttt 13

<210> SEQ ID NO 94
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 94
tttctcgtgc agct 14

<210> SEQ ID NO 95
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 95
ttctggcgcg tgcc 14

<210> SEQ ID NO 96
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 96
ccctcgtgga gctc 14

<210> SEQ ID NO 97
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 97
gcccgcgcgc agcg 14

<210> SEQ ID NO 98
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 98
cggctccacc ttct 14

<210> SEQ ID NO 99
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 99
ctggcggtag agct 14

<210> SEQ ID NO 100
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 100
gctcgtgcag cttc 14

<210> SEQ ID NO 101
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 101
cagcttctgg cgcg 14

<210> SEQ ID NO 102
<211> LENGTH: 14
<212> TYPE: DNA
<213> ORGANISM: Artificial sequence
<220> FEATURE:
<223> OTHER INFORMATION: Antisense oligonucleotide

<400> SEQUENCE: 102
gcgcgcagcg gctc 14

<210> SEQ ID NO 103
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 103
tccaccttct ggcg 14

<210> SEQ ID NO 104
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 104
cggtgtagag ctcc 14

<210> SEQ ID NO 105
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 105
ccatctcctc ctgc 14

<210> SEQ ID NO 106
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 106
gaagtcgtcc agatccaaa 19

<210> SEQ ID NO 107
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 107
aagtcgtcca gatccaaat 19

<210> SEQ ID NO 108
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 108
agtcgtccag atccaaatg 19

<210> SEQ ID NO 109
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 109
gtcgtccaga tccaaatgg 19

<210> SEQ ID NO 110
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 110
tcgtccagat ccaaatggc 19

<210> SEQ ID NO 111
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 111
cgtccagatc caaatggca 19

<210> SEQ ID NO 112
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 112
gtccagatcc aaatggcaa 19

<210> SEQ ID NO 113
<211> LENGTH: 19

-continued

<212> TYPE: DNA
<213> ORGANISM: Artificial Sequence
<220> FEATURE:
<223> OTHER INFORMATION: Antisense oligonucleotide

<400> SEQUENCE: 113
tccagatcca aatggcaaa 19

<210> SEQ ID NO 114
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 114
cagatccaaa tg 12

<210> SEQ ID NO 115
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 115
agatccaaat ggcaaa 16

<210> SEQ ID NO 116
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 116
agatccaaat gg 12

<210> SEQ ID NO 117
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 117
gatccaaatg gc 12

<210> SEQ ID NO 118
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 118
atccaaatgg ca 12

<210> SEQ ID NO 119
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 119
tccaaatggc aa 12

<210> SEQ ID NO 120
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 120
ccaaatggca aa 12

<210> SEQ ID NO 121
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 121
ccaaatggca aaccttctt 19

<210> SEQ ID NO 122
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 122
atggcaaatc ttcttcatc 19

<210> SEQ ID NO 123
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 123
aaatggcaaa ccttcttca 19

<210> SEQ ID NO 124
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 124
aaatggcaaa tcttcttca 19

<210> SEQ ID NO 125
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 125
atggcaaacc ttcttcatc 19

<210> SEQ ID NO 126
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 126
ccaaatggca aatcttctt 19

<210> SEQ ID NO 127
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 127
atggcaaacc ttctt 15

<210> SEQ ID NO 128
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 128
atggcaaatc ttctt 15

<210> SEQ ID NO 129
<211> LENGTH: 11
<212> TYPE: DNA
<213> ORGANISM: Artificial Sequence
<220> FEATURE:
<223> OTHER INFORMATION: Antisense oligonucleotide

<400> SEQUENCE: 129
cttcttcatc c 11

<210> SEQ ID NO 130
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 130
ccaggaccca acccaca 17

<210> SEQ ID NO 131
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 131
gctacttatt gctg 14

<210> SEQ ID NO 132
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 132
tgctggaaac ctac 14

<210> SEQ ID NO 133
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 133
ttccttggat tgaa 14

<210> SEQ ID NO 134
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 134
gcccacagca cttgca 16

<210> SEQ ID NO 135
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 135
caccaacagt gggtac 16

<210> SEQ ID NO 136
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 136
caacagacta gc 12

<210> SEQ ID NO 137
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 137
gaagaagggg tcct 14

<210> SEQ ID NO 138
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 138
gaattatgct ctcc 14

<210> SEQ ID NO 139
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 139
ctccagactt tcta 14

<210> SEQ ID NO 140
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 140
aagtcacaca ggaagg 16

<210> SEQ ID NO 141
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 141
gaaactagag aaaa 14

<210> SEQ ID NO 142
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 142
aataattttt gaag 14

<210> SEQ ID NO 143
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 143
gaagtattga aagt 14

<210> SEQ ID NO 144
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 144
tgaaagtaca cggt 14

<210> SEQ ID NO 145
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 145
ctggggcagg ggtg 14

<210> SEQ ID NO 146

<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 146
ggggtggagg gcag 14

<210> SEQ ID NO 147
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 147
tgctccttcc tcag 14

<210> SEQ ID NO 148
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 148
acccgggact tgctc 15

<210> SEQ ID NO 149
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 149
tgtcagtgac agct 14

<210> SEQ ID NO 150
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 150
tgtcagtgac agctagtgt 19

<210> SEQ ID NO 151
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 151
gtcagtgaca gctagtgtg 19

<210> SEQ ID NO 152
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 152
tcagtgacag ctagtgtga 19

<210> SEQ ID NO 153
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 153
agtgacagct agtgtgagt 19

<210> SEQ ID NO 154
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 154
tgacagctag tgtga 15

<210> SEQ ID NO 155
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 155
tgacagctag tgtgagtac 19

<210> SEQ ID NO 156
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 156
gacagctagt gtgagtact 19

<210> SEQ ID NO 157
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 157
cagctagtgt gagtactct 19

<210> SEQ ID NO 158
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 158
agctagtgtg agtactctt 19

<210> SEQ ID NO 159
<211> LENGTH: 19
<212> TYPE: DNA

-continued

<213> ORGANISM: Artificial Sequence
<220> FEATURE:
<223> OTHER INFORMATION: Antisense oligonucleotide

<400> SEQUENCE: 159
gctagtgtga gtactctta 19

<210> SEQ ID NO 160
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 160
ctagtgtgag tactcttat 19

<210> SEQ ID NO 161
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 161
ctagtgtgag tact 14

<210> SEQ ID NO 162
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 162
tagtgtgagt actcttatg 19

<210> SEQ ID NO 163
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 163
agtgtgagta ctcttatgt 19

<210> SEQ ID NO 164
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 164
gtgtgagtac tcttatgtt 19

<210> SEQ ID NO 165
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 165
tgtgagtact cttatgttc 19

<210> SEQ ID NO 166
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 166
gtgagtactc ttatgttca 19

<210> SEQ ID NO 167
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 167
tgagtactct tatgttcag 19

<210> SEQ ID NO 168
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 168
actcttatgt tcag 14

<210> SEQ ID NO 169
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 169
tacctcttga cttt 14

<210> SEQ ID NO 170
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 170
gactttgggg acaa 14

<210> SEQ ID NO 171
<211> LENGTH: 13
<212> TYPE: DNA
<213> ORGANISM: Artificial Sequence
<220> FEATURE:
<223> OTHER INFORMATION: Antisense oligonucleotide

<400> SEQUENCE: 171
aaactgagct cca 13

<210> SEQ ID NO 172
<211> LENGTH: 14
<212> TYPE: DNA
<213> ORGANISM: Artificial Sequence
<220> FEATURE:

<223> OTHER INFORMATION: Antisense oligonucleotide

<400> SEQUENCE: 172
agctgcacga gaaa 14

<210> SEQ ID NO 173
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 173
ggcacgcgcc agaa 14

<210> SEQ ID NO 174
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 174
gagctccacg aggg 14

<210> SEQ ID NO 175
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 175
cgctgcgcgc gggc 14

<210> SEQ ID NO 176
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 176
agaaggtgga gccg 14

<210> SEQ ID NO 177
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 177
agctctaccg ccag 14

<210> SEQ ID NO 178
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 178
gaagctgcac gagc 14

-continued

<210> SEQ ID NO 179
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 179
cgcgccagaa gctg 14

<210> SEQ ID NO 180
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 180
gagccgctgc gcgc 14

<210> SEQ ID NO 181
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 181
cgccagaagg tgga 14

<210> SEQ ID NO 182
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 182
ggagctctac accg 14

<210> SEQ ID NO 183
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 183
gcaggaggag atgg 14

<210> SEQ ID NO 184
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 184
tttggatctg gacgacttc 19

<210> SEQ ID NO 185
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 185
atttggatct ggacgactt 19

<210> SEQ ID NO 186
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 186
catttggatc tggacgact 19

<210> SEQ ID NO 187
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 187
ccatttggat ctggacgac 19

<210> SEQ ID NO 188
<211> LENGTH: 19
<212> TYPE: DNA
<213> ORGANISM: Artificial sequence
<220> FEATURE:
<223> OTHER INFORMATION: Antisense oligonucleotide

<400> SEQUENCE: 188
gccatttgga tctggacga 19

<210> SEQ ID NO 189
<211> LENGTH: 19
<212> TYPE: DNA
<213> ORGANISM: Artificial sequence
<220> FEATURE:
<223> OTHER INFORMATION: Antisense oligonucleotide

<400> SEQUENCE: 189
tgccatttgg atctggacg 19

<210> SEQ ID NO 190
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 190
ttgccatttg gatctggac 19

<210> SEQ ID NO 191
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 191
tttgccattt ggatctgga 19

<210> SEQ ID NO 192
<211> LENGTH: 12

<212> TYPE: DNA
<213> ORGANISM: Artificial Sequence
<220> FEATURE:
<223> OTHER INFORMATION: Antisense oligonucleotide

<400> SEQUENCE: 192
catttggatc tg 12

<210> SEQ ID NO 193
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 193
tttgccattt ggatct 16

<210> SEQ ID NO 194
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 194
ccatttggat ct 12

<210> SEQ ID NO 195
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 195
gccatttgga tc 12

<210> SEQ ID NO 196
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 196
tgccatttgg at 12

<210> SEQ ID NO 197
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 197
tgccatttgg at 12

<210> SEQ ID NO 198
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 198

-continued

```
tttgccattt gg                                                         12


<210> SEQ ID NO 199
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 199

aagaaggttt gccatttgg                                                  19


<210> SEQ ID NO 200
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 200

gatgaagaag atttgccat                                                  19


<210> SEQ ID NO 201
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 201

tgaagaaggt ttgccattt                                                  19


<210> SEQ ID NO 202
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 202

tgaagaagat ttgccattt                                                  19


<210> SEQ ID NO 203
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 203

gatgaagaag gtttgccat                                                  19


<210> SEQ ID NO 204
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 204

aagaagattt gccatttgg                                                  19


<210> SEQ ID NO 205
<211> LENGTH: 15
<212> TYPE: DNA
<213> ORGANISM: Artificial Sequence
```

<220> FEATURE:
<223> OTHER INFORMATION: Antisense oligonucleotide

<400> SEQUENCE: 205
aagaaggttt gccat 15

<210> SEQ ID NO 206
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 206
aagaagattt gccat 15

<210> SEQ ID NO 207
<211> LENGTH: 11
<212> TYPE: DNA
<213> ORGANISM: Artificial Sequence
<220> FEATURE:
<223> OTHER INFORMATION: Antisense oligonucleotide

<400> SEQUENCE: 207
ggatgaagaa g 11

<210> SEQ ID NO 208
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 208
tgtgggttgg gtcctgg 17

<210> SEQ ID NO 209
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 209
cagcaataag tagc 14

<210> SEQ ID NO 210
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 210
gtaggtttcc agca 14

<210> SEQ ID NO 211
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 211
ttcaatccaa ggaa 14

<210> SEQ ID NO 212
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 212
tgcaagtgct gtgggc                                              16

<210> SEQ ID NO 213
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 213
gtacccactg ttggtg                                              16

<210> SEQ ID NO 214
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 214
gctagtctgt tg                                                  12

<210> SEQ ID NO 215
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 215
aggacccctt cttc                                                14

<210> SEQ ID NO 216
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 216
ggagagcata attc                                                14

<210> SEQ ID NO 217
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 217
tagaaagtct ggag                                                14

<210> SEQ ID NO 218
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 218
ccttcctgtg tgactt 16

<210> SEQ ID NO 219
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 219
ttttctctag tttc 14

<210> SEQ ID NO 220
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 220
cttcaaaaat tatt 14

<210> SEQ ID NO 221
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 221
actttcaata cttc 14

<210> SEQ ID NO 222
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 222
accgtgtact ttca 14

<210> SEQ ID NO 223
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 223
cacccctgcc ccag 14

<210> SEQ ID NO 224
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 224
ctgccctcca cccc 14

<210> SEQ ID NO 225

<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 225
ctgaggaagg agca 14

<210> SEQ ID NO 226
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 226
gagcaagtcc cgggt 15

<210> SEQ ID NO 227
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 227
agctgtcact gaca 14

<210> SEQ ID NO 228
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 228
acactagctg tcactgaca 19

<210> SEQ ID NO 229
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 229
cacactagct gtcactgac 19

<210> SEQ ID NO 230
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 230
tcacactagc tgtcactga 19

<210> SEQ ID NO 231
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 231
actcacacta gctgtcact 19

<210> SEQ ID NO 232
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 232
tcacactagc tgtca 15

<210> SEQ ID NO 233
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 233
gtactcacac tagctgtca 19

<210> SEQ ID NO 234
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 234
agtactcaca ctagctgtc 19

<210> SEQ ID NO 235
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 235
agagtactca cactagctg 19

<210> SEQ ID NO 236
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 236
aagagtactc acactagct 19

<210> SEQ ID NO 237
<211> LENGTH: 19
<212> TYPE: DNA
<213> ORGANISM: Artificial sequence
<220> FEATURE:
<223> OTHER INFORMATION: Antisense oligonucleotide

<400> SEQUENCE: 237
taagagtact cacactagc 19

<210> SEQ ID NO 238
<211> LENGTH: 19
<212> TYPE: DNA

-continued

<213> ORGANISM: Artificial Sequence
<220> FEATURE:
<223> OTHER INFORMATION: Antisense oligonucleotide

<400> SEQUENCE: 238
ataagagtac tcacactag 19

<210> SEQ ID NO 239
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 239
agtactcaca ctag 14

<210> SEQ ID NO 240
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 240
cataagagta ctcacacta 19

<210> SEQ ID NO 241
<211> LENGTH: 19
<212> TYPE: DNA
<213> ORGANISM: Artificial Seqiuence
<220> FEATURE:
<223> OTHER INFORMATION: Antisense oligonucleotide

<400> SEQUENCE: 241
acataagagt actcacact 19

<210> SEQ ID NO 242
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 242
aacataagag tactcacac 19

<210> SEQ ID NO 243
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 243
gaacataaga gtactcaca 19

<210> SEQ ID NO 244
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 244
tgaacataag agtactcac 19

<210> SEQ ID NO 245
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 245
ctgaacataa gagtactca 19

<210> SEQ ID NO 246
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 246
ctgaacataa gagt 14

<210> SEQ ID NO 247
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 247
aaagtcaaga ggta 14

<210> SEQ ID NO 248
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 248
ttgtccccaa agtc 14

<210> SEQ ID NO 249
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 249
aagaaggttt gccat 15

<210> SEQ ID NO 250
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 250
tcacactagc tgtca 15

<210> SEQ ID NO 251
<211> LENGTH: 15
<212> TYPE: DNA
<213> ORGANISM: Artificial Sequence
<220> FEATURE:

<223> OTHER INFORMATION: Antisense oligonucleotide

<400> SEQUENCE: 251
aagaaggttt gccat 15

<210> SEQ ID NO 252
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 252
tcacactagc tgtca 15

<210> SEQ ID NO 253
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 253
ctcctcctgc cacttcttct g 21

<210> SEQ ID NO 254
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 254
ctggtggatg aagaaggttt gc 22

<210> SEQ ID NO 255
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 255
tttggatctg gacgacttc 19

<210> SEQ ID NO 256
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 256
caataagtag cctgt 15

<210> SEQ ID NO 257
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 257
cacgctagtc tgttg 15

-continued

<210> SEQ ID NO 258
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 258
cttccttcct gtgtg 15

<210> SEQ ID NO 259
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 259
caggctgagt taccg 15

<210> SEQ ID NO 260
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 260
gctagtctgt tg 12

<210> SEQ ID NO 261
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 261
gtctgatgga ga 12

<210> SEQ ID NO 262
<211> LENGTH: 6
<212> TYPE: DNA
<213> ORGANISM: Artificial Sequence
<220> FEATURE:
<223> OTHER INFORMATION: Antisense oligonucleotide

<400> SEQUENCE: 262 gctagt 6

<210> SEQ ID NO 263
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 263
tgccatttgg atctggacg 19

<210> SEQ ID NO 264
<211> LENGTH: 25
<212> TYPE: DNA
<213> ORGANISM: Artificial Sequence
<220> FEATURE:
<223> OTHER INFORMATION: Reverse complement of the antisense
oligonucleotide SEQ ID NO: 23

<400> SEQUENCE: 264
cugacaccaa gcucauacuu uacaa 25

<210> SEQ ID NO 265
<211> LENGTH: 25
<212> TYPE: DNA
<213> ORGANISM: Artificial Sequence
<220> FEATURE:
<223> OTHER INFORMATION: Reverse complement of the antisense oligonucleotide SEQ ID NO: 24

<400> SEQUENCE: 265
cccagagaga gaacagccau ugatt 25

<210> SEQ ID NO 266
<211> LENGTH: 25
<212> TYPE: DNA
<213> ORGANISM: Artificial Sequence
<220> FEATURE:
<223> OTHER INFORMATION: Reverse complement of the antisense oligonucleotide SEQ ID NO: 25

<400> SEQUENCE: 266
cucucaaagu gcuggaauua uaggt 25

<210> SEQ ID NO 267
<211> LENGTH: 25
<212> TYPE: DNA
<213> ORGANISM: Artificial Sequence
<220> FEATURE:
<223> OTHER INFORMATION: Reverse complement of the antisense oligonucleotide SEQ ID NO: 41

<400> SEQUENCE: 267
gucuggugug gcugugacug accac 25

<210> SEQ ID NO 268
<211> LENGTH: 25
<212> TYPE: DNA
<213> ORGANISM: Artificial Sequence
<220> FEATURE:
<223> OTHER INFORMATION: Reverse complement of the antisense oligonucleotide SEQ ID NO: 42

<400> SEQUENCE: 268
gucacagugu ggugggagaa gggac 25

<210> SEQ ID NO 269
<211> LENGTH: 25
<212> TYPE: DNA
<213> ORGANISM: Artificial Sequence
<220> FEATURE:
<223> OTHER INFORMATION: Reverse complement of the antisense oligonucleotide SEQ ID NO: 43

<400> SEQUENCE: 269
guagguggua gcugugucag ugctg 25

<210> SEQ ID NO 270
<211> LENGTH: 25
<212> TYPE: DNA
<213> ORGANISM: Artificial Sequence
<220> FEATURE:
<223> OTHER INFORMATION: Reverse complement of the antisense oligonucleotide SEQ ID NO: 44

<400> SEQUENCE: 270
gcagauccau ccucagugaa gcaca 25

<210> SEQ ID NO 271
<211> LENGTH: 25
<212> TYPE: DNA
<213> ORGANISM: Artificial Sequence
<220> FEATURE:
<223> OTHER INFORMATION: Reverse complement of the antisense
oligonucleotide SEQ ID NO: 45

<400> SEQUENCE: 271
gguggugucu gaugagcguu ucuct 25

<210> SEQ ID NO 272
<211> LENGTH: 25
<212> TYPE: DNA
<213> ORGANISM: Artificial Sequence
<220> FEATURE:
<223> OTHER INFORMATION: Reverse complement of the antisense
oligonucleotide SEQ ID NO: 46

<400> SEQUENCE: 272
ggcucagccu cuugugcuuc cuaag 25

<210> SEQ ID NO 273
<211> LENGTH: 25
<212> TYPE: DNA
<213> ORGANISM: Artificial Sequence
<220> FEATURE:
<223> OTHER INFORMATION: Reverse complement of the antisense
oligonucleotide SEQ ID NO: 47

<400> SEQUENCE: 273
gagcaaggug ggacagggag ccagg 25

<210> SEQ ID NO 274
<211> LENGTH: 25
<212> TYPE: DNA
<213> ORGANISM: Artificial Sequence
<220> FEATURE:
<223> OTHER INFORMATION: Reverse complement of the antisense
oligonucleotide SEQ ID NO: 48

<400> SEQUENCE: 274
guugaagcug gguguggaaa ugaac 25

<210> SEQ ID NO 275
<211> LENGTH: 19
<212> TYPE: DNA
<213> ORGANISM: Artificial Sequence
<220> FEATURE:
<223> OTHER INFORMATION: Probe Sequence

<400> SEQUENCE: 275
tttggatctg gacgacttc 19

<210> SEQ ID NO 276
<211> LENGTH: 21
<212> TYPE: DNA
<213> ORGANISM: Artificial Sequence
<220> FEATURE:
<223> OTHER INFORMATION: Forward Primer

<400> SEQUENCE: 276
ctcctcctgc cacttcttct g 21

```
<210> SEQ ID NO 277
<211> LENGTH: 22
<212> TYPE: DNA
<213> ORGANISM: Artificial Sequence
<220> FEATURE:
<223> OTHER INFORMATION: Reverse Primer

<400> SEQUENCE: 277

ctggtggatg aagaaggttt gc                                              22


<210> SEQ ID NO 278
<211> LENGTH: 12
<212> TYPE: DNA
<213> ORGANISM: Artificial sequence
<220> FEATURE:
<223> OTHER INFORMATION: Antisense oligonucleotide

<400> SEQUENCE: 278

gctagtctgt tg                                                         12


<210> SEQ ID NO 279
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 279

gtctgatgga ga                                                         12
```

TREATMENT OF LCAT GENE RELATED DISEASES BY INHIBITION OF A NATURAL ANTISENSE TRANSCRIPT TO LCAT

The present Application is a Continuation of U.S. Ser. No. 14/814,895, filed Jul. 31, 2015, which is a Divisional of U.S. Ser. No. 13/318,713 filed Nov. 3, 2011, now U.S. Pat. No. 9,155,754, which is a 371 of International Application No. PCT/US2010/033908 filed May 6, 2010, which claims the priority to U.S. Provisional Patent Application Nos. 61/175,930 filed May 6, 2009, 61/176,267 filed May 7, 2009, 61/180,646 filed May 22, 2009, 61/235,227 filed Aug. 19, 2009, and 61/248,212 filed Oct. 2, 2009, which are incorporated herein by reference in their entireties.

FIELD OF THE INVENTION

Embodiments of the invention comprise oligonucleotides modulating expression and/or function of a Lipid transport and metabolism gene and associated molecules.

BACKGROUND

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, VITRAVENE™ (for treatment of cytomegalovirus retinitis), reflecting that antisense has therapeutic utility.

SUMMARY

This Summary is provided to present a summary of the invention to briefly indicate the nature and substance of the invention. It is submitted with the understanding that it will not be used to interpret or limit the scope or meaning of the claims.

In one embodiment, the invention provides methods for inhibiting the action of a natural antisense transcript by using antisense oligonucleotide(s) targeted to any region of the natural antisense transcript resulting in up-regulation of the corresponding sense gene. It is also contemplated herein that inhibition of the natural antisense transcript can be achieved by siRNA, ribozymes and small molecules, which are considered to be within the scope of the present invention.

One embodiment provides a method of modulating function and/or expression of a Lipid transport and metabolism gene polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of a polynucleotide comprising 5 to 30 consecutive nucleotides within nucleotides 1 to 1299 of SEQ ID NO: 8, 1 to 918 of SEQ ID NO: 9, 1 to 1550 of SEQ ID NO: 10, 1 to 329 of SEQ ID NO: 11, 1 to 1826 of SEQ ID NO: 12, 1 to 536 of SEQ ID NO: 13, 1 to 551 of SEQ ID NO: 14, 1 to 672 of SEQ ID NO: 15, 1 to 616 of SEQ ID NO: 16, 1 to 471 of SEQ ID NO: 17, 1 to 707 of SEQ ID NO: 18, 1 to 741 of SEQ ID NO: 19, 1 to 346 of SEQ ID NO: 20, 1 to 867 of SEQ ID NO: 21, 1 to 563 of SEQ ID NO: 22 (FIG. 3) thereby modulating function and/or expression of the Lipid transport and metabolism gene polynucleotide in patient cells or tissues in vivo or in vitro.

In another preferred embodiment, an oligonucleotide targets a natural antisense sequence of a Lipid transport and metabolism gene polynucleotide, for example, nucleotides set forth in SEQ ID NO: 8 to 22, and any variants, alleles, homologs, mutants, derivatives, fragments and complementary sequences thereto. Examples of antisense oligonucleotides are set forth as SEQ ID NOS: 23 to 263 (FIGS. 4 to 9).

Another embodiment provides a method of modulating function and/or expression of a Lipid transport and metabolism gene polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of the an antisense of the Lipid transport and metabolism gene polynucleotide; thereby modulating function and/or expression of the Lipid transport and metabolism gene polynucleotide in patient cells or tissues in vivo or in vitro.

Another embodiment provides a method of modulating function and/or expression of a Lipid transport and metabolism gene polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to a Lipid transport and metabolism gene antisense polynucleotide; thereby modulating function and/or expression of the Lipid transport and metabolism gene polynucleotide in patient cells or tissues in vivo or in vitro.

In a preferred embodiment, a composition comprises one or more antisense oligonucleotides which bind to sense and/or antisense Lipid transport and metabolism gene polynucleotides.

In another preferred embodiment, the oligonucleotides comprise one or more modified or substituted nucleotides.

In another preferred embodiment, the oligonucleotides comprise one or more modified bonds.

In yet another embodiment, the modified nucleotides comprise modified bases comprising phosphorothioate, methylphosphonate, peptide nucleic acids, 2'-O-methyl, fluoro- or carbon, methylene or other locked nucleic acid (LNA) molecules. Preferably, the modified nucleotides are locked nucleic acid molecules, including .alpha.-L-LNA.

In another preferred embodiment, the oligonucleotides are administered to a patient subcutaneously, intramuscularly, intravenously or intraperitoneally.

In another preferred embodiment, the oligonucleotides are administered in a pharmaceutical composition. A treatment regimen comprises administering the antisense compounds at least once to patient; however, this treatment can be modified to include multiple doses over a period of time. The treatment can be combined with one or more other types of therapies.

In another preferred embodiment, the oligonucleotides are encapsulated in a liposome or attached to a carrier molecule (e.g. cholesterol, TAT peptide).

Other aspects are described infra.

BRIEF DESCRIPTION OF THE DRAWINGS

FIG. 2 shows

Figure 1A:
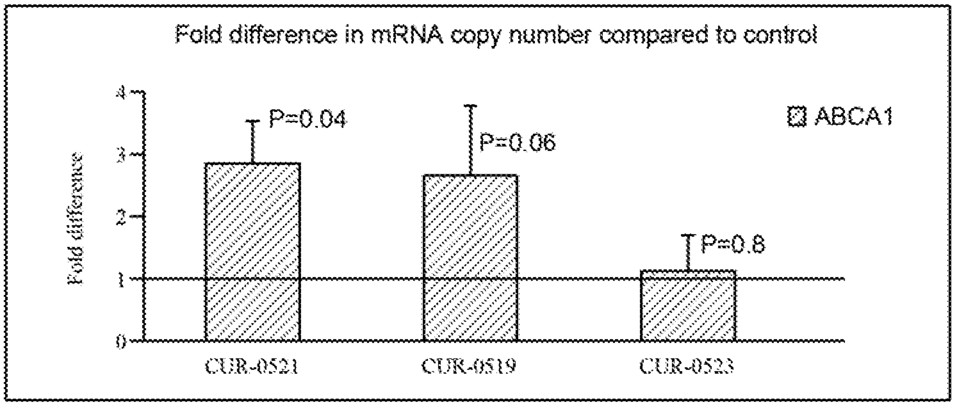
FIG. 1A is a graph of real time PCR results showing the fold change+standard deviation in ABCA1 mRNA after treatment of 518A2 cells with siRNA oligonucleotides introduced using Lipofectamine 2000, as compared to control. Real time PCR results show that the levels of ABCA1 mRNA in 518A2 cells are significantly increased 48 h after treatment with one of the siRNAs designed to ABCA1 antisense AK311445. Bars denoted as CUR-0521, CUR-0519 and CUR-0523 correspond to samples treated with SEQ ID NOS: 23 to 25 respectively.

SEQ ID NO: 1: *Homo sapiens* ATP-binding cassette, sub-family A (ABC1), member 1 (ABCA1), mRNA (NCBI Accession No.: NM.sub.—005502).

SEQ ID NO: 2: *Homo sapiens* lecithin-cholesterol acyltransferase (LCAT), mRNA (NCBI Accession No.: NM.sub.—000229.1).

SEQ ID NO: 3: *Homo sapiens* low density lipoprotein receptor-related protein 1 (LRP1), mRNA (NCBI Accession No.: NM.sub.—002332.2).

SEQ ID NO: 4: *Mus musculus* low density lipoprotein receptor-related protein 1 (Lrp1), mRNA (NCBI Accession No.: NM.sub.—008512.2).

SEQ ID NO: 5: *Homo sapiens* low density lipoprotein receptor (LDLR), mRNA (NCBI Accession No.: NM.sub.—000527.3).

SEQ ID NO: 6: *Homo sapiens* apolipoprotein E (APOE), mRNA (NCBI Accession No.: NM.sub.—000041.2).

SEQ ID NO: 7: *Homo sapiens* apolipoprotein A-I (APOA1), mRNA (NCBI Accession No.: NM.sub.—000039).

FIG. 3 shows

SEQ ID NO: 8: Human Natural ABCA1 antisense sequence (AK311445)

SEQ ID NO: 9: Mouse Natural ABCA1 antisense sequence (BF133827)

SEQ ID NO: 10: Human Natural LCAT antisense sequence (Hs.668679)

SEQ ID NO: 11: Human Natural LCAT antisense sequence (Hs.593769)

SEQ ID NO: 12: Human Natural LCAT antisense sequence (Hs.387239)

SEQ ID NO: 13: Human Natural LRP1 antisense sequence (Hs.711951)

SEQ ID NO: 14: Human Natural LRP1 antisense sequence (DC401271)

SEQ ID NO: 15: Human Natural LRP1 antisense sequence (BM933147)

SEQ ID NO: 16: Mouse Natural LRP1 antisense sequence (CK626173)

SEQ ID NO: 17: Mouse Natural LRP1 antisense sequence (AW544265) SEQ ID NO: 18: Human Natural ABCA1 antisense sequence (bloflor.aApr07)

SEQ ID NO: 19: Human Natural ABCA1 antisense sequence (sherflor.aApr07)

SEQ ID NO: 20: Natural APOE antisense sequence (Hs.626623)

SEQ ID NO: 21: Natural APOE antisense sequence (Hs.714236)

SEQ ID NO: 22: Natural APOA1 antisense sequence (DA327409 extended)

FIG. 4 shows the ABCA1 antisense oligonucleotides, SEQ ID NOs: 23 to 40. 'r' indicates RNA and * indicates phosphothioate bond.

FIG. 5 shows the LCAT antisense oligonucleotides, SEQ ID NOs: 41 to 58. 'r' indicates RNA and * indicates phosphothioate bond.

FIG. 6 shows the LRP1 antisense oligonucleotides, SEQ ID NOs: 59 to 73. * indicates phosphothioate bond.

FIG. 7 shows the LDLR antisense oligonucleotides, SEQ ID NOs: 74 to 83. * indicates phosphothioate bond.

FIG. 8 shows the ApoE antisense oligonucleotides, SEQ ID NOs: 84 to 92. * indicates phosphothioate bond.

FIG. 9 shows the ApoA1 antisense oligonucleotides, SEQ ID NOs: 93 to 263. 'r' indicates RNA and * indicates phosphothioate bond.

FIG. 10 shows the ABCA1 sense oligonucleotides, SEQ ID NOs: 264 to 266. The sense oligonucleotides SEQ ID NO: 264 to 266 are the reverse complements of the antisense oligonucleotides SEQ ID NO: 23 to 24 respectively. 'r' indicates RNA.

FIG. 11 shows the LCAT sense oligonucleotides, SEQ ID NOs: 275 to 282. The sense oligonucleotides SEQ ID NO:

267 to 274 are the reverse complements of the antisense oligonucleotides SEQ ID NO: 41 to 48 respectively. 'r' indicates RNA.

FIG. 12 shows:

SEQ ID NOs: 275 to 277: correspond to the probe sequence, forward primer sequence and the reverse primer sequence respectively with respect to the custom designed assay for ApoA1 antisense DA327409ext SEQ ID NO: 278: corresponds to CUR 962, * indicates phosphothioate bond and + indicates LNA.

SEQ ID NO: 279: corresponds to CUR 963, * indicates phosphothioate bond and + indicates LNA.

DETAILED DESCRIPTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "mRNA" means the presently known mRNA transcript(s) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA (Eguchi et al., (1991) Ann. Rev. Biochem. 60, 631-652). An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoogsteen or reverse Hogsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register" that is, when the monomers are linked consecutively, as in native DNA, or linked via spacers. The spacers are intended to constitute a covalent "bridge" between the regions and have in preferred cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alphahelices.

As used herein "Lipid transport and metabolism genes" are inclusive of all family members, mutants, alleles, fragments, species, coding and noncoding sequences, sense and antisense polynucleotide strands, etc.

As used herein, the words ATP-binding cassette 1; Lipid transport and metabolism gene; ABC transporter 1; cholesterol efflux regulatory protein (CERP), ABCA1, ABC-1, ABC1, CERP; F1114958; HDLDT1; TGD are used interchangeably in the present application.

As used herein, the words Lecithin-cholesterol acyltransferase, LCAT, Phosphatidylcholine-sterol acyltransferase, Phospholipid-cholesterol acyltransferase are used interchangeably in the present application.

As used herein, the words A2MR, Alpha-2-macroglobulin receptor, APOER, Apolipoprotein E receptor, APR, CD91, F1116451, IGFBP3R, LRP, LRP-1, MGC88725, Prolow-density lipoprotein receptor-related protein 1, TGFBR5 are used interchangeably in the present application.

As used herein, the words LDLR, FH, FHC, LDLCQ2, LDL receptor, Low-density lipoprotein receptor are used interchangeably in the present application.

As used herein, the words AD2, Apo-E, ApoE, Apolipoprotein E, LDLCQ5, LPG, MGC1571 are used interchangeably in the present application.

As used herein, the words ApoA1, Apo-A1, Apolipoprotein A1, MGC117399 are used interchangeably in the present application.

As used herein, the term "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term "target nucleic acid" encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences (Caplen, N.J., et al. (2001) Proc. Natl. Acad. Sci. USA 98:9742-9747). In certain embodiments of the present invention, the mediators are 5-25 nucleotide "small interfering" RNA duplexes (siRNAs). The siRNAs are derived from the processing of dsRNA by an RNase enzyme known as Dicer (Bernstein, E., et al. (2001) Nature 409:363-366). siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion (Bernstein, E., et al. (2001) Nature 409:363-366; Boutla, A., et al. (2001) Curr Biol. 11:1776-1780). Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" is meant an RNA molecule with enzymatic activity (Cech, (1988) J. American. Med. Assoc. 260, 3030-3035). Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al. (1990) Cell, 63, 601-608). This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphornates, phosphoroselenoate, phosphoramidate, and the like, as more fully described below.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in Benner et al., U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Kornberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties (see e.g., described generally by Scheit, Nucleotide Analogs, John Wiley, New York, 1980; Freier & Altmann, (1997) Nucl. Acid. Res., 25(22), 4429-4443, Toulme, J. J., (2001) Nature Biotechnology 19:17-18; Manoharan M., (1999) Biochemica et Biophysica Acta 1489:117-139; Freier S. M., (1997) Nucleic Acid Research, 25:4429-4443, Uhlman, E., (2000) Drug Discovery & Development, 3: 203-213, Herdewin P., (2000) Antisense & Nucleic Acid Drug Dev., 10:297-310); 2'-0, 3'-C-linked [3.2.0] bicycloarabinonucleosides (see e.g. N. K Christiensen., et al, (1998) J. Am. Chem. Soc., 120: 5458-5463; Prakash T P, Bhat B. (2007) Curr Top Med Chem. 7(7):641-9; Cho E J, et al. (2009) Annual Review of Analytical Chemistry, 2, 241-264). Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick, Hoogsteen or reversed Hoogsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15M) of salts with inorganic cations such as Na++ or K++(i.e., low ionic strength), temperature higher than 20.degree. C.-25.degree. C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1.times. sodium chloride-sodium citrate buffer (SSC)/0.1% (w/v) SDS at 60.degree. C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., (1990) J. Mol. Biol., 215, 403-410; Zhang and Madden, (1997) Genome Res., 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., (1981) 2, 482-489).

As used herein, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30.degree. C. for short oligonucleotides (e.g., 10 to 50 nucleotide). Stringent conditions may also be achieved with the addition of destabilizing agents such as formamide.

As used herein, "modulation" means either an increase (stimulation) or a decrease (inhibition) in the expression of a gene.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein, "cancer" refers to all types of cancer or neoplasm or malignant tumors found in mammals, including, but not limited to: leukemias, lymphomas, melanomas, carcinomas and sarcomas. The cancer manifests itself as a "tumor" or tissue comprising malignant cells of the cancer. Examples of tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Additional cancers which can be treated by the disclosed composition according to the invention include but not limited to, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

"Neurological disease or disorder" refers to any disease or disorder of the nervous system and/or visual system. "Neurological disease or disorder" include disease or disorders that involve the central nervous system (brain, brainstem and cerebellum), the peripheral nervous system (including cranial nerves), and the autonomic nervous system (parts of which are located in both central and peripheral nervous system). Examples of neurological disorders include but are not limited to, headache, stupor and coma, dementia, seizure, sleep disorders, trauma, infections, neoplasms, neuroopthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological disorder. The following is a list of several neurological disorders, symptoms, signs and syndromes that can be treated using compositions and methods according to the present invention: acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; DandyWalker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactic a polyneuritiformis; herpes zoster oticus; herpes zoster; Hirayama syndrome; HIV associated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Keams-Sayre syndrome; Kennedy disease Kinsboume syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease—neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; p muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Neurodegenerative disease or disorder (Parkinson's disease, Huntington's disease, Alzheimer's disease, amyotrophic lateral sclerosis (ALS), dementia, multiple sclerosis and other diseases and disorders associated with neuronal cell death); paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocalleukoencephalopathy; progressive sclerosing poliodystrophy; progressive supranuclear palsy; pseudotumor cerebri; Ramsay-Hunt syndrome (types I and 11); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; and Zellweger syndrome.

An "Inflammation" refers to systemic inflammatory conditions and conditions associated locally with migration and attraction of monocytes, leukocytes and/or neutrophils. Examples of inflammation include, but are not limited to, Inflammation resulting from infection with pathogenic organisms (including gram-positive bacteria, gram-negative bacteria, viruses, fungi, and parasites such as protozoa and helminths), transplant rejection (including rejection of solid organs such as kidney, liver, heart, lung or cornea, as well as rejection of bone marrow transplants including graft-versus-host disease (GVHD)), or from localized chronic or acute autoimmune or allergic reactions. Autoimmune diseases include acute glomerulonephritis; rheumatoid or reactive arthritis; chronic glomerulonephritis; inflammatory bowel diseases such as Crohn's disease, ulcerative colitis and necrotizing enterocolitis; granulocyte transfusion associated syndromes; inflammatory dermatoses such as contact dermatitis, atopic dermatitis, psoriasis; systemic lupus erythematosus (SLE), autoimmune thyroiditis, multiple sclerosis, and some forms of diabetes, or any other autoimmune state where attack by the subject's own immune system results in pathologic tissue destruction. Allergic reactions include allergic asthma, chronic bronchitis, acute and delayed hypersensitivity. Systemic inflammatory disease states include inflammation associated with trauma, burns, reperfusion following ischemic events (e.g. thrombotic events in heart, brain, intestines or peripheral vasculature, including myocardial infarction and stroke), sepsis, ARDS or multiple organ dysfunction syndrome. Inflammatory cell recruitment also occurs in atherosclerotic plaques. Inflammation includes, but is not limited to, Non-Hodgkin's lymphoma, Wegener's granulomatosis, Hashimoto's thyroiditis, hepatocellular carcinoma, thymus atrophy, chronic pancreatitis, rheumatoid arthritis, reactive lymphoid hyperplasia, osteoarthritis, ulcerative colitis, papillary carcinoma, Crohn's disease, ulcerative colitis, acute cholecystitis, chronic cholecystitis, cirrhosis, chronic sialadenitis, peritonitis, acute pancreatitis, chronic pancreatitis, chronic Gastritis, adenomyosis, endometriosis, acute cervicitis, chronic cervicitis, lymphoid hyperplasia, multiple sclerosis, hypertrophy secondary to idiopathic thrombocytopenic purpura, primary IgA nephropathy, systemic lupus erythematosus, psoriasis, pulmonary emphysema, chronic pyelonephritis, and chronic cystitis.

A cardiovascular disease or disorder includes those disorders that can either cause ischemia or are caused by reperfusion of the heart. Examples include, but are not limited to, atherosclerosis, coronary artery disease, granulomatous myocarditis, chronic myocarditis (non-granulomatous), primary hypertrophic cardiomyopathy, peripheral artery disease (PAD), stroke, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, but not limited to, tissue damage related to a Lipid transport and metabolism gene activation. CVS diseases include, but are not limited to, atherosclerosis, granulomatous myocarditis, myocardial infarction, myocardial fibrosis secondary to valvular heart disease, myocardial fibrosis without infarction, primary hypertrophic cardiomyopathy, and chronic myocarditis (non-granulomatous).

A 'Metabolic disease or disorder' refers to a wide range of diseases and disorders of the endocrine system including, for example, insulin resistance, diabetes, obesity, impaired glucose tolerance, high blood cholesterol, hyperglycemia, hyperinsulinemia, dyslipidemia and hyperlipidemia.

Polynucleotide and Oligonucleotide Compositions and Molecules

Targets

In one embodiment, the targets comprise nucleic acid sequences of a Lipid transport and metabolism genes, including without limitation sense and/or antisense noncoding and/or coding sequences associated with a Lipid transport and metabolism gene.

In one embodiment, the targets comprise nucleic acid sequences of ABCA1, including without limitation sense and/or antisense noncoding and/or coding sequences associated with ABCA1 gene.

In one embodiment, the targets comprise nucleic acid sequences of LCAT, including without limitation sense and/or antisense noncoding and/or coding sequences associated with LCAT gene.

In one embodiment, the targets comprise nucleic acid sequences of LRP1, including without limitation sense and/or antisense noncoding and/or coding sequences associated with LRP1 gene.

In one embodiment, the targets comprise nucleic acid sequences of low density lipoprotein receptor (LDLR), including without limitation sense and/or antisense noncoding and/or coding sequences associated with LDLR.

In one embodiment, the targets comprise nucleic acid sequences of apolipoprotein (ApoA1), including without limitation sense and/or antisense noncoding and/or coding sequences associated with ApoA. Human apolipoprotein A-I (ApoA-I) is the major protein constituent of high-density lipoproteins (HDL and lymph chylomicrons. In human plasma four major circulating lipoproteins have been named: chylomicrons (CM), very low-density lipoproteins (VLDL), low-density lipoproteins (LDL), and high-density lipoproteins (HDL). HDL is involved in the removal of cholesterol from peripheral tissues by transporting it to the liver or to other lipoproteins.

ATP-binding cassette, sub family-A (ABCAI) member I ABCAI functions as a cholesterol efflux pump in the cellular lipid removal pathway.

ATP-binding cassette transporters (ABC-transporter) are members of a protein superfamily that is one of the largest and most ancient families with representatives in all extant phyla from prokaryotes to humans. ABC transporters are transmembrane proteins that utilize the energy of adenosine triphosphate (ATP) hydrolysis to carry out certain biological processes including translocation of various substrates across membranes and non-transport-related processes such as translation of RNA and DNA repair. They transport a wide variety of substrates across extra- and intracellular membranes, including metabolic products, lipids and sterols, and drugs. Proteins are classified as ABC transporters based on the sequence and organization of their ATP-binding cassette (ABC) domain(s). ABC transporters are involved in tumor resistance, cystic fibrosis, bacterial multidrug resistance, and a range of other inherited human diseases.

The membrane-associated protein encoded by ABC1 gene is a member of the superfamily of ATP-binding cassette (ABC) transporters. ABC proteins transport various molecules across extra- and intracellular membranes. ABC genes are divided into seven distinct subfamilies (ABCA, MDRITAP, MRP, ALD, OABP, GCN20, White). This protein is a member of the ABCA subfamily. Members of the ABCA subfamily comprise the only major ABC subfamily found exclusively in multicellular eukaryotes. With cholesterol as its substrate, this protein functions as a cholesterol efflux pump in the cellular lipid removal pathway.

In preferred embodiments, antisense oligonucleotides are used to prevent or treat diseases or disorders associated with ATP-Binding cassette molecules. ATP-binding cassette transporter ABC1 (member 1 of human transporter subfamily ABCA), also known as the cholesterol efflux regulatory protein (CERP) is a protein which in humans is encoded by the ABC1 gene. This transporter is a major regulator of cellular cholesterol and phospholipid homeostasis.

ABC1 is present in high-density lipoproteins (HDL) which permits the removal of excessive cholesterol and phospholipids from human cell membranes. Since this protein is needed throughout the body it is synthesis ubiquitously as a 220-kDa protein. It is present in higher quantities in tissues that shuttle or are involved in the turnover of lipids such as the liver, the small intestine and adipose tissue.

Factors that act upon the ABC1 transporter's expression or its posttranslational modification are also molecules that are involved in its subsequent function like fatty acids, cholesterol and also cytokines and cyclic adenosine monophosphate.

Low-density lipoprotein receptor-related protein 1 (LPR1) is about 4544 amino acids; 504575 Da. It is a heterodimer of an 85-kDa membrane-bound carboxyl subunit and a noncovalently attached 515-kDa amino-terminal subunit. Intracellular domain interacts with MAFB. LPR1 is found in a complex with PIDIIPCLI1, LRP1 and CUBNI. Interacts with SNX17, PIDIIPCLI1, PDGF, LRPAP1 and CUBN. The intracellular domain interacts with SHC1, GULP1 and DAB 1.

LRP1 is an endocytic receptor involved in endocytosis and in phagocytosis of apoptotic cells; early embryonic development; cellular lipid homeostasis; plasma clearance of chylomicron remnants and activated LRPAP1 (alpha 2-macroglobulin); local metabolism of complexes between plasminogen activators and their endogenous inhibitors. Without wishing to be bound by theory, it may modulate cellular events, such as APP metabolism, kinase-dependent intracellular signaling, neuronal calcium signaling as well as neurotransmission.

High density lipoprotein (HDL) picks up extra cholesterol in the blood and returns it to the liver Low density lipoprotein (or LDL) is the main transporter of cholesterol in the body. But too much LDL over many years can result in atherosclerosis (the narrowing and hardening of arteries) and lead to heart disease or a heart attack. The ratio is determined by dividing the LDL cholesterol into the HDL cholesterol. For example, if a person has an HDL cholesterol of 50 mg/dL and an LDL cholesterol of 150 mg/dL, the HDL/LDL ratio would be 0.33. The goal is to keep the HDL/LDL ratio above 0.3, with the ideal HDL/LDL ratio being above 0.4.

HDL are synthesized de novo in both the liver and small intestine as protein-rich disc-shaped particles. The primary apoproteins of HDL are apoA-I, apoA-II, apoC-I, apoC-II, and apoE. Newly formed HDL contain very little cholesterol and cholesteryl esters. HDL are converted from their initial discoidal shape into spherical lipoprotein particles through the accumulation of cholesteryl esters in the neutral core of the lipoprotein particle. Cholesterol is accumulated by HDL from chylomicron remnants VLDL remnants (also called intermediate density Lipoproteins or IDL) and directly from cell surface membranes. The cholesterol is esterified through the action of an HDL-associated enzyme lecithin:cholesterol acyltransferase ("LCAT"). For LCAT to transfer a fatty acid from lecithin (phosphatidylcholine) to the C-3-OH group of cholesterol, interaction with ApoA-I found on the HDL surface is required. This accumulation of core cholesteryl esters converts nascent HDL to HDL2 and HDL3. See R. I. Levy et al., "The structure, function and metabolism of high-density lipoproteins: A status report," Circulation, vol. 62, pp. IV4-8 (1980); and D. I. Silverman et al., "High-density lipoprotein subfractions," Am. J. Med., vol. 94, pp. 636-45 (1993).

HDL are usually isolated from the plasma by ultracentrifugation. The normal HDL density range is from 1.063 g/mL to 1.21 g/mL, which divides roughly into two ranges HDL2 (1.063 g/mL to 1.125 g/mL) and HDL3 (1.125 g/mL to 1.21 g/mL). More recently, two major populations of particles in HDL have been identified by two dimensional electrophoresis followed by immunoblotting and enzyme-linked differential antibody immunosorbent assay. One of these populations contains particles with apoA-I alone, and the other contains particles with both apoA-I and apoA-II. The relative proportion of apoA-I particles is highest in the HDL2 fraction, while HDL3 is more a combination of apoA-I and apoA-II. See J. C. Fruchart et al., "Apolipoprotein A-containing lipoprotein particles: physiological role, quantification, and clinical significance," Clin. Chem., vol. 38, pp. 793-7 (1992); and B. F. Asztalos et al., "Normolipidemic subjects with low HDL cholesterol levels have altered HDL subpopulations," Arteriosder. Thromb. Vasc. Biol., vol. 17, pp. 1885-1893 (1997).

Human apolipoprotein A-I (ApoA-I) is the major protein constituent of HDL and lymph chylomicrons. ApoA-I is primarily synthesized in the liver and small intestine as a precursor protein (preproapo A-I). Preproapo A-I is cleaved intracellularly to form proapo A-I, the form secreted into the plasma and lymph. In the plasma, six amino acids are cleaved from proapo A-I to form mature ApoA-I.

Mature ApoA-I is a single unglycosylated polypeptide composed of 243 amino acids of known sequence. ApoA-I serves as a cofactor of a plasma enzyme (lecithin-cholesterol acyltransferase (LCAT)), responsible for the formation of most cholesterol esters in plasma. Decreased levels of ApoA-I may result in disorders of the plasma lipid transport system and in the development of coronary heart disease. Low levels of both ApoA-I and HDL has been shown to be a strong risk factor for heart attacks and other atherosclerotic vascular diseases. See U.S. Pat. Nos. 5,059,528 and 6,258,596.

Apolipoprotein E (ApoE) is an apoprotein found in the chylomicron and intermediate-density lipoproteins (IDLs) that binds to a specific receptor on liver cells and peripheral cells. Intermediate-density lipoproteins belong to the lipoprotein particle family and are formed from the degradation of very low-density lipoproteins. IDL is one of the five major groups of lipoproteins (chylomicrons, VLDL, IDL, LDL, HDL) that enable fats and cholesterol to move within the water-based solution of the bloodstream. Apolipoprotein E (ApoE) is important for the normal catabolism of triglyceride-rich lipoprotein constituents.

The APOE gene, ApoE, is mapped to chromosome 19 in a cluster with Apolipoprotein C1 and Apolipoprotein C2. ApoE consists of four exons and three introns, totaling 3597 base pairs. In melanocytic cells APOE gene expression may be regulated by microphthalmia-associated transcription factor (MITF). The gene is polymorphic with three major alleles, ApoE2, ApoE3, ApoE4, which translate into three isoforms of the protein: normal—ApoE-E3; dysfunctional—ApoE-E2 and ApoE-E4. These isoforms differ from each other only by single amino acid substitutions at positions 112 and 158.

Lecithin-cholesterol acyltransferase (LCAT), is a plasma enzyme produced by the liver and catalyzes the conversion of cholesterol to cholesteryl esters on lipoproteins by the transacylation of fatty acid from the sn-2 position of phosphatidylcholine to the 3-hydroxyl group on the A-ring of cholesterol. Most LCAT activity is found on high-density lipoprotein (HDL) but approximately 30% is also on apolipoprotein (Apo) B-containing lipoproteins.

The apolipoprotein E gene is polymorphic with three major alleles, ApoE2, ApoE3, ApoE4. E2 is associated with the genetic disorder type III hyperlipoproteinemia and with both increased and decreased risk for atherosclerosis. E3 is found in approximately 64 percent of the population. It is considered the "neutral" Apo E genotype. E4 may contribute to atherosclerosis and Alzheimer's disease, impaired cognitive function, and reduced neurite outgrowth.

LCAT promotes the reverse cholesterol transport pathway, the pathway by which excess cellular cholesterol is returned to the liver for excretion. Without wishing to be bound by theory, mechanisms include, for example LCAT increases the level of HDL, which in itself may increase the flux of cholesterol from cells by increasing the amount of extracellular acceptors of cholesterol. Also, esterification of cholesterol by LCAT on HDL could limit the spontaneous back exchange of cholesterol from HDL to cells and promotes the net delivery of cholesterol on HDL and on to the liver.

In preferred embodiments, antisense oligonucleotides are used to prevent or treat diseases or disorders associated with Lipid transport and metabolism gene family members. Exemplary Lipid transport and metabolism gene mediated diseases and disorders which can be treated with cell/tissues regenerated from stem cells obtained using the antisense compounds comprise: a cardiovascular disease or disorder, a metabolic disease or disorder (e.g., diabetes, obesity, dyslipidemia, hyperglycemia, hyperinsulinemia, hypercholesterolemia etc.), a disease or disorder associated with impaired lipid metabolism, a coronary artery disease, atherosclerosis, an HDL metabolism disease or disorder (e.g., familial HDL deficiency (FHD), Sea-blue histiocytosis, Tangier's Disease, Fish-eye disease, LCAT deficiency, low-HDL cholesterolemia etc.), a disease or disorder associated with cellular cholesterol and/or phospholipid homeostasis, Familial amyloid nephropathy, a disease or disorder associated with impaired cholesterol regulation, a disease or disorder associated with a deficiency of the Lipid transport and metabolism gene transporter, Apolipoprotein A-I deficiency, a disease or disorder associated with abnormally fast or abnormally slow rate of cholesterol efflux in a cell, a disease or disorder associated with pancreatic beta cell function, diabetes, a metabolic disease or disorder, arthritis, inflammation, an autoimmune disease or disorder, acquired immune deficiency syndrome (AIDS), inflammation, a neurological disease or disorder, a neurodegenerative disease or disorder, cancer, dyslipidiemia, metabolic syndrome, a senile plaque, cerebral amyloid angiopathy, Amyloidosis, glioblastoma, a disease or disorder associated with amyloid deposition, neurofibrillary tangles, choriocarcinoma, astrocytoma, amyloidosis, hyperlipidemia, neoplastic transformation, atherosclerotic plaque, obstruction, metastasis, pulmonary fibrosis, necrosis, shock, melanoma, genetic susceptibility, psoriasis, glioma, neuropathology, a vascular disease, cell damage, Nonsmall cell lung carcinomas (NSCLCs), liposarcoma, an immunodeficiency disease or disorder, an organ transplant rejection, an allergy, glomerulonephritis, venous thrombosis, pathological processes or leukemia, a skeletal disease or disorder, a muscular disease or disorder, a disease or disorder associated with infectious organisms, an immune related disease or disorder, nerve repair and paralysis, neuroendocrine differentiation, systemic non-neuropathic amyloidosis, an amyloid disease, tumor growth dependent on angiogenesis, non-cancerous diseases with symptoms include an increase in angiogenesis, e.g., psoriasis, retinopathy of prematurity, a Choroid disease, neovascular glaucoma, diabetic retinopathy, substance abuse, impaired cognitive function, and reduced neurite outgrowth, ApoE abnormal expression, function, activity as compared to a normal control, psoriasis, a disease or disorder caused by foreign organisms such as viral, bacterial, parasitic, fungal, and the like.

In a preferred embodiment the Lipid transport and metabolism gene antisense oligonucleotides are therapeutically used in organ transplantation (e.g., liver transplant, kidney transplant, bone marrow transplant, heart transplant etc.).

In a preferred embodiment, the oligonucleotides are specific for polynucleotides of a Lipid transport and metabolism gene, which includes, without limitation noncoding regions. The Lipid transport and metabolism gene targets comprise variants of a Lipid transport and metabolism gene; mutants of a Lipid transport and metabolism gene, including SNPs; noncoding sequences of a Lipid transport and metabolism gene; alleles, fragments and the like. Preferably the oligonucleotide is an antisense RNA molecule.

In accordance with embodiments of the invention, the target nucleic acid molecule is not limited to a Lipid transport and metabolism gene polynucleotides alone but extends to any of the isoforms, receptors, homologs, non-coding regions and the like of a Lipid transport and metabolism gene.

In another preferred embodiment, an oligonucleotide targets a natural antisense sequence (natural antisense to the coding and non-coding regions) of a Lipid transport and metabolism gene targets, including, without limitation, variants, alleles, homologs, mutants, derivatives, fragments and complementary sequences thereto. Preferably the oligonucleotide is an antisense RNA or DNA molecule.

In another preferred embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound.

These compounds are then tested using the methods described herein to determine their ability to inhibit expression of a target nucleic acid.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired. Such conditions include, i.e., physiological conditions in the case of in vivo assays or therapeutic treatment, and conditions in which assays are performed in the case of in vitro assays.

An antisense compound, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarily to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In another preferred embodiment, targeting of a Lipid transport and metabolism gene including without limitation, antisense sequences which are identified and expanded, using for example, PCR, hybridization etc., one or more of the sequences set forth as SEQ ID NO: 8 to 22, and the like, modulate the expression or function of a Lipid transport and metabolism gene. In one embodiment, expression or function is up-regulated as compared to a control. In another preferred embodiment, expression or function is down-regulated as compared to a control.

In another preferred embodiment, oligonucleotides comprise nucleic acid sequences set forth as SEQ ID NOS: 23 to 263 including antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes a Lipid transport and metabolism gene.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In a preferred embodiment, the antisense oligonucleotides bind to the natural antisense sequences of a Lipid transport and metabolism gene and modulate the expression and/or function of a Lipid transport and metabolism gene (SEQ ID NO: 1). Examples of antisense sequences include SEQ ID NOS: 8 to 263.

In another preferred embodiment, the antisense oligonucleotides bind to one or more segments of a Lipid transport and metabolism gene polynucleotide and modulate the expression and/or function of a Lipid transport and metabolism gene. The segments comprise at least five consecutive nucleotides of a Lipid transport and metabolism gene sense or antisense polynucleotides.

In another preferred embodiment, the antisense oligonucleotides are specific for natural antisense sequences of a Lipid transport and metabolism gene wherein binding of the oligonucleotides to the natural antisense sequences of a Lipid transport and metabolism gene modulate expression and/or function of a Lipid transport and metabolism gene.

In another preferred embodiment, oligonucleotide compounds comprise sequences set forth as SEQ ID NOS: 23 to 263, antisense sequences which are identified and expanded, using for example, PCR, hybridization etc These oligonucleotides can comprise one or more modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding a Lipid transport and metabolism gene, regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. Another target region for this invention is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In another preferred embodiment, the antisense oligonucleotides bind to coding and/or non-coding regions of a target polynucleotide and modulate the expression and/or function of the target molecule.

In another preferred embodiment, the antisense oligonucleotides bind to natural antisense polynucleotides and modulate the expression and/or function of the target molecule.

In another preferred embodiment, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

Target segments 5-100 nucleotides in length comprising a stretch of at least five (5) consecutive nucleotides selected from within the illustrative preferred target segments are considered to be suitable for targeting as well.

Target segments can include DNA or RNA sequences that comprise at least the 5 consecutive nucleotides from the 5'-terminus of one of the illustrative preferred target segments (the remaining nucleotides being a consecutive stretch of the same DNA or RNA beginning immediately upstream of the 5'-terminus of the target segment and continuing until the DNA or RNA contains about 5 to about 100 nucleotides). Similarly preferred target segments are represented by DNA or RNA sequences that comprise at least the 5 consecutive nucleotides from the 3'-terminus of one of the illustrative preferred target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment, it is preferred to target specific nucleic acids by antisense oligonucleotides. Targeting an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or a non coding polynucleotide such as for example, non coding RNA (ncRNA).

RNAs can be classified into (1) messenger RNAs (mRNAs), which are translated into proteins, and (2) non-protein-coding RNAs (ncRNAs). ncRNAs comprise microRNAs, antisense transcripts and other Transcriptional Units (TU) containing a high density of stop codons and lacking any extensive "Open Reading Frame". Many ncRNAs appear to start from initiation sites in 3' untranslated regions (3'UTRs) of protein-coding loci. ncRNAs are often rare and at least half of the ncRNAs that have been sequenced by the FANTOM consortium seem not to be polyadenylated. Most researchers have for obvious reasons focused on polyadenylated mRNAs that are processed and exported to the cytoplasm. Recently, it was shown that the set of non-polyadenylated nuclear RNAs may be very large, and that many such transcripts arise from so-called intergenic regions (Cheng, J. et al. (2005) Science 308 (5725), 1149-1154; Kapranov, P. et al. (2005). Genome Res 15 (7), 987-997). The mechanism by which ncRNAs may regulate gene expression is by base pairing with target transcripts. The RNAs that function by base pairing can be grouped into (1) cis encoded RNAs that are encoded at the same genetic location, but on the opposite strand to the RNAs they act upon and therefore display perfect complementarity to their target, and (2) trans-encoded RNAs that are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping parts of the antisense transcript resulting in its knockdown or sequestration. Coding as well as non-coding antisense can be targeted in an identical manner and that either category is capable of regulating the corresponding sense transcripts—either in a concordant or disconcordant manner. The strategies that are employed in identifying new oligonucleotides for use against a target can be based on the knockdown of antisense RNA transcripts by antisense oligonucleotides or any other means of modulating the desired target.

Strategy 1: In the case of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2: In the case of concordant regulation, one could concomitantly knock down both antisense and sense transcripts and thereby achieve synergistic reduction of the conventional (sense) gene expression. If, for example, an antisense oligonucleotide is used to achieve knockdown, then this strategy can be used to apply one antisense oligonucleotide targeted to the sense transcript and another antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

In another preferred embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs). It is currently not known whether RNAa is conserved in other organisms.

Small double-stranded RNA (dsRNA), such as small interfering RNA (siRNA) and microRNA (miRNA), have been found to be the trigger of an evolutionary conserved mechanism known as RNA interference (RNAi). RNAi invariably leads to gene silencing via remodeling chromatin to thereby suppress transcription, degrading complementary mRNA, or blocking protein translation. However, in instances described in detail in the examples section which follows, oligonucleotides are shown to increase the expression and/or function of the Lipid transport and metabolism gene polynucleotides and encoded products thereof dsRNAs may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In a further embodiment, the "preferred target segments" identified herein may be employed in a screen for additional compounds that modulate the expression of a Lipid transport and metabolism gene polynucleotide. "Modulators" are those compounds that decrease or increase the expression of a nucleic acid molecule encoding a Lipid transport and metabolism gene and which comprise at least a 5-nucleotide portion that is complementary to a preferred target segment. The screening method comprises the steps of contacting a preferred target segment of a nucleic acid molecule encoding sense or natural antisense polynucleotides of a Lipid transport and metabolism gene with one or more candidate modulators, and selecting for one or more candidate modulators which decrease or increase the expression of a nucleic acid molecule encoding a Lipid transport and metabolism gene polynucleotide, e.g. SEQ ID NOS: 23 to 263. Once it is shown that the candidate modulator or modulators are capable of modulating (e.g. either decreasing or increasing) the expression of a nucleic acid molecule encoding a Lipid transport and metabolism gene polynucleotide, the modulator may then be employed in further investigative studies of the function of a Lipid transport and metabolism gene polynucleotide, or for use as a research, diagnostic, or therapeutic agent in accordance with the present invention.

Targeting the natural antisense sequence preferably modulates the function of the target gene. For example, the Lipid transport and metabolism gene (e.g. accession numbers NM.sub.—005502, NM.sub.—000229, NM.sub.—002332, NM.sub.—008512, NM.sub.—000527.3, NM.sub.—000041, NM.sub.—000039, FIG. 2). In a preferred embodiment, the target is an antisense polynucleotide of the Lipid transport and metabolism gene. In a preferred embodiment, an antisense oligonucleotide targets sense and/or natural antisense sequences of a Lipid transport and metabolism gene polynucleotide (e.g. accession numbers NM.sub.—005502, NM.sub.—000229, NM.sub.—002332, NM.sub.—008512, NM.sub.—000527, NM.sub.—000041, NM.sub.—000039, FIG. 2), variants, alleles, isoforms, homologs, mutants, derivatives, fragments and complementary sequences thereto. Preferably the oligonucleotide is an antisense molecule and the targets include coding and non-coding regions of antisense and/or sense Lipid transport and metabolism gene polynucleotides.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., (1998) Nature, 391, 806-811; Timmons and Fire, (1998) Nature, 395, 854;

Timmons et al., (2001) Gene, 263, 103-112; Tabara et al., (1998) Science, 282, 430-431; Montgomery et al., (1998) Proc. Natl. Acad. Sci. USA, 95, 15502-15507; Tuschl et al., (1999) Genes Dev., 13, 3191-3197; Elbashir et al., (2001) Nature, 411, 494-498; Elbashir et al., (2001) Genes Dev. 15, 188-200). For example, such double-stranded moieties have been shown to inhibit the target by the classical hybridization of antisense strand of the duplex to the target, thereby triggering enzymatic degradation of the target (Tijsterman et al., (2002) Science, 295, 694-697).

In a preferred embodiment, an antisense oligonucleotide targets Lipid transport and metabolism gene polynucleotides (e.g. accession numbers NM.sub.—005502, NM.sub.—000229, NM.sub.—002332, NM.sub.—008512. NM.sub.—000527, NM.sub.—000041, NM.sub.—000039), variants, alleles, isoforms, homologs, mutants, derivatives, fragments and complementary sequences thereto. Preferably the oligonucleotide is an antisense molecule.

In accordance with embodiments of the invention, the target nucleic acid molecule is not limited to Lipid transport and metabolism gene alone but extends to any of the isoforms, receptors, homologs and the like of a Lipid transport and metabolism gene molecule.

In another preferred embodiment, an oligonucleotide targets a natural antisense sequence of a Lipid transport and metabolism gene polynucleotide, for example, polynucleotides set forth as SEQ ID NO: 8 to 22, and any variants, alleles, homologs, mutants, derivatives, fragments and complementary sequences thereto. Examples of antisense oligonucleotides are set forth as SEQ ID NOS: 23 to 263.

In one embodiment, the oligonucleotides are complementary to or bind to nucleic acid sequences of a Lipid transport and metabolism gene antisense, including without limitation noncoding sense and/or antisense sequences associated with a Lipid transport and metabolism gene polynucleotide and modulate expression and/or function of a Lipid transport and metabolism gene molecule.

In another preferred embodiment, the oligonucleotides are complementary to or bind to nucleic acid sequences of a Lipid transport and metabolism gene natural antisense, set forth as SEQ ID NO: 8 to 22 and modulate expression and/or function of a Lipid transport and metabolism gene molecule.

In a preferred embodiment, oligonucleotides comprise sequences of at least 5 consecutive nucleotides of SEQ ID NOS: 23 to 263 and modulate expression and/or function of a Lipid transport and metabolism gene molecule.

The polynucleotide targets comprise Lipid transport and metabolism gene, including family members thereof, variants of a Lipid transport and metabolism gene; mutants of a Lipid transport and metabolism gene, including SNPs; noncoding sequences of a Lipid transport and metabolism gene; alleles of a Lipid transport and metabolism gene; species variants, fragments and the like. Preferably the oligonucleotide is an antisense molecule.

In another preferred embodiment, the oligonucleotide targeting Lipid transport and metabolism gene polynucleotides, comprise: antisense RNA, interference RNA (RNAi), short interfering RNA (siRNA); micro interfering RNA (miRNA); a small, temporal RNA (stRNA); or a short, hairpin RNA (shRNA); small RNA-induced gene activation (RNAa); or, small activating RNA (saRNA).

In another preferred embodiment, targeting of a Lipid transport and metabolism gene polynucleotide, e.g. SEQ ID NO: 8 to 22 modulate the expression or function of these targets. In one embodiment, expression or function is up-regulated as compared to a control. In another preferred embodiment, expression or function is down-regulated as compared to a control.

In another preferred embodiment, antisense compounds comprise sequences set forth as SEQ ID NOS: 23 to 263. These oligonucleotides can comprise one or more modified nucleotides, shorter or longer fragments, modified bonds and the like.

In another preferred embodiment, SEQ ID NOS: 23 to 263 comprise one or more LNA nucleotides.

The modulation of a desired target nucleic acid can be carried out in several ways known in the art. For example, antisense oligonucleotides, siRNA etc. Enzymatic nucleic acid molecules (e.g., ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript (Zaug et al., 324, Nature 429 1986; Cech, 260 JAMA 3030, 1988; and Jefferies et al., 17 Nucleic Acids Research 1371, 1989).

Because of their sequence-specificity, trans-cleaving enzymatic nucleic acid molecules show promise as therapeutic agents for human disease (Usman & McSwiggen, (1995) Ann. Rep. Med. Chem. 30, 285-294; Christoffersen and Marr, (1995) J. Med. Chem. 38, 2023-2037). Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, (1979) Proc. R. Soc. London, B 205, 435) have been used to evolve new nucleic acid catalysts capable of catalyzing a variety of reactions, such as cleavage and ligation of phosphodiester linkages and amide linkages, (Joyce, (1989) Gene, 82, 83-87; Beaudry et al., (1992) Science 257, 635-641; Joyce, (1992) Scientific American 267, 90-97; Breaker et al., (1994) TIBTECH 12, 268; Bartel et al., (1993) Science 261:1411-1418; Szostak, (1993) TIBS 17, 89-93; Kumar et al., (1995) FASEB J., 9, 1183; Breaker, (1996) Curr. Op. Biotech., 7, 442).

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 mM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain selfcleaving ribozymes may be optimized to give maximal catalytic activity, or that entirely new RNA motifs can be made that display significantly faster rates for RNA phosphodiester cleavage.

Intermolecular cleavage of an RNA substrate by an RNA catalyst that fits the "hammerhead" model was first shown in 1987 (Uhlenbeck, O. C. (1987) Nature, 328: 596-600). The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalytic RNA to maintain necessary base pairing with the target sequences (Haseloff and Gerlach, (1988) Nature, 334, 585; Walbot and Bruening, (1988) Nature, 334, 196; Uhlenbeck, O. C. (1987) Nature, 328: 596-600; Koizumi, M., et al. (1988) FEBS Left., 228: 228-230). This has allowed use of the catalytic RNA to cleave specific target sequences and indicates that catalytic RNAs designed according to the "hammerhead" model may possibly cleave specific substrate RNAs in vivo. (see Haseloff and Gerlach, (1988) Nature, 334, 585; Walbot and Bruening, (1988) Nature, 334, 196; Uhlenbeck, O. C. (1987) Nature, 328: 596-600).

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and permit the use of regulated and tissue specific promoters for gene expression.

In a preferred embodiment, an oligonucleotide or antisense compound comprises an oligomer or polymer of ribonucleic acid (RNA) and/or deoxyribonucleic acid (DNA), or a mimetic, chimera, analog or homolog thereof. This term includes oligonucleotides composed of naturally occurring nucleotides, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines (Hammond et al., (1991) Nat. Rev. Genet., 2, 110-119; Matzke et al., (2001) Curr. Opin. Genet. Dev., 11, 221-227; Sharp, (2001) Genes Dev., 15, 485-490). When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound of the invention comprises from 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length.

In one embodiment, the antisense or oligonucleotide compounds of the invention have antisense portions of 12 or 13 to 30 nucleotides in length. One having ordinary skill in the art will appreciate that this embodies antisense compounds having antisense portions of 12, 13, 14, 15, 16, 17, 18, 19, 20, 21, 22, 23, 24, 25, 26, 27, 28, 29 or 30 nucleotides in length, or any range therewithin.

In another preferred embodiment, the oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In another preferred embodiment, the antisense oligonucleotides, such as for example, nucleic acid molecules set forth in SEQ ID NOS: 8 to 263 comprise one or more substitutions or modifications. In one embodiment, the nucleotides are substituted with locked nucleic acids (LNA).

In another preferred embodiment, the oligonucleotides target one or more regions of the nucleic acid molecules sense and/or antisense of coding and/or non-coding sequences associated with Lipid transport and metabolism gene and the sequences set forth as SEQ ID NOS: 1 to 7 and 8 to 22. The oligonucleotides are also targeted to overlapping regions of SEQ ID NOS: 1 to 7 and 8 to 22.

Certain preferred oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one preferred embodiment, a chimeric oligonucleotide comprises at least one region modified to increase target binding affinity, and, usually, a region that acts as a substrate for RNAse H Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target.

Chimeric antisense compounds of the invention may be formed as composite structures of two or more oligonucleotides, modified oligonucleotides, oligonucleosides and/or oligonucleotides mimetics as described above. Such; compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In another preferred embodiment, the region of the oligonucleotide which is modified comprises at least one nucleotide modified at the 2' position of the sugar, most preferably a 2'-Oalkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. Some desirable modifications can be found in De Mesmaeker et al. (1995) Acc. Chem. Res., 28:366-374.

Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, —N(CH3)-O—CH2 [known as a methylene (methylimino) or MMI backbone], CH2-O—N(CH3)-CH2, CH2-N(CH3)-N(CH3)-CH2 and O—N(CH3)-CH2-CH2 backbones, wherein the native phosphodiester backbone is represented as O—P—O—CH,). The amide backbones disclosed by De Mesmaeker et al. (1995) Acc. Chem. Res. 28:366-374 are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone (Nielsen et al. (1991) Science 254, 1497). Oligonucleotides may also comprise one or more substituted sugar moieties. Preferred oligonucleotides comprise one of the following at the 2' position: OH, SH, SCH3, F, OCN, OCH3 OCH3, OCH3O (CH2)n CH3, O(CH2)n NH2 or O(CH2)n CH3 where n is from 1 to about 10; C1 to C10 lower alkyl, alkoxyalkoxy, substituted lower alkyl, alkaryl or aralkyl; Cl; Br; CN; CF3; OCF3; S—, or N-alkyl; S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH2 CH2 OCH3, also known as 2'-O-(2-methoxyethyl)] (Martin et al., (1995) Helv. Chim. Acta, 78, 486). Other preferred modifications include 2'-methoxy (2'-O—CH3), 2'-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleotides, e.g., 2-amino adenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. (Kornberg, A., DNA Replication, W. H. Freeman & Co., San Francisco, 1980, pp 75-77; Gebeyehu, G., (1987) et al. Nucl. Acids Res. 15:4513). A "universal" base known in the art, e.g., inosine, may be included. 5-Me-C substitutions have been shown to increase nucleic acid duplex stability by 0.6-1.2.degree. C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., (1989) Proc. Natl. Acad. Sci. USA 86, 6553), cholic acid (Manoharan et al. (1994) Bioorg. Med. Chem. Let. 4, 1053), a thioether, e.g., hexyl-S-tritylthiol (Manoharan et al. (1992) Ann. N.Y. Acad. Sci. 660, 306; Manoharan et al. (1993) Bioorg. Med. Chem. Let. 3, 2765), a thiocholesterol (Oberhauser et al., (1992) Nucl. Acids Res. 20, 533), an aliphatic chain, e.g., dodecandiol or undecyl residues (Saison-Behmoaras et al. EMBO J. 1991, 10, 111; Kabanov et al. (1990) FEBS Left. 259, 327; Svinarchuk et al. (1993) Biochimie 75, 49), a phospholipid, e.g., di-hexadecyl-rac-glycerol or triethylammonium 1,2-di-O-hexadecyl-rac-glycero-3-H-phosphonate (Manoharan et al. (1995) Tetrahedron Left. 36, 3651; Shea et al. (1990) Nucl. Acids Res. 18, 3777), a polyamine or a polyethylene glycol chain (Manoharan et al. (1995) Nucleosides & Nucleotides, 14, 969), or adamantane acetic acid (Manoharan et al. (1995) Tetrahedron Left. 36, 3651). Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc (Uhlman, et al. (2000) Current Opinions in Drug Discovery & Development Vol. 3 No 2). This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 5 and 25 nucleotides, more preferably between about 12 and 20 nucleotides.

Preferred modified oligonucleotide backbones comprise, but not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264, 562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen, et al. (1991) Science 254, 1497-1500.

In another preferred embodiment of the invention the oligonucleotides with phosphorothioate backbones and oligonucleosides with heteroatom backbones, and in particular—CH2-NH—O—CH2-, —CH2-N(CH3)-O—CH2— known as a methylene (methylimino) or MMI backbone, —CH2-O—N(CH3)-CH2-, —CH2N(CH3)-N(CH3) CH2-and-O—N(CH3)-CH2-CH2- wherein the native phosphodiester backbone is represented as —O—P—O—CH2- of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; S—, or N-alkyl; S—, or N-alkenyl; O-, S- or N-alkynyl; or O alkyl-O-alkyl, wherein the alkyl, alkenyl and alkynyl may be substituted or unsubstituted C to CO alkyl or C2 to CO alkenyl and alkynyl. Particularly preferred are O(CH2)n OmCH3, O(CH2)n, OCH3, O(CH2)nNH2, O(CH2)nCH3, O(CH2)nONH2, and O(CH2nON(CH2)nCH3)2 where n and m can be from 1 to about 10. Other preferred oligonucleotides comprise one of the following at the 2' position: C to CO, (lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification comprises 2'-methoxyethoxy (2'-O—CH2CH2OCH3, also known as 2'-O-(2-methoxyethyl) or 2'-MOE) (Martin et al., (1995) Helv. Chim. Acta, 78, 486-504) i.e., an alkoxyalkoxy group. A further preferred modification comprises 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2.

Other preferred modifications comprise 2'-methoxy (2'-OCH3), 2'-aminopropoxy (2'-OCH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646, 265;

5,658,873; 5,670,633; and 5,700,920, each of which is herein incorporated by reference.

Oligonucleotides may also comprise nucleobase (often referred to in the art simply as "base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleotides are particularly useful for increasing the binding affinity of the oligomeric compounds of the invention. These comprise 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-Omethoxyethyl sugar modifications.

Representative United States patents that teach the preparation of the above noted modified nucleotides as well as other modified nucleotides comprise, but are not limited to, U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety (Letsinger et al., (1989) Proc. Natl. Acad. Sci. USA, 86, 6553-6556), cholic acid (Manoharan et al., (1994) Bioorg. Med. Chem. Let., 4, 1053-1060), a thioether, e.g., hexyl-S-tritylthiol (Manoharan et al., (1992) Ann. N. Y. Acad. Sci., 660, 306-309; Manoharan et al., (1993) Bioorg. Med. Chem. Let., 3, 2765-2770), a thiocholesterol (Oberhauser et al., (1992) Nucl. Acids Res., 20, 533-538), an aliphatic chain, e.g., dodecandiol or undecyl residues (Kabanov et al., (1990) FEBS Left., 259, 327-330; Svinarchuk et al., (1993) Biochimie 75, 49-54), a phospholipid, e.g., di-hexadecyl-rac-glycerol or triethylammonium 1,2-di-O-hexadecyl-rac-glycero-3-H-phosphonate (Manoharan et al., (1995) Tetrahedron Left., 36, 3651-3654; Shea et al., (1990) Nucl. Acids Res., 18, 3777-3783), a polyamine or a polyethylene glycol chain (Mancharan et al., (1995) Nucleosides & Nucleotides, 14, 969-973), or adamantane acetic acid (Manoharan et al., (1995) Tetrahedron Left., 36, 3651-3654), a palmityl moiety (Mishra et al., (1995) Biochim. Biophys. Acta, 1264, 229-237), or an octadecylamine or hexylamino-carbonyl-t oxycholesterol moiety (Crooke et al., (1996) J. Pharmacol. Exp. Ther., 277, 923-937).

Representative United States patents that teach the preparation of such oligonucleotides conjugates comprise, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486, 603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203; 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, each of which is herein incorporated by reference.

Drug Discovery:

The compounds of the present invention can also be applied in the areas of drug discovery and target validation. The present invention comprehends the use of the compounds and preferred target segments identified herein in drug discovery efforts to elucidate relationships that exist between a Lipid transport and metabolism gene polynucleotide and a disease state, phenotype, or condition. These methods include detecting or modulating a Lipid transport and metabolism gene polynucleotide comprising contacting a sample, tissue, cell, or organism with the compounds of the present invention, measuring the nucleic acid or protein level of a Lipid transport and metabolism gene polynucleotide and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up Regulation or Inhibition of Gene Expression:

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly(A) signal. These plasmids would produce an mRNA with a reporter gene in the upstream portion of the gene and a potential RNAi target in the 3' non-coding region. The effectiveness of individual antisense oligonucleotides would be assayed by modulation of the reporter gene. Reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

Lipid transport and metabolism gene protein and mRNA expression can be assayed using methods known to those of skill in the art and described elsewhere herein. For example, immunoassays such as the ELISA can be used to measure protein levels. Lipid transport and metabolism gene antibodies for ELISAs are available commercially, e.g., from R&D Systems (Minneapolis, Minn.), Abcam, Cambridge, Mass.

In embodiments, Lipid transport and metabolism gene expression (e.g., mRNA or protein) in a sample (e.g., cells or tissues in vivo or in vitro) treated using an antisense oligonucleotide of the invention is evaluated by comparison with Lipid transport and metabolism gene expression in a control sample. For example, expression of the protein or nucleic acid can be compared using methods known to those of skill in the art with that in a mock-treated or untreated sample. Alternatively, comparison with a sample treated with a control antisense oligonucleotide (e.g., one having an altered or different sequence) can be made depending on the information desired. In another embodiment, a difference in the expression of the Lipid transport and metabolism gene protein or nucleic acid in a treated vs. an untreated sample can be compared with the difference in expression of a different nucleic acid (including any standard deemed appropriate by the researcher, e.g., a housekeeping gene) in a treated sample vs. an untreated sample.

Observed differences can be expressed as desired, e.g., in the form of a ratio or fraction, for use in a comparison with control. In embodiments, the level of a Lipid transport and metabolism gene mRNA or protein, in a sample treated with an antisense oligonucleotide of the present invention, is increased or decreased by about 1.25-fold to about 10-fold or more relative to an untreated sample or a sample treated with a control nucleic acid. In embodiments, the level of a Lipid transport and metabolism gene mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

Kits, Research Reagents, Diagnostics, and Therapeutics

The compounds of the present invention can be utilized for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or the entire complement of genes expressed within cells and tissues.

As used herein the term "biological system" or "system" is defined as any organism, cell, cell culture or tissue that expresses, or is made competent to express products of the Lipid transport and metabolism genes. These include, but are not limited to, humans, transgenic animals, cells, cell cultures, tissues, xenografts, transplants and combinations thereof.

As one non limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined These analyses can be performed on stimulated or unstimulated cells and in the presence or absence of other compounds that affect expression patterns.

Examples of methods of gene expression analysis known in the art include DNA arrays or microarrays (Brazma and Vilo, (2000) FEBS Left., 480, 17-24; Celis, et al., (2000) FEBS Lett., 480, 2-16), SAGE (serial analysis of gene expression) (Madden, et al., (2000) Drug Discov. Today, 5, 415-425), READS (restriction enzyme amplification of digested cDNAs) (Prashar and Weissman, (1999) Methods Enzymol., 303, 258-72), TOGA (total gene expression analysis) (Sutcliffe, et al., (2000) Proc. Natl. Acad. Sci. U.S.A., 97, 1976-81), protein arrays and proteomics (Celis, et al., (2000) FEBS Left., 480, 2-16; Jungblut, et al., Electrophoresis, 1999, 20, 2100-10), expressed sequence tag (EST) sequencing (Celis, et al., FEBS Left., 2000, 480, 2-16; Larsson, et al., J. Biotechnol., 2000, 80, 143-57), subtractive RNA fingerprinting (SuRF) (Fuchs, et al., (2000) Anal. Biochem. 286, 91-98; Larson, et al., (2000) Cytometry 41, 203-208), subtractive cloning, differential display (DD) (Jurecic and Belmont, (2000) Curr Opin. Microbiol. 3, 316-21), comparative genomic hybridization (Carulli, et al., (1998) J. Cell Biochem. Suppl., 31, 286-96), FISH (fluorescent in situ hybridization) techniques (Going and Gusterson, (1999) Eur. J. Cancer, 35, 1895-904) and mass spectrometry methods (To, Comb. (2000) Chem. High Throughput Screen, 3, 235-41).

The compounds of the invention are useful for research and diagnostics, because these compounds hybridize to nucleic acids encoding a Lipid transport and metabolism gene. For example, oligonucleotides that hybridize with such efficiency and under such conditions as disclosed herein as to be effective Lipid transport and metabolism gene modulators are effective primers or probes under conditions favoring gene amplification or detection, respectively. These primers and probes are useful in methods requiring the specific detection of nucleic acid molecules encoding a Lipid transport and metabolism gene and in the amplification of said nucleic acid molecules for detection or for use in further studies of a Lipid transport and metabolism gene. Hybridization of the antisense oligonucleotides, particularly the primers and probes, of the invention with a nucleic acid encoding a Lipid transport and metabolism gene can be detected by means known in the art. Such means may include conjugation of an enzyme to the oligonucleotide, radiolabeling of the oligonucleotide, or any other suitable detection means. Kits using such detection means for detecting the level of a Lipid transport and metabolism gene in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of a Lipid transport and metabolism gene polynucleotide is treated by administering antisense compounds in accordance with this invention. For example, in one non-limiting embodiment, the methods comprise the step of administering to the animal in need of treatment, a therapeutically effective amount of a Lipid transport and metabolism gene modulator. The Lipid transport and metabolism gene modulators of the present invention effectively modulate the activity of a Lipid transport and metabolism gene or modulate the expression of a Lipid transport and metabolism gene protein. In one embodiment, the activity or expression of a Lipid transport and metabolism gene in an animal is inhibited by about 10% as compared to a control. Preferably, the activity or expression of a Lipid transport and metabolism gene in an animal is inhibited by about 30%. More preferably, the activity or expression of a Lipid transport and metabolism gene in an animal is inhibited by 50% or more. Thus, the oligomeric compounds modulate expression of a Lipid transport and metabolism gene mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

In one embodiment, the activity or expression of a Lipid transport and metabolism gene and/or in an animal is increased by about 10% as compared to a control. Preferably, the activity or expression of a Lipid transport and metabolism gene in an animal is increased by about 30%. More preferably, the activity or expression of a Lipid transport and metabolism gene in an animal is increased by 50% or more. Thus, the oligomeric compounds modulate expression of a Lipid transport and metabolism gene mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

For example, the reduction of the expression of a Lipid transport and metabolism gene may be measured in serum, blood, adipose tissue, liver or any other body fluid, tissue or organ of the animal. Preferably, the cells contained within said fluids, tissues or organs being analyzed contain a nucleic acid molecule encoding Lipid transport and metabolism gene peptides and/or the Lipid transport and metabolism gene protein itself The compounds of the invention can be utilized in pharmaceutical compositions by adding an effective amount of a compound to a suitable pharmaceutically acceptable diluent or carrier. Use of the compounds and methods of the invention may also be useful prophylactically.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-Hphosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotides conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Although, the antisense oligonucleotides do not need to be administered in the context of a vector in order to modulate a target expression and/or function, embodiments of the invention relates to expression vector constructs for the expression of antisense oligonucleotides, comprising promoters, hybrid promoter gene sequences and possess a strong constitutive promoter activity, or a promoter activity which can be induced in the desired case.

In an embodiment, invention practice involves administering at least one of the foregoing antisense oligonucleotides with a suitable nucleic acid delivery system. In one embodiment, that system includes a non-viral vector operably linked to the polynucleotide. Examples of such nonviral vectors include the oligonucleotide alone (e.g. any one or more of SEQ ID NOS: 23 to 263) or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutinatin virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al., (1995) J. Neurochem, 64: 487; Lim, F., et al., in DNA Cloning: Mammalian Systems, D. Glover, Ed. (Oxford Univ. Press, Oxford England) (1995); Geller, A. I. et al., (1993) Proc Natl. Acad. Sci.: U.S.A.: 90 7603; Geller, A. I., et al., (1990) Proc Natl. Acad. Sci USA: 87:1149], Adenovirus Vectors (LeGal LaSalle et al., Science, 259:988 (1993); Davidson, et al., (1993) Nat. Genet. 3: 219; Yang, et al., (1995) J. Virol. 69: 2004) and Adeno-associated Virus Vectors (Kaplitt, M. G., et al., (1994) Nat. Genet. 8:148).

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein by reference.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

For treating tissues in the central nervous system, administration can be made by, e.g., injection or infusion into the cerebrospinal fluid. Administration of antisense RNA into cerebrospinal fluid is described, e.g., in U.S. Pat. App. Pub. No. 2007/0117772, "Methods for slowing familial ALS disease progression," incorporated herein by reference in its entirety.

When it is intended that the antisense oligonucleotide of the present invention be administered to cells in the central nervous system, administration can be with one or more agents capable of promoting penetration of the subject antisense oligonucleotide across the blood-brain barrier. Injection can be made, e.g., in the entorhinal cortex or hippocampus. Delivery of neurotrophic factors by administration of an adenovirus vector to motor neurons in muscle tissue is described in, e.g., U.S. Pat. No. 6,632,427, "Adenoviral-vector-mediated gene transfer into medullary motor neurons," incorporated herein by reference. Delivery of vectors directly to the brain, e.g., the striatum, the thalamus, the hippocampus, or the substantia nigra, is known in the art and described, e.g., in U.S. Pat. No. 6,756,523, "Adenovirus vectors for the transfer of foreign genes into cells of the central nervous system particularly in brain," incorporated herein by reference. Administration can be rapid as by injection or made over a period of time as by slow infusion or administration of slow release formulations.

The subject antisense oligonucleotides can also be linked or conjugated with agents that provide desirable pharmaceutical or pharmacodynamic properties. For example, the antisense oligonucleotide can be coupled to any substance, known in the art to promote penetration or transport across the blood-brain barrier, such as an antibody to the transferrin receptor, and administered by intravenous injection. The antisense compound can be linked with a viral vector, for example, that makes the antisense compound more effective and/or increases the transport of the antisense compound across the blood-brain barrier. Osmotic blood brain barrier disruption can also be accomplished by, e.g., infusion of sugars including, but not limited to, meso erythritol, xylitol, D(+) galactose, D(+) lactose, D(+) xylose, dulcitol, myo-inositol, L(−) fructose, D(−) mannitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids including, but not limited to, glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 4,866,042, "Method for the delivery of genetic material across the blood brain barrier," U.S. Pat. No. 6,294,520, "Material for passage through the blood-brain barrier," and U.S. Pat. No. 6,936, 589, "Parenteral delivery systems," all incorporated herein by reference in their entirety.

The subject antisense compounds may be admixed, encapsulated, conjugated or otherwise associated with other molecules, molecule structures or mixtures of compounds, for example, liposomes, receptor-targeted molecules, oral, rectal, topical or other formulations, for assisting in uptake, distribution and/or absorption. For example, cationic lipids may be included in the formulation to facilitate oligonucleotide uptake. One such composition shown to facilitate uptake is LIPOFECTIN (available from GIBCO-BRL, Bethesda, Md.).

Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 .mu.m in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287, 860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposomeslacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoyl-phosphatidyl DOPE ethanolamine, dimyristoylphosphatidyl choline DMPC, distearolyphosphatidyl choline) negative (e.g. dimyristoylphosphatidyl glycerol DMPG) and cationic (e.g.

dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein by reference. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bischloroethyl-nitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclo-phosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be a particular antisense sequence of a Lipid transport and metabolism gene, and the second target may be a region from another nucleotide sequence. Alternatively, compositions of the invention may contain two or more antisense compounds targeted to different regions of the same Lipid transport and metabolism gene nucleic acid target. Numerous examples of antisense compounds are illustrated herein and others may be selected from among suitable compounds known in the art. Two or more combined compounds may be used together or sequentially.

Dosing:

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in in vitro and in vivo animal models. In general, dosage is from 0.01 .mu.g to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 .mu.g to 100 g per kg of body weight, once or more daily, to once every 20 years.

In embodiments, a patient is treated with a dosage of drug that is at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100 mg/kg body weight. Certain injected dosages of antisense oligonucleotides are described, e.g., in U.S. Pat. No. 7,563,884, "Antisense modulation of PTP1B expression," incorporated herein by reference in its entirety.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1 Design of Antisense Oligonucleotides Specific for a Nucleic Acid Molecule Antisense to a Lipid Transport and Metabolism Gene and/or a Sense Strand of a Lipid Transport and Metabolism Gene Polynucleotide As indicated above the term "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays The hybridization properties of the oligonucleotides described herein can be determined by one or more in vitro assays as known in the art. For example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecular interactions, for example, a melting curve assay.

Melting curve assay determines the temperature at which a rapid transition from double-stranded to single-stranded conformation occurs for the natural antisense/Molecule complex. This temperature is widely accepted as a reliable measure of the interaction strength between the two molecules.

A melting curve assay can be performed using a cDNA copy of the actual natural antisense RNA molecule or a synthetic DNA or RNA nucleotide corresponding to the binding site of the Molecule. Multiple kits containing all necessary reagents to perform this assay are available (e.g. Applied Biosystems Inc. MeltDoctor kit). These kits include a suitable buffer solution containing one of the double strand DNA (dsDNA) binding dyes (such as ABI HRM dyes, SYBR Green, SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined by the particular manufacturer's protocols. The mixture is heated to 95.degree. C. to dissociate all pre-formed dsDNA complexes, then slowly cooled to room temperature or other lower temperature defined by the kit manufacturer to allow the DNA molecules to anneal. The newly formed complexes are then slowly heated to 95.degree. C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g. ABI's StepOne Plus Real Time PCR System or LightTyper instrument, Roche Diagnostics, Lewes, UK).

Melting peaks are constructed by plotting the negative derivative of fluorescence with respect to temperature (-d (Fluorescence)/dT) on the y-axis) against temperature (x-axis) using appropriate software (for example LightTyper (Roche) or SDS Dissociation Curve, ABI). The data is analyzed to identify the temperature of the rapid transition from dsDNA complex to single strand molecules. This temperature is called Tm and is directly proportional to the strength of interaction between the two molecules. Typically, Tm will exceed 40.degree. C.

Example 2 Modulation of a Lipid Transport and Metabolism Gene Polynucleotide Treatment of 518A2 Cells with Antisense Oligonucleotides 518A2 cells obtained from Albert Einstein-Montefiore Cancer Center, NY were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CI)) at 37.degree. C. and 5% CO2. One day before the experiment the cells were replated at the density of 1.5.times.105/ml into 6 well plates and incubated at 37.degree. C. and 5% CO2. On the day of the experiment the media in the 6 well plates was changed to fresh growth media. All antisense oligonucleotides were diluted to the concentration of 20 nM. Two .mu.l of this solution was incubated with 400 .mu.l of Opti-MEM media (Gibco cat #31985-070) and 4 .mu.l of Lipofectamine 2000 (Invitrogen cat #11668019) at room temperature for 20 min and applied to each well of the 6 well plates with 518A2 cells. A Similar mixture including 2 .mu.l of water instead of the oligonucleotide solution was used for the mock-transfected controls. After 3-18 h of incubation at 37.degree. C. and 5% CO2 the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813 as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay by Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Results

Real time PCR results show that the levels of ABCA1 mRNA in 518A2 cells are significantly increased 48 h after treatment with one of the siRNAs designed to ABCA1 antisense AK311445 (FIG. 1A).

Figure 1B:
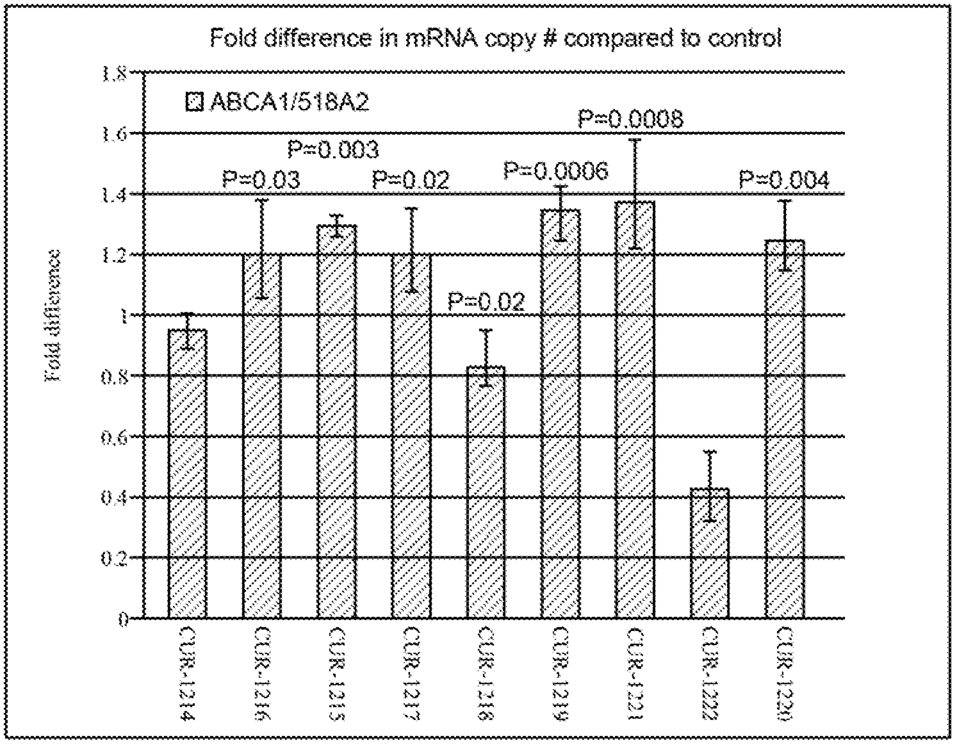
FIG. 1B is a graph of real time PCR results showing the fold change+standard deviation in ABCA1 mRNA after treatment of 518A2 cells with phosphorothioate oligonucleotides introduced using Lipofectamine 2000, as compared to control. Real time PCR results show that the levels of ABCA1 mRNA in 518A2 cells are significantly increased 48 h after treatment with six of the oligos designed to ABCA1 antisense AK311445. Bars denoted as CUR-1214 to CUR-1222 correspond to samples treated with SEQ ID NOS: 26 to 34 respectively.

Real time PCR results show that the levels of ABCA1 mRNA in 518A2 cells are significantly increased 48 h after treatment with six of the oligos designed to ABCA1 antisense AK311445 (FIG. 1B).

Treatment of 3T3 Cells with Antisense Oligonucleotides

3T3 cells from ATCC (cat #CRL-1658) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CI)) at 37.degree. C. and 5% CO.sub.2. One day before the experiment the cells were replated at the density of 1.5.times.10.sup.5/ml into 6 well plates and incubated at 37.degree. C. and 5% CO.sub.2. On the day of the experiment the media in the 6 well plates was changed to fresh growth media. All antisense oligonucleotides were diluted to the concentration of 20 .mu.M. Two .mu.l of this solution was incubated with 400 .mu.l of Opti-MEM media (Gibco cat #31985-070) and 4 .mu.l of Lipofectamine 2000 (Invitrogen cat #11668019) at room temperature for 20 min and applied to each well of the 6 well plates with 3T3 cells. A Similar mixture including 2 .mu.l of water instead of the oligonucleotide solution was used for the mock-transfected controls. After 3-18 h of incubation at 37.degree. C. and 5% CO.sub.2 the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay by Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Figure 1C:
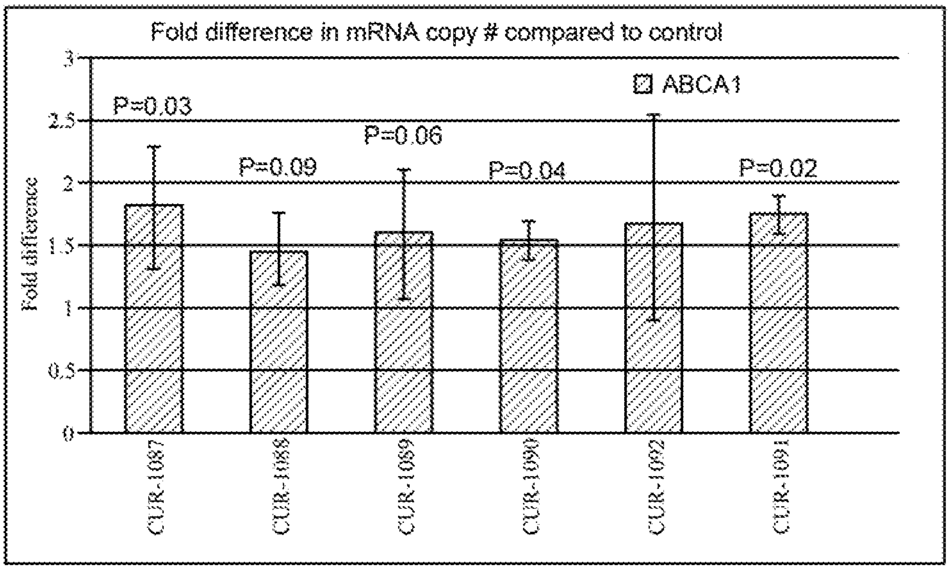
FIG. 1C is a graph of real time PCR results showing the fold change+standard deviation in ABCA1 mRNA after treatment of 3T3 cells with phosphorothioate oligonucleotides introduced using Lipofectamine 2000, as compared to control. Real time PCR results show that the levels of ABCA1 mRNA in 3T3 cells are significantly increased 48 h after treatment with three of the oligos designed to mouse ABCA1 antisense BF133827. Bars denoted as CUR-1087 to CUR-1090, CUR-1092 and CUR-1091 correspond to samples treated with SEQ ID NOS: 35 to 38, 40 and 39 respectively.

Results:

Real time PCR results show that the levels of ABCA1 mRNA in 3T3 cells are significantly increased 48 h after treatment with three of the oligos designed to mouse ABCA1 antisense BF133827 (FIG. 1C).

Figure 1D:
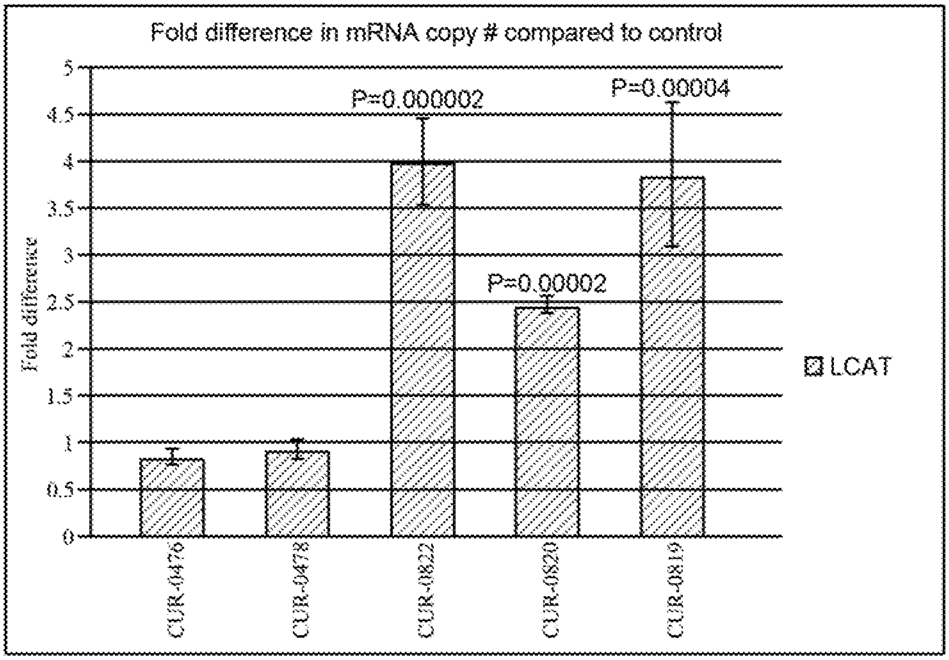
FIG. 1D is a graph of real time PCR results showing the fold change+standard deviation in LCAT mRNA after treatment of Hek293 cells with siRNA and phosphorothioate oligonucleotides introduced using Lipofectamine 2000, as compared to control. Real time PCR results show that the levels of the LCAT mRNA in Hek293 cells are significantly increased 48 h after treatment with three of the oligos designed to LCAT antisense Hs.668679. Bars denoted as CUR-0476, CUR-0478, CUR-0822, CUR-0820 and CUR-0819 correspond to samples treated with SEQ ID NOS: 41, 42, 58, 56 and 55 respectively.
Figure 1E:
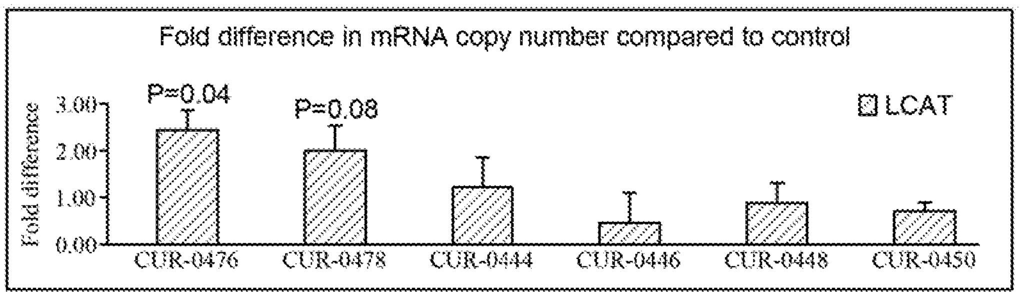
FIG. 1E is a graph of real time PCR results showing the fold change+standard deviation in LCAT mRNA after treatment of HepG2 cells with siRNA oligonucleotides introduced using Lipofectamine 2000, as compared to control. Real time PCR results show that the levels of the LCAT mRNA in HepG2 cells are significantly increased 48 h after treatment with two of the oligos designed to LCAT antisense Hs.668679. Bars denoted as CUR-0476, CUR-0478, CUR-0444, CUR-0446, CUR-0448 and CUR-0450 correspond to samples treated with SEQ ID NOS: 41, 42, and 44 to 47 respectively. CUR-0444, CUR-0446, CUR-0448, CUR-0450 correspond to oligonucleotides that targeted SEQ ID NO: 11 (CUR-0444 and CUR-0446) and SEQ ID NO: 12 (CUR-0448 and CUR-0450).
Figure 1F:
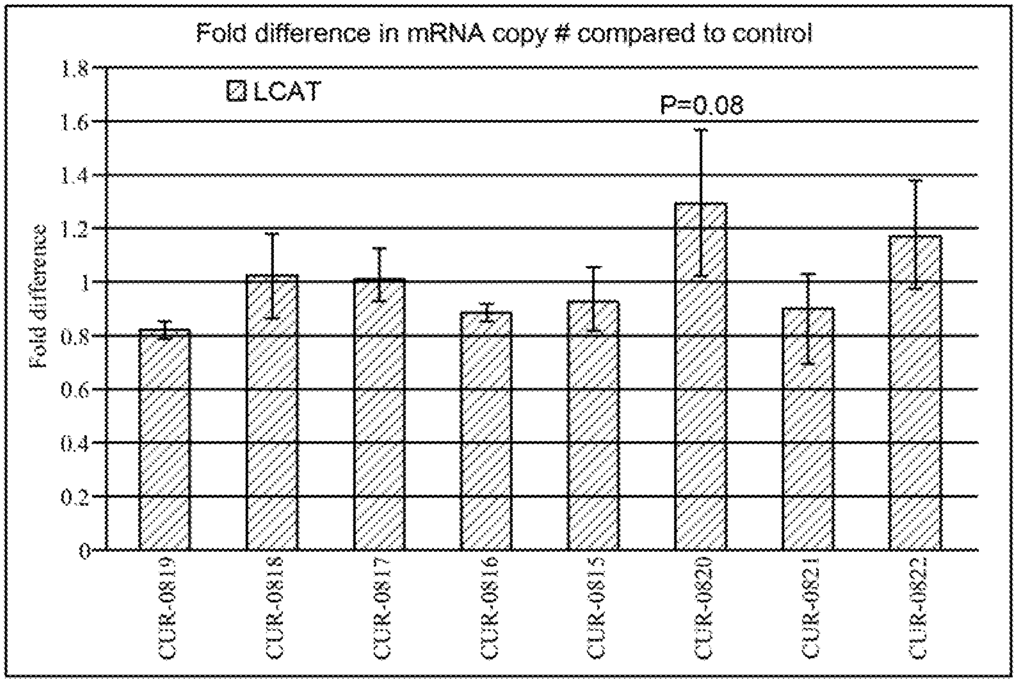
FIG. 1F is a graph of real time PCR results showing the fold change+standard deviation in LCAT mRNA after treatment of HepG2 cells with phosphorothioate oligonucleotides introduced using Lipofectamine 2000, as compared to control. Real time PCR results show that the levels of the LCAT mRNA in HepG2 cells are significantly increased 48 h after treatment with one of the oligos designed to LCAT antisense Hs.668679. Bars denoted as CUR-0819, CUR-0818, CUR-0817, CUR-0816, CUR-0815, CUR-0820, CUR-0821 and CUR-0822 correspond to samples treated with SEQ ID NOS: 55, 54, 53, 52, 51 and 56 to 58 respectively.
Figure 1G:
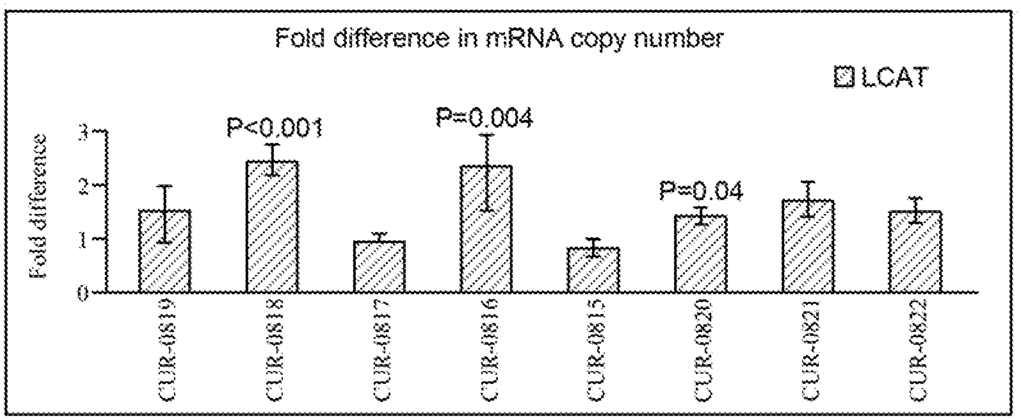
FIG. 1G is a graph of real time PCR results showing the fold change+standard deviation in LCAT mRNA after treatment of Vero cells with phosphorothioate oligonucleotides introduced using Lipofectamine 2000, as compared to control. Real time PCR results show that the levels of the LCAT mRNA in Vero cells are significantly increased 48 h after treatment with one of the oligos designed to LCAT antisense Hs.668679. Bars denoted as CUR-0819, CUR-0818, CUR-0817, CUR-0816, CUR-0815, CUR-0820, CUR-0821 and CUR-0822 correspond to samples treated with SEQ ID NOS: 55, 54, 53, 52, 51 and 56 to 58 respectively.
Figure 1H:
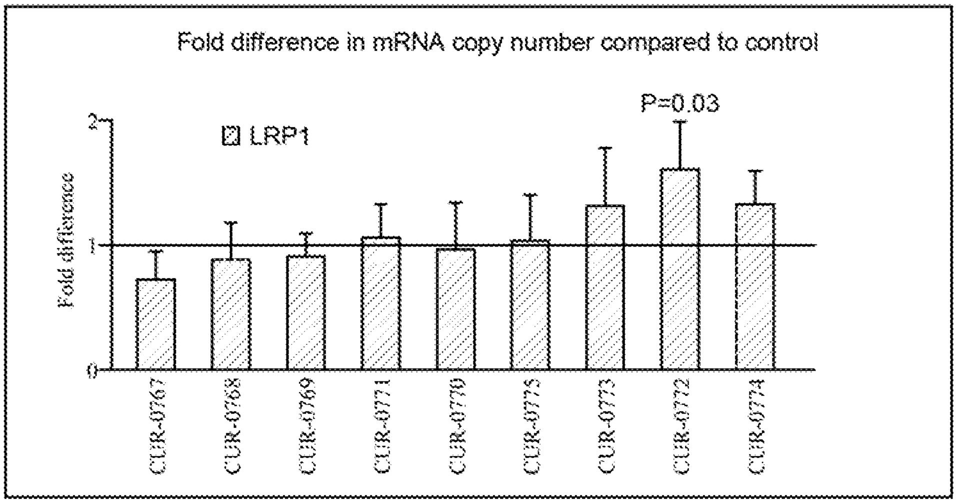
FIG. 1H is a graph of real time PCR results showing the fold change+standard deviation in LRP1 mRNA after treatment of HepG2 cells with phosphorothioate oligonucleotides introduced using Lipofectamine 2000, as compared to control. Real Time PCR results show that levels of LRP1 mRNA in HepG2 cells are significantly increased 48 h after treatment with oligos to LRP1 antisense DC401271. Bars denoted as CUR-0767 to CUR-0769, CUR-0771, CUR-0770, CUR-0775, CUR-0773, CUR-0772 and CUR-0774 correspond to samples treated with SEQ ID NOS: 59 to 61, 63, 62, 67, 65, 64 and 66 respectively.
Figure 1I:
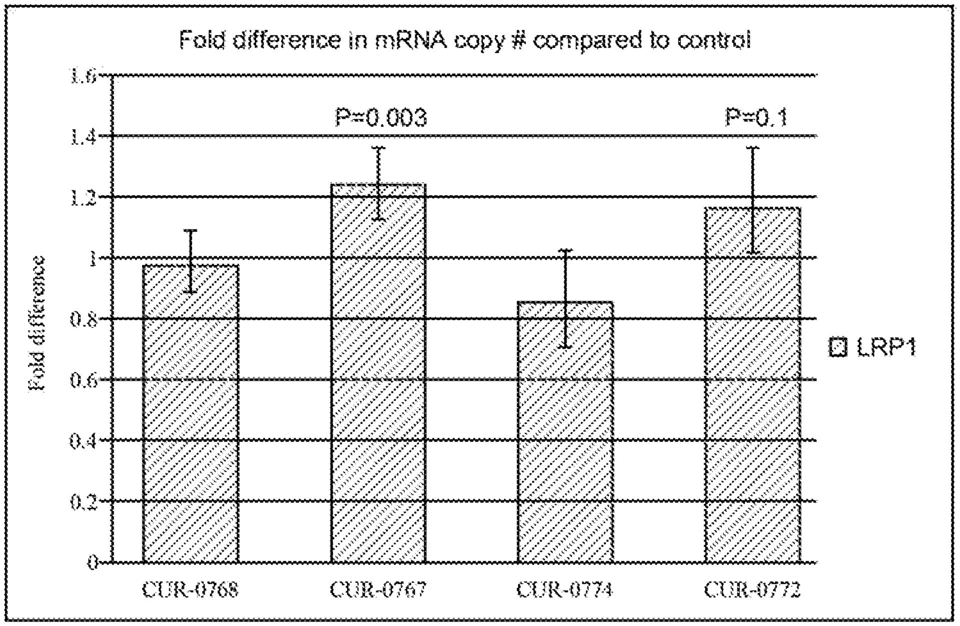
FIG. 1I is a graph of real time PCR results showing the fold change+standard deviation in LRP1 mRNA after treatment of Vero cells with phosphorothioate oligonucleotides introduced using Lipofectamine 2000, as compared to control. Real Time PCR results show that levels of LRP1 mRNA in Vero cells are significantly increased 48 h after treatment with oligos to LRP1 antisense DC401271 and Hs.711951. Bars denoted as CUR-0768, CUR-0767, CUR-0774 and CUR-0772 correspond to samples treated with SEQ ID NOS: 60, 59, 66 and 64 respectively.
Figure 1J:
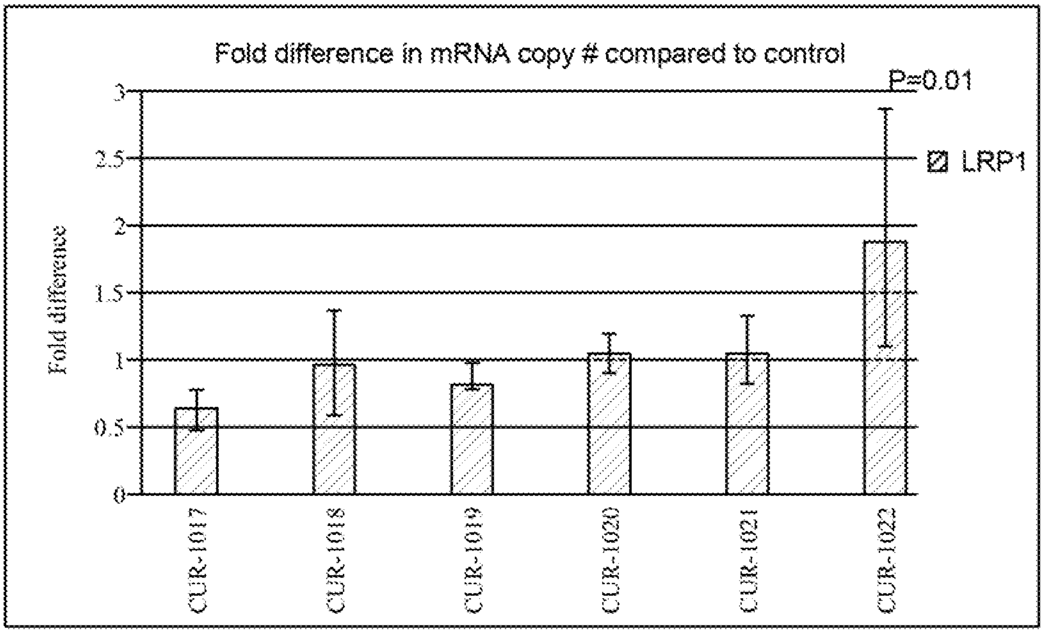
FIG. 1J is a graph of real time PCR results showing the fold change+standard deviation in LRP1 mRNA after treatment of 3T3 cells with phosphorothioate oligonucleotides introduced using Lipofectamine 2000, as compared to control. Real Time PCR results show that levels of LRP1 mRNA in 3T3 cells are significantly increased 48 h after treatment with oligos to LRP1 antisense DC401271 and AW544265. Bars denoted as CUR-1017 to CUR-1022 correspond to samples treated with SEQ ID NOS: 68 to 73 respectively.

Real Time PCR results show that levels of LRP1 mRNA in 3T3 cells are significantly increased 48 h after treatment with oligos to LRP1 antisense DC401271 and AW544265 (FIG. 1J).

Treatment of HepG2 Cells with Antisense Oligonucleotides

Method 1: Treatment of HepG2 Cells with Naked Antisense Oligonucleotides:

HepG2 cells from ATCC (cat #HB-8065) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CI)) at 37.degree. C. and 5% CO.sub.2. One day before the experiment the cells were replated at the density of 0.5.times.10.sup.4/ml into 6 well plates and incubated at 37.degree. C. and 5% CO.sub.2. On the day of the experiment the media in the 6 well plates was replaced with 1.5 ml/well of fresh growth media. All antisense oligonucleotides were diluted in water to the concentration of 20 .mu.M. 2 .mu.l of this solution was mixed with 400 .mu.l of fresh growth media and applied to each well of the 6 well plates with HepG2 cells. A similar mixture including 2 .mu.l of water instead of the oligonucleotide solution was used for the mock-treated controls. After 3-18 h of incubation at 37.degree. C. and 5% CO.sub.2 the media was changed to fresh growth media. 72 h after addition of antisense oligonucleotides the cells were redosed as described in above. 48-72 h after second dosing the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using Mx4000 thermal cycler (Stratagene). Fold change in gene expression after treatment with antisense oligonucleotides was calculated based on the difference in 18S-normalized dCt values between treated and mock-transfected samples.

Method Two: Treatment of HepG2 Cells with Antisense Oligonucleotides:

HepG2 cells from ATCC (cat #HB-8065) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CI)) at 37.degree. C. and 5% CO.sub.2. One day before the experiment the cells were replated at the density of 1.5.times.10.sup.5/ml into 6 well plates and incubated at 37.degree. C. and 5% CO.sub.2. On the day of the experiment the media in the 6 well plates was changed to fresh growth media. All antisense oligonucleotides were diluted to the concentration of 20 .mu.M. 2 .mu.l of this solution was incubated with 400 .mu.l of Opti-MEM media (Gibco cat #31985-070) and 4 .mu.l of Lipofectamine 2000 (Invitrogen cat #11668019) at room temperature for 20 min and applied to each well of the 6 well plates with HepG2 cells. A similar mixture including 2 .mu.l of water instead of the oligonucleotide solution was used for the mock-transfected controls. After 3-18 h of incubation at 37.degree. C. and 5% CO.sub.2 the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using Mx4000 thermal cycler (Stratagene). Fold change in gene expression after treatment with antisense oligonucleotides was calculated based on the difference in 18S-normalized dCt values between treated and mock-transfected samples.

Results

Real time PCR results show that the levels of the LCAT mRNA in HepG2 cells are significantly increased 48 h after treatment with two of the oligos designed to LCAT antisense Hs.668679 (FIG. 1E).

Real time PCR results show that the levels of the LCAT mRNA in HepG2 cells are significantly increased 48 h after treatment with one of the oligos designed to LCAT antisense Hs.668679 (FIG. 1F).

Real Time PCR results show that levels of LRP1 mRNA in HepG2 cells are significantly increased 48 h after treatment with oligos to LRP1 antisense DC401271 (FIG. 1H).

Figure 1K:
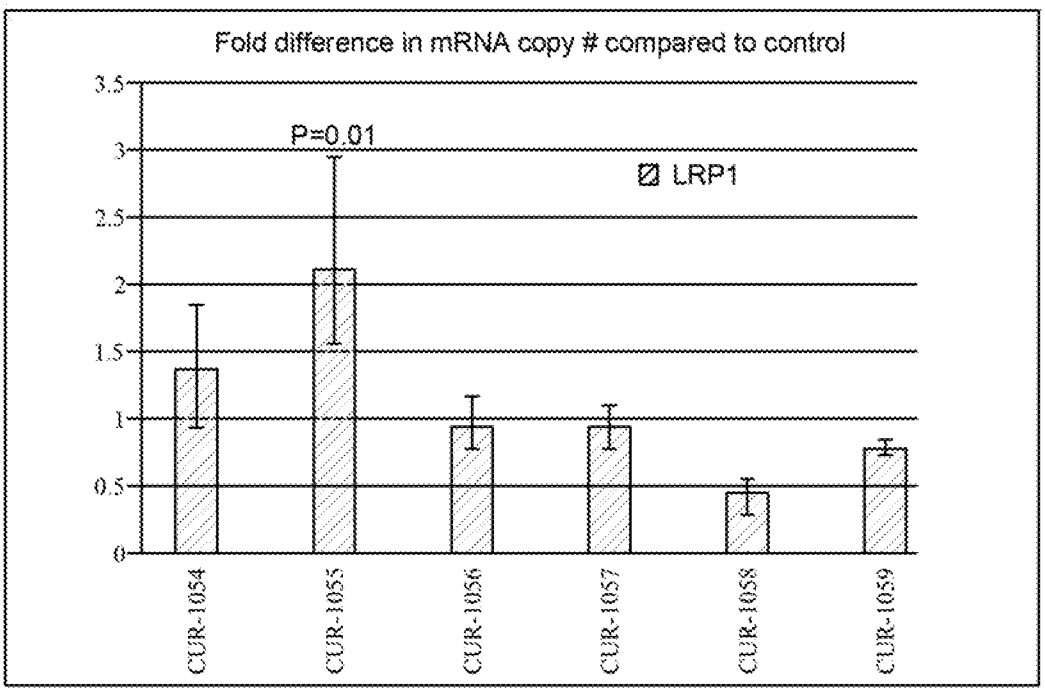
FIG. 1K is a graph of real time PCR results showing the fold change+standard deviation in LDLR mRNA after treatment of HepG2 cells with phosphorothioate oligonucleotides introduced using Lipofectamine 2000, as compared to control. Real Time PCR results show that levels of LDLR mRNA in HepG2 cells are significantly increased 48 h after treatment with antisense oligos to LDLR antisense sherflor.aApr07. Bars denoted as CUR-1054 to CUR-1059 correspond to samples treated with SEQ ID NOS: 74 to 79 respectively.
Figure 1L:
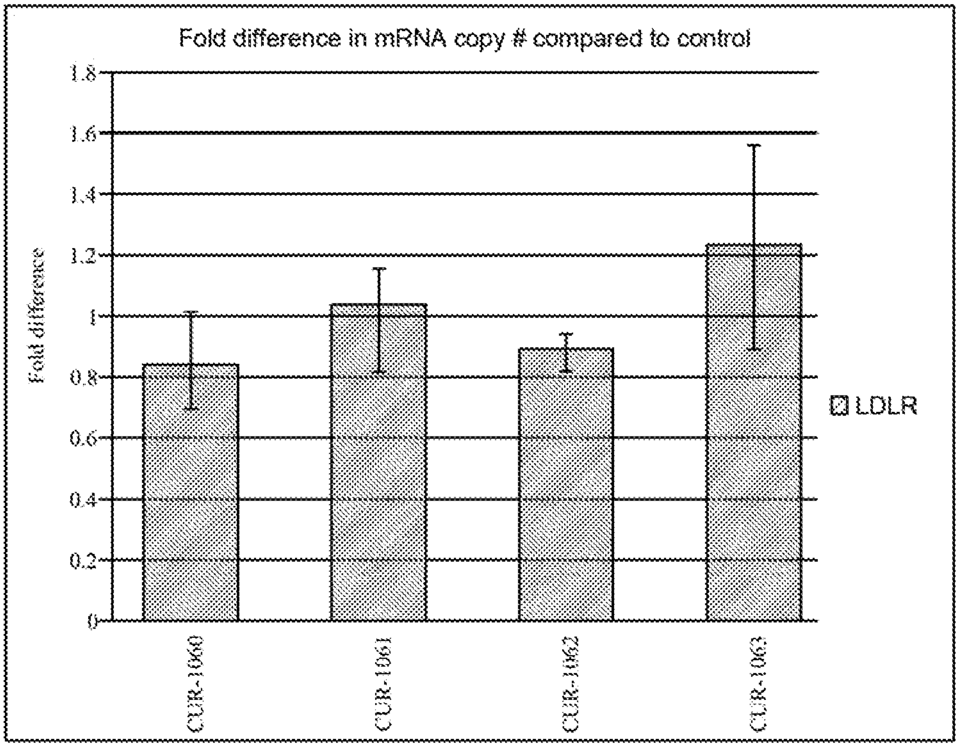
FIG. 1L is a graph of real time PCR results showing the fold change+standard deviation in LDLR mRNA after treatment of HepG2 cells with phosphorothioate oligonucleotides introduced using Lipofectamine 2000, as compared to control. Real Time PCR results show that levels of LDLR mRNA in HepG2 cells after treatment with antisense oligos to LDLR antisense bloflor.aApr07. Bars denoted as CUR- 1059 to CUR-1063 correspond to samples treated with SEQ ID NOS: 79 to 83 respectively.

Real Time PCR results show that levels of LDLr mRNA in HepG2 cells are significantly increased 48 h after treatment with antisense oligos to LDLR antisense sherflor.aApr07.Oligos designed to LDLr antisense bloflor.aAprO7 (CUR-1059-CUR-1063) did not elevate LDLr levels (FIGS. 1K and 1L).

Figure 1M:
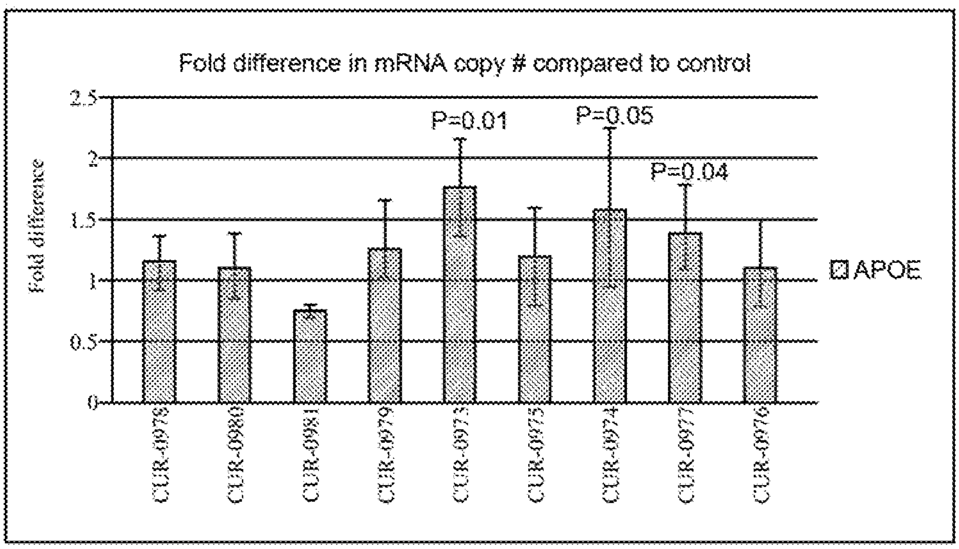
FIG. 1M is a graph of real time PCR results showing the fold change+standard deviation in ApoE mRNA after treatment of HepG2 cells with phosphorothioate oligonucleotides introduced using Lipofectamine 2000, as compared to control. Real time PCR results show that the levels of APOE mRNA in HepG2 cells are significantly increased 48 h after treatment with three of the antisense oligos designed to APOE antisense Hs.626623. Bars denoted as CUR-0978, CUR-0980, CUR-0981, CUR-0979, CUR-0973, CUR-0975, CUR-0974, CUR-0977 and CUR-0976 correspond to samples treated with SEQ ID NOS: 89, 91, 92, 90, 84, 86, 85, 88 and 87 respectively.

Real time PCR results show that the levels of APOE mRNA in HepG2 cells are significantly increased 48 h after treatment with three of the antisense oligos designed to APOE antisense Hs.626623. Oligos designed to APOE4 antisense Hs.714236 did not significantly elevate APOE mRNA (FIG. 1M).

Figure 1N:
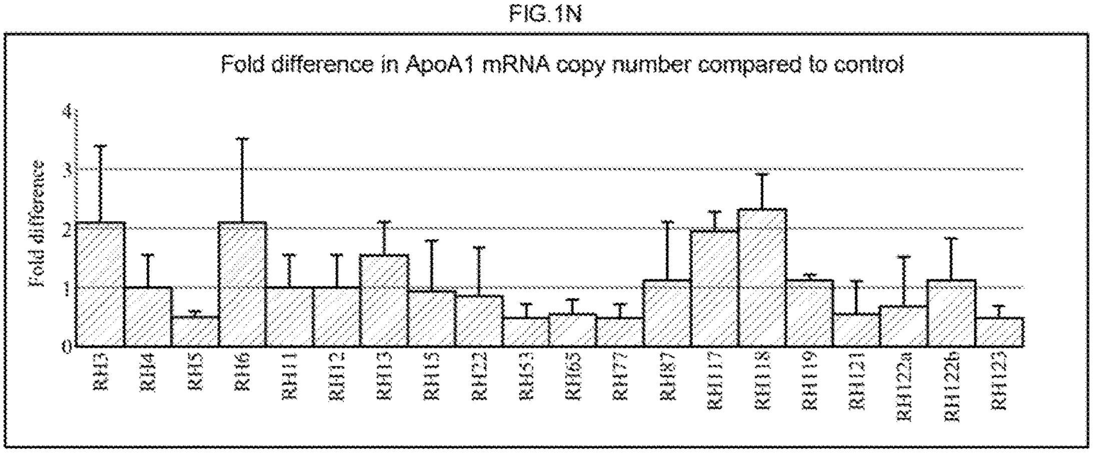
FIG. 1N to FIG. 1P represent a graphs of real time PCR results showing the fold change+standard deviation in ApoA1 mRNA after treatment of HepG2 cells with phosphorothioate oligonucleotides introduced using Lipofectamine 2000, as compared to control. Real time PCR results show that the levels of ApoA1 mRNA in HepG2 cells are significantly increased 48 h after treatment with some of the antisense oligonucleotides to ApoA1 antisense DA327409ext. Bars RH3-RH597, correspond to samples treated with SEQ ID NOS 171 to 248 respectively.
Figure 1O:
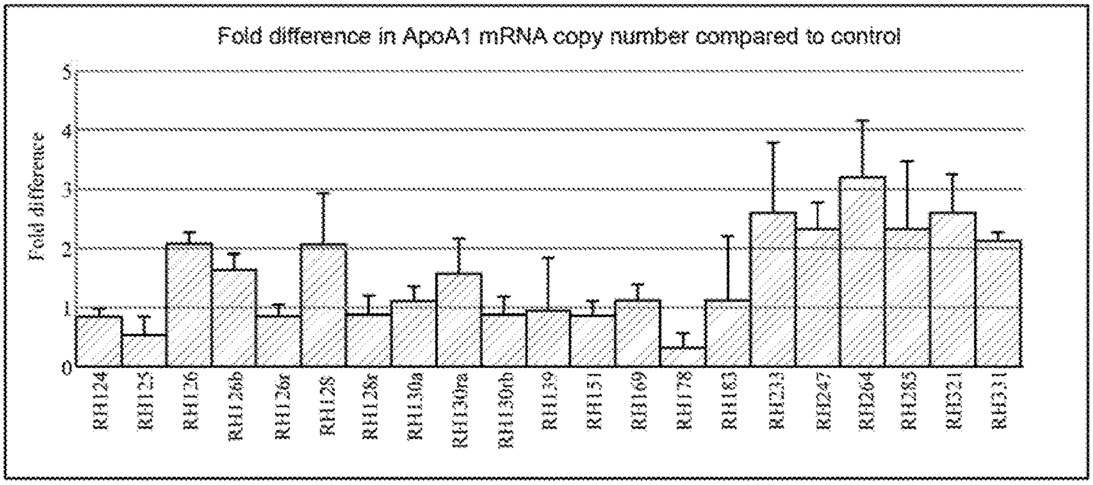
Figure 1P:
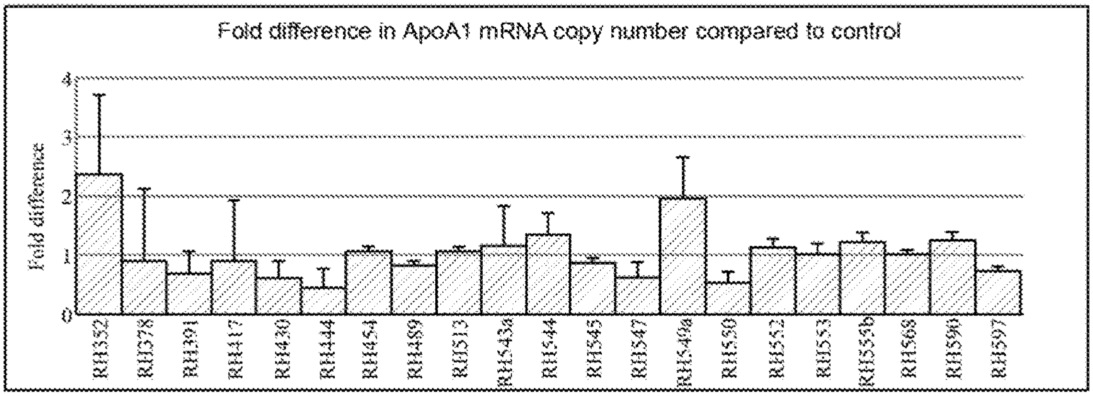

Real time PCR results show that the levels of ApoA1 mRNA in HepG2 cells are significantly increased 48 h after treatment with some of the antisense oligonucleotides to ApoA1 antisense DA327409ext (FIG. 1N to FIG. 1P).

Figure 1Q:
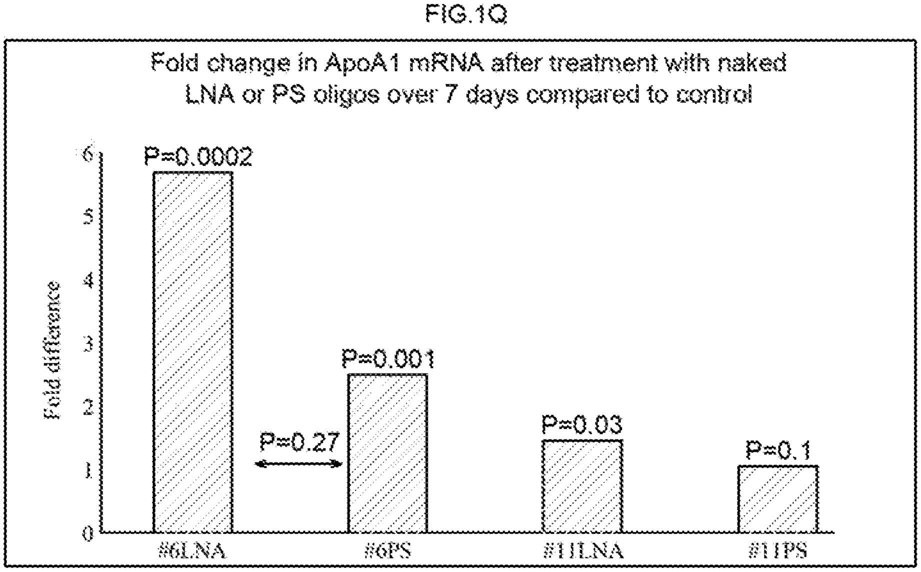
FIG. 1Q is a graph of real time PCR results showing the fold change in ApoA1 mRNA (top panel) and ApoA1 natural antisense DA327409ext RNA (bottom panel) after treatment of HepG2 cells with naked LNA or phosphothioate oligonucleotides over 7 days as compared to control. Bars denoted as #6LNA, #11LNA, #6P5 and #11PS represent SEQ ID NOS 249 to 252 respectively.
Figure 1Q:
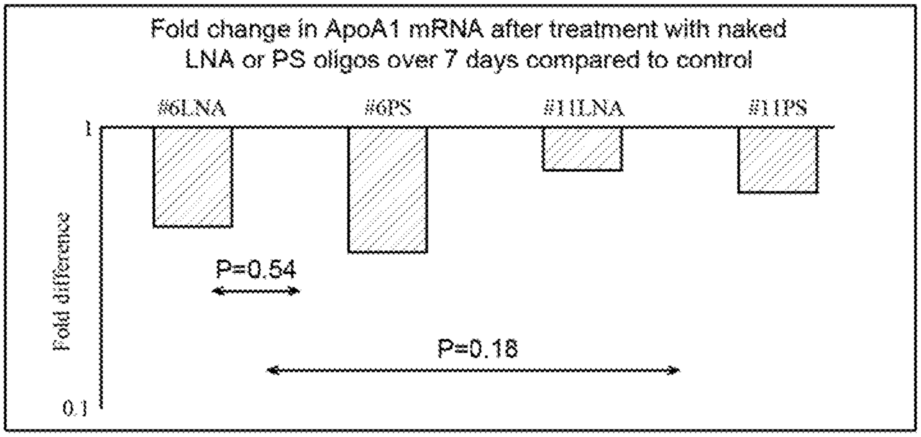

Real time PCR results showing the fold change in ApoA1 mRNA (top panel) and ApoA1 natural antisense DA327409ext RNA (bottom panel) after treatment of HepG2 cells with naked LNA or phosphothioate oligonucleotides over 7 days as compared to control (FIG. 1Q).

Figure 1R:
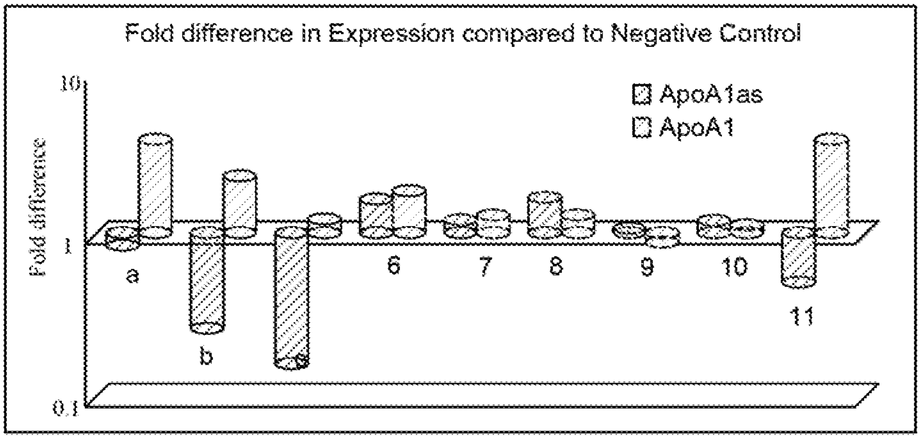
FIG. 1R is a graph of real time PCR results showing the fold change in ApoA1 mRNA (orange bars) and ApoA1 natural antisense DA327409ext RNA (blue bars) after treatment of HepG2 cells with LNA oligonucleotides. Bars denoted as 6-11 correspond to SEQ ID NOS 249, 257 to 260 and 250.

Real time PCR results showing the fold change in ApoA1 mRNA (orange bars) and ApoA1 natural antisense DA327409ext RNA (blue bars) after treatment of HepG2 cells with LNA oligonucleotides (FIG. 1R). Treatment of Hek293 Cells with Antisense Oligonucleotides Hek293 cells from ATCC (cat #CRL-1573) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CI)) at 37.degree. C. and 5% CO.sub.2. One day before the experiment the cells were replated at the density of 1.5.times.10.sup.5/ml into 6 well plates and incubated at 37.degree. C. and 5% CO.sub.2. On the day of the experiment the media in the 6 well plates was changed to fresh growth media. All antisense oligonucleotides were diluted to the concentration of 20 .mu.M. Two .mu.l of this solution was incubated with 400 .mu.l of Opti-MEM media (Gibco cat #31985-070) and 4 .mu.l of Lipofectamine 2000 (Invitrogen cat #11668019) at room temperature for 20 min and applied to each well of the 6 well plates with Hek293 cells. A Similar mixture including 2 .mu.l of water instead of the oligonucleotide solution was used for the mock-transfected controls. After 3-18 h of incubation at 37.degree. C. and 5% CO.sub.2 the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay by Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using using Mx4000 thermal cycler (Stratagene) or StepOne Plus Real Time PCR Machine (Applied Biosystems).

Fold change in gene expression after treatment with antisense oligonucleotides was calculated based on the difference in 18S-normalized dCt values between treated and mock-transfected samples.

Results:

Real Time PCR Results Show that the Levels of the LCAT mRNA in Hek293 Cells are Significantly Increased 48 h after Treatment with Three of the Oligos Designed to LCAT Antisense Hs.668679 (FIG. 1D).

Treatment of Vero 76 Cells with Antisense Oligonucleotides

Vero 76 cells from ATCC (cat #CRL-1587) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat

#MT30-002-CI)) at 37.degree. C. and 5% CO.sub.2. One day before the experiment the cells were replated at the density of 1.5.times.10.sup.5/ml into 6 well plates and incubated at 37.degree. C. and 5% CO.sub.2. On the day of the experiment the media in the 6 well plates was changed to fresh growth media. All antisense oligonucleotides were diluted to the concentration of 20 .mu.M. Two .mu.l of this solution was incubated with 400 .mu.l of Opti-MEM media (Gibco cat #31985-070) and 4 .mu.l of Lipofectamine 2000 (Invitrogen cat #11668019) at room temperature for 20 min and applied to each well of the 6 well plates with Vero 76 cells. A Similar mixture including 2 .mu.l of water instead of the oligonucleotide solution was used for the mock-transfected controls. After 3-18 h of incubation at 37.degree. C. and 5% CO.sub.2 the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay by Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using using Mx4000 thermal cycler (Stratagene) or StepOne Plus Real Time PCR Machine (Applied Biosystems).

Fold change in gene expression after treatment with antisense oligonucleotides was calculated based on the difference in 18S-normalized dCt values between treated and mock-transfected samples.

Results:

Real time PCR results show that the levels of the LCAT mRNA in Vero cells are significantly increased 48 h after treatment with one of the oligos designed to LCAT antisense Hs.668679 (FIG. 1G).

Real Time PCR results show that levels of LRP1 mRNA in Vero cells are significantly increased 48 h after treatment with oligos to LRP1 antisense DC401271 and Hs.711951 (FIG. 1I).

Detection Probes Used in Applied Biosystems Gene Expression Assays:

ABCA1: Hs00194045_ml (human), Mm01350760_ml (mouse)

LCAT: Hs00173415 ml

LRP1: Hs00233856_ml (human), Mm00464608_ml (mouse)

LDLR: Hs00181192 ml

ApoE: Hs00171168_ml

ApoA1: Hs00163641_ml, 18S cat #4319413E

Custom Designed Assay for ApoA1 Antisense DA327409ext:

```
Fam labeled:
                                (SEQ ID NO: 275)
TTTGGATCTGGACGACTTC
```

Example 3 Modulation of a Lipid Transport and Metabolism Gene Expression

Materials and Methods

Cells were treated with either of the following methods:

Method 1: Treatment of HepG2 Cells with Naked Antisense Oligonucleotides:

HepG2 cell were grown in MEM/EBSS (Hyclone cat #SH30024)+10% FBS+penicillin+streptomycin at 37.degree. C. and 5% CO.sub.2. One day before the experiment the cells were replated at the density of 1.5.times.10.sup.4/ml into 6 well plates and left at 37.degree. C. and 5% CO.sub.2. On the day of the experiment the media in the 6 well plates was changed to fresh MEM/EBSS+10% FBS. All antisense oligonucleotides manufactured by IDT were diluted to the concentration of 20 .mu.M. 2 .mu.l of this solution was incubated with 400 .mu.l of Opti-MEM media (Gibco cat #31985-070) and applied to each well of the 6 well plates with HepG2 cells. Similar mixture including 2 .mu.l of water instead of the oligonucleotide solution was used for the mock-transfected controls. 72 h after addition of antisense oligonucleotides the media was removed and the dosing procedure was repeated as described in above.

48-72 h after repeated dosing RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using Mx4000 thermal cycler (Stratagene).

Fold change in gene expression after treatment with antisense oligonucleotides was calculated based on the difference in 18S-normalized dCt values between treated and mock-transfected samples.

Primers and probe for the custom designed Taqman assay for the ApoA1 natural antisense DA327409ext. Capital letters indicate unmodified deoxyribonucleotides

```
Probe sequence (FAM labeled)
                                (SEQ ID NO: 275)
TTTGGATCTGGACGACTTC

Forward Primer Seq.
                                (SEQ ID NO: 276)
CTCCTCCTGCCACTTCTTCTG

Reverse Primer Seq.
                                (SEQ ID NO: 277)
CTGGTGGATGAAGAAGGTTTGC
```

Method Two: Treatment of HepG2 Cells with Antisense Oligonucleotides:

HepG2 cells from ATCC (cat #HB-8065) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CI)) at 37.degree. C. and 5% CO.sub.2. One day before the experiment the cells were replated at the density of 1.5.times.10.sup.5/ml into 6 well plates and incubated at 37.degree. C. and 5% CO.sub.2. On the day of the experiment the media in the 6 well plates was changed to fresh growth media. All antisense oligonucleotides were diluted to the concentration of 20 .mu.M. 2 .mu.l of this solution was incubated with 400 .mu.l of Opti-MEM media (Gibco cat #31985-070) and 4 .mu.l of Lipofectamine 2000 (Invitrogen cat #11668019) at room temperature for 20 min and applied to each well of the 6 well plates with HepG2 cells. Similar mixture including 2 .mu.l of water instead of the oligonucleotide solution was used for the mock-transfected controls. After 3-18 h of incubation at 37.degree. C. and 5% CO.sub.2 the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions.

600 ng of RNA was added to the reverse transcription reaction performed using Verso cDNA kit from Thermo Scientific (cat #AB1453B) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using Mx4000 thermal cycler (Stratagene). Fold change in gene expression after treatment with antisense oligonucleotides was calculated based on the difference in 18S-normalized dCt values between treated and mock-transfected samples.

Primers and probe for the custom designed Taqman assay for the ApoA1 natural antisense DA327409ext. Capital letters indicate unmodified deoxyribonucleotides

```
Probe sequence (FAM labeled)
                              (SEQ ID NO: 275)
TTTGGATCTGGACGACTTC

Forward Primer Seq.
                              (SEQ ID NO: 276)
CTCCTCCTGCCACTTCTTCTG

Reverse Primer Seq.
                              (SEQ ID NO: 277)
CTGGTGGATGAAGAAGGTTTGC
```

Treatment of Primary Monkey Hepatocytes

Primary monkey hepatocytes were introduced into culture by RxGen Inc. and plated in 6 well plates. They were treated with oligonucleotides as follows. The media in the 6 well plates was changed to fresh growth media consisting of William's Medium E (Sigma cat #W4128) supplemented with 5% FBS, 50 U/ml penicillin and 50 ug/ml streptomycin, 4 ug/ml insulin, 1 uM dexamethasone, 10 ug/ml Fungin (InVivogen, San Diego Calif.). All antisense oligonucleotides were diluted to the concentration of 20 .mu.M. 2 .mu.l of this solution was incubated with 400 .mu.l of Opti-MEM media (Gibco cat #31985-070) and 4 .mu.l of Lipofectamine 2000 (Invitrogen cat #11668019) at room temperature for 20 min and applied to each well of the 6 well plates with cells. Similar mixture including 2 .mu.l of water instead of the oligonucleotide solution was used for the mock-transfected controls. After 3-18 h of incubation at 37.degree. C. and 5% CO.sub.2 the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Inc., Foster City Calif.). The following PCR cycle was used: 50.degree. C. for 2 min, 95.degree. C. for 10 min, 40 cycles of (95.degree. C. for 15 seconds, 60.degree. C. for 1 min) using Mx4000 thermal cycler (Stratagene). Fold change in gene expression after treatment with antisense oligonucleotides was calculated based on the difference in 18S-normalized dCt values between treated and mock-transfected samples. ELISA was conducted using MabTech Inc. ApoA1 ELISA kit cat #3710-11-6 according to manufacturer's instructions.

Figure 1S:
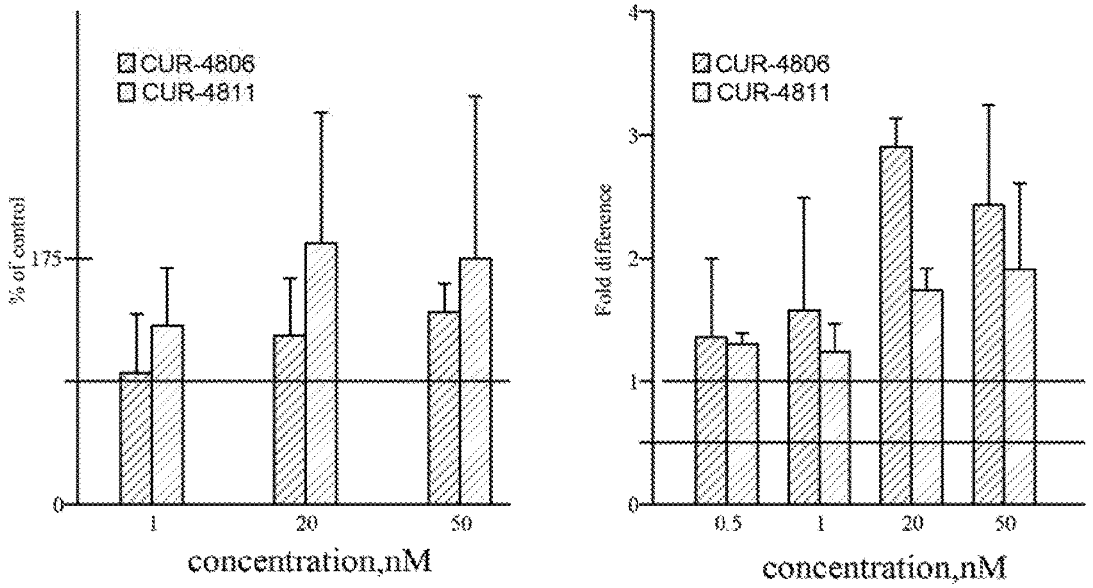
FIG. 1S shows dose dependent increase in ApoA1 mRNA (bottom panel) and protein (top panel) after treatment of HepG2 cells with oligonucleotides. Bars denoted CUR-4806 and CUR-4811 correspond to SEQ ID NOS 249 and 250 respectively.
Figure 1T:
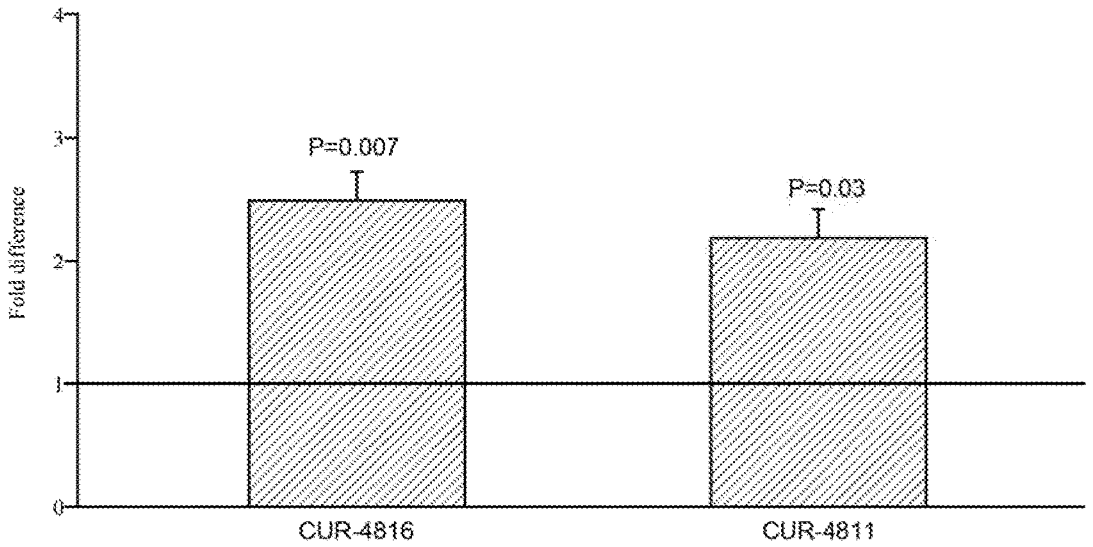
FIG. 1T is a graph of the real time PCR results showing upregulation of the ApoA1 mRNA in primary African green monkey hepatocytes after treatment with oligonucleotides against natural ApoA1 antisense DA327409ext. Bars denoted CUR-4816 and CUR-4811 correspond to SEQ ID NOS: 263 and 250 respectively.

The results are shown in FIG. 1Q to FIG. 1T. FIG. 1Q shows that both oligonucleotides with the phosphothioate backbone, i.e. internucleotide linkages and LNA oligonucleotides were effective in modulating the target gene expression as measured by ApoA1 mRNA (top panel) and ApoA1 antisense DA327409ext RNA (bottom panel) amounts detected. FIG. 1R shows the levels of ApoA1 mRNA (orange bars) and ApoA1 antisense DA327409ext RNA (blue bars) in HepG2 cells treated with oligonucleotides designed against DA327409ext. FIG. 1S shows dose dependent upregulation of ApoA1 mRNA (bottom panel) and protein (top panel) in HepG2 cultures treated with oligonucleotides designed against DA327409ext. Fig. T shows upregulation of ApoA1 mRNA in primary African green monkey hepatocytes after treatment with oligonucleotides designed against DA327409ext.

Example 4: Efficacy and Duration of Action Study of CUR-962 in the African Green Monkey The objective of this study was to assess and compare the effect of antisense knockdown of the discordant noncoding antisense sequences that regulate a Lipid transport and metabolism gene following intravenous administration in a nonhuman primate model. The antisense oligonucleotide test articles designed to inhibit the APOA1 regulatory sequences were designated as CUR-962.

```
CUR-962:
                                        (SEQ ID NO: 278)
+G* + C*T* A*G*T* C*T*G* + T* + T* + G

CUR-963 (control):
                                        (SEQ ID NO: 279)
+G* + T*C* T*G*A* T*G*G* + A* G* + A
```

Regulatory Test Guidelines

This study was designed in accordance with accepted toxicological principles and to comply with International Conference of Harmonization (ICH) Harmonized Tripartite Guidelines (Non-Clinical Safety Studies for the Conduct of Human Clinical Trials for Pharmaceuticals ICH M3(m), 2000 Nov. 9), and generally accepted procedures for the testing of therapeutic agents.

Test and Control Articles

Test Article Identity and Preparation

The test article, CUR-962, is a chemically stabilized antisense oligonucleotide. The vehicle for intravenous delivery is phosphate-buffered saline (PBS).

Vehicle Characterization

For the PBS vehicle, the composition, batch number, expiry date and storage conditions (temperature and light/dark) was obtained from the supplier.

Test Article Storage and Handling

The test substance and vehicle were stored according to the received storage conditions supplied by the Sponsor and manufacturer, accordingly.

Analysis of the Test Article Formulations

Samples of the test article formulation will be cryopreserved for analysis of the concentration, stability and homogeneity of the test substance formulations.

Test System Rationale

The primate is a suitable non rodent species, acceptable to regulatory authorities as an indicator of potential hazards, and for which extensive background data are available. The African green monkey specifically is a highly clinically relevant model of multiple human physiologic and disease states.

The intravenous route of administration corresponds to a possible human therapeutic route. The dose of the test articles was based on the results of the dose finding studies of analogous compounds previously performed in the African green monkey.

African green monkey were chosen as the primate of choice as the test substances' target sequence are conserved across species with 100% homology in primates. Additionally, the test substance is a synthetic oligonucleotide. Consequently, dosing in primates allows for a superior assessment of the efficacy of these compounds that would be more reflective of the uptake likely to be seen in humans than in any other species.

Animals

Species: *Chlorocebus sabaeus*, non-human primate

Breed: African green monkey indigenous to St. Kitts.

Source: RxGen, Lower Bourryeau, St. Kitts, West Indies.

Expected Age: The test animals were adults.

Expected Body Weight: The monkeys weigh approximately 3-4 kg. The actual range may vary but will be documented in the data.

Sex: The test animals were adult females.

Number of Animals: Ten animals were screened to ensure identification of 8 animals appropriate for enrollment in the study.

Number on Study: Females: 8

Justification for Number on Study:

This study was designed to use the fewest number of animals possible, consistent with the primary objective of evaluating the therapeutic efficacy of the test article in the African green monkey and prior studies of the systemic administration of this type of oligonucleotide in this species.

Animal Specification:

Ten adult African Green monkeys in the weight range of 3 to 4 kg, were employed in the study. The monkeys were drug-naive adult animals humanely trapped from the feral population that inhabits the island. Trapped monkeys were treated with antihelminthics to eliminate any possible intestinal parasite burden and were observed in quarantine for a minimum of 4 weeks prior to screening for study enrollment. The age of trapped monkeys were estimated by size and dentation, with the exclusion of older animals from the study. Prior to study enrollment, a clinical exam was performed on each monkey, including evaluation of locomotion and dexterity. Blood samples were taken and sent to Antech Diagnostics (Memphis, Tenn.) for comprehensive clinical chemistries and a complete blood count and lipid profiles (see sections 9.2 and 319567928 for specifications). Monkeys with abnormal lab values, as determined by comparison to the established normal range for monkeys in the St. Kitts colony, were excluded from the study. In order to identify 8 monkeys that satisfy this criterion, 10 monkeys were screened, with the screening of additional animals as needed. Before study initiation, the selected monkeys will be transferred to individual cages to acclimate to individual housing for a one-week period. Only animals deemed suitable for experimentation will be enrolled in the study. The actual (or estimated) age and weight ranges at the start of the study will be detailed in the raw data and final report.

Animal Health and Welfare

The highest standards of animal welfare were followed and adhered to guidelines stipulated by the St. Kitts Department of Agriculture and the U.S. Department of Health and Human Services. All studies will be conducted in accordance with these requirements and all applicable codes of practice for the care and housing of laboratory animals. All applicable standards for veterinary care, operation, and review as contained in the NIH Guide for the Care and Use of Animals. The St. Kitts facility maintains an animal research committee that reviews the protocols and inspects the facilities as required by the Guide. The Foundation has an approved assurance filed with the Office of Laboratory Animal Welfare, as required by the Guide, #A4384-01 (Axion Research Foundation/St. Kitts Biomedical Foundation). There are no special nonhuman primate veterinary care issues and biohazard issues raised by the research specified in this study.

Housing and Environment

To allow detection of any treatment-related clinical signs, the animals were housed individually prior to surgery and postoperatively until sacrifice. The primate building in which the individual cages were situated were illuminated entirely by ambient light, which at 17 degrees north latitude approximates a 12 hr:12 hr light-dark cycle as recommended in the U.S. D.H.H.S guidelines. The RxGen primate building was completely ventilated to the outside. Additional air movement was assured by ceiling fans to maintain a constant target temperature of 23-35.degree. C., as is typical of St. Kitts throughout the year. Twenty-four hour extremes of temperature and relative humidity (which also will not be controlled) were measured daily. During the study, the cages were cleaned at regular intervals.

Diet and Water

Each animal was offered approximately 90 grams per day of a standard monkey chow diet (TekLad, Madison, Wis.). The specific nutritional composition of the diet was recorded. The water was periodically analyzed for microbiological purity. The criteria for acceptable levels of contaminants in stock diet and water supply were within the analytical specifications established by the diet manufacturer and the periodic facility water evaluations, respectively. The water met all criteria necessary for certification as acceptable for human consumption.

Experimental Design

Animal Identification and Randomization

Allocation was done by means of a stratified randomization procedure based on bodyweight and plasma cholesterol profiles. Prior to and after allocation to a group, each animal was identified by a tattoo on the abdomen. Tattoos are placed on all colony animals as a means of identification in the course of routine health inspections. A cage plan was drawn up to identify the individuals housed within, and individual monkeys were further identified by a labeled tag attached to their respective cage.

Group Sizes, Doses and Identification Numbers

The animals were assigned to 2 treatment groups, comprised of 4 monkeys in each group. Specific animal identification numbers were provided to each monkey according to the facility numbering system. This system uniquely identifies each monkey by a letter followed by a three-digit number, e.g. Y032.

Route and Frequency of Administration

Animals were dosed once daily on Days 1, 3, and 5 delivered intravenously by manual infusion over .about.10 min. The infusion rate will be 24 mL/kg/h. The animals were sedated with ketamine and xylazine prior to and during the dosing procedure. A venous catheter (Terumo mini vein infusion set, 20 gauge needle, or similar appropriate infusion set) was inserted into the saphenous vein. Dosing took place in each monkey between 8:00 and 10:00 a.m. shortly after the animals wake and prior to feeding. A blood sample to assess plasma cholesterol and other lipid levels as described in Blood Chemistry section below, was collected just prior to each infusion. Blood collection preceded feeding at both sampling intervals to minimize dietary effects on cholesterol measurements.

Clinical Observations

All visible signs of reaction to treatment were recorded on each day of dosing. In addition, the animals were examined at least once each week for physical attributes such as appearance and general condition.

Body Weights

Body weights were recorded at weekly intervals during the treatment and post-treatment periods.

Food Consumption

Individual food consumption was not be quantified. Feeding patterns, however, were be monitored and a note made of any major changes.

Mortality and Morbidity

Mortality and morbidity will be recorded. Any decision regarding premature sacrifice will be made after consultation with the Study Director and with the Sponsor's Monitoring Scientist, if possible Animals that are found dead or killed prematurely will be subjected to necropsy with collection of liver, kidney, heart and spleen lung tissues for histopathology. In the event of premature sacrifice a blood sample will also be taken (if possible) and the parameters determined. Animals that are found dead after regular working hours will be refrigerated overnight and necropsies performed at the start of the next working day. If the condition of an animal requires premature sacrifice, it will be euthanized by intravenous overdose of sodium pentobarbital. All research is governed by the Principles for Use of Animals. RxGen is required by law to comply with the U.S. Department of Health and Human Services standards for primate facility, which dictates the levels of severity that the procedures within this study, specified as mild, must abide.

Clinical Laboratory Studies

Blood Samples

Three blood samples were obtained from all animals prior to treatment, to establish a plasma cholesterol baseline. Blood samples were collected post treatment and were taken via superficial venipuncture. The volume collected at any one sampling time point was not to exceed 8 ml, which represents approximately 4% total blood volume of an adult monkey.

Animals had blood drawn at two baseline time points and on study days 1, 3, 5, 7, 9, 11, 13 and 15, with continued weekly collection thereafter until total plasma cholesterol normalizes in group 1 (APOA1), if a perturbation is appreciated. Eight milliliters of blood were collected on days 1, 6 and 11 to allow for assessment of clinical chemistries, lipid profiles and coagulation profiles. On all other days only 5 mls of blood were collected, sufficient for clinical chemistries and lipid profiles.

Blood samples were split into three parts on days on which both chemistry and hematology measures will be made. One sample was collected into plasma collection tubes containing 25 .mu.l of heparin and labeled with the study number, dose level, day number, date, unique animal identification number. Following separation 1 ml of plasma was removed to a sterile cryotube carrying the above details and stored appropriately until shipment, for blood chemistry analysis. One aliquot of the plasma (0.5 ml) was removed to a sterile cryotube labeled with the details described above and stored appropriately until shipment for plasma cholesterol distribution and Lipid profile analysis. An additional 1 ml and 0.5 ml aliquot of plasma was flash frozen and stored in liquid nitrogen to serve as back-up samples for potential additional analyses.

Two additional whole blood sample aliquots (2.5 ml each) were treated with acid citrate dextrose (ACD) anticoagulant and labeled, and stored at 4.degree. C. until shipped for coagulation and CBC measures detailed below.

The samples were shipped to arrive within 24 h of sampling, or stored under stable conditions for shipment at a time determined appropriate.

Repeat samples were taken only if the method of sampling or the method of assay was thought to be outside normal quality limits Samples were taken into labeled tubes.

Hematology

A complete blood count (CBC), Prothrombin Time, PTT, Fibrinogen and D-Dimer were measured on all samples collected on days 1, 6 and 11 (and on additional days if perturbations are detected at any of these time points). Blood counts were assessed on 1 ml of whole blood collected in vacutainers containing EDTA. Coagulation profile determinations were performed on approximately 2.0 mL blood collected in vacutainers containing acid citrate dextrose (ACD) anticoagulant.

Blood Chemistry

Glucose, Blood Urea Nitrogen, Creatinine, Total protein, Albumin, Total bilirubin, Alkaline Phosphatase, Alanine aminotransferase (ALT), Aspartate aminotransferase (AST), Cholesterol, Calcium, Phosphorus, Sodium, Potassium, Chloride, A/G ratio, BUN/Creatine (calculated) Globulins (calculated), Lipase, Amylase, Triglycerides, CPK, Lactate dehydrogenase, Gamma glutamyl transferase (GGT), Magnesium, Total Cholesterol LDL, VLDL, HDL, ApoA1, ApoA2, ApoB, ApoE, ApoLp(a). Superchemistries and LDL and HDL measures were made on every plasma sample. ApoA1 measures were made on select samples after assessment of the LDL and HDL data.

Determinations were performed on approximately 1.0 mL plasma for the superchemistry and 0.5 ml plasma for the cholesterol distribution and Lipid transport and metabolism gene measures. An additional aliquot of plasma was collected and stored for possible future analyses.

Liver Biopsies

A percutaneous liver biopsy was performed on all monkeys at baseline and on days 7 and 17. A 14 gauge biopsy needle (INRAD) will be employed to obtain 2 core biopsies (.about.1.0 cm in length) from both the right and left lobe of the liver. Successful biopsy was confirmed by visual inspection of the biopsy sample on the biopsy needle prior to subdividing as indicated below.

The samples were pooled and then split in the following manner. Half of one biopsy (.about.0.5 cm) from the left lobe was immersed in paraformaldehyde for sectioning for histopathology and in situ analysis. The remaining half of each of the divided biopsies, as well the other two intact biopsies were immediately immersed in a labeled cryotube containing 2 mls of RNAlater (Qiagen) and incubated at 4.degree. C. overnight, following which the RNAlater was aspirated and the sample tube flash frozen in liquid nitrogen. Following transportation in liquid nitrogen total RNA was isolated employing the Trizol or TriReagent method, with an expected yield of .about.40 .mu.g per 1.0 cm 14 g core biopsy (.about.80-100 .mu.g total for the pooled RNA derived from all 4 pooled core biopsies from a single monkey, absent the component saved for histopathology and in situ). 5 .mu.g of the RNA fraction were used for target-specific real-time qPCR (TaqMan miRNA assay, ABI). The remaining RNA fraction was reserved for possible genome wide expression analysis.

The fixed tissue was processed for paraffin embedding. Sections were stained for H&E and histopathological findings reported under Gross Histological findings. All slides generated in this work carried a label with the study number, dose level, day number, date, unique animal identification number.

Statistical Analysis

Statistics

Descriptive statistics on hematology, clinical chemistries and lipid profiles were performed. Appropriate bioinformatic analyses was conducted on expression data.

Sample Size

Sample size determinations were made on the basis of prior experiments administering modified anti-sense oligonucleotides to African green monkeys and resulting clinical chemistry and lipid profile changes and associated variability. The total number of subjects for efficacy evaluation were twenty enrolled animals, with four animals per treatment group, and four additional screened animals.

Figure 1U:
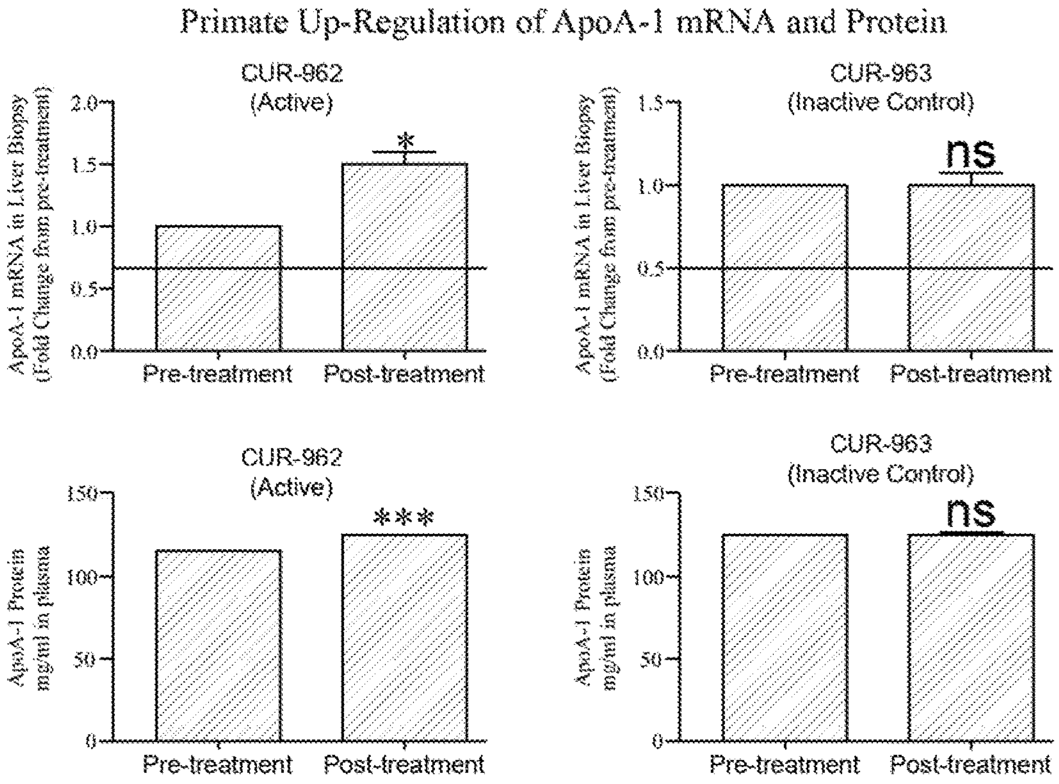
FIG. 1U is a graph showing that ApoA1 mRNA and protein levels increased in monkey liver biopsies after treatment with CUR-962, an oligonucleotide designed to ApoA1 antisense DA327409ext, compared to the baseline levels, as determined by real time PCR and ELISA respectively (right panels). ApoA1 mRNA or protein levels did not change after the same period of time in the control group dosed with an oligonucleotide that showed no effect on ApoA1 levels in vitro (CUR-963) (left panels). Bars denoted CUR-962 and CUR-963 correspond to SEQ ID NOS 260 and 261 respectively.

Results:

The results are shown in the following figures. FIG. 1U: ApoA1 mRNA (top panels) and protein (bottom panels) levels increased in monkey liver biopsies after treatment with CUR-962, an oligonucleotide designed to ApoA1 antisense DA327409ext, compared to the baseline levels, as determined by real time PCR and ELISA respectively (two left panels). ApoA1 mRNA and protein levels did not change after the same period of time in the control group dosed with an oligonucleotide that showed no effect on ApoA1 levels in vitro (CUR-963, two right panels).

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A method of upregulating a function of and/or the expression of a lecithin-cholesterol acetyltransferase (LCAT) gene in mammalian cells or tissues in vivo or in vitro comprising: contacting said cells or tissues with at least one modified antisense oligonucleotide of 12 to 30 nucleotides in length that targets, is 100% complementary with and specifically hybridizes to a complementary region within nucleotides 1 to 1550 of a natural antisense polynucleotide of the LCAT gene wherein said natural antisense polynucleotide consists of SEQ ID NO: 10, thereby upregulating a function of and/or the expression of the LCAT gene in mammalian cells or tissues in vivo or in vitro.

2. The method of claim 1, wherein expression of the LCAT gene is increased in cells in vitro relative to cells of a mock-transfected control.

3. The method of claim 1, wherein the at least one modified antisense oligonucleotide comprises at least one modification selected from the group consisting of at least one modified sugar moiety, at least one modified internucleoside linkage, at least one modified nucleotide, and combinations thereof.

4. The method of claim 1, wherein the complementary region of the natural antisense polynucleotide is complementary to a sequence within a coding region of a LCAT RNA.

5. The method of claim 1, wherein the 12-30 nucleotides of the at least one modified antisense oligonucleotide are 100% complementary to an equal length sequence of the natural antisense that is complementary to both coding and non-coding sequences of a LCAT RNA.

6. The method of claim 1, wherein the at least one modified antisense oligonucleotide is 12 to 24 nucleotides in length and comprises one or more modifications selected from: at least one modified sugar moiety, at least one modified internucleoside linkage, at least one modified nucleotide, and combinations thereof.

7. The method of claim 6, wherein the one or more modifications comprise at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and combinations thereof.

8. The method of claim 6, wherein the one or more modifications comprise at least one modified internucleoside linkage selected from: a phosphorothioate, alkylphosphonate, phosphorodithioate, alkylphosphonothioate, phosphoramidate, carbamate, carbonate, phosphate triester, acetamidate, carboxymethyl ester, and combinations thereof.

9. The method of claim 6, wherein the one or more modifications comprise at least one modified nucleotide selected from: a peptide nucleic acid (PNA), a locked nucleic acid (LNA), or an arabino-nucleic acid (FANA).

10. The method of claim 1, wherein the at least one oligonucleotide comprises at least one oligonucleotide sequence selected from the group consisting of SEQ ID NOS: 41, 42, 52, 54, 55, 56, and 58.

11. A method of upregulating a function of and/or the expression of a LCAT gene in mammalian cells or tissues in vivo or in vitro comprising: contacting said cells or tissues with at least one short interfering RNA (siRNA) oligonucleotide 19 to 30 nucleotides in length, wherein said at least one siRNA oligonucleotide comprises an oligonucleotide strand that is sufficiently complementary to a portion of SEQ ID NO: 10 to specifically hybridize under physiological conditions to a natural antisense transcripts that is the RNA version of SEQ ID NO: 10, wherein the portion of the natural antisense transcript to which the siRNA oligonucleotide strand can hybridize is not complementary to LCAT mRNA.

12. A method of treating a disease associated with an LCAT gene in a patient in need of treatment thereof, comprising: administering to said patient a therapeutically effective dose of at least one modified antisense oligonucleotide of 10 to 30 nucleotides in length that binds and specifically hybridizes to a complementary region of a natural antisense sequence of said LCAT gene consisting of SEQ ID NO: 10 and upregulates expression of said LCAT gene thereby treating the disease associated with the LCAT gene, wherein the disease associated with the LCAT gene is Fish Eye disease.

* * * * *